US010723952B2

(12) United States Patent
Horiguchi et al.

(10) Patent No.: US 10,723,952 B2
(45) Date of Patent: Jul. 28, 2020

(54) POLYMERIZABLE COMPOUND AND OPTICALLY ANISOTROPIC BODY

(71) Applicant: DIC Corporation, Tokyo (JP)

(72) Inventors: Masahiro Horiguchi, Kita-adachi-gun (JP); Yutaka Kadomoto, Kita-adachi-gun (JP); Tetsuo Kusumoto, Kita-adachi-gun (JP)

(73) Assignee: DIC CORPORATION, Tokyo (JP)

( * ) Notice: Subject to any disclaimer, the term of this patent is extended or adjusted under 35 U.S.C. 154(b) by 0 days.

(21) Appl. No.: 15/517,441

(22) PCT Filed: Oct. 6, 2015

(86) PCT No.: PCT/JP2015/078322
§ 371 (c)(1),
(2) Date: Apr. 6, 2017

(87) PCT Pub. No.: WO2016/056542
PCT Pub. Date: Apr. 14, 2016

(65) Prior Publication Data
US 2017/0306233 A1    Oct. 26, 2017

(30) Foreign Application Priority Data

Oct. 9, 2014    (JP) ................... 2014-208048

(51) Int. Cl.
*G02F 1/1333* (2006.01)
*C09K 19/38* (2006.01)
(Continued)

(52) U.S. Cl.
CPC ............... *C09K 19/38* (2013.01); *A61K 8/37* (2013.01); *A61K 8/40* (2013.01); *A61K 8/46* (2013.01); *A61K 8/49* (2013.01); *A61K 8/4966* (2013.01); *A61K 8/69* (2013.01); *A61Q 19/00* (2013.01); *C07C 251/86* (2013.01); *C07C 251/88* (2013.01); *C07C 255/55* (2013.01); *C07C 323/52* (2013.01); *C07D 277/50* (2013.01); *C07D 277/66* (2013.01); *C07D 277/82* (2013.01); *C07D 277/84* (2013.01); *C07D 303/22* (2013.01); *C07D 303/48* (2013.01); *C07D 305/06* (2013.01); *C07D 339/06* (2013.01); *C07D 409/04* (2013.01); *C07D 417/04* (2013.01); *C07D 417/12* (2013.01); *C07D 513/04* (2013.01); *C08F 20/18* (2013.01); *C08F 20/30* (2013.01); *C08G 59/20* (2013.01); *C08G 65/18* (2013.01); *C08G 65/2612* (2013.01); *C09K 19/32* (2013.01); *C09K 19/34* (2013.01); *C09K 19/3486* (2013.01); *C09K 19/3497* (2013.01); *C09K 19/54* (2013.01);
(Continued)

(58) Field of Classification Search
CPC ............... C09K 19/54; C09K 19/3497; C09K 19/3486; C09K 19/34; C09K 19/32; C09K 19/38; C09K 2019/0448; G02F 1/1333; G02F 1/13363; A61K 8/37; A61K 8/40; A61K 8/46; A61K 8/49; A61K 8/4966; A61K 8/69; A61K 47/22; A61K 2800/10; A61Q 19/00; C07C 251/86; C07C 251/88; C07C 255/55; C07C 323/52; C07C 2603/24; C07C 2603/32; C07C 2603/18; C07C 2601/14; C07D 277/50; C07D 277/66; C07D 277/82; C07D 277/84; C07D 303/48; C07D 305/06; C07D 339/06; C07D 409/04; C07D 417/04; C07D 417/12; C07D 513/04; C08F 20/18; C08F 20/30; C08G 59/20; C08G 65/18; C08G 65/2612
USPC .................................................. 252/299.01
See application file for complete search history.

(56) References Cited

U.S. PATENT DOCUMENTS 5,445,854 A    8/1995  Newsham et al.
2007/0111199 A1    5/2007  Housey
(Continued)

FOREIGN PATENT DOCUMENTS

CN    101279901 A    10/2008
GB      1016964 A     1/1966
(Continued)

OTHER PUBLICATIONS

International Search Report dated Dec. 22, 2015, issued in counterpart International Application No. PCT/JP2015/078322 (3 pages).
(Continued)

*Primary Examiner* — Geraldina Visconti
(74) *Attorney, Agent, or Firm* — Westerman, Hattori, Daniels & Adrian, LLP

(57) ABSTRACT

The present invention provides a polymerizable compound that reduces, for example, the likelihood of crystals precipitating in a polymerizable composition including the polymerizable compound and enables the polymerizable composition to have high preservation stability and a polymerizable composition including the polymerizable compound which reduces the likelihood of inconsistencies being formed in a film-like polymer produced by polymerizing the polymerizable composition. Also provided are a polymer produced by polymerizing the polymerizable composition and an optically anisotropic body including the polymer. The present invention provides the compound represented by General Formula (I), a composition including the compound, a polymer produced by polymerizing the composition, and an optically anisotropic body including the polymer.

12 Claims, No Drawings

(51) Int. Cl.

| | | |
|---|---|---|
| A61K 8/49 | (2006.01) | |
| C07D 277/82 | (2006.01) | |
| C07C 251/88 | (2006.01) | |
| C08F 20/18 | (2006.01) | |
| C08G 65/18 | (2006.01) | |
| C07D 305/06 | (2006.01) | |
| A61K 8/40 | (2006.01) | |
| C08G 59/20 | (2006.01) | |
| C07C 251/86 | (2006.01) | |
| C09K 19/54 | (2006.01) | |
| C07C 323/52 | (2006.01) | |
| C09K 19/32 | (2006.01) | |
| C09K 19/34 | (2006.01) | |
| C08G 65/26 | (2006.01) | |
| C07D 513/04 | (2006.01) | |
| C07C 255/55 | (2006.01) | |
| C07D 277/84 | (2006.01) | |
| C07D 417/12 | (2006.01) | |
| A61Q 19/00 | (2006.01) | |
| A61K 8/69 | (2006.01) | |
| A61K 8/46 | (2006.01) | |
| A61K 8/37 | (2006.01) | |
| C07D 277/50 | (2006.01) | |
| C07D 303/22 | (2006.01) | |
| C07D 303/48 | (2006.01) | |
| C07D 277/66 | (2006.01) | |
| C07D 339/06 | (2006.01) | |
| C07D 409/04 | (2006.01) | |
| C07D 417/04 | (2006.01) | |
| C08F 20/30 | (2006.01) | |
| C09K 19/04 | (2006.01) | |
| A61K 47/22 | (2006.01) | |
| G02F 1/13363 | (2006.01) | |

(52) U.S. Cl.
CPC .......... *A61K 47/22* (2013.01); *A61K 2800/10* (2013.01); *C07C 2601/14* (2017.05); *C07C 2603/18* (2017.05); *C07C 2603/24* (2017.05); *C07C 2603/32* (2017.05); *C09K 2019/0448* (2013.01); *G02F 1/13363* (2013.01)

(56) References Cited

U.S. PATENT DOCUMENTS

| | | |
|---|---|---|
| 2007/0176145 A1 | 8/2007 | Nishikawa et al. |
| 2012/0224245 A1 | 9/2012 | Adlem |
| 2014/0107247 A1 | 4/2014 | Sakamoto et al. |
| 2014/0142266 A1 | 5/2014 | Sakamoto et al. |
| 2014/0200320 A1 | 7/2014 | Sakamoto et al. |
| 2014/0309396 A1 | 10/2014 | Sakamoto et al. |
| 2015/0115199 A1 | 4/2015 | Choi et al. |
| 2015/0175564 A1 | 6/2015 | Sakamoto et al. |
| 2015/0183902 A1 | 7/2015 | Sakamoto et al. |
| 2015/0274647 A1 | 10/2015 | Sakamoto et al. |
| 2015/0274872 A1 | 10/2015 | Sakamoto et al. |
| 2015/0277007 A1 | 10/2015 | Matsuyama et al. |
| 2015/0277010 A1 | 10/2015 | Aimatsu et al. |
| 2015/0285979 A1 | 10/2015 | Aimatsu |
| 2016/0002374 A1 | 1/2016 | Sakamoto et al. |
| 2016/0200841 A1 | 7/2016 | Sakamoto |
| 2016/0257659 A1 | 9/2016 | Sakamoto et al. |
| 2017/0003418 A1 | 1/2017 | Yamamoto et al. |
| 2017/0008833 A1 | 1/2017 | Sakamoto et al. |
| 2017/0369783 A1* | 12/2017 | Horiguchi ............ C07C 69/753 |
| 2018/0022716 A1* | 1/2018 | Horiguchi ............ C07D 277/82 |

FOREIGN PATENT DOCUMENTS

| | | |
|---|---|---|
| JP | 63-55543 A | 3/1988 |
| JP | 2005-289980 A | 10/2005 |
| JP | 2007-328053 A | 12/2007 |
| JP | 2009-029795 A | 2/2009 |
| JP | 2009-506125 A | 2/2009 |
| JP | 2009-062508 A | 3/2009 |
| JP | 2010-31223 A | 2/2010 |
| JP | 2010-100541 A | 5/2010 |
| JP | 2011-006361 A | 1/2011 |
| JP | 2011-207765 A | 10/2011 |
| JP | 2011-246381 A | 12/2011 |
| JP | 2012-077055 A | 4/2012 |
| JP | 2013-509458 A | 3/2013 |
| JP | 2015-200877 A | 11/2015 |
| JP | 2016-113583 A | 6/2016 |
| WO | 2005/112540 A2 | 12/2005 |
| WO | 2012/141245 A1 | 10/2012 |
| WO | 2012/147904 A1 | 11/2012 |
| WO | 2012/176679 A1 | 12/2012 |
| WO | 2013/157888 A1 | 10/2013 |
| WO | 2013/180217 A1 | 12/2013 |
| WO | 2014010325 A1 | 1/2014 |
| WO | 2014/061709 A1 | 4/2014 |
| WO | 2014/065176 A1 | 5/2014 |
| WO | 2014/065243 A1 | 5/2014 |
| WO | 2014069515 A1 | 5/2014 |
| WO | 2014/126113 A1 | 8/2014 |
| WO | 2014/132978 A1 | 9/2014 |
| WO | 2015/025793 A1 | 2/2015 |
| WO | 2015/064698 A1 | 5/2015 |
| WO | 2015/098702 A1 | 7/2015 |
| WO | 2015/122384 A1 | 8/2015 |
| WO | 2015/122385 A1 | 8/2015 |
| WO | 2016/56542 A1 | 4/2016 |
| WO | 2016/056542 A1 | 4/2016 |
| WO | 2016/088749 A1 | 6/2016 |

OTHER PUBLICATIONS

Calvin, Joel et al., "Rhodium-Catalyzed and Zinc(II)-Triflate-Promoted Asymmetric Hydrogenation of Tetrasubstituted a, b-Unsaturated Ketones", Oranic Letters, 2012, vol. 14, No. 4, pp. 1038-1041.

Szelinski, Helga et al., "Porphyrins Linked to High Acceptor Strength Cyano Quinones as Models for the Photosynthetic Reaction Center", Pergamon, Tetrahedron, vol. 52, No. 25, pp. 8497-8516.

Kallitsis, J.K. et al., "Soluble Polymers with Laterally Attached Oligophenyl Units for Potential Use as Blue Luminescent Materials", Macromolecules, 1997, vol. 30, No. 10, pp. 2989-2996.

Benbow John W. et al., "An Approach to Dibenzofuran Heterocycles. 1. Electron-Transfer Processes en Route to Dibenzofuran-1, 4-diones", J. Org. Chem, Jul. 1, 1997, vol. 62, No. 26, pp. 9345-9347.

Yu, Sze-Chit et al., "Self-Assembled Electroluminescent Polymers Derived from Terpyridine-Based Moieties", Advanced Materials, Oct. 2, 2003, vol. 15, No. 19, pp. 1643-1647.

Benbow, John W. et al., "Biaryl Formation Using the Suzuki Protocol: Considerations of Base, Halide, and Protecting Group", Pergamon, Tetrahedron Letters, 1996, vol. 37, No. 49, pp. 8829-8832.

MacDonald, Dwight et al., "Substituted 2, 2-bisaryl-bicycloheptanes as novel and potent inhibitors of 5-lipoxygenase activating protein", Elsevier, Bioorganic & Medicinal Chemistry Letters, Jan. 29, 2008, pp. 2023-2027.

International Search Report dated Feb. 16, 2016, issued in counterpart Application No. PCT/JP2015/085342, with English translation (17 pages).

International Search Report dated May 17, 2016, issued in counterpart International Application No. PCT/JP2016/054399 (2 pages).

Notification of Reasons for Refusal dated Jan. 24, 2017, issued in counterpart Japanese Patent Application No. 2016-567448, wlEnglish translation (8 pages).

(56) References Cited

OTHER PUBLICATIONS

Decision to Grant a Patent dated May 25, 2017, issued in counterpart Japanese Patent Application No. 2016-567448, w/English translation (6 pages).

* cited by examiner

POLYMERIZABLE COMPOUND AND OPTICALLY ANISOTROPIC BODY

TECHNICAL FIELD

The present invention relates to a compound including a polymerizable group, a polymerizable composition and a polymerizable liquid crystal composition that include the compound, and an optically anisotropic body produced using the polymerizable liquid crystal composition.

BACKGROUND ART

Compounds including a polymerizable group (polymerizable compounds) have been used for producing various optical materials. For example, a polymer having a uniform orientation can be prepared by polymerizing a polymerizable composition including a polymerizable compound which has been arranged in a pattern while being in a liquid crystal state. Such a polymer can be used for producing polarizing plates, phase-difference plates, and the like, which are necessary in the production of displays. The polymerizable composition typically includes two or more polymerizable compounds in order to meet the demands for optical properties, polymerization velocity, solubility, melting point, glass transition temperature, and the transparency, mechanical strength, surface hardness, heat resistance, and lightfastness of the polymer. The polymerizable compounds included in the polymerizable composition are required to enhance physical properties of the polymerizable composition without degrading the other properties of the polymerizable composition.

There has been a demand for phase-difference films having a low- or inverse-wavelength dependence of birefringence in order to increase the viewing angles of liquid crystal displays. Accordingly, various polymerizable liquid crystal compounds having an inverse- or low-wavelength dependence have been developed as a material for such phase-difference films. However, when the polymerizable compounds are added to a polymerizable composition, the polymerizable compounds cause crystals to precipitate, that is, the polymerizable compounds degrade the preservation stability of the polymerizable composition (PTL 3). Furthermore, when the polymerizable composition is applied to a base material and polymerization is subsequently performed, inconsistencies are likely to be formed in the resulting film (PTL 1 to PTL 3). If the film having inconsistencies is used as a material for, for example, displays, nonuniformity in the brightness of the screen and unnatural colors may occur. This significantly degrades the quality of displays. Consequently, the development of a polymerizable liquid crystal compound having an inverse- or low-wavelength dependence, with which the above issues may be addressed, has been anticipated.

CITATION LIST

Patent Literature

PTL 1: WO2012/147904A1
PTL 2: WO2012/141245A1
PTL 3: Japanese Unexamined Patent Application Publication No. 2010-031223

SUMMARY OF INVENTION

Technical Problem

It is an object of the present invention to provide a polymerizable compound that reduces, for example, the likelihood of crystals precipitating in a polymerizable composition including the polymerizable compound and enables the polymerizable composition to have high preservation stability and a polymerizable composition including the polymerizable compound which reduces the likelihood of inconsistencies being formed in a film-like polymer produced by polymerizing the polymerizable composition. Another object of the present invention is to provide a polymer produced by polymerizing the polymerizable composition and an optically anisotropic body including the polymer.

Solution to Problem

In order to address the foregoing issues, the inventors of the present invention conducted extensive studies and, as a result, developed the compound represented by General Formula (I) below. Specifically, the present invention provides a compound represented by General Formula (I) below.

[Chem. 1]

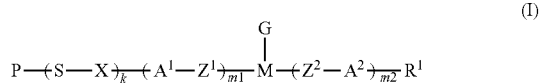

(I)

(wherein, P represents a polymerizable group;
S represents a spacer group or a single bond and, when a plurality of S groups are present, they may be identical to or different from one another;
X represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond and, when a plurality of X groups are present, they may be identical to or different from one another (note that, P—(S—X)$_k$— does not include an —O—O— bond);
A$^1$ and A$^2$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, the above groups may be optionally substituted with one or more L substituents, and, when a plurality of A$^1$ groups and/or a plurality of A$^2$ groups are present, they may be identical to or different from one another;
L represents a fluorine atom, a chlorine atom, a bromine atom, an iodine atom, a pentafluorosulfanyl group, a nitro group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, when a plurality of L substituents are present, they may be identical to or different from one another, and some hydrogen atoms included in the alkyl group may be replaced with fluorine atoms;

$Z^1$ and $Z^2$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, or a single bond, and, when a plurality of $Z^1$ groups and/or a plurality of $Z^2$ groups are present, they may be identical to or different from one another;

M represents a group selected from Formulae (M-1) to (M-8) below,

[Chem. 2]

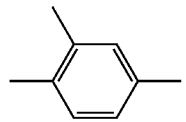
(M-1)

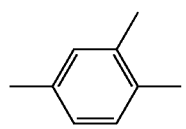
(M-2)

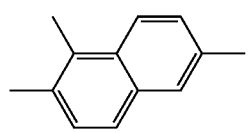
(M-3)

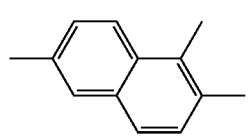
(M-4)

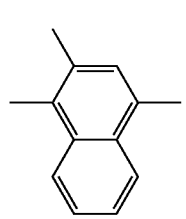
(M-5)

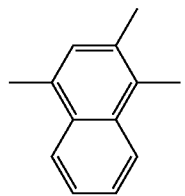
(M-6)

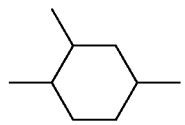
(M-7)

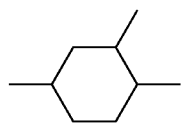
(M-8)

the above groups may be optionally substituted with one or more $L^M$ substituents, $L^M$ represents a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, some hydrogen atoms included in the alkyl group may be replaced with fluorine atoms, and, when a plurality of $L^M$ substituents are present, they may be identical to or different from one another;

$R^1$ represents a hydrogen atom, a fluorine atom, a chlorine atom, a bromine atom, an iodine atom, a pentafluorosulfanyl group, a cyano group, a nitro group, an isocyano group, a thioisocyano group, or a linear or branched alkyl group having 1 to 20 carbon atoms in which one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—, —CF=CF—, or —C≡C— and some hydrogen atoms included in the alkyl group may be replaced with fluorine atoms; G represents a group selected from Formulae (G-1) and (G-2) below,

[Chem. 3]

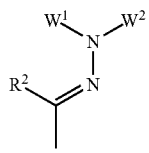
(G-1)

-continued

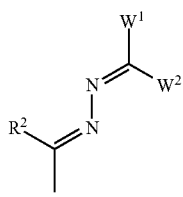

(G-2)

(wherein, R² represents a hydrogen atom or a linear or branched alkyl group having 1 to 20 carbon atoms in which one —CH₂— group or two or more —CH₂— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C— and some hydrogen atoms included in the alkyl group may be replaced with fluorine atoms;

W¹ represents a group having 2 to 30 carbon atoms, the group including at least one aromatic group, the group may be optionally substituted with one or more L^W substituents, L^W represents a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —CH₂— group or two or more —CH₂— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, some hydrogen atoms included in the alkyl group may be replaced with fluorine atoms, and, when a plurality of L^W substituents are present, they may be identical to or different from one another;

W² represents a hydrogen atom or a linear or branched alkyl group having 1 to 20 carbon atoms in which one —CH₂— group or two or more —CH₂— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C— and some hydrogen atoms included in the alkyl group may be replaced with fluorine atoms, or W² represents a group having 2 to 30 carbon atoms, the group including at least one aromatic group, the group may be optionally substituted with one or more L^W substituents; and W¹ and W² may form a ring structure together), and k represents an integer of 0 to 8, m1 and m2 each independently represent an integer of 0 to 5, and m1+m2 is an integer of 1 to 5). The present invention also provides a polymerizable composition and a polymerizable liquid crystal composition that include the above-described compound, a polymer produced by polymerizing the polymerizable liquid crystal composition, and an optically anisotropic body including the polymer.

Advantageous Effects of Invention

The compound according to the present invention enables a polymerizable composition including the compound to have high preservation stability and is suitably used as a component of a polymerizable composition. An optically anisotropic body produced using a polymerizable liquid crystal composition including the compound according to the present invention reduces the occurrence of inconsistencies and is suitably used for producing optical materials such as phase-difference films.

DESCRIPTION OF EMBODIMENTS

The present invention provides the compound represented by General Formula (I), a polymerizable composition and a polymerizable liquid crystal composition that include the compound, a polymer produced by polymerizing the polymerizable liquid crystal composition, and an optically anisotropic body including the polymer.

In General Formula (I), P represents a polymerizable group. P preferably represents a group selected from Formulae (P-1) to (P-20) below.

[Chem. 4]

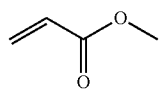

(P-1)

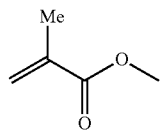

(P-2)

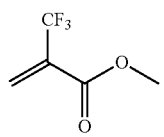

(P-3)

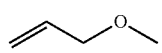

(P-4)

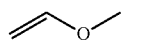

(P-5)

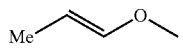

(P-6)

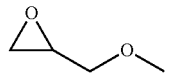

(P-7)

(P-8)

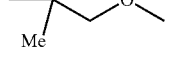

(P-9)

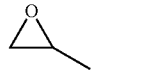

(P-10)

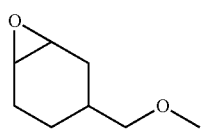 (P-11)

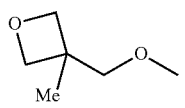 (P-12)

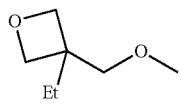 (P-13)

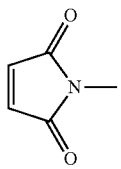 (P-14)

 (P-15)

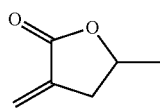 (P-16)

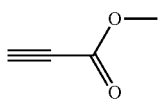 (P-17)

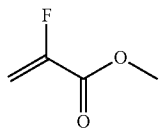 (P-18)

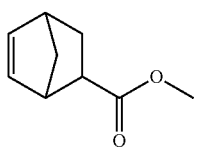 (P-19)

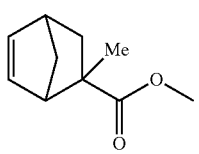 (P-20)

The above polymerizable groups are polymerized by radical polymerization, radical addition polymerization, cationic polymerization, or anionic polymerization. In particular, in the case where ultraviolet polymerization is performed for performing polymerization, Formulae (P-1), (P-2), (P-3), (P-4), (P-5), (P-7), (P-11), (P-13), (P-15), and (P-18) are preferable, Formulae (P-1), (P-2), (P-7), (P-11), and (P-13) are more preferable, Formulae (P-1), (P-2), and (P-3) are further preferable, and Formulae (P-1) and (P-2) are particularly preferable.

S represents a spacer group or a single bond. When a plurality of S groups are present, they may be identical to or different from one another. The spacer group is preferably an alkylene group having 1 to 20 carbon atoms in which one —$CH_2$— group or two or more —$CH_2$— groups that are not adjacent to one another may be each independently replaced with —O—, —COO—, —OCO—, —OCO—O—, —CO—NH—, —NH—CO—, —CH=CH—, or —C≡C—. In consideration of the availability of raw materials and ease of synthesis, S more preferably independently represents an alkylene group having 1 to 10 carbon atoms in which one —$CH_2$— group or two or more —$CH_2$— groups that are not adjacent to one another may be each independently replaced with —O—, —COO—, or —OCO— or a single bond and, when a plurality of S groups are present, they may be identical to or different from one another. S further preferably independently represents an alkylene group having 1 to 10 carbon atoms or a single bond and, when a plurality of S groups are present, they may be identical to or different from one another. S particularly preferably independently represents an alkylene group having 1 to 8 carbon atoms.

X represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C—, or a single bond. When a plurality of X groups are present, they may be identical to or different from one another (note that, P—$(S-X)_k$— does not include an —O—O— bond). In consideration of the availability of raw materials and ease of synthesis, X preferably independently represents —O—, —S—, —$OCH_2$—, —$CH_2O$—, —COO—, —OCO—, —CO—S—, —S—CO—, —O—CO—O—, —CO—NH—, —NH—CO—, —COO—$CH_2CH_2$—, —OCO—$CH_2CH_2$—, —$CH_2CH_2$—COO—, —$CH_2CH_2$—OCO—, or a single bond and, when a plurality of X groups are present, they may be identical to or different from one another. X more preferably independently represents —O—, —$OCH_2$—, —$CH_2O$—, —COO—, —OCO—, —COO—$CH_2CH_2$—, —OCO—$CH_2CH_2$—, —$CH_2CH_2$—COO—, —$CH_2CH_2$—OCO—, or a single bond. X particularly preferably independently represents —O—, —COO—, —OCO—, or a single bond and, when a plurality of X groups are present, they may be identical to or different from one another.

$A^1$ and $A^2$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group. The above groups may be optionally substituted with one or more L substituents. When a plurality of $A^1$ groups and/or a plurality of $A^2$ groups are present, they may be identical to or different from one another. In consideration of the availability of raw materials and ease of synthesis, $A^1$ and $A^2$ preferably each independently represent a 1,4-phenylene group, a 1,4-cyclohexylene group, or naphthalene-2,6-diyl which may be optionally substituted with one or more L substituents. $A^1$ and $A^2$ more preferably each independently represent a group selected from Formulae (A-1) to (A-11) below.

[Chem. 5]

(A-1) 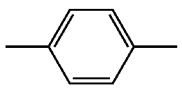

(A-2) 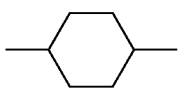

(A-3) 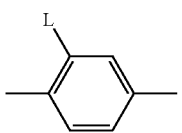

(A-4) 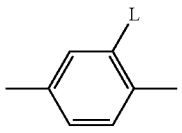

(A-5) 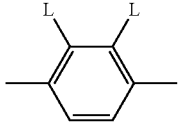

(A-6) 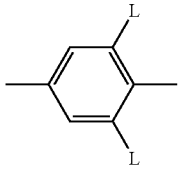

(A-7) 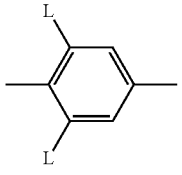

(A-8) 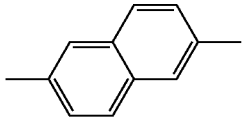

(A-9) 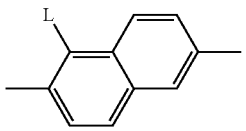

(A-10) 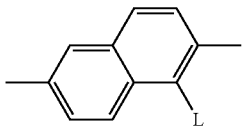

(A-11) 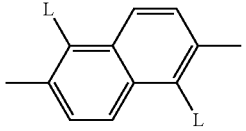

$A^1$ and $A^2$ further preferably each independently represent a group selected from Formulae (A-1) to (A-8) and particularly preferably each independently represent a group selected from Formulae (A-1) to (A-4).

$Z^1$ and $Z^2$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH═CH—COO—, —CH═CH—OCO—, —COO—CH═CH—, —OCO—CH═CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH═CH—, —N═N—, —CH═N—, —N═CH—, —CH═N—N═CH—, —CF═CF—, —C≡C—, or a single bond. When a plurality of $Z^1$ groups and/or a plurality of $Z^2$ groups are present, they may be identical to or different from one another. In consideration of the liquid crystal properties of the compound, the availability of raw materials, and ease of synthesis, the plurality of $Z^1$ groups and the plurality of $Z^2$ groups preferably each independently represent a single bond, —OCH$_2$—, —CH$_2$O—, —COO—, —OCO—, —CF$_2$O—, —OCF$_2$—, —CH$_2$CH$_2$—, —CF$_2$CF$_2$—, —CH═CH—COO—, —CH═CH—OCO—, —COO—CH═CH—, —OCO—CH═CH—, —COO—CH$_2$CH$_2$—, —OCO—CH$_2$CH$_2$—, —CH$_2$CH$_2$—COO—, —CH$_2$CH$_2$—OCO—, —CH═CH—, —CF═CF—, —C≡C—, or a single bond, more preferably each independently represent —OCH$_2$—, —CH$_2$O—, —CH$_2$CH$_2$—, —COO—, —OCO—, —COO—CH$_2$CH$_2$—, —OCO—CH$_2$CH$_2$—, —CH$_2$CH$_2$—COO—, —CH$_2$CH$_2$—OCO—, —CH═CH—, —C≡C—, or a single bond, further preferably each independently represent —OCH$_2$—, —CH$_2$O—, —CH$_2$CH$_2$—, —COO—, —OCO—, —COO—CH$_2$CH$_2$—, —OCO—CH$_2$CH$_2$—, —CH$_2$CH$_2$—COO—, —CH$_2$CH$_2$—OCO—, or a single bond, further preferably each independently represent —OCH$_2$—, —CH$_2$O—, —COO—, —OCO—, —COO—CH$_2$CH$_2$—, —OCO—CH$_2$CH$_2$—, —CH$_2$CH$_2$—COO—, —CH$_2$CH$_2$—OCO—, or a single bond, and particularly preferably each independently represent —OCH$_2$—, —CH$_2$O—, —COO—, —OCO—, or a single bond.

M represents a group selected from Formulae (M-1) to (M-8) below.

[Chem. 6]

(M-1) 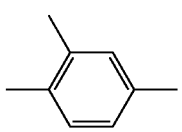

(M-2) 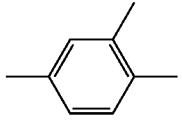

(M-3)

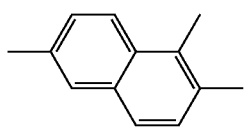
(M-4)

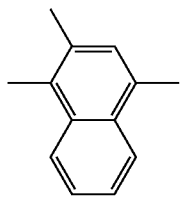
(M-5)

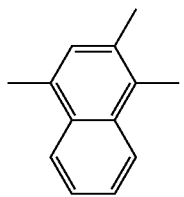
(M-6)

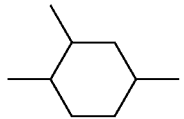
(M-7)

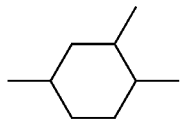
(M-8)

The above groups may be optionally substituted with one or more $L^M$ substituents. In consideration of the availability of raw materials and ease of synthesis, M preferably each independently represents a group selected from Formulae (M-1) and (M-2) which may optionally be substituted with one or more $L^M$ and Formulae (M-3) to (M-6) which are not substituted, more preferably represents a group selected from Formulae (M-1) and (M-2) which may optionally be substituted with one or more $L^M$, and particularly preferably represents a group selected from Formulae (M-1) and (M-2) which are not substituted.

$R^1$ represents a hydrogen atom, a fluorine atom, a chlorine atom, a bromine atom, an iodine atom, a pentafluorosulfanyl group, a cyano group, a nitro group, an isocyano group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—, —CF=CF—, or —C≡C— and some hydrogen atoms included in the alkyl group may be replaced with fluorine atoms. In order to enhance liquid crystal properties and increase ease of synthesis, $R^1$ preferably represents a hydrogen atom, a fluorine atom, a chlorine atom, a cyano group, or a linear or branched alkyl group having 1 to 12 carbon atoms in which one —$CH_2$— group or two or more —$CH_2$— groups that are not adjacent to one another may be each independently replaced with —O—, —COO—, —OCO—, or —O—CO—O—, more preferably represents a hydrogen atom, a fluorine atom, a chlorine atom, a cyano group, or a linear alkyl or alkoxy group having 1 to 12 carbon atoms, further preferably represents a hydrogen atom or a linear alkyl or alkoxy group having 1 to 12 carbon atoms, and particularly preferably represents a linear alkyl or alkoxy group having 1 to 12 carbon atoms, G represents a group selected from Formulae (G-1) and (G-2) below,

[Chem. 7]

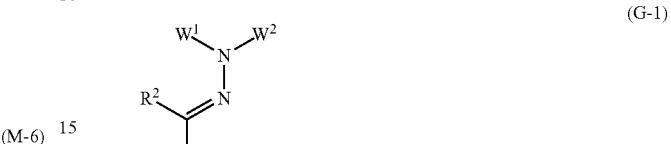
(G-1)

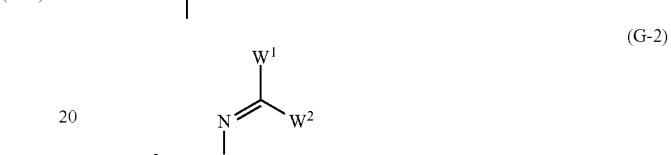
(G-2)

(In Formulae (G-1) and (G-2), $R^2$ represents a hydrogen atom or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C— and some hydrogen atoms included in the alkyl group may be replaced with fluorine atoms; $W^1$ represents a group having 2 to 30 carbon atoms, the group including at least one aromatic group, the group may be optionally substituted with one or more $L^W$ substituents, $L^W$ represents a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, some hydrogen atoms included in the alkyl group may be replaced with fluorine atoms, and, when a plurality of $L^W$ substituents are present, they may be identical to or different from one another; $W^2$ represents a hydrogen atom or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C— and some hydrogen atoms included in the alkyl group may be replaced with fluorine atoms, or W² represents a group having 2 to 30 carbon atoms, the group including at least one aromatic group, and the group may be optionally substituted with one or more L$^W$ substituents; and W¹ and W² may form a ring structure together).

R² represents a hydrogen atom or a linear or branched alkyl group having 1 to 20 carbon atoms in which one —CH₂— group or two or more —CH₂— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C— and some hydrogen atoms included in the alkyl group may be replaced with fluorine atoms. In consideration of liquid crystal properties and ease of synthesis, R² preferably represents a hydrogen atom or a linear or branched alkyl group having 1 to 12 carbon atoms in which some hydrogen atoms may be replaced with fluorine atoms and one —CH₂— group or two or more —CH₂— groups that are not adjacent to one another may be each independently replaced with —O—, —COO—, or —OCO—, more preferably represents a hydrogen atom or a linear or branched alkyl group having 1 to 12 carbon atoms in which some hydrogen atoms may be replaced with fluorine atoms, further preferably represents a hydrogen atom or a linear or branched alkyl group having 1 to 12 carbon atoms, and particularly preferably represents a hydrogen atom.

W¹ represents a group having 2 to 30 carbon atoms, the group including at least one aromatic group. The group may be optionally substituted with one or more L$^W$ substituents. The aromatic group included in W¹ may be an aromatic hydrocarbon group, an aromatic hetero group, or a group including an aromatic hydrocarbon group and an aromatic hetero group. The above aromatic groups may be bonded with a single bond or a linking group or form a condensed ring. W¹ may further include, in addition to an aromatic group, an acyclic structure and/or a cyclic structure other than an aromatic group. In consideration of the availability of raw materials and ease of synthesis, the group represented by W¹ is preferably selected from Formulae (W-1) to (W-19) below which may optionally be substituted with one or more L$^W$ substituents.

[Chem. 8]

(W-1)

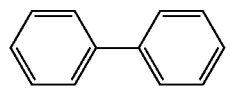
(W-2)

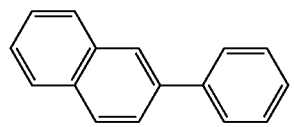
(W-3)

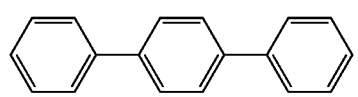
(W-4)

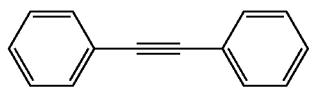
(W-5)

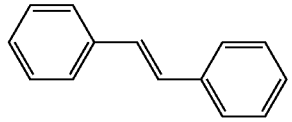
(W-6)

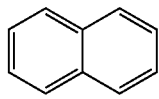
(W-7)

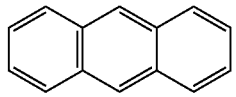
(W-8)

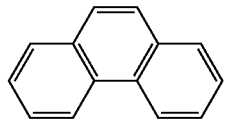
(W-9)

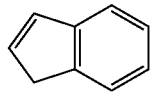
(W-10)

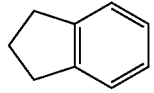
(W-11)

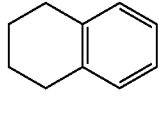
(W-12)

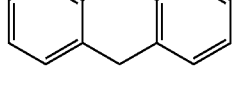
(W-13)

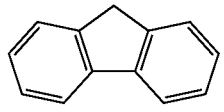
(W-14)

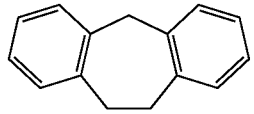
(W-15)

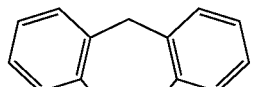
(W-16)

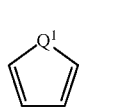
(W-17)

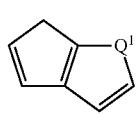
(W-18)

-continued (W-19)

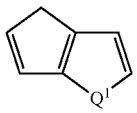

(in Formulae (W-1) to (W-19), the above groups may include a bond at any position; two or more groups selected from the above groups may be connected to one another with a single bond to form another group; $Q^1$ represents —O—, —S—, —NR$^3$— (where $R^3$ represents a hydrogen atom or an alkyl group having 1 to 8 carbon atoms), or —CO—; —CH= groups included in the above groups may be each independently replaced with a —N= group; —CH$_2$— groups included in the above groups may be each independently replaced with —O—, —S—, —NR$^4$— (where $R^4$ represents a hydrogen atom or an alkyl group having 1 to 8 carbon atoms), or —CO— providing that an —O—O— bond is not included. The group represented by Formula (W-1) is preferably a group selected from Formulae (W-1-1) to (W-1-8) below which may optionally be substituted with one or more $L^W$,

[Chem. 9]

(W-1-1)

(W-1-2)

(W-1-3)

(W-1-4)

(W-1-5)

(W-1-6)

(W-1-7)

(W-1-8)

(in Formulae (W-1-1) to (W-1-8), the above groups may include a bond at any position). The group represented by Formula (W-7) is preferably a group selected from Formulae (W-7-1) to (W-7-7) below which may optionally be substituted with one or more $L^W$,

[Chem. 10]

(W-7-1)

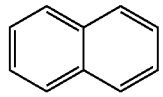

(W-7-2)

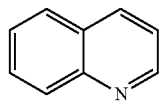

(W-7-3)

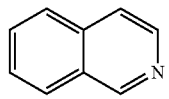

(W-7-4)

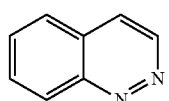

(W-7-5)

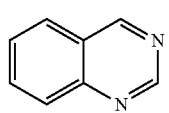

(W-7-6)

(W-7-7)

(in Formulae (W-7-1) to (W-7-7), the above groups may include a bond at any position). The group represented by Formula (W-10) is preferably a group selected from Formulae (W-10-1) to (W-10-8) below which may optionally be substituted with one or more $L^W$,

[Chem. 11]

(W-10-1)

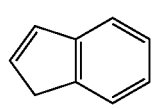

(W-10-2)

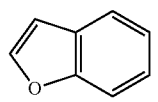

(W-10-3)

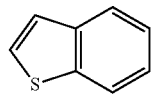

(W-10-4)

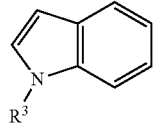

(W-10-5)
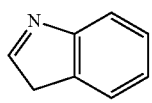

(W-10-6)
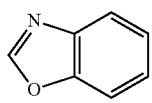

(W-10-7)
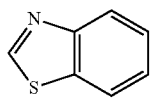

(W-10-8)
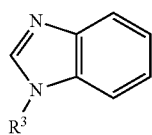

(in Formulae (W-10-1) to (W-10-8), the above groups may include a bond at any position, and $R^3$ represents a hydrogen atom or an alkyl group having 1 to 8 carbon atoms). The group represented by Formula (W-11) is preferably a group selected from Formulae (W-11-1) to (W-11-13) below which may optionally be substituted with one or more $L^W$,

[Chem. 12]

(W-11-1)
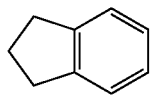

(W-11-2)
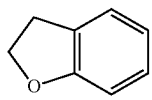

(W-11-3)
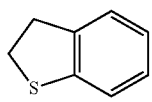

(W-11-4)
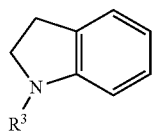

(W-11-5)
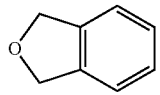

(W-11-6)
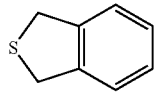

(W-11-7)
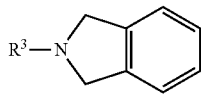

(W-11-8)
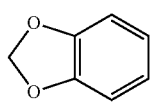

(W-11-9)
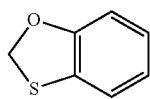

(W-11-10)
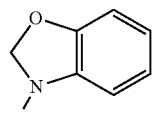

(W-11-11)
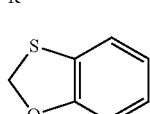

(W-11-12)
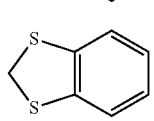

(W-11-13)
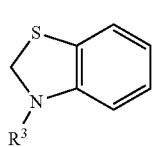

(in Formulae (W-11-1) to (W-11-13), the above groups may include a bond at any position, and $R^3$ represents a hydrogen atom or an alkyl group having 1 to 8 carbon atoms). The group represented by Formula (W-12) is preferably a group selected from Formulae (W-12-1) to (W-12-19) below which may optionally be substituted with one or more $L^W$,

[Chem. 13]

(W-12-1)
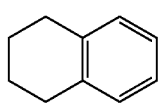

(W-12-2)
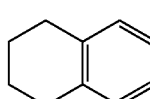

(W-12-3)
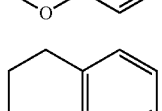

(W-12-4)
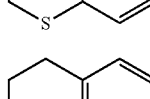

(W-12-5)
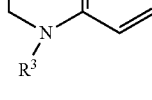

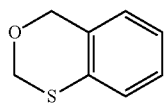 (W-12-6)
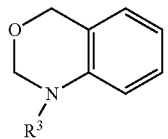 (W-12-7)
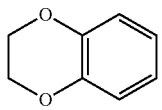 (W-12-8)
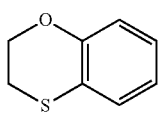 (W-12-9)
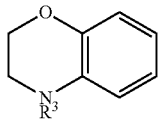 (W-12-10)
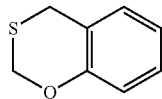 (W-12-11)
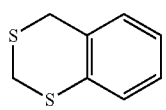 (W-12-12)
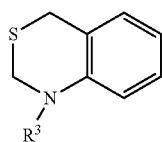 (W-12-13)
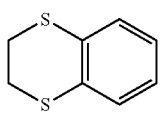 (W-12-14)
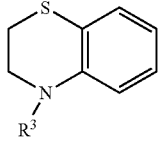 (W-12-15)
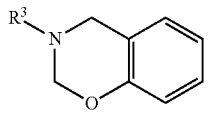 (W-12-16)
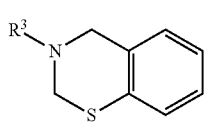 (W-12-17)
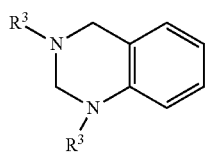 (W-12-18)
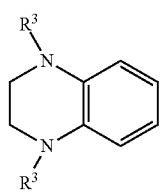 (W-12-19)
(in Formulae (W-12-1) to (W-12-19), the above groups may include a bond at any position, and $R^3$ represents a hydrogen atom or an alkyl group having 1 to 8 carbon atoms). The group represented by Formula (W-13) is preferably a group selected from Formulae (W-13-1) to (W-13-10) below which may optionally be substituted with one or more $L^W$,
[Chem. 14]
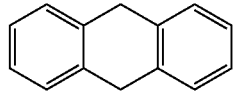 (W-13-1)
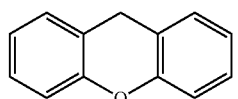 (W-13-2)
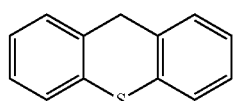 (W-13-3)
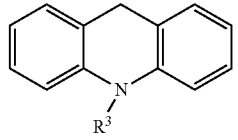 (W-13-4)
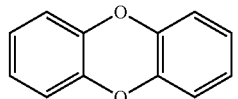 (W-13-5)
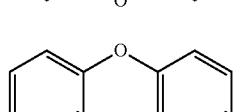 (W-13-6)
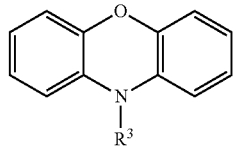 (W-13-7)

(W-13-8)

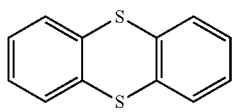

(W-13-9)

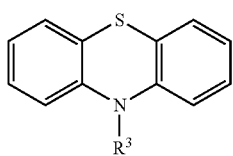

(W-13-10)

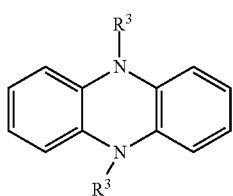

(in Formulae (W-13-1) to (W-13-10), the above groups may include a bond at any position, and R³ represents a hydrogen atom or an alkyl group having 1 to 8 carbon atoms). The group represented by Formula (W-14) is preferably a group selected from Formulae (W-14-1) to (W-14-4) below which may optionally be substituted with one or more $L^W$,

[Chem. 15]

(W-14-1)

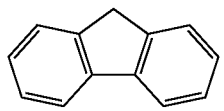

(W-14-2)

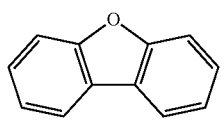

(W-14-3)

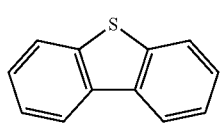

(W-14-4)

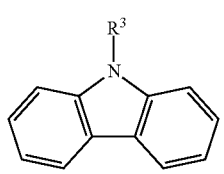

(in Formulae (W-14-1) to (W-14-4), the above groups may include a bond at any position, and R³ represents a hydrogen atom or an alkyl group having 1 to 8 carbon atoms). The group represented by Formula (W-15) is preferably a group selected from Formulae (W-15-1) to (W-15-18) below which may optionally be substituted with one or more $L^W$,

[Chem. 16]

(W-15-1)

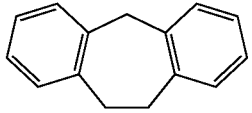

(W-15-2)

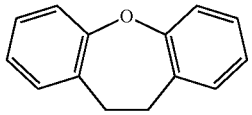

(W-15-3)

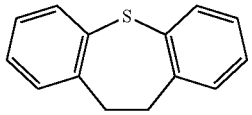

(W-15-4)

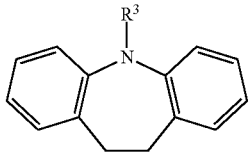

(W-15-5)

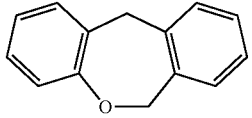

(W-15-6)

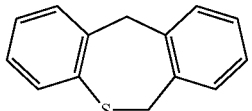

(W-15-7)

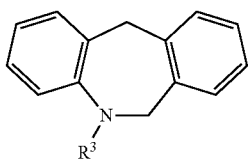

(W-15-8)

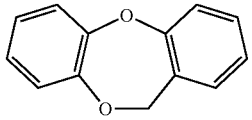

(W-15-11)

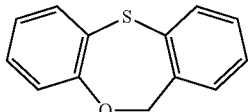

(W-15-12)

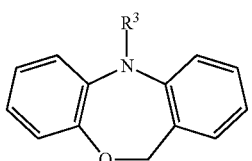

(in Formulae (W-15-1) to (W-15-18), the above groups may include a bond at any position, and R³ represents a hydrogen atom or an alkyl group having 1 to 8 carbon atoms). The group represented by Formula (W-16) is preferably a group selected from Formulae (W-16-1) to (W-16-4) below which may optionally be substituted with one or more $L^W$,

[Chem. 17]

(in Formulae (W-16-1) to (W-16-4), the above groups may include a bond at any position, and R³ represents a hydrogen atom or an alkyl group having 1 to 8 carbon atoms). The group represented by Formula (W-17) is preferably a group selected from Formulae (W-17-1) to (W-17-6) below which may optionally be substituted with one or more $L^W$,

[Chem. 18]

(in Formulae (W-17-1) to (W-17-6), the above groups may include a bond at any position, and R³ represents a hydrogen atom or an alkyl group having 1 to 8 carbon atoms). The group represented by Formula (W-18) is preferably a group selected from Formulae (W-18-1) to (W-18-6) below which may optionally be substituted with one or more $L^W$,

[Chem. 19]

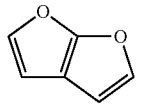
(W-18-1)

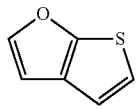
(W-18-2)

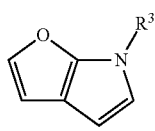
(W-18-3)

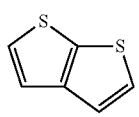
(W-18-4)

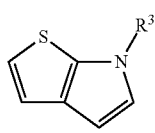
(W-18-5)

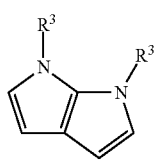
(W-18-6)

(in Formulae (W-18-1) to (W-18-6), the above groups may include a bond at any position, and $R^3$ represents a hydrogen atom or an alkyl group having 1 to 8 carbon atoms). The group represented by Formula (W-19) is preferably a group selected from Formulae (W-19-1) to (W-19-9) below which may optionally be substituted with one or more $L^W$,

[Chem. 20]

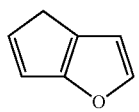
(W-19-1)

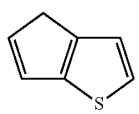
(W-19-2)

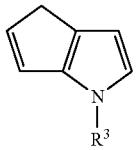
(W-19-3)

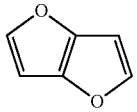
(W-19-4)

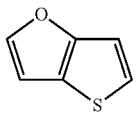
(W-19-5)

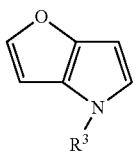
(W-19-6)

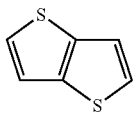
(W-19-7)

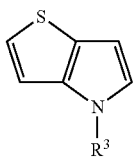
(W-19-8)

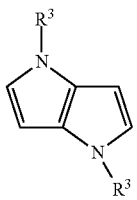
(W-19-9)

(in Formulae (W-19-1) to (W-19-9), the above groups may include a bond at any position, and $R^3$ represents a hydrogen atom or an alkyl group having 1 to 8 carbon atoms). The aromatic group included in $W^1$ is more preferably a group selected from Formulae (W-1-1), (W-7-1), (W-7-2), (W-7-7), (W-8), (W-10-6), (W-10-7), (W-10-8), (W-11-8), (W-11-9), (W-11-10), (W-11-11), (W-11-12), and (W-11-13) which may optionally be substituted with one or more $L^W$, is particularly preferably a group selected from Formulae (W-1-1), (W-7-1), (W-7-2), (W-7-7), (W-10-6), (W-10-7), and (W-10-8) which may optionally be substituted with one or more $L^W$, and is further preferably a group selected from Formulae (W-a-1) to (W-a-6) below,

[Chem. 21]

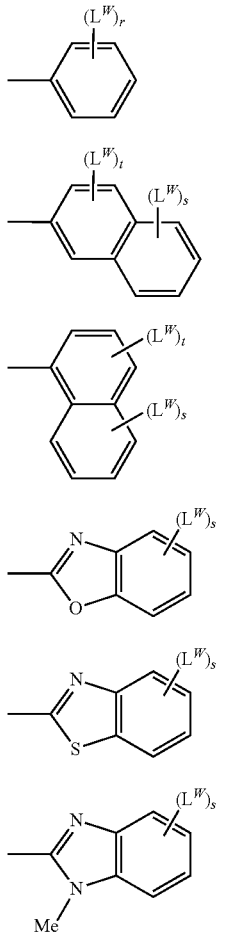

(in Formulae (W-a-1) to (W-a-6), r represents an integer of 0 to 5, s represents an integer of 0 to 4, and t represents an integer of 0 to 3).

$W^2$ represents a hydrogen atom or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—. Some hydrogen atoms included in the alkyl group may be replaced with fluorine atoms. In another case, $W^2$ represents a group having 2 to 30 carbon atoms, the group including at least one aromatic group. The group may be optionally substituted with one or more $L^W$ substituents. $W^1$ and $W^2$ may form a ring structure together. In consideration of the availability of raw materials and ease of synthesis, $W^2$ preferably represents a hydrogen atom or a linear or branched alkyl group having 1 to 20 carbon atoms in which one —$CH_2$— group or two or more —$CH_2$— groups that are not adjacent to one another may be each independently replaced with —O—, —CO—, —COO—, —OCO—, —CH=CH—COO—, —OCO—CH=CH—, —CH=CH—, —CF=CF—, or —C≡C— and some of hydrogen atoms may be replaced with fluorine atoms, more preferably represents a hydrogen atom or a linear or branched alkyl group having 1 to 20 carbon atoms in which one —$CH_2$— group or two or more —$CH_2$— groups that are not adjacent to one another may be each independently replaced with —O—, and further preferably represents a hydrogen atom or a linear alkyl group having 1 to 12 carbon atoms in which one —$CH_2$— group or two or more —$CH_2$— groups that are not adjacent to one another may be each independently replaced with —O—. In order to reduce the likelihood of impurities having large molecular weights being produced when the compound is dissolved in a solvent or formed into a composition, $W^2$ particularly preferably represents a linear alkyl group having 1 to 12 carbon atoms in which one —$CH_2$— group or two or more —$CH_2$— groups that are not adjacent to one another may be each independently replaced with —O—. In the case where $W^2$ represents a group having 2 to 30 carbon atoms, the group including at least one aromatic group, which may be optionally substituted with one or more $L^W$ substituents, $W^2$ may be identical to $W^1$ or different from $W^1$. In such a case, preferable example of the group represented by $W^2$ are the same as those described above as examples of the group represented by $W^1$. In the case where $W^1$ and $W^2$ form a ring structure together, the cyclic group represented by —$NH^1W^2$ is preferably a group selected from Formulae (W-b-1) to (W-b-42) below which may optionally be substituted with one or more $L^W$ substituents,

[Chem. 22]

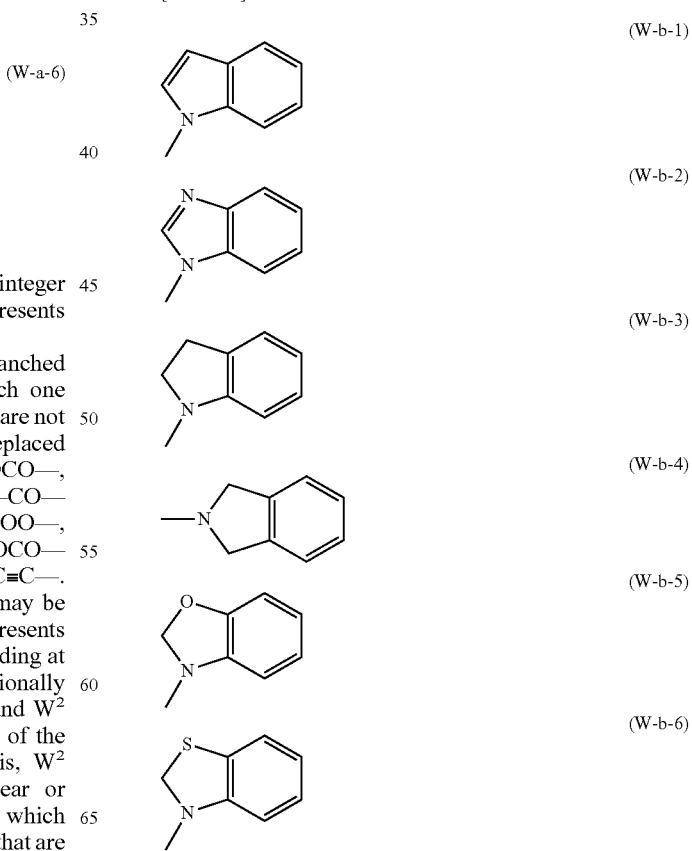

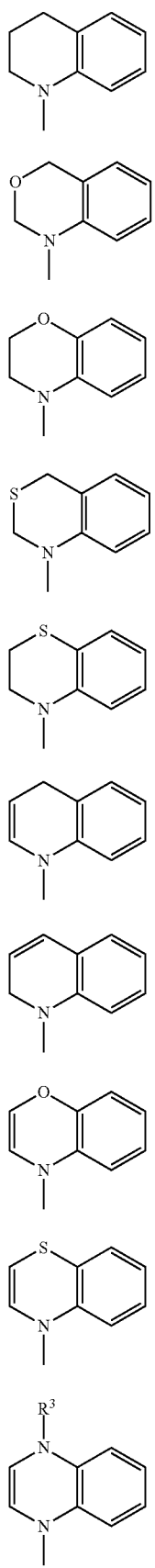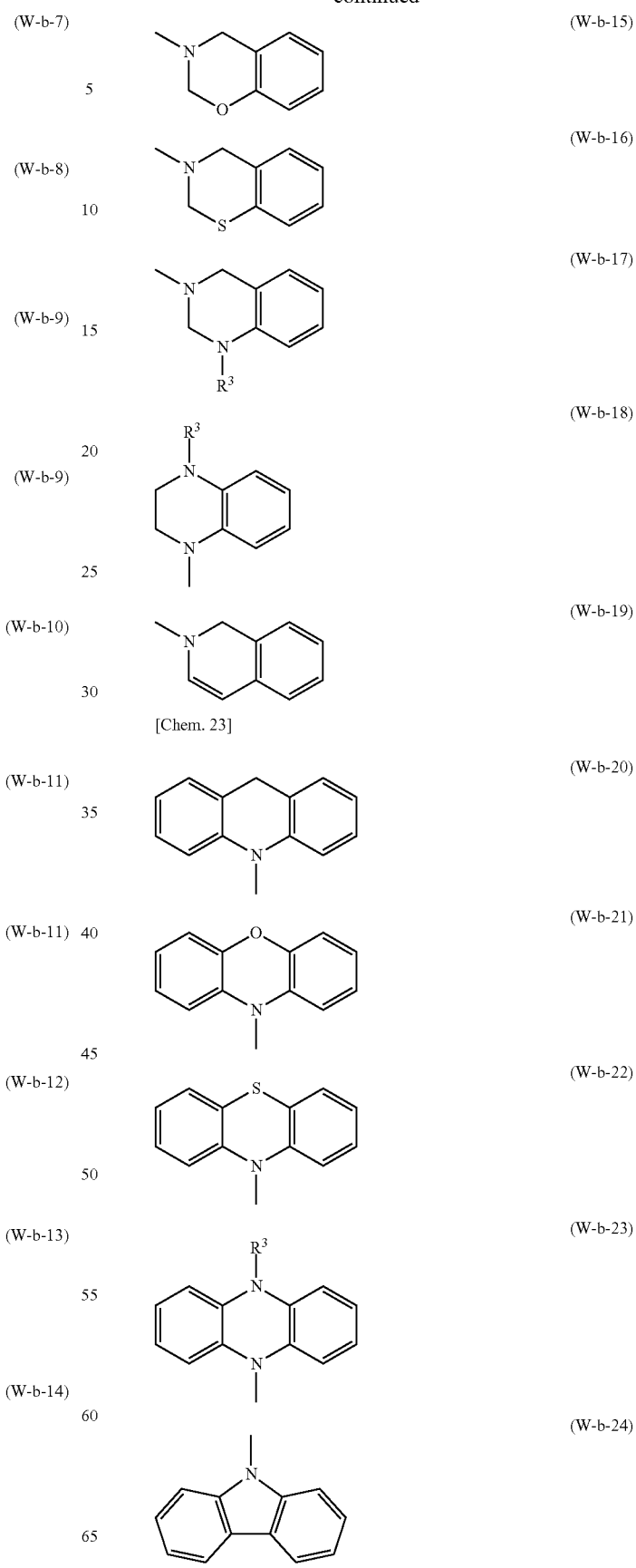

(W-b-25) 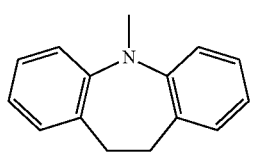

(W-b-26) 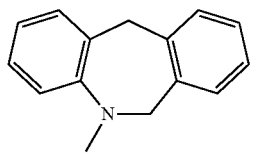

(W-b-27) 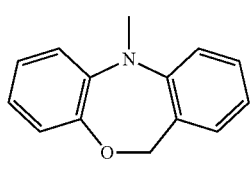

(W-b-28) 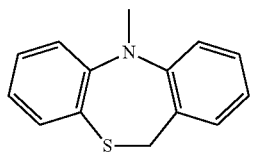

(W-b-29) 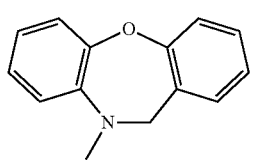

(W-b-30) 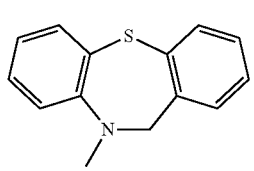

(W-b-31) 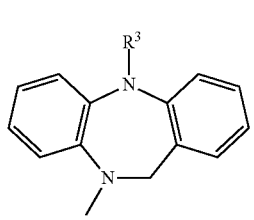

(W-b-32) 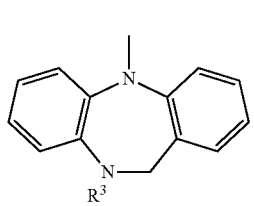

(W-b-33) 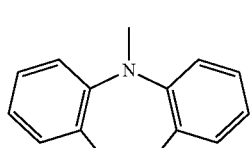

(W-b-34) 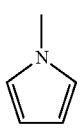

(W-b-35) 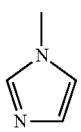

(W-b-36) 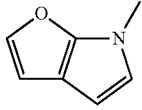

(W-b-37) 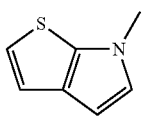

(W-b-38) 

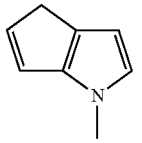

(W-b-39) 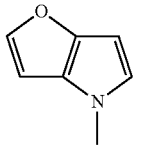

(W-b-40)

(W-b-41)

(W-b-42) 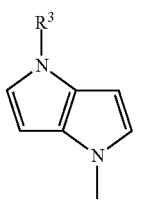

(in Formulae (W-b-1) to (W-b-42), $R^3$ represents a hydrogen atom or an alkyl group having 1 to 8 carbon atoms). In consideration of the availability of raw materials and ease of synthesis, the cyclic group represented by —$NW^1W^2$ is particularly preferably a group selected from Formulae (W-b-20), (W-b-21), (W-b-22), (W-b-23), (W-b-24), (W-b-25), and (W-b-33) which may optionally be substituted with one or more $L^W$ substituents.

The cyclic group represented by =CW¹W² is preferably a group selected from Formulae (W-c-1) to (W-c-81) below which may optionally be substituted with one or more $L^W$ substituents,
[Chem. 24]
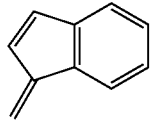 (W-c-1)
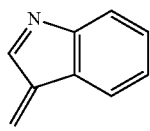 (W-c-2)
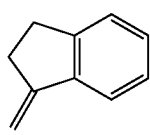 (W-c-3)
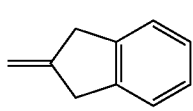 (W-c-4)
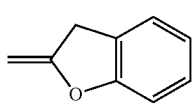 (W-c-5)
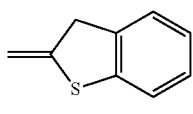 (W-c-6)
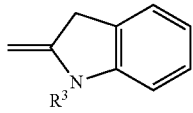 (W-c-7)
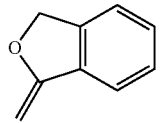 (W-c-8)
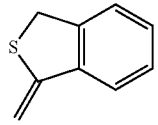 (W-c-9)
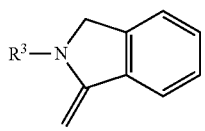 (W-c-9)
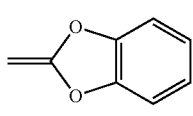 (W-c-10)
-continued
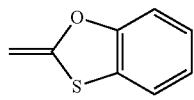 (W-c-11)
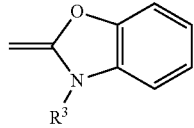 (W-c-11)
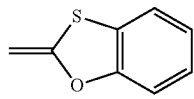 (W-c-12)
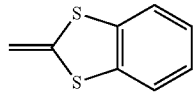 (W-c-13)
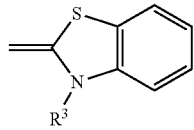 (W-c-14)
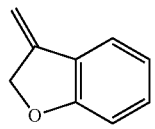 (W-c-15)
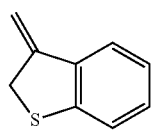 (W-c-16)
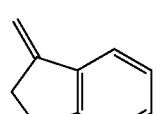 (W-c-17)
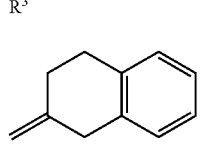 (W-c-18)
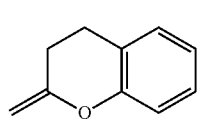 (W-c-19)
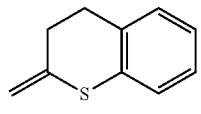 (W-c-20)
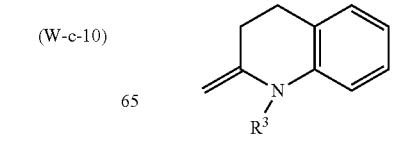 (W-c-21)

(W-c-22) 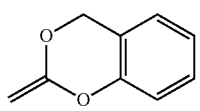
(W-c-23) 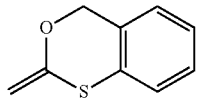
(W-c-24) 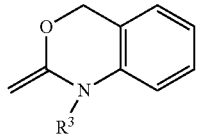
(W-c-25) 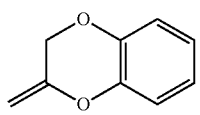
(W-c-26) 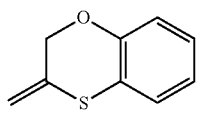
(W-c-27) 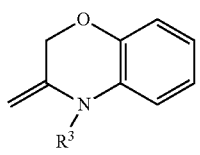
(W-c-28) 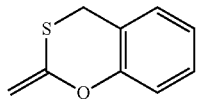
[Chem. 25]
(W-c-29) 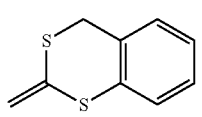
(W-c-30) 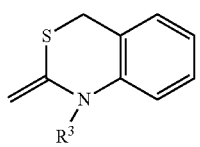
(W-c-31) 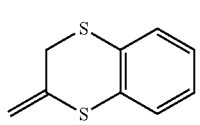
(W-c-32) 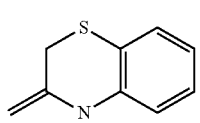
(W-c-33) 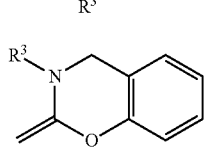
(W-c-34) 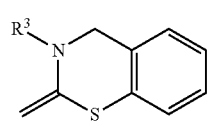
(W-c-35) 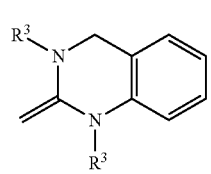
(W-c-36) 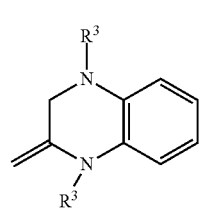
(W-c-37) 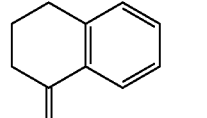
(W-c-38) 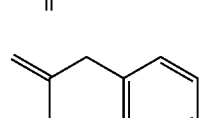
(W-c-39) 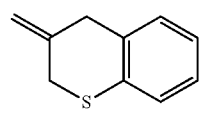
(W-c-40) 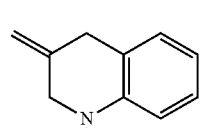
(W-c-41) 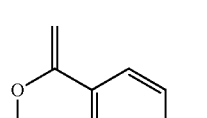
(W-c-42) 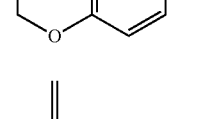
(W-c-43) 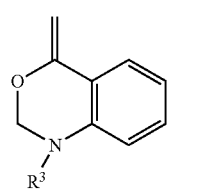

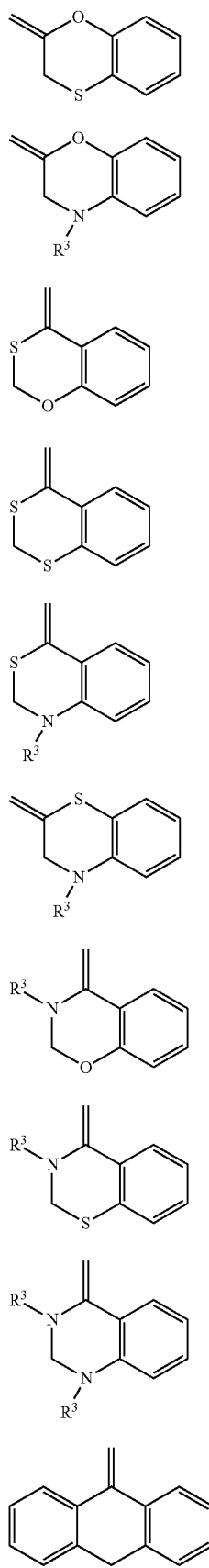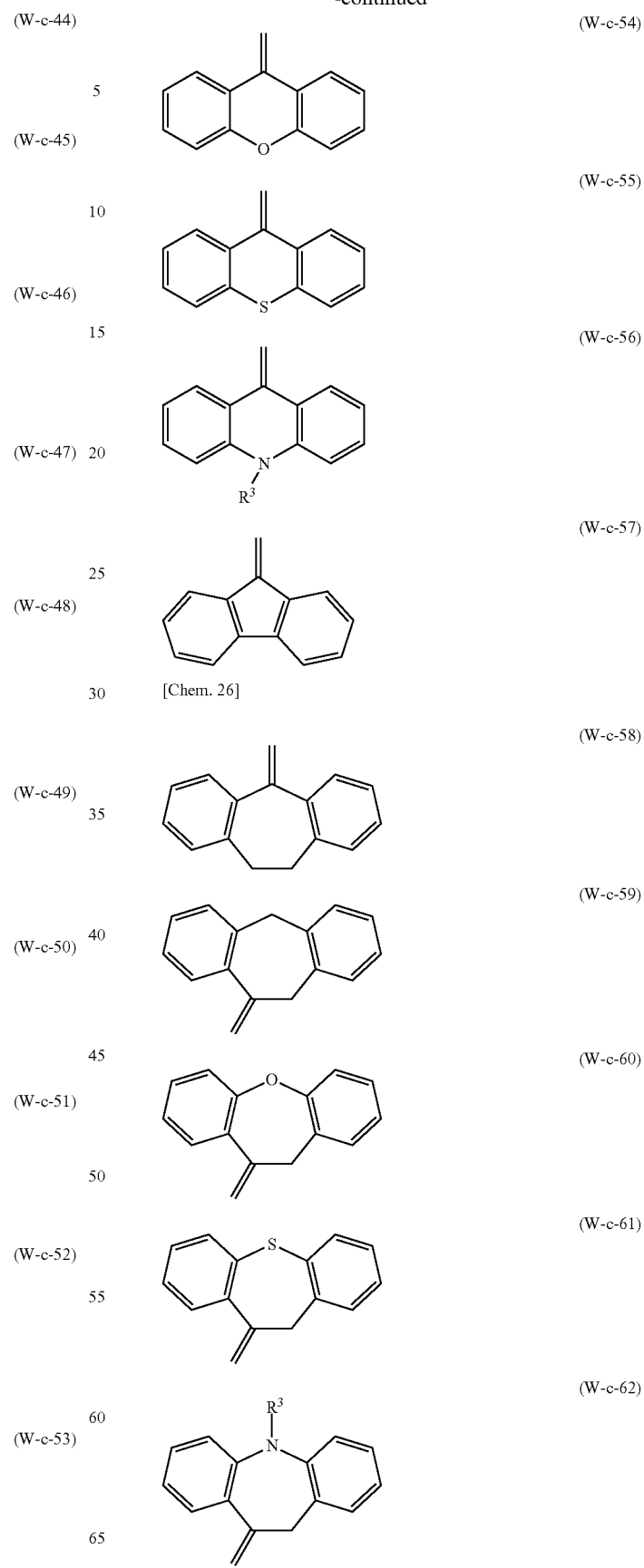

-continued
(W-c-63)
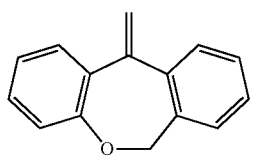
(W-c-64)
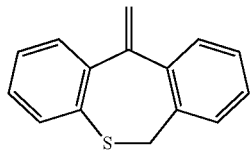
(W-c-65)
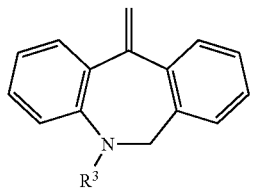
(W-c-66)
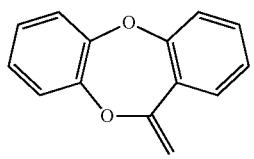
(W-c-67)
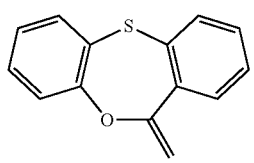
(W-c-68)
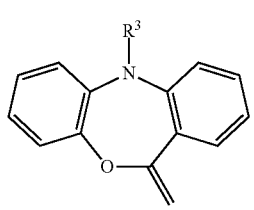
(W-c-69)
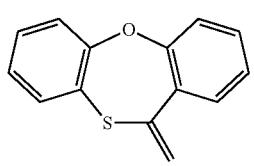
(W-c-70)
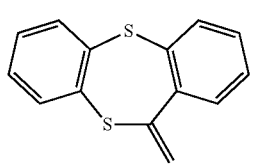
(W-c-71)
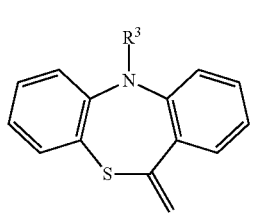
-continued
(W-c-72)
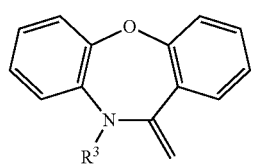
(W-c-73)
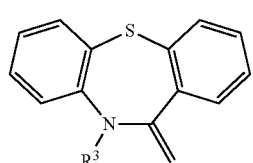
(W-c-74)
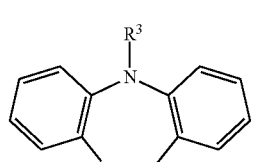
(W-c-75)
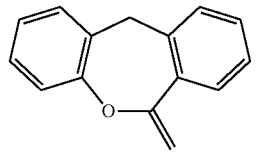
(W-c-76)
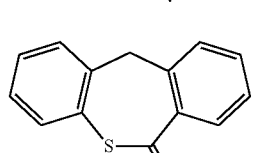
(W-c-77)

(W-c-78)
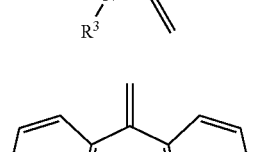
(W-c-79)
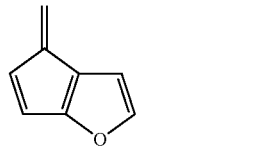
(W-c-80)
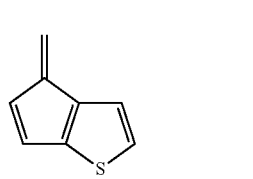

-continued

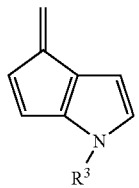
(W-c-81)

(in Formulae (W-c-1) to (W-c-81), $R^3$ represents a hydrogen atom or an alkyl group having 1 to 8 carbon atoms). In consideration of the availability of raw materials and ease of synthesis, the cyclic group represented by =$CW^1W^2$ is particularly preferably a group selected from Formulae (W-c-11), (W-c-12), (W-c-13), (W-c-14), (W-c-53), (W-c-54), (W-c-55), (W-c-56), (W-c-57), and (W-c-78) which may optionally be substituted with one or more $L^W$ substituents.

The total number of π electrons included in $W^1$ and $W^2$ is preferably 4 to 24 in consideration of wavelength dependency, preservation stability, liquid crystal properties, and ease of synthesis.

L represents a fluorine atom, a chlorine atom, a bromine atom, an iodine atom, a pentafluorosulfanyl group, a nitro group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—. Some hydrogen atoms included in the alkyl group may be replaced with fluorine atoms. In consideration of liquid crystal properties and ease of synthesis, L preferably represents a fluorine atom, a chlorine atom, a pentafluorosulfanyl group, a nitro group, a methylamino group, a dimethylamino group, a diethylamino group, a diisopropylamino group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —O—CO—O—, —CH=CH—, —CF=CF—, or —C≡C— and some hydrogen atoms may be replaced with fluorine atoms, more preferably represents a fluorine atom, chlorine atom, or a linear or branched alkyl group having 1 to 12 carbon atoms in which one —$CH_2$— group or two or more —$CH_2$— groups that are not adjacent to one another may be each independently replaced with —O—, —COO—, or —OCO— and some hydrogen atoms may be replaced with fluorine atoms, further preferably represents a fluorine atom, a chlorine atom, or a linear or branched alkyl or alkoxy group having 1 to 12carbon atoms in which some hydrogen atoms may be replaced with fluorine atoms, and particularly preferably represents a fluorine atom, a chlorine atom, or a linear alkyl or alkoxy group having 1 to 8 carbon atoms.

k represents an integer of 0 to 8. In consideration of liquid crystal properties, the availability of raw materials, and ease of synthesis, k preferably represents an integer of 0 to 4, more preferably represents an integer of 0 to 2, further preferably represents 0 or 1, and particularly preferably represents 1.

m1 and m2 each independently represent an integer of 0 to 5. m1+m2 is an integer of 1 to 5. In consideration of liquid crystal properties, ease of synthesis, and preservation stability, m1 and m2 each independently represent an integer of 1 to 4, more preferably represent an integer of 1 to 3, and particularly preferably represent 1 or 2. m1+m2 is preferably an integer of 1 to 4 and particularly preferably 2 or 3.

More specifically, the compound represented by General Formula (I) is more preferably a compound selected from General Formulae (I-A) to (I-D) below in consideration of inverse dependency, solubility in solvents, ease of synthesis, availability of raw materials, and liquid crystal properties,

[Chem. 27]

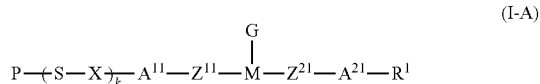
(I-A)

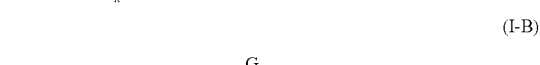
(I-B)

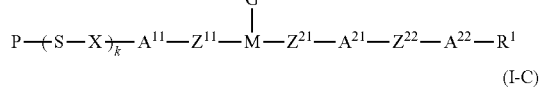
(I-C)

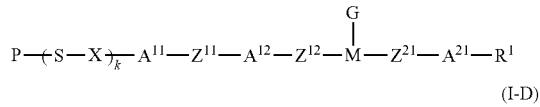
(I-D)

(in General Formulae (I-A) to (I-D), P, S, X, k, M, G, and $R^1$ represent the same things as in General Formula (I); $A^{11}$ and $A^{12}$ each independently represent the same things as $A^1$ of General Formula (I); $Z^{11}$ and $Z^{12}$ each independently represent the same things as $Z^1$ of General Formula (I); $A^{21}$ and $A^{22}$ each independently represent the same things as $A^2$ of General Formula (I); and $Z^{21}$ and $Z^{22}$ each independently represent the same things as $Z^2$ of General Formula (I). Preferable structures of the above groups are as in General Formula (I)). In consideration of the balance between the anisotropy of refractive index and inverse dependency, in General Formulae (I-A) and (I-B), $A^{11}$ further preferably represents a 1,4-phenylene group that may optionally be substituted with the substituent L and, in General Formulae (I-C) and (I-D), $A^{11}$ further preferably represents a 1,4-phenylene group that may optionally be substituted with the substituent L and $A^{12}$ further preferably represents a 1,4-cyclohexylene group that may optionally be substituted with the substituent L. In General Formulae (I-A) to (I-D), $A^{21}$ further preferably represents a 1,4-phenylene group or 1,4-cyclohexylene group which may optionally be substituted with the substituent L and $A^{22}$ further preferably represents a 1,4-cyclohexylene group which may optionally be substituted with the substituent L. Among General Formulae (I-A) to (I-D), compounds represented by General Formulae (I-A) to (I-C) are more preferable and compounds represented by Formulae (I-A) and (I-C) are particularly preferable in consideration of liquid crystal properties, ease of synthesis, and preservation stability. In the case where a higher nematic-isotropic phase transition temperature TNI is anticipated, a compound represented by General Formula (I-C) is particularly preferable.

Further specifically, the compound represented by General Formula (I) is further preferably a compound selected from General Formulae (I-A-1) to (I-D-2) below in consideration of inverse dependency, solubility in solvents, ease of synthesis, availability of raw materials, and liquid crystal properties,

[Chem. 28]

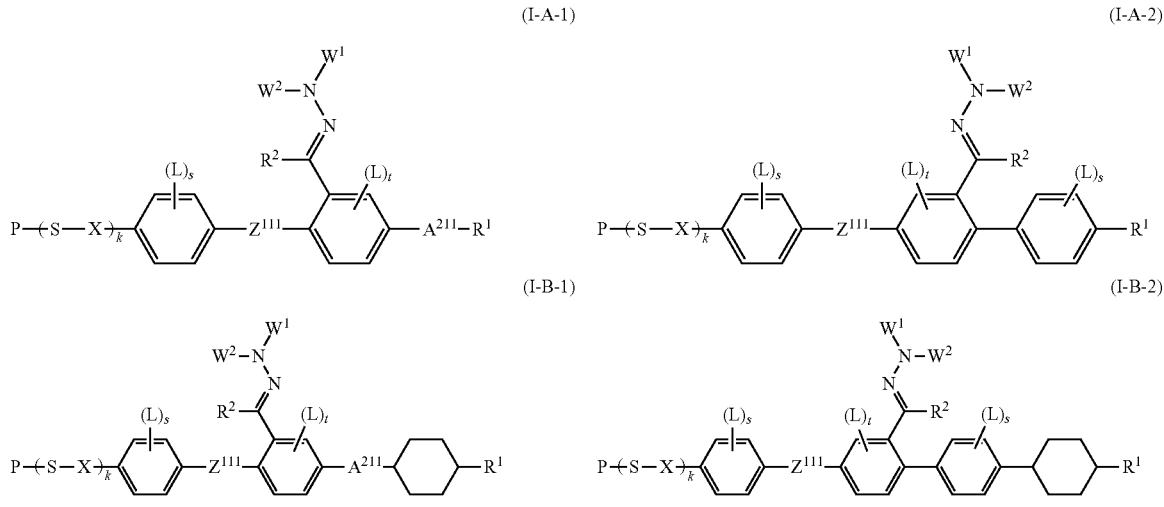

[Chem. 29]

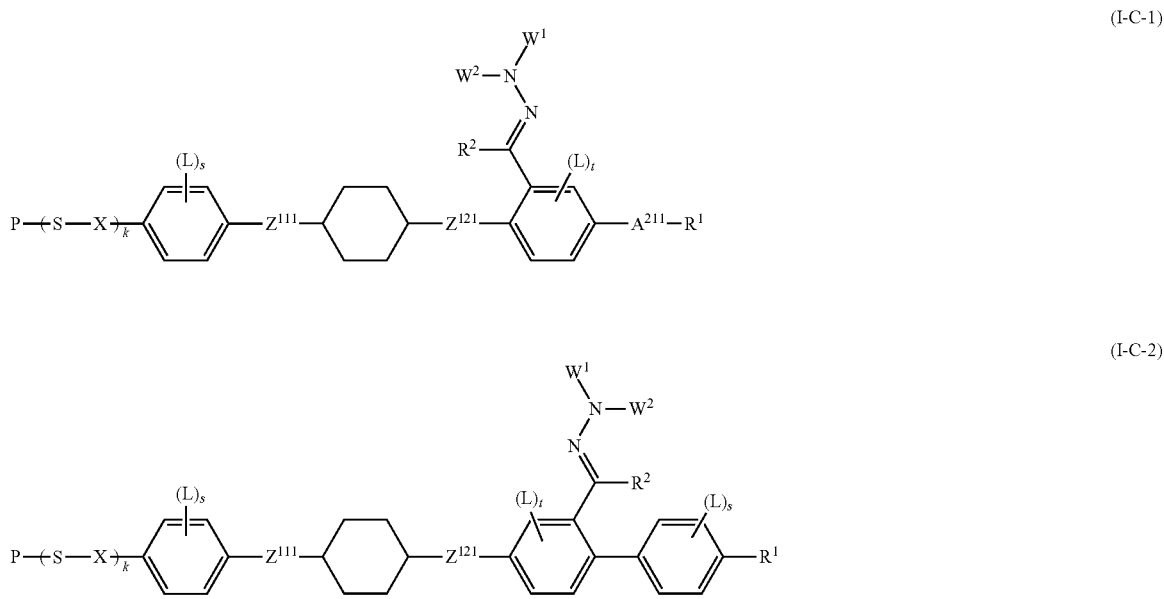

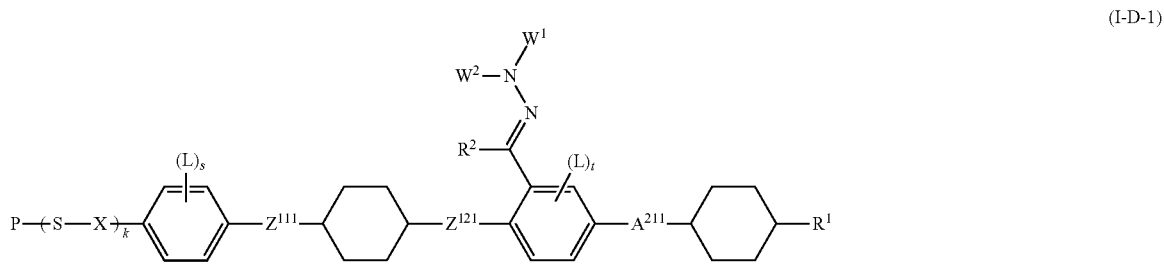

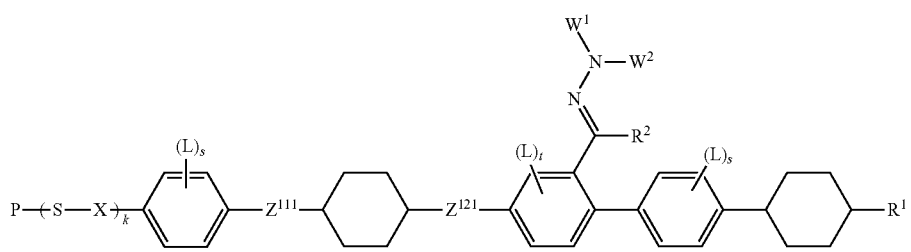

(I-D-2)

(in General Formulae (I-A-1) to (I-D-2), P, S, X, k, L, $R^2$, $W^1$, $W^2$, and $R^1$ represent the same things as in General Formula (I); s represents an integer of 0 to 4; t represents an integer of 0 to 3; $A^{211}$ represents the same thing as $A^2$ of General Formula (I); $Z^{111}$ and $Z^{121}$ each independently represent the same thing as $Z^1$ of General Formula (I); and preferable structures of the above groups are as in General Formula (I)). Among General Formulae (I-A-1) to (I-D-2), in consideration of liquid crystal properties, ease of synthesis, and preservation stability, compounds represented by General Formulae (I-A-1) to (I-C-2) are more preferable and compounds represented by General Formulae (I-A-1), (I-A-2), (I-C-1), and (I-C-2) are particularly preferable. In the case where inverse wavelength dependency on the short-wavelength side is anticipated, compounds represented by General Formulae (I-A-1) and (I-C-1) are particularly preferable. In the case where both inverse wavelength dependency and the anisotropy of refractive index are required in a balanced manner, compounds represented by General Formulae (I-A-2) and (I-C-2) are particularly preferable. In the case where a higher nematic-isotropic phase transition temperature TNI is anticipated, compounds represented by General Formula (I-C-1) and (I-C-2) are particularly preferable. In the case where inverse wavelength dependency on the long-wavelength side is anticipated, a compound represented by General Formula (I-C-1) is particularly preferable.

Specifically, the compound represented by General Formula (I) is preferably selected from the compounds represented by Formulae (I-1) to (I-134) below.

[Chem. 30]

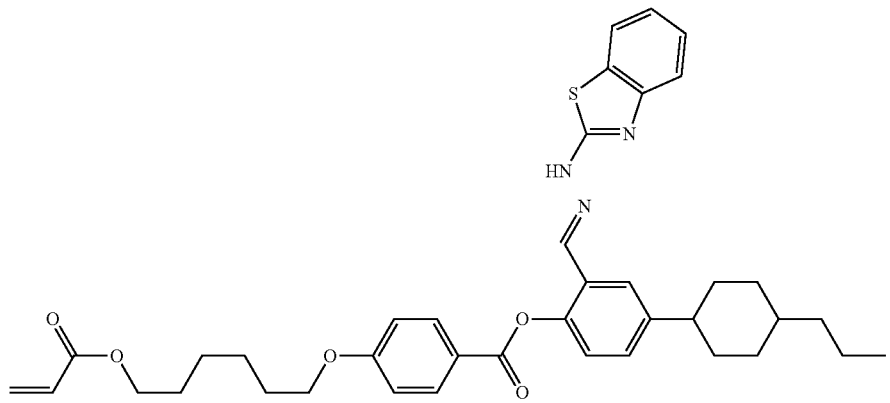

(I-1)

(I-2)

(I-3)
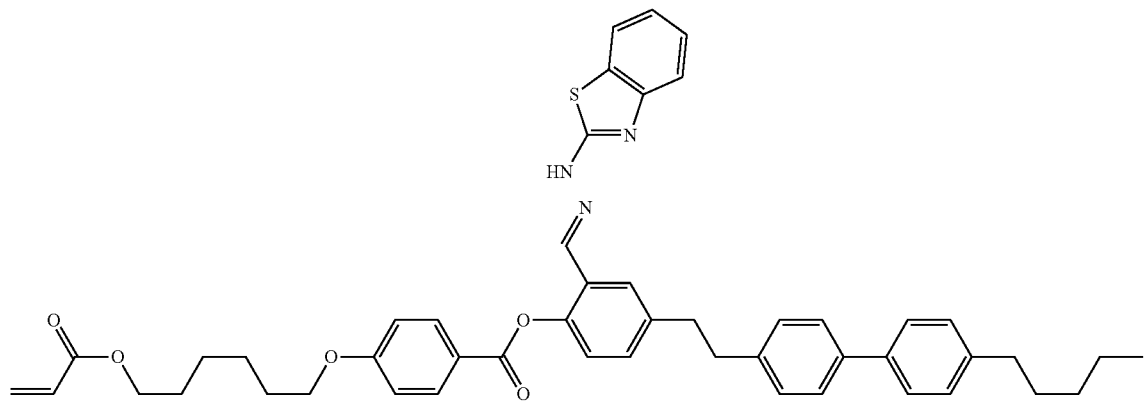
(I-4)
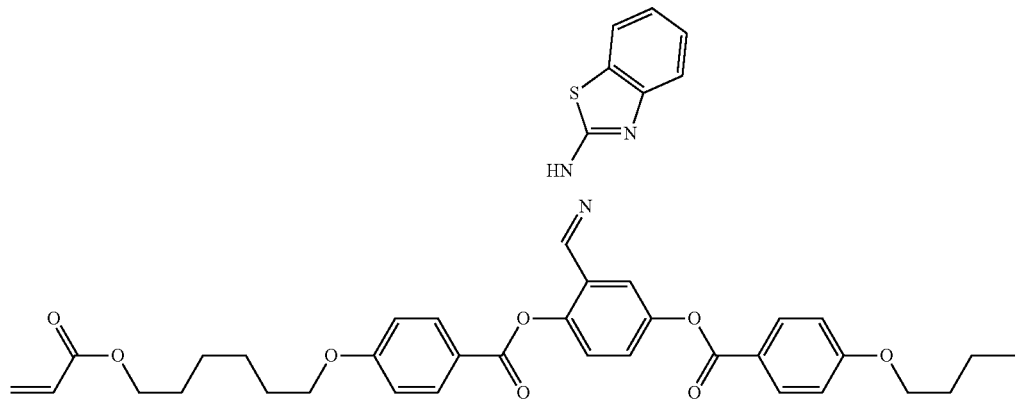
(I-5)
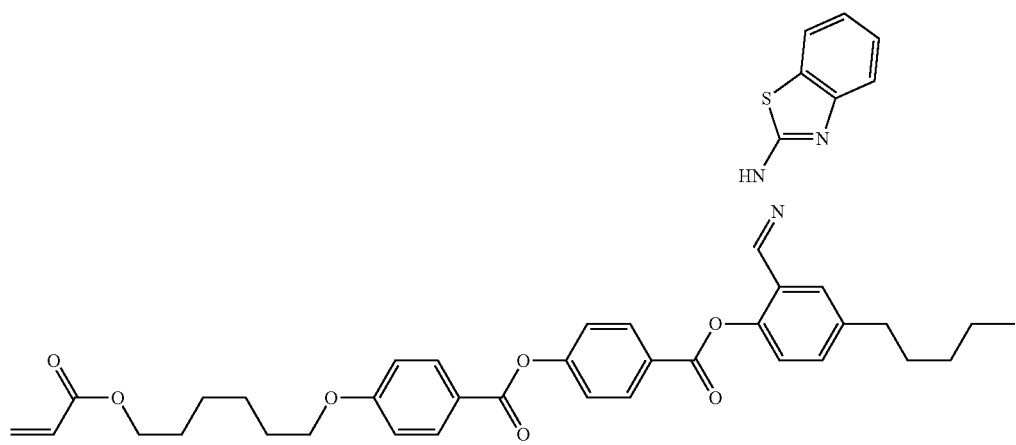

-continued
[Chem. 31]
(I-6)
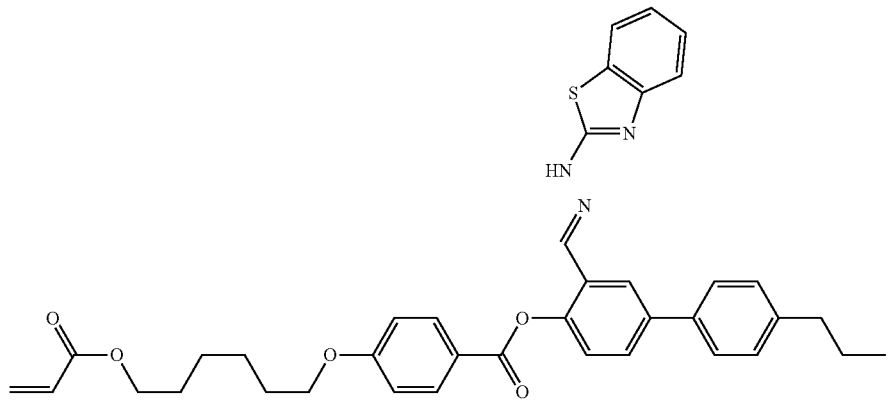
(I-7)
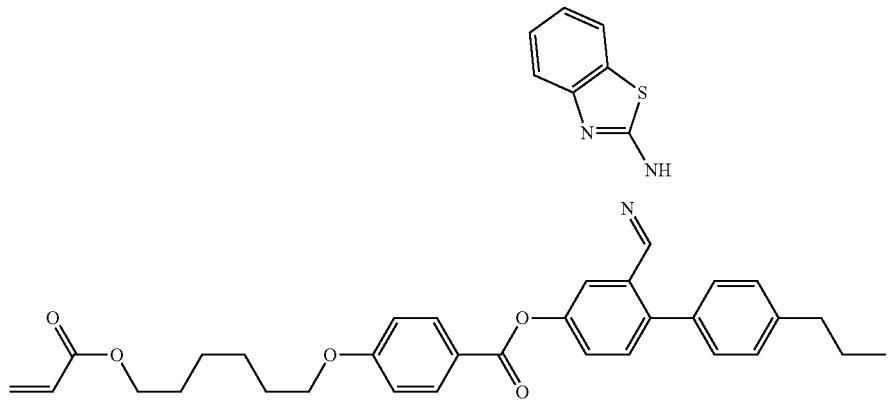
(I-8)
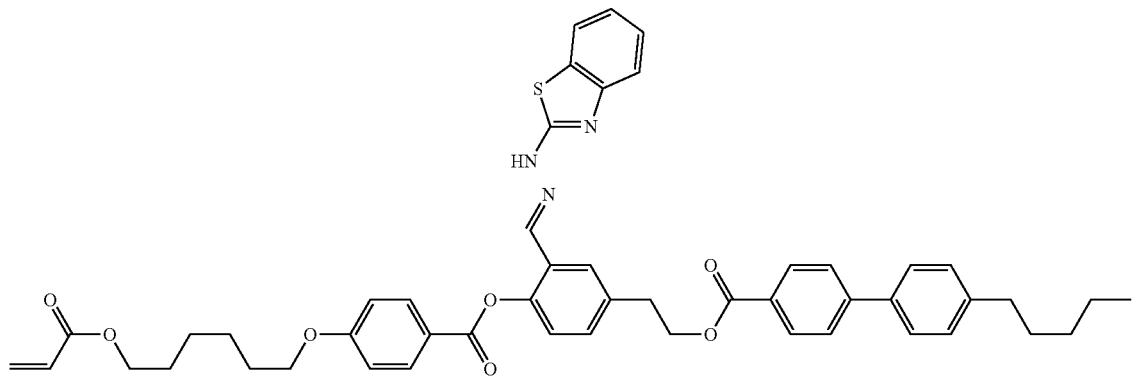

(I-9)
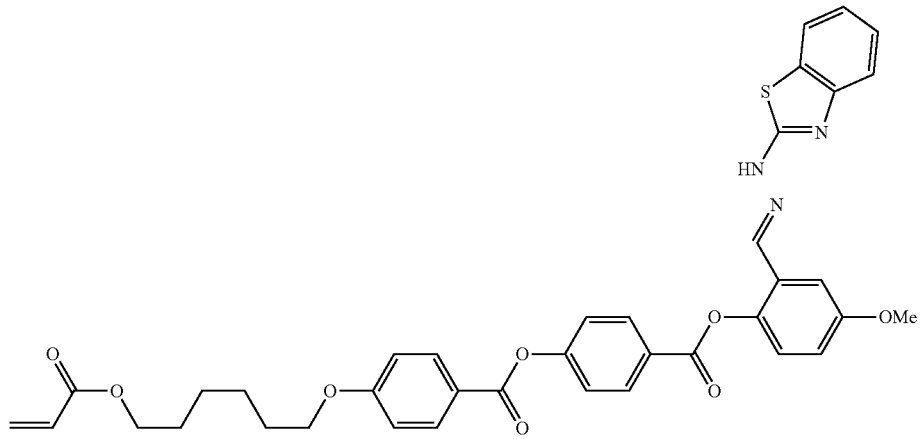
(I-10)
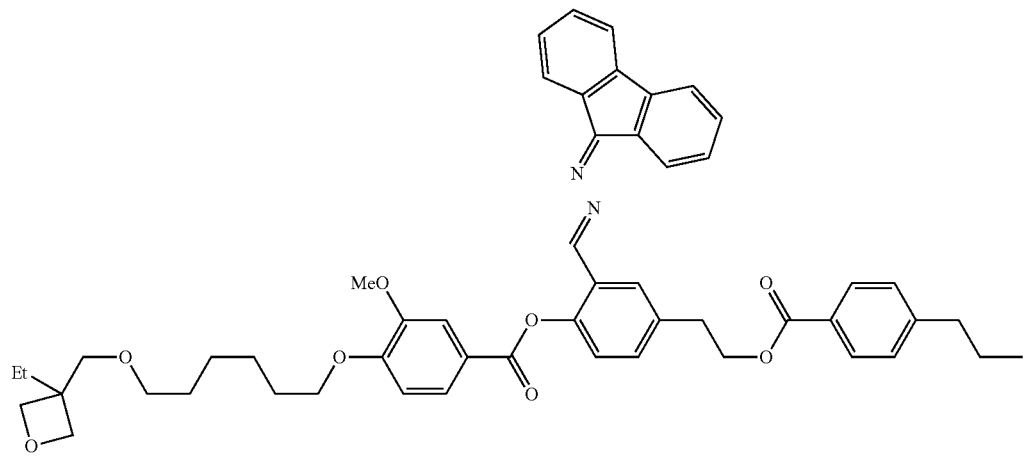
[Chem. 32]
(I-11)
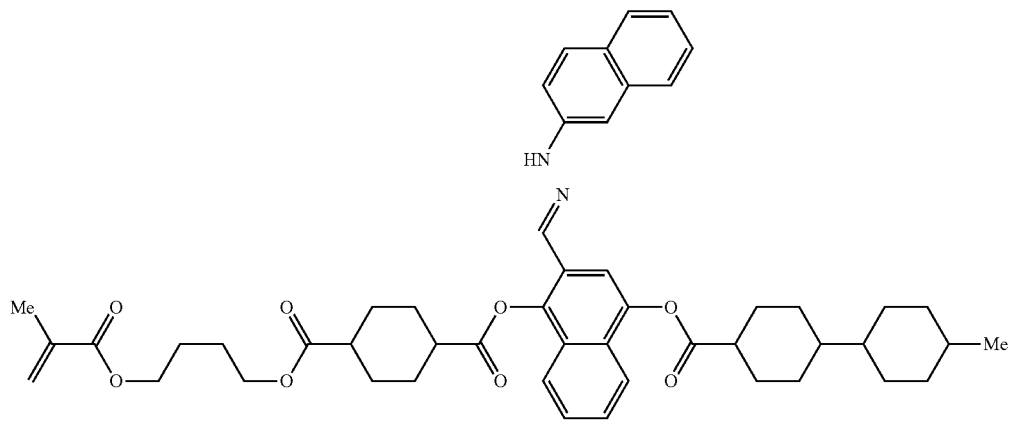

-continued
(I-12)
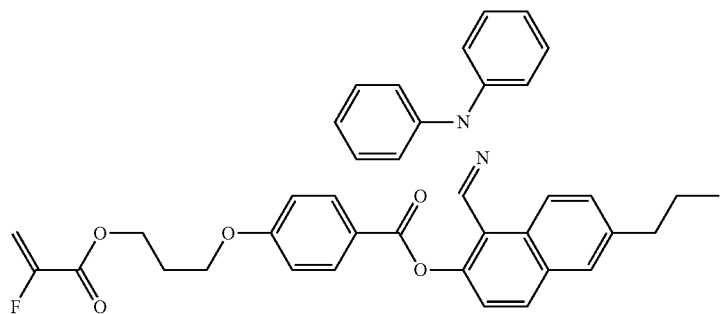
(I-13)
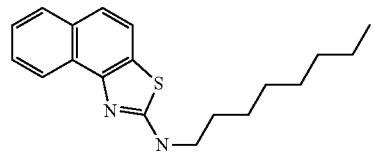
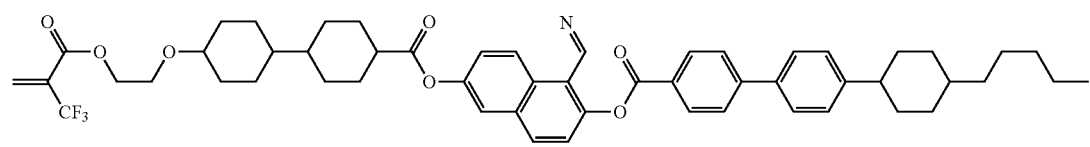
(I-14)
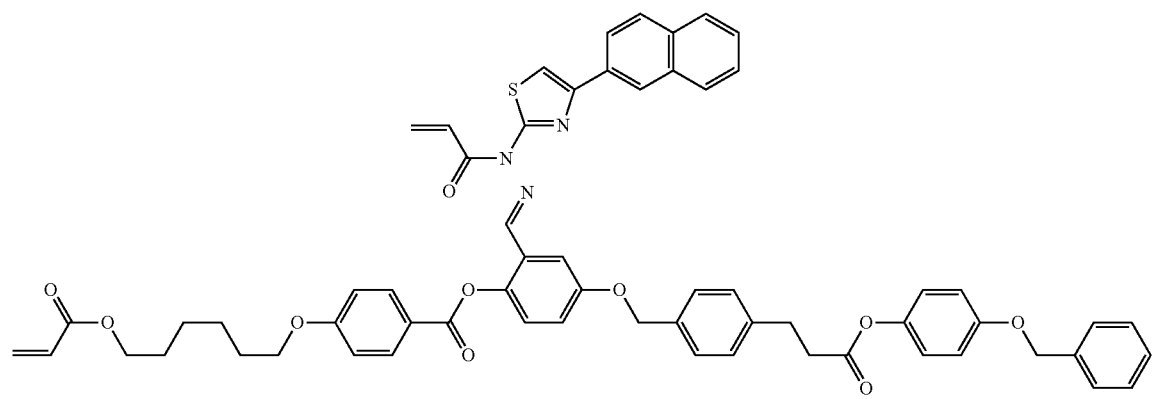
(I-15)
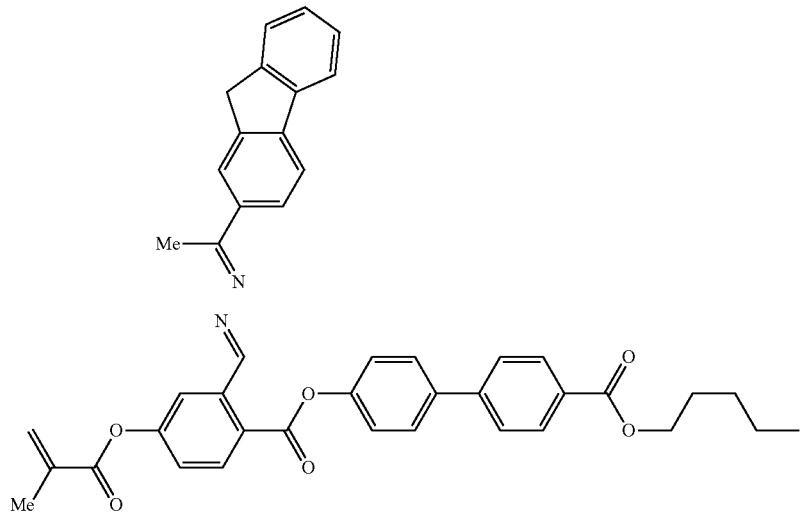

[Chem. 33]
(I-16)
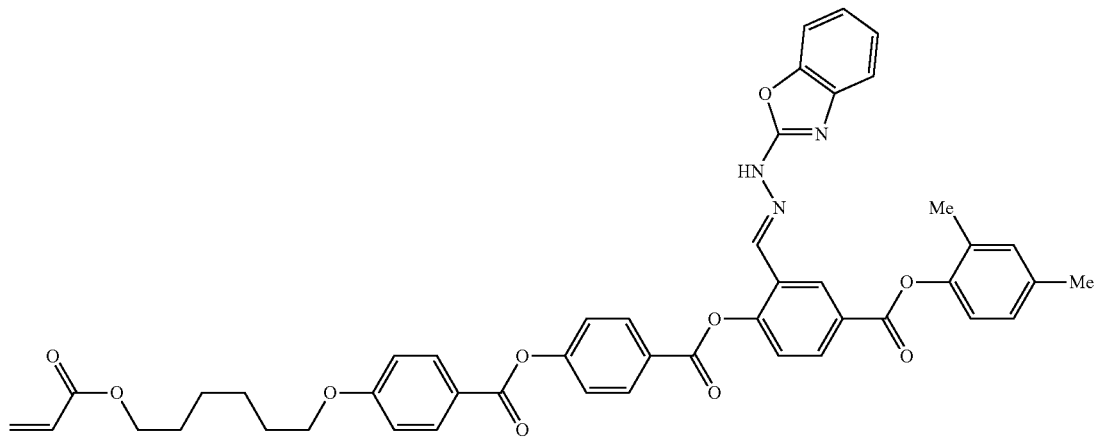
(I-17)
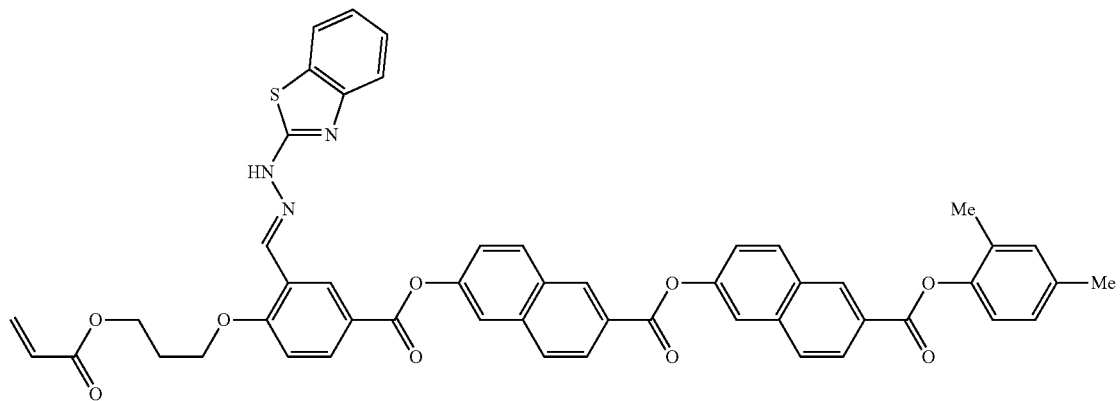
(I-18)
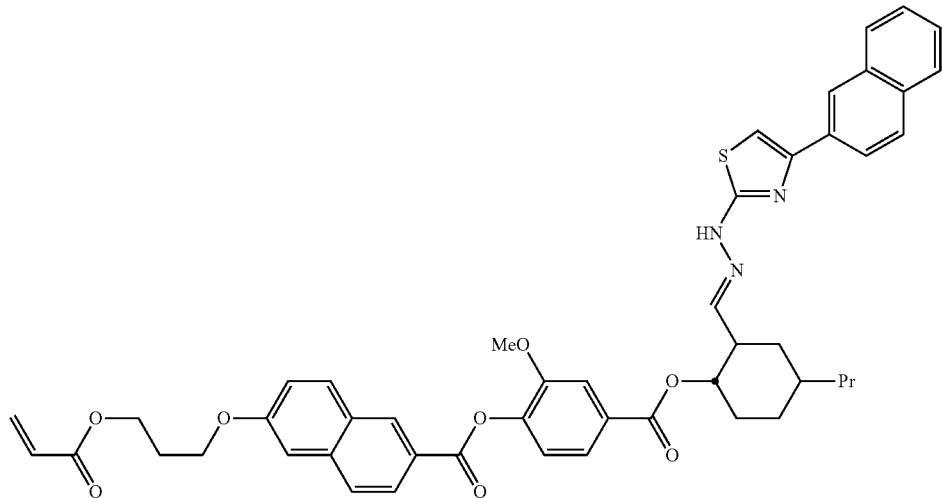

-continued
(I-19)
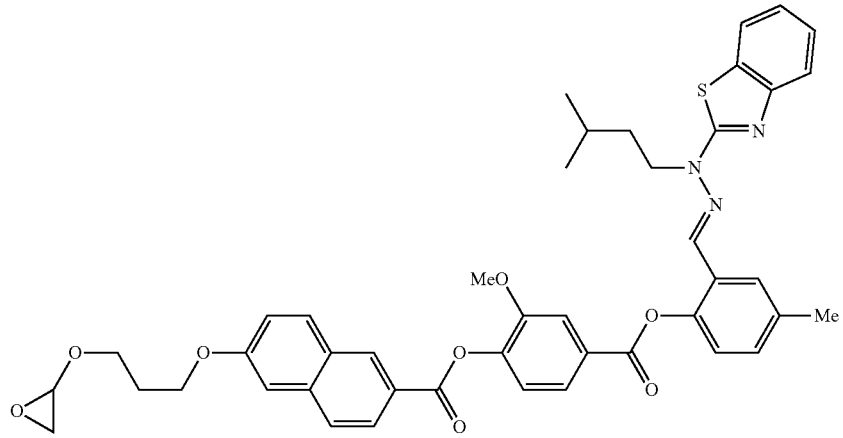
(I-20)
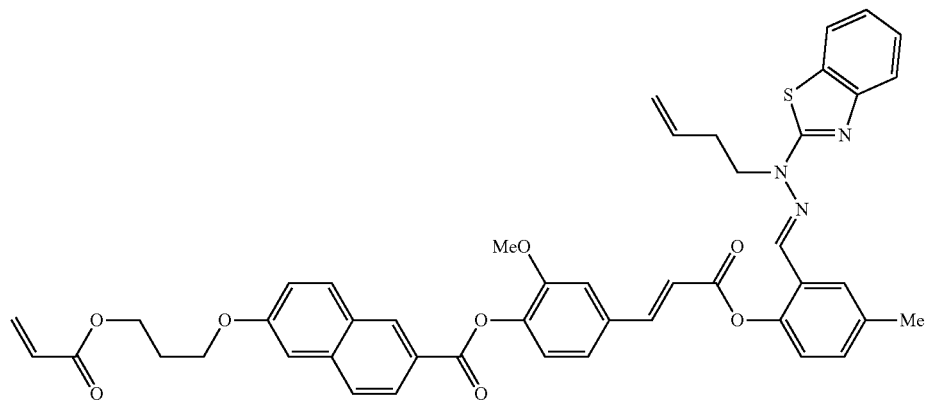
[Chem. 34]
(I-21)
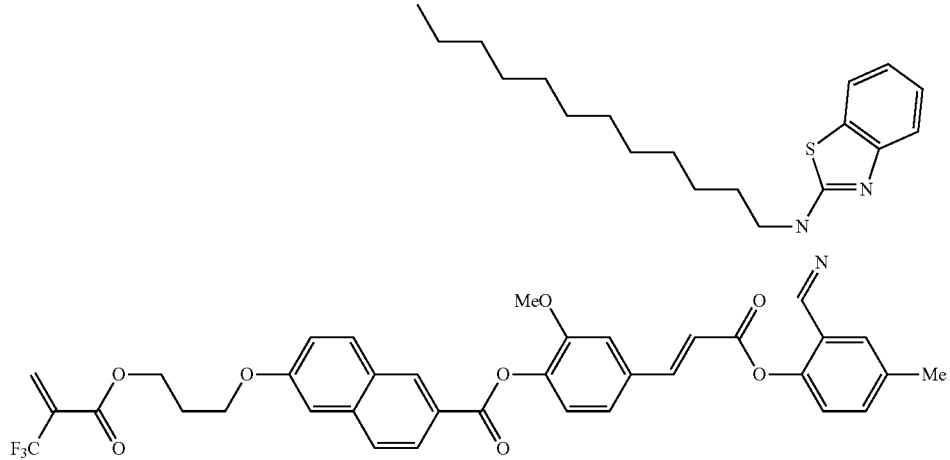

(I-22)
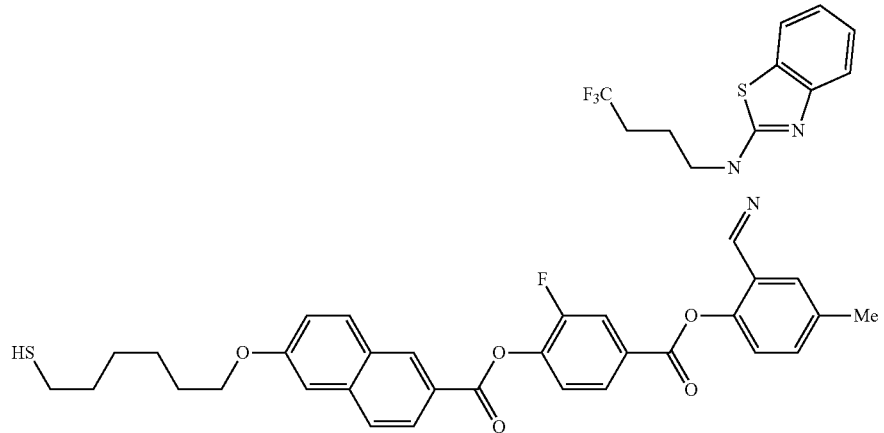
(I-23)
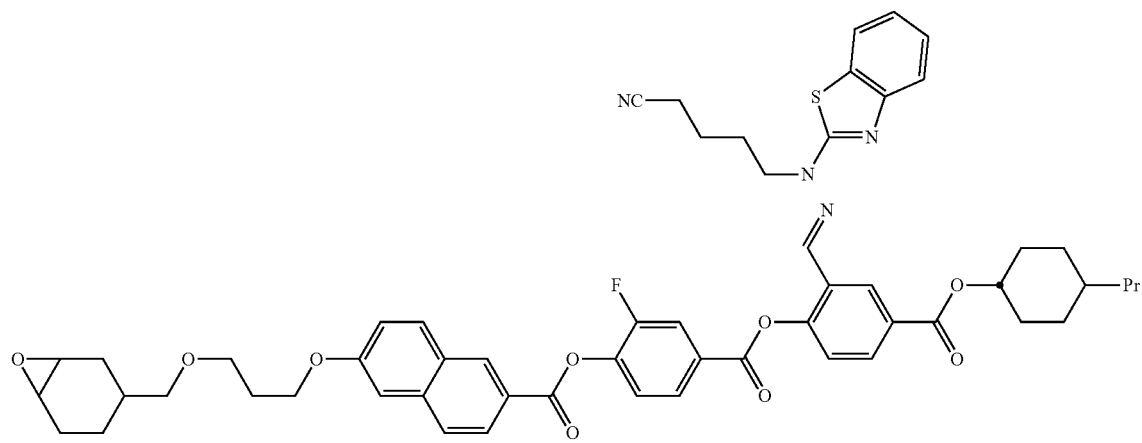
(I-24)
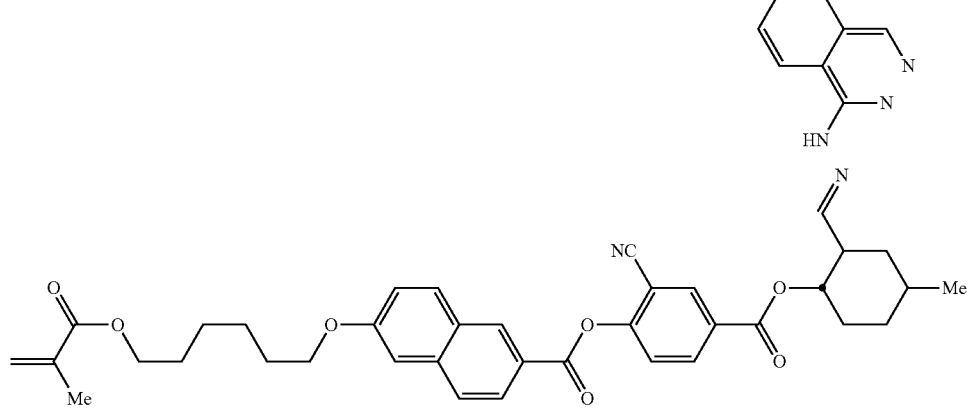

-continued
(I-25)
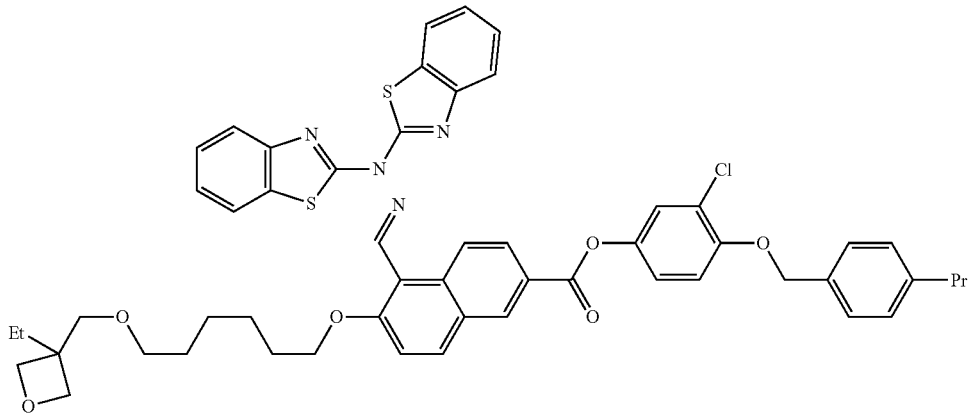
[Chem. 35]
(I-26)
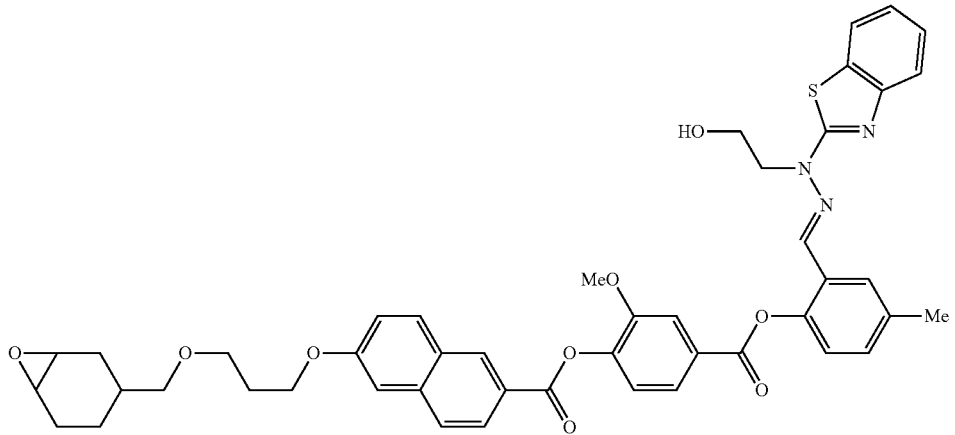
(I-27)
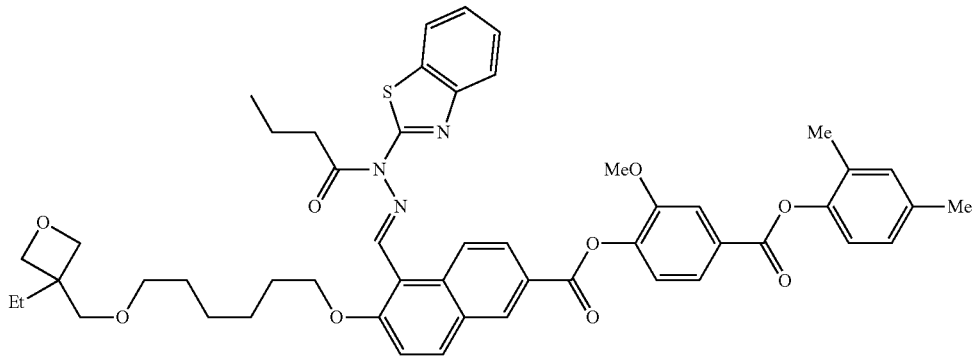

(I-28)
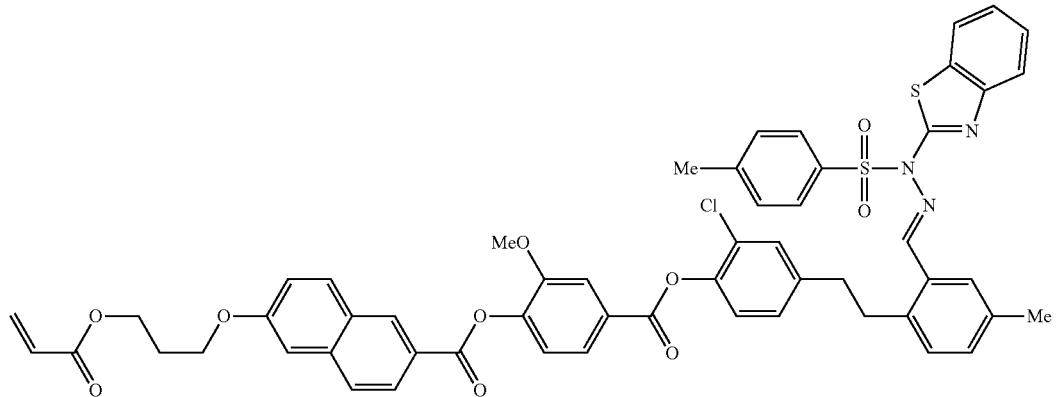
(I-29)
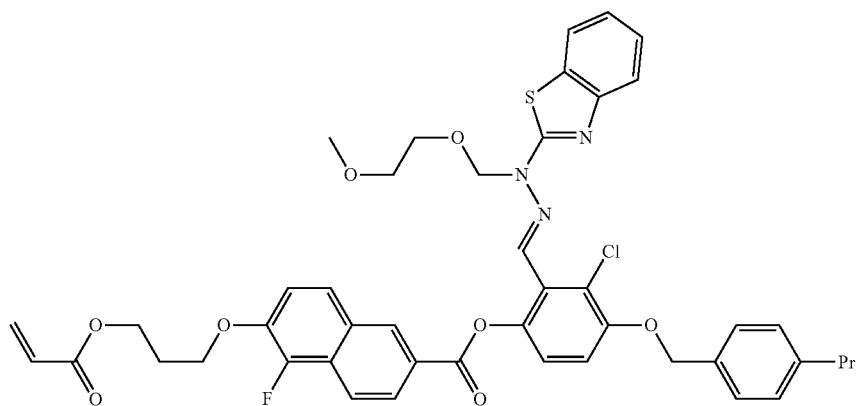
(I-30)
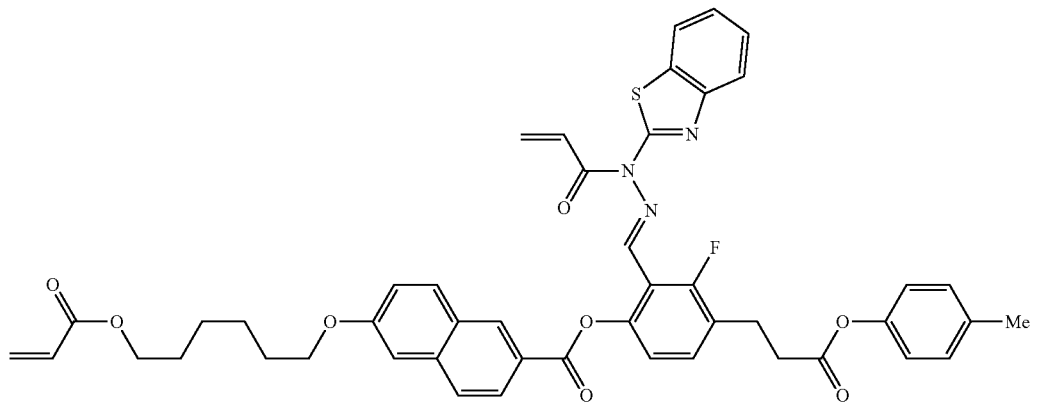

-continued
[Chem. 36]
(I-31)
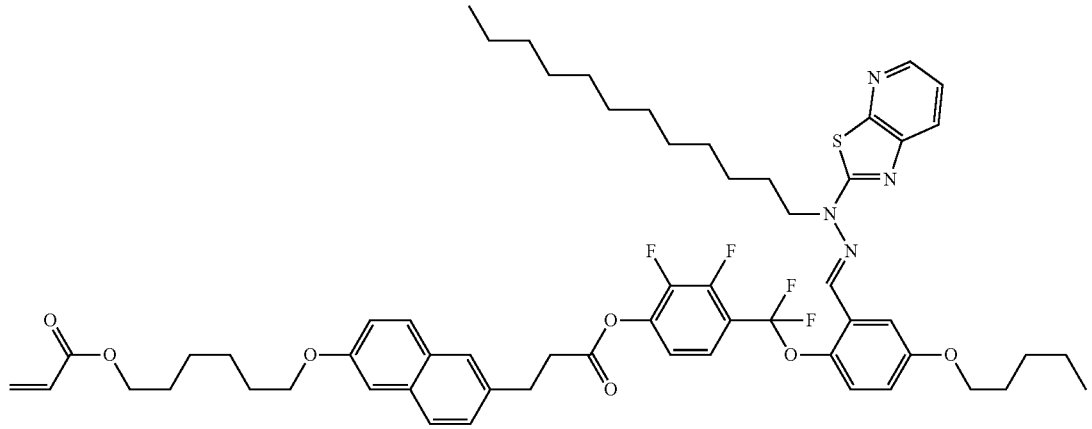
(I-32)
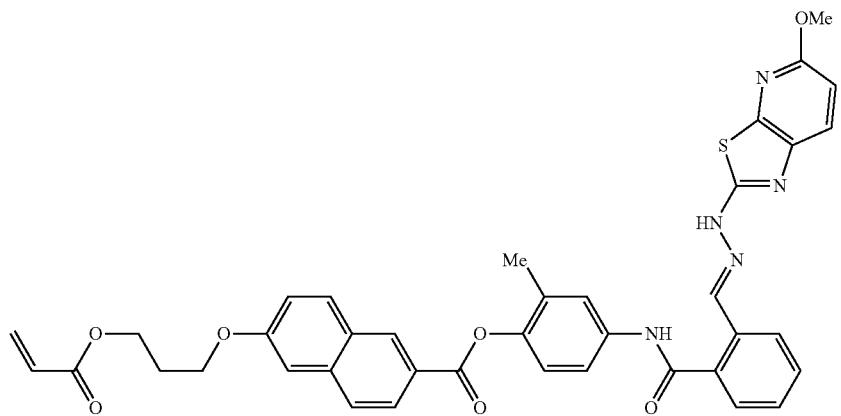
(I-33)
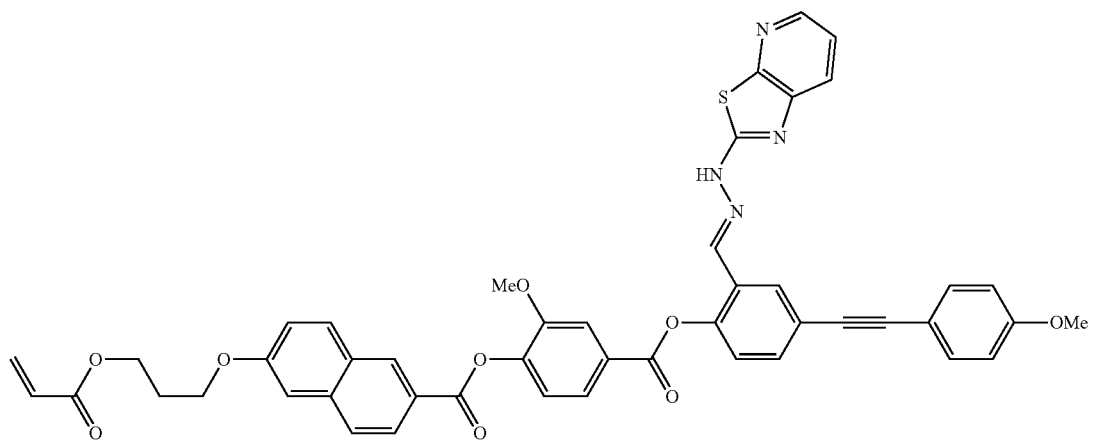

(I-34)
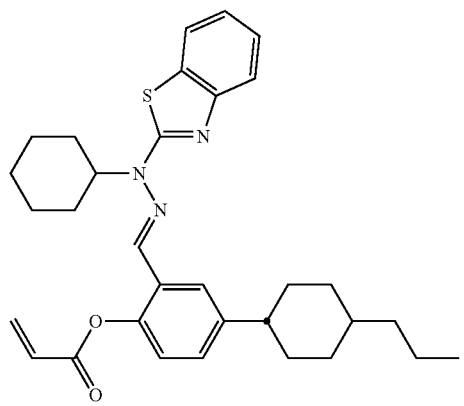
(I-35)
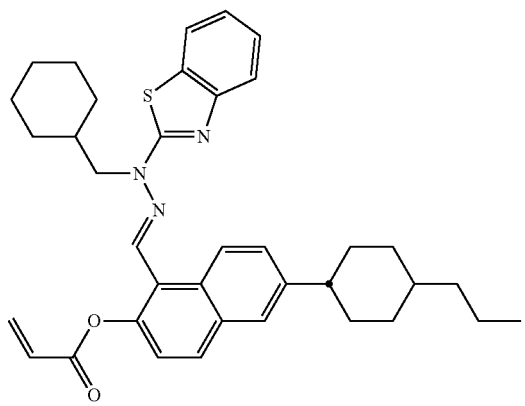
[Chem. 37]
(I-36)
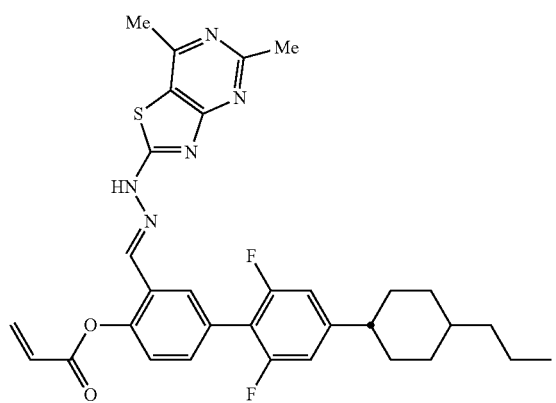
(I-37)
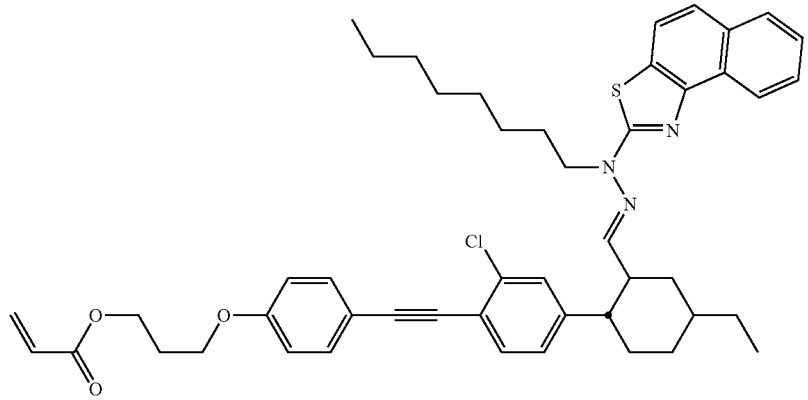

-continued
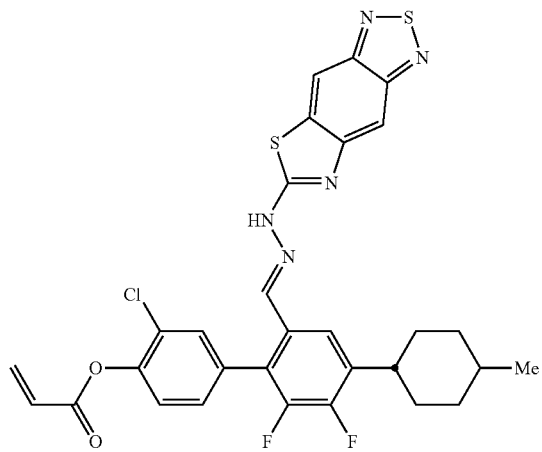
(I-38)
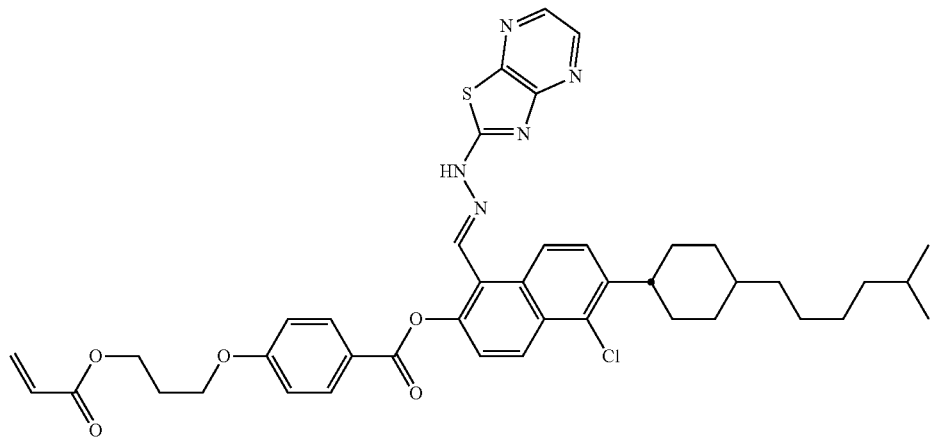
(I-39)
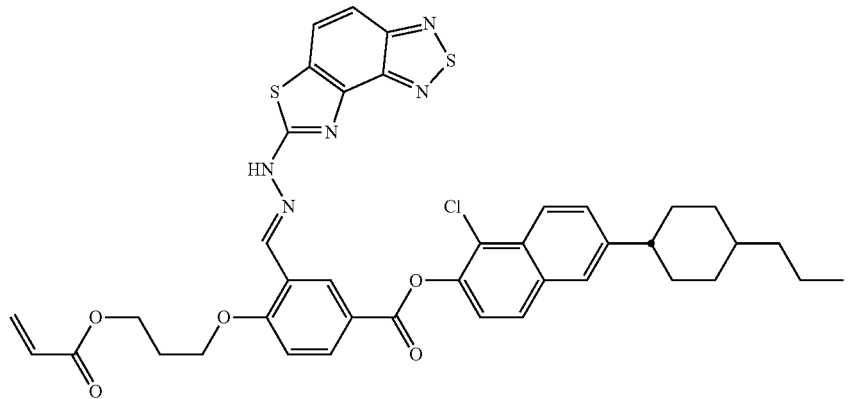
(I-40)

-continued
[Chem. 38]
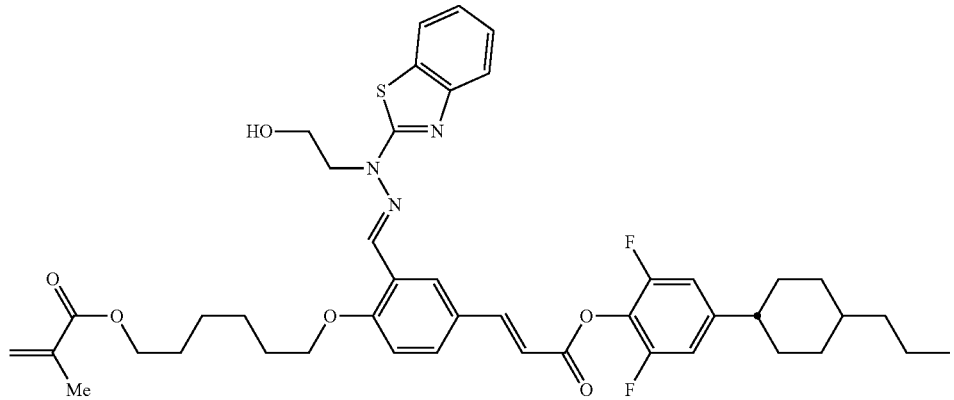
(I-41)
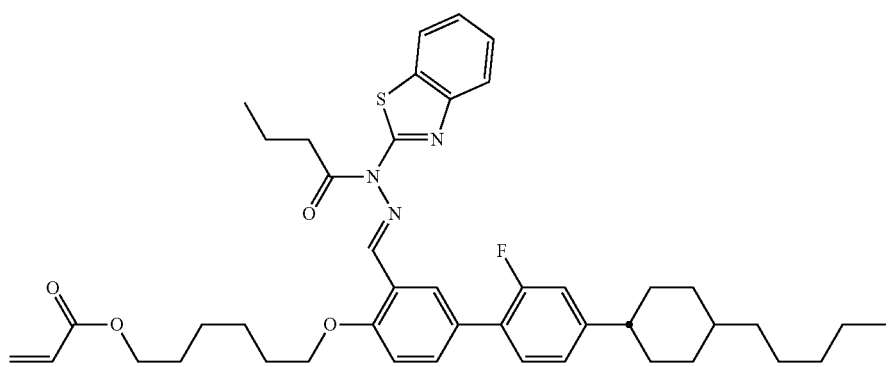
(I-42)
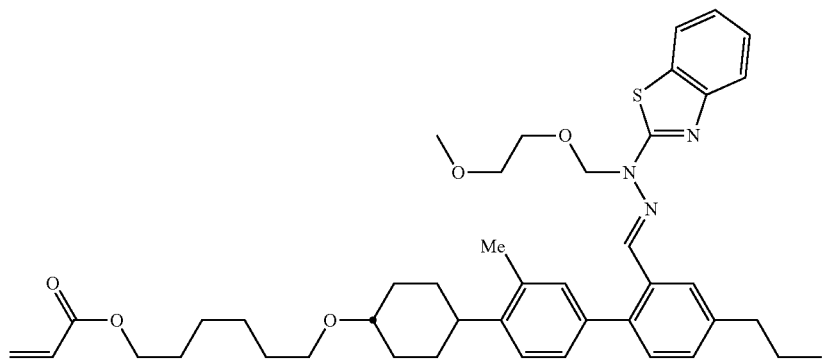
(I-43)
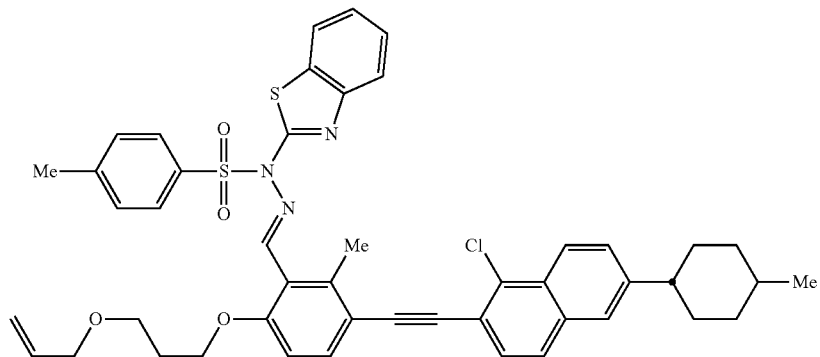
(I-44)

(I-45)
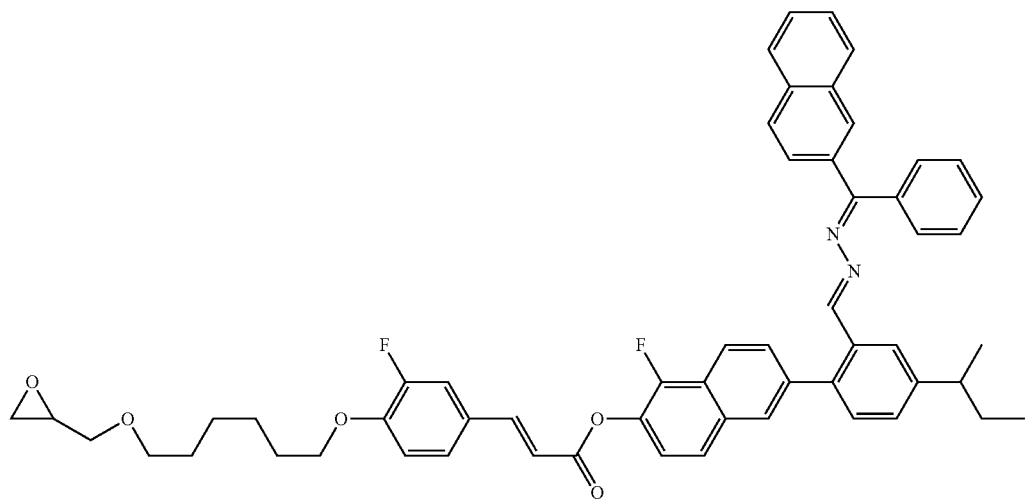
(I-46)
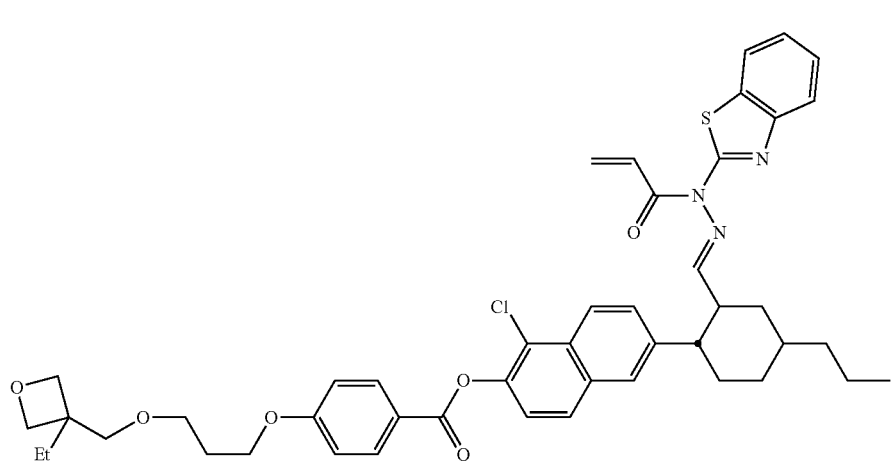
(I-47)
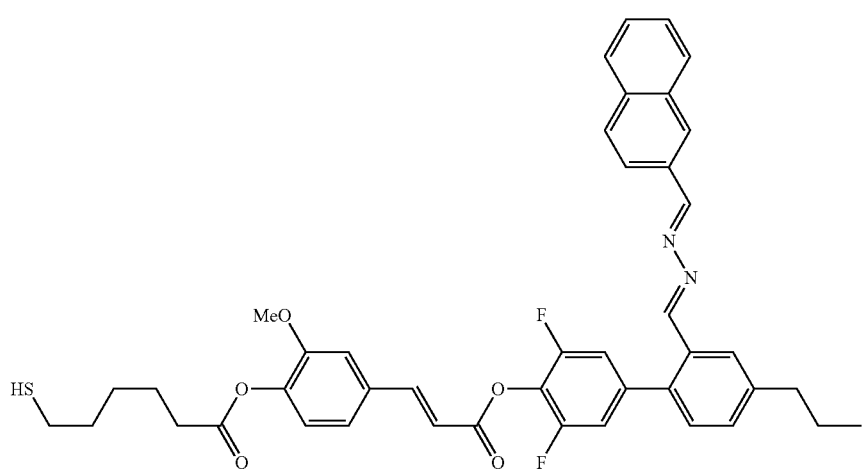

(I-48)
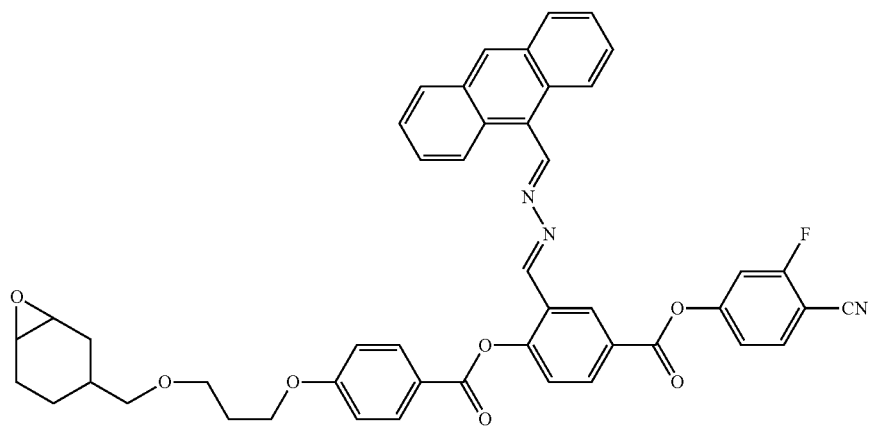
(I-49)
(I-50)
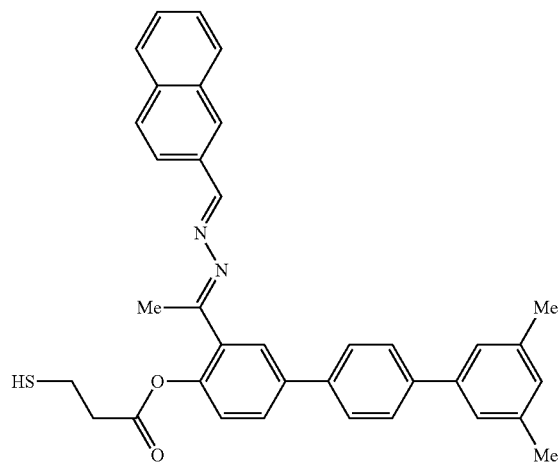

[Chem. 40]
(I-51)
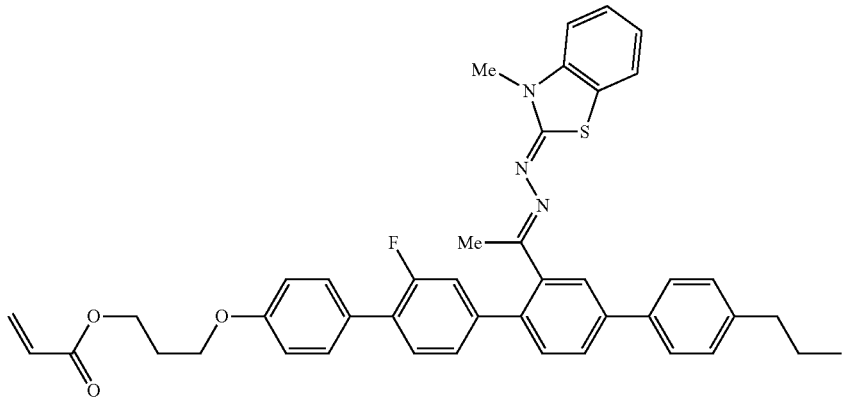
(I-52)
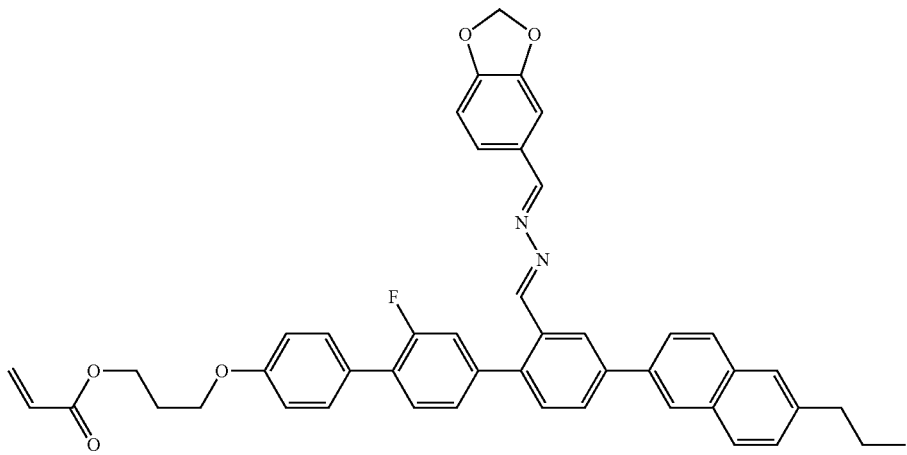
(I-53)
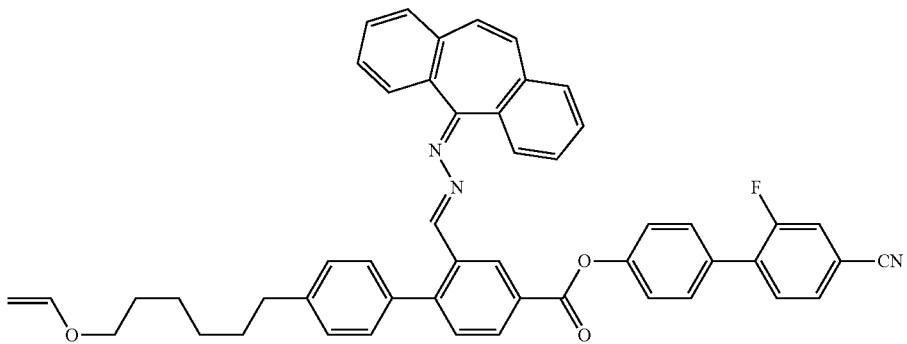

(I-54)
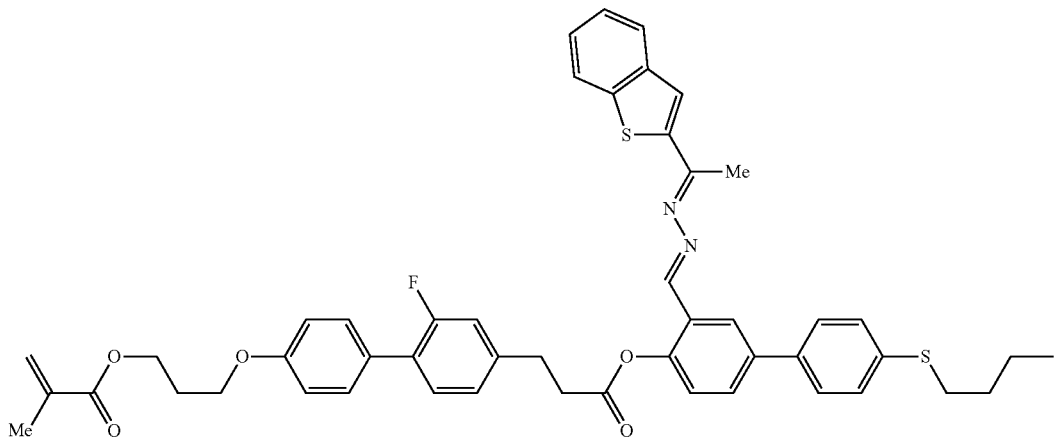
(I-55)
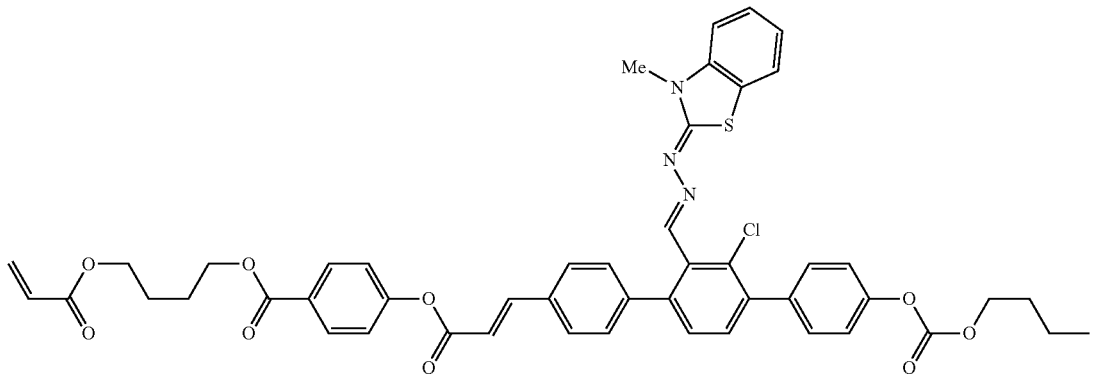
[Chem. 41]
(I-56)
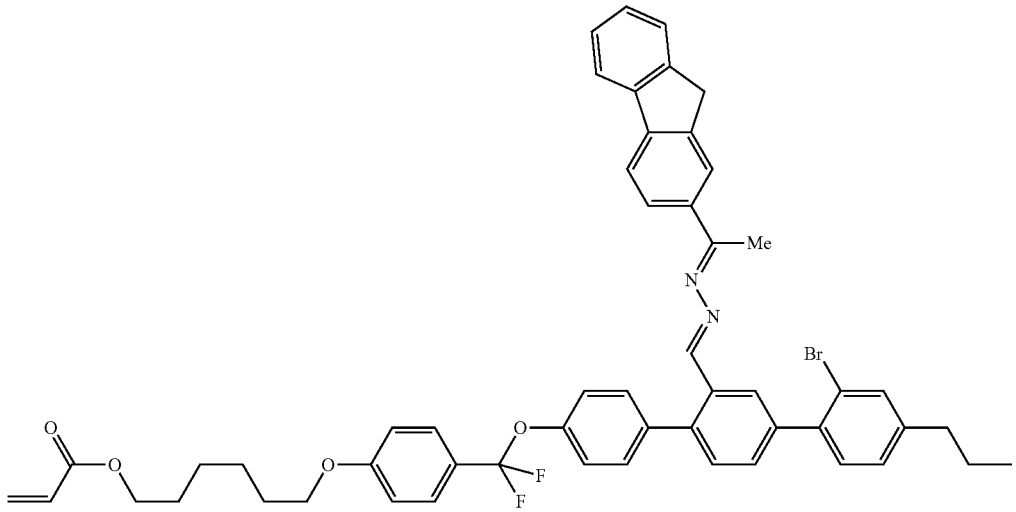

(I-57)
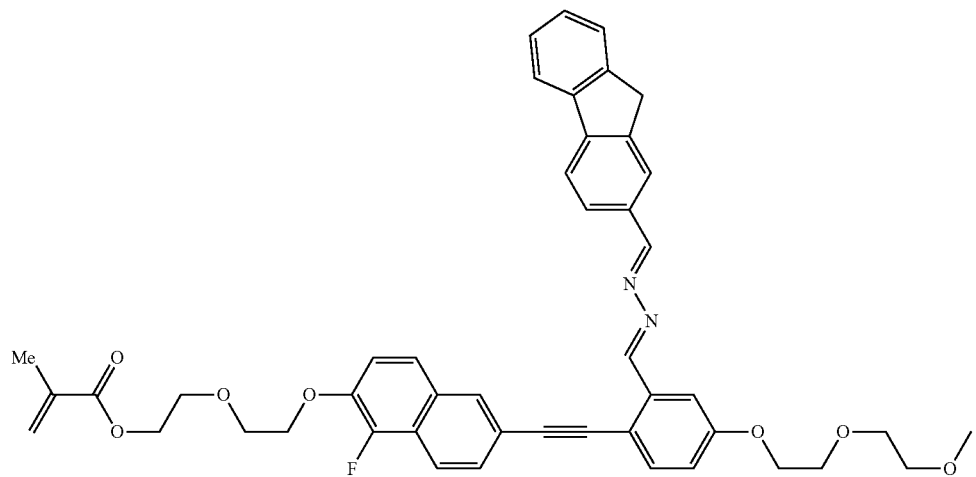
(I-58)
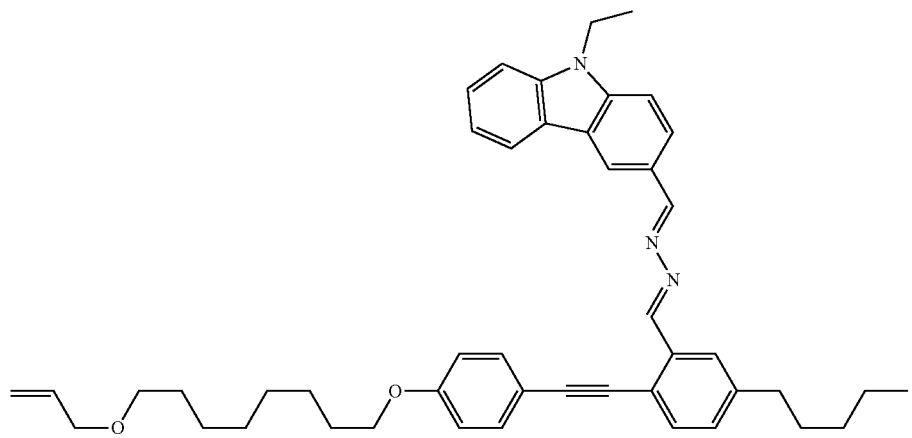
(I-59)
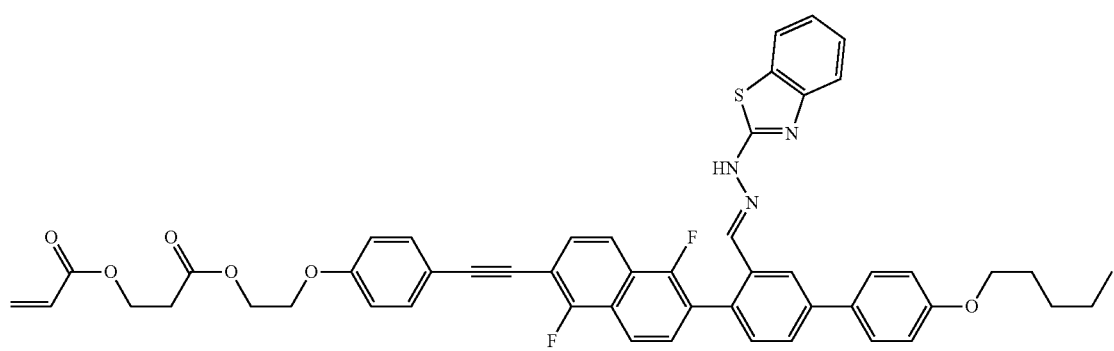

(I-60)
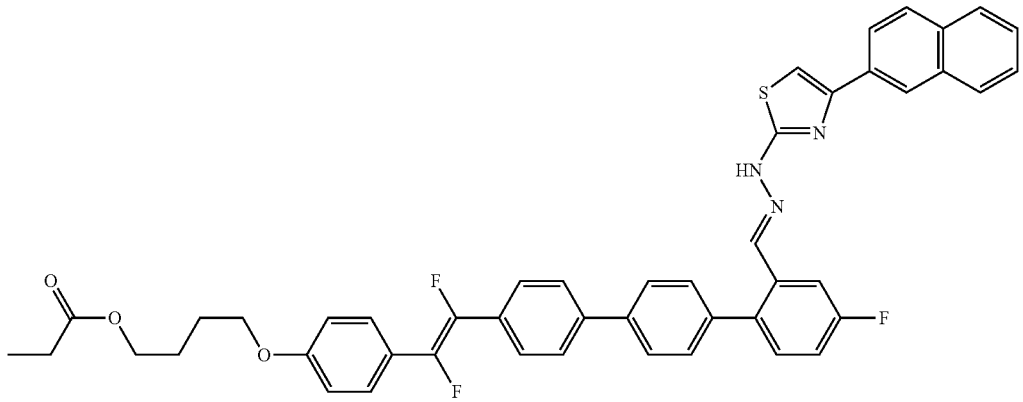
[Chem. 42]
(I-61)
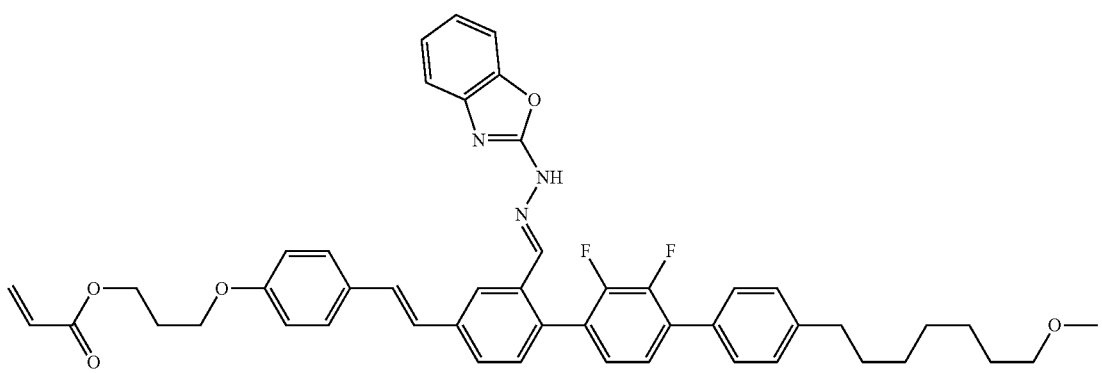
(I-62)
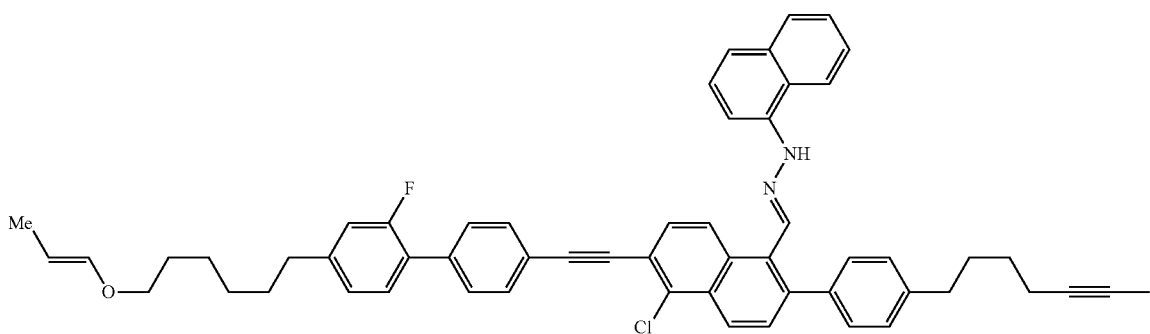
(I-63)
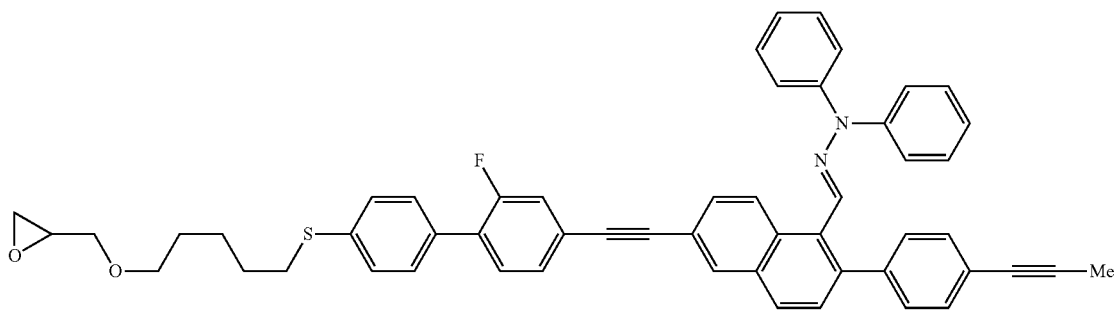

(I-64)
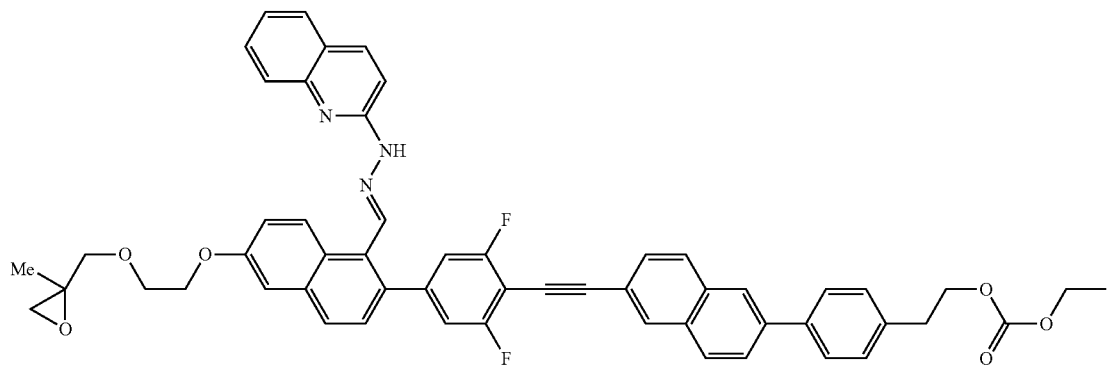
(I-65)
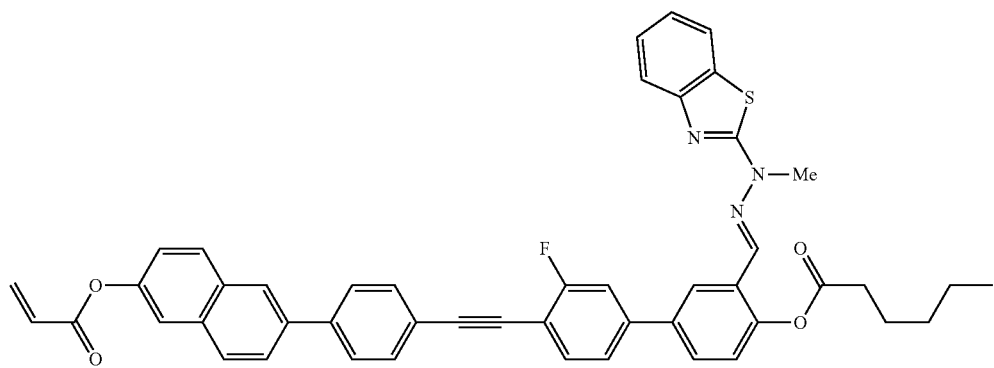
[Chem. 43]
(I-66)
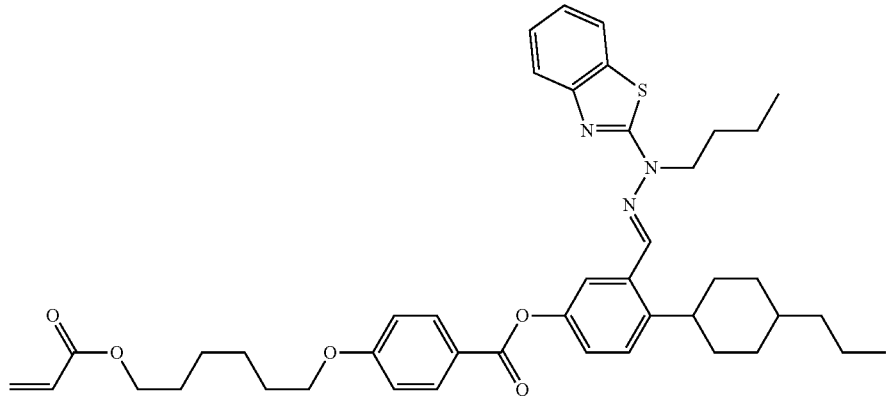
(I-67)
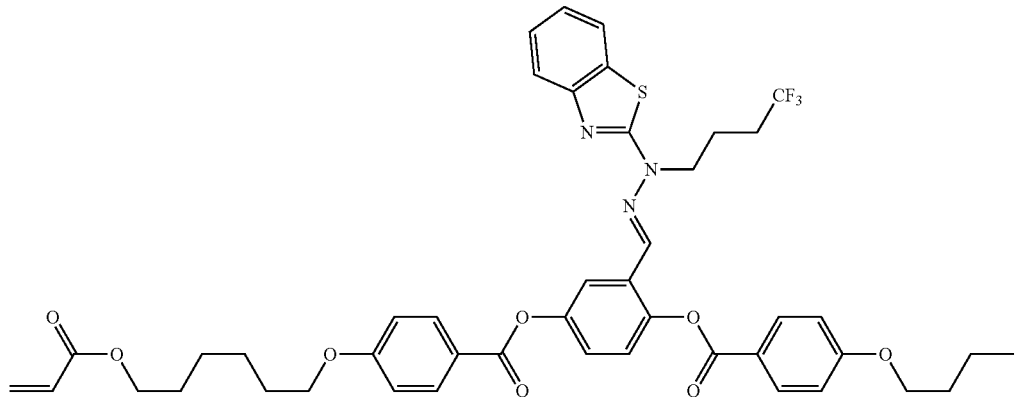

(I-68)
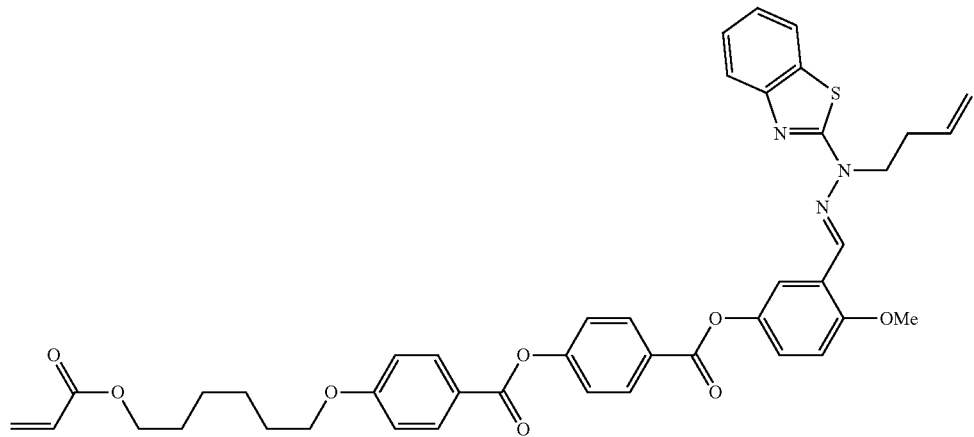
(I-69)
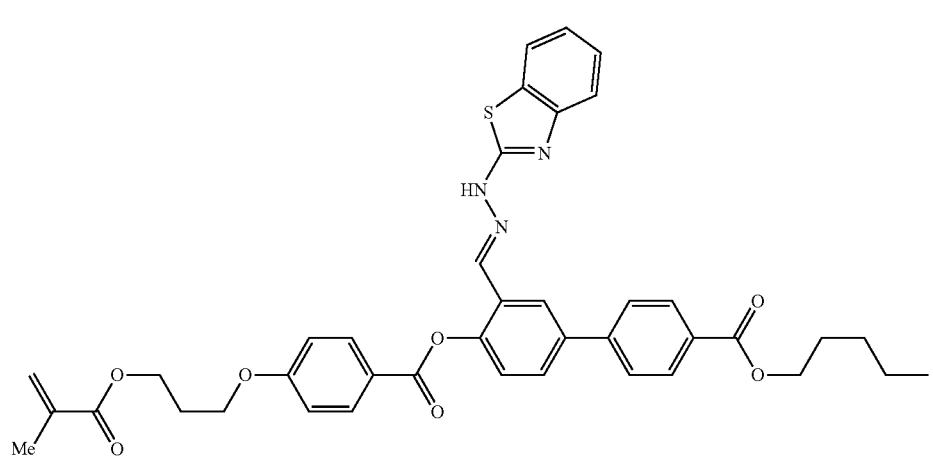
(I-70)
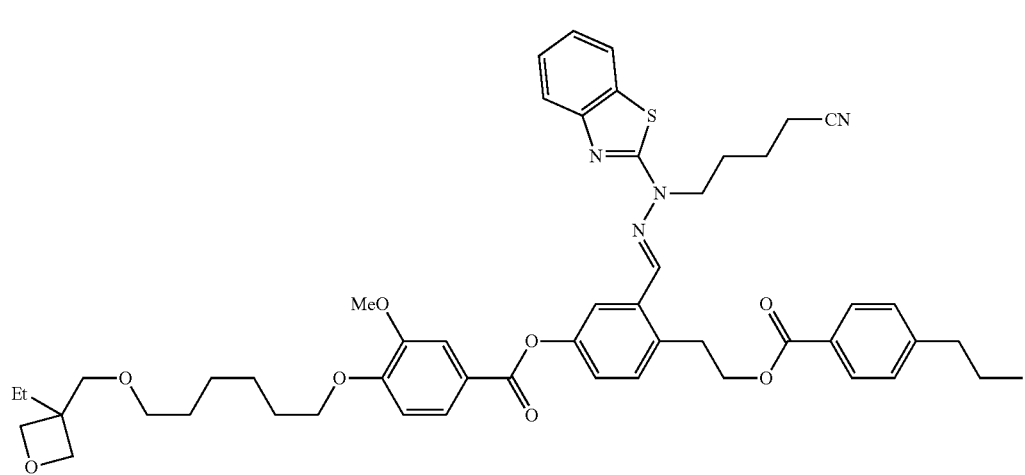

[Chem. 44]
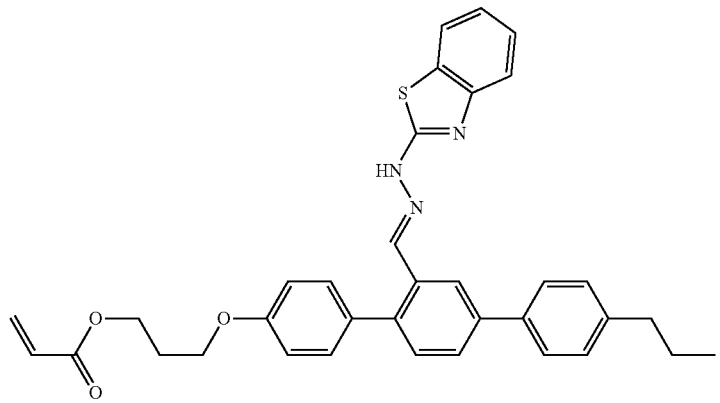
(I-71)
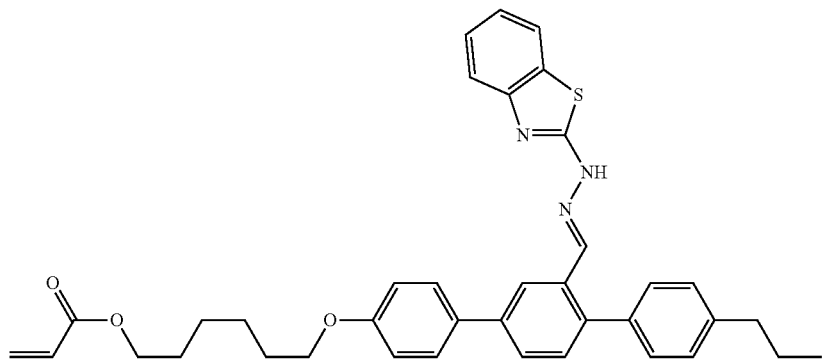
(I-72)
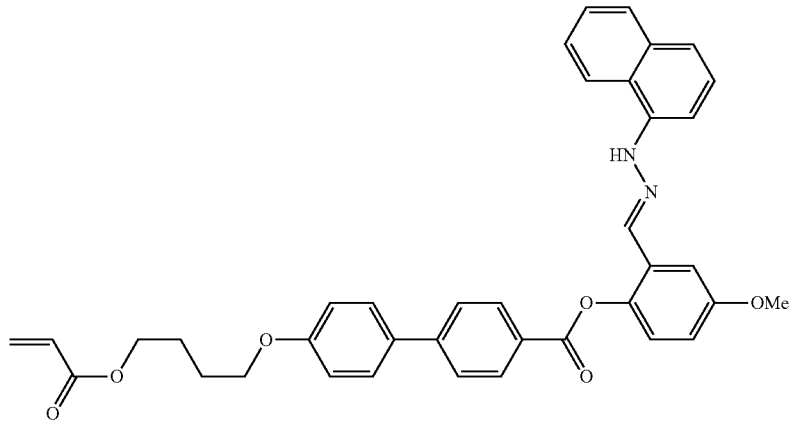
(I-73)

-continued
(I-74)
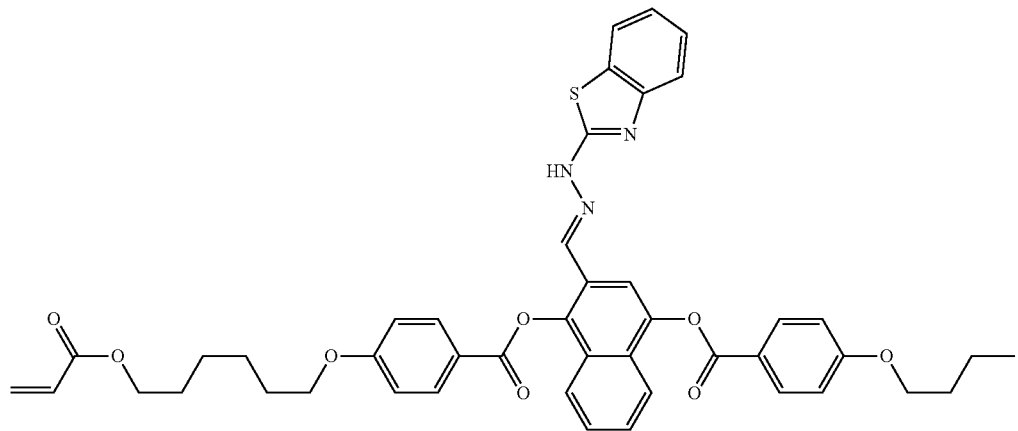
(I-75)
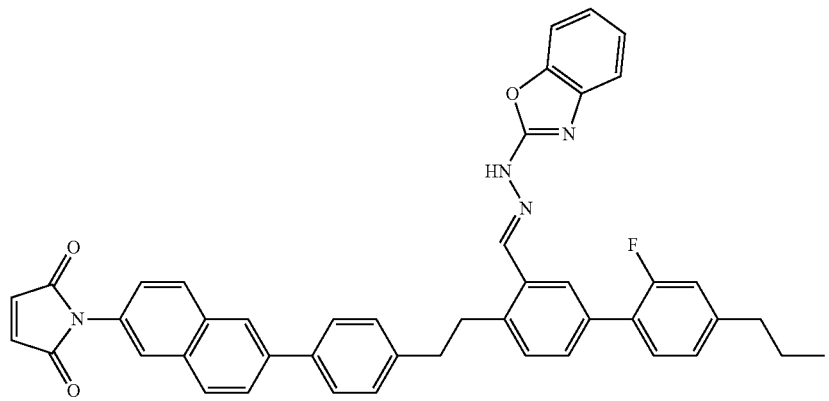
[Chem. 45]
(I-76)
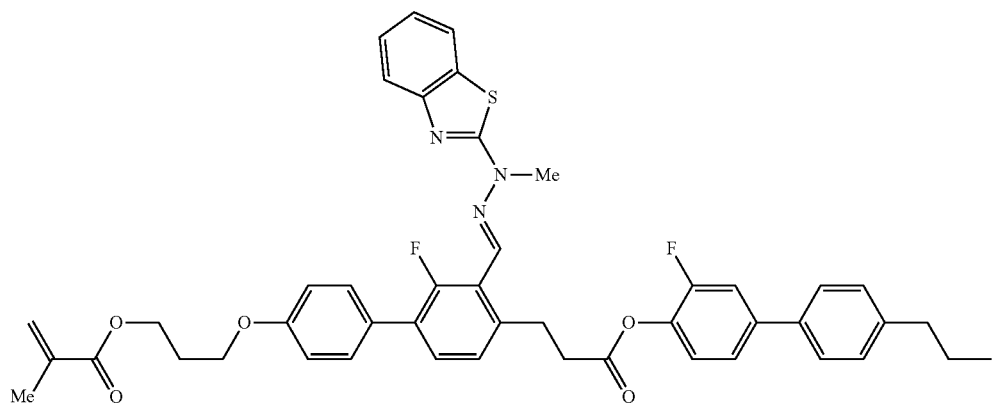

-continued
(I-77)
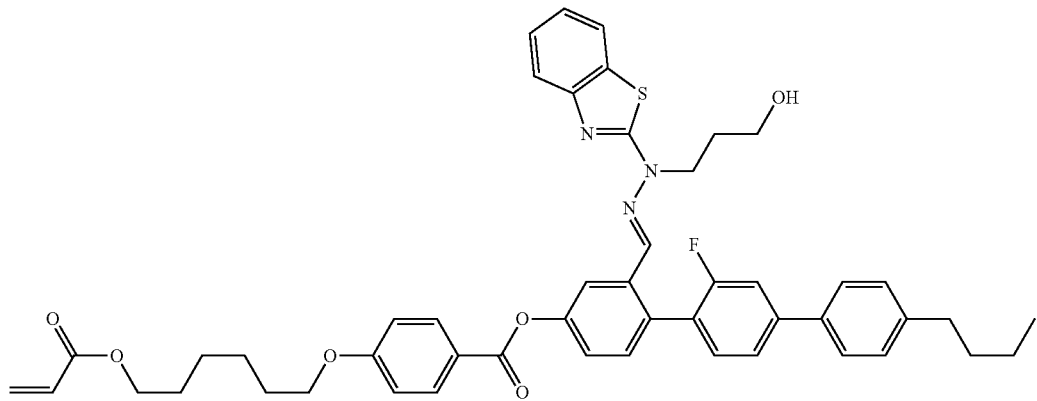
(I-78)
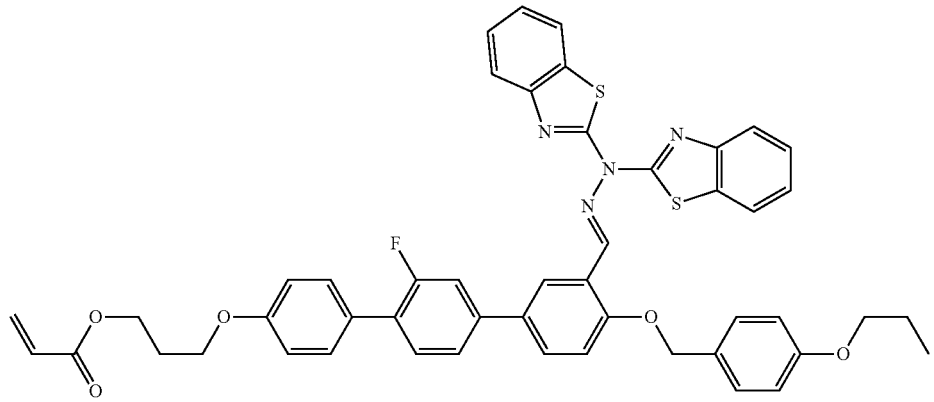
(I-79)
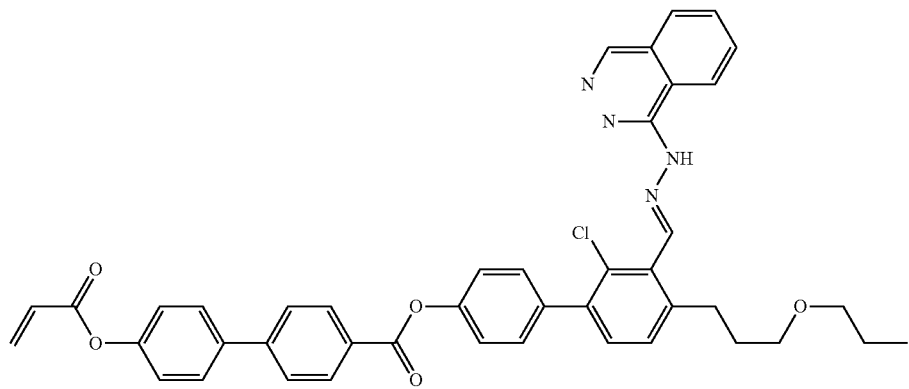
(I-80)
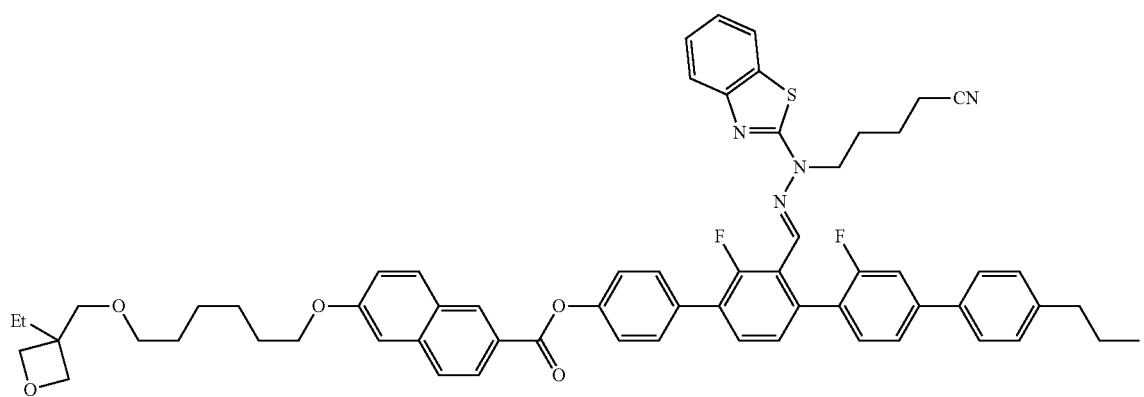

-continued
[Chem. 46]
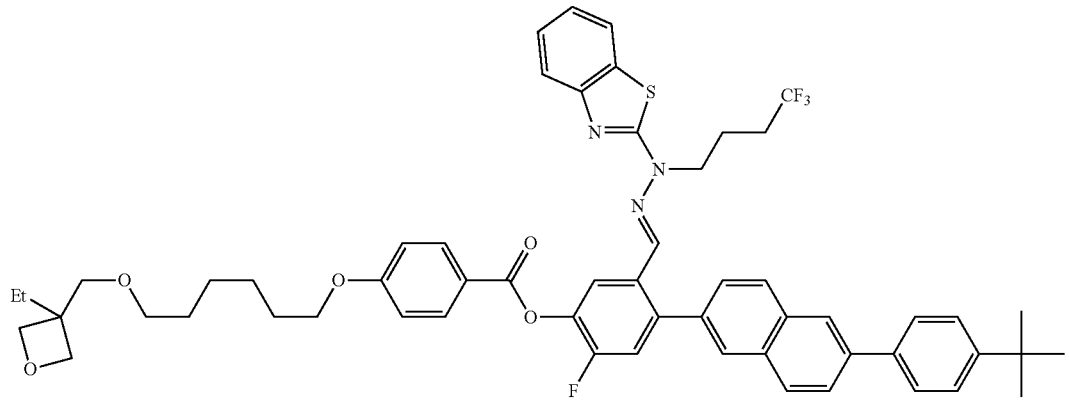
(I-81)
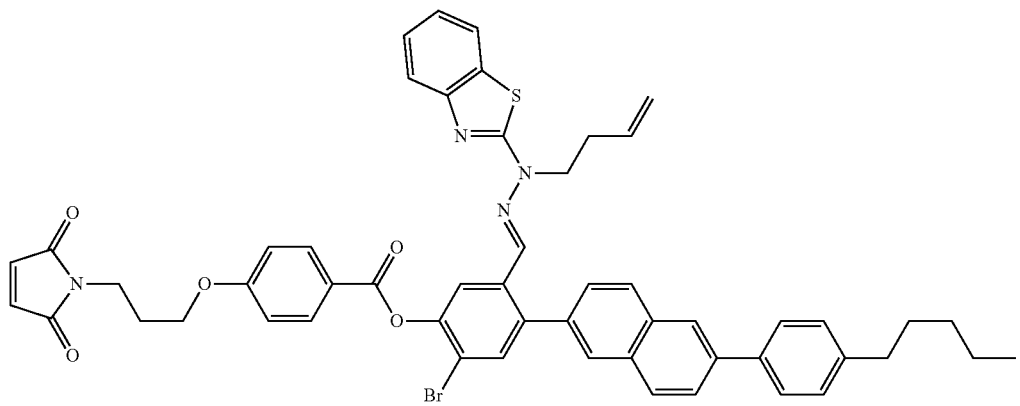
(I-82)
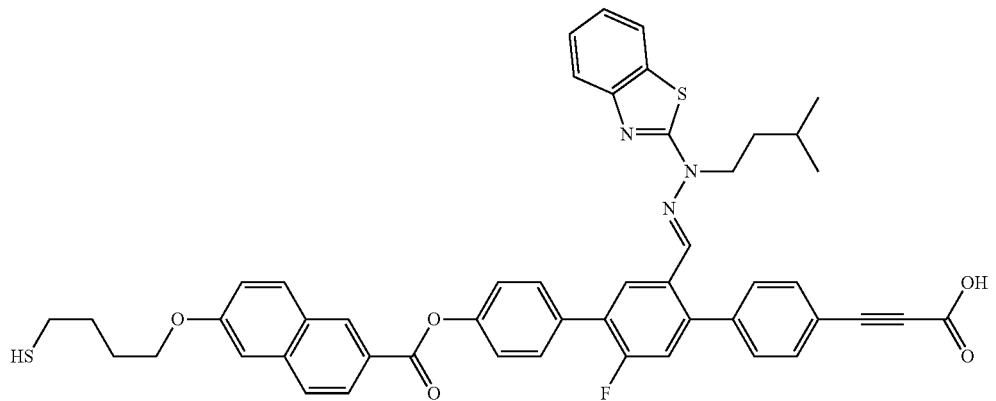
(I-83)
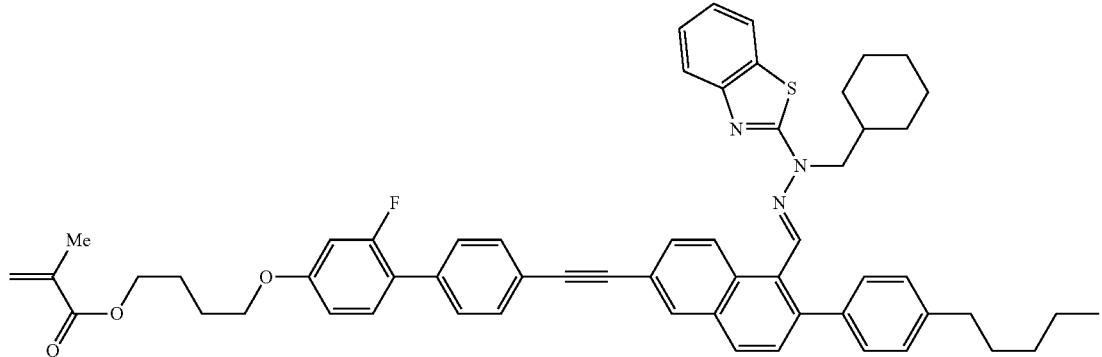
(I-84)

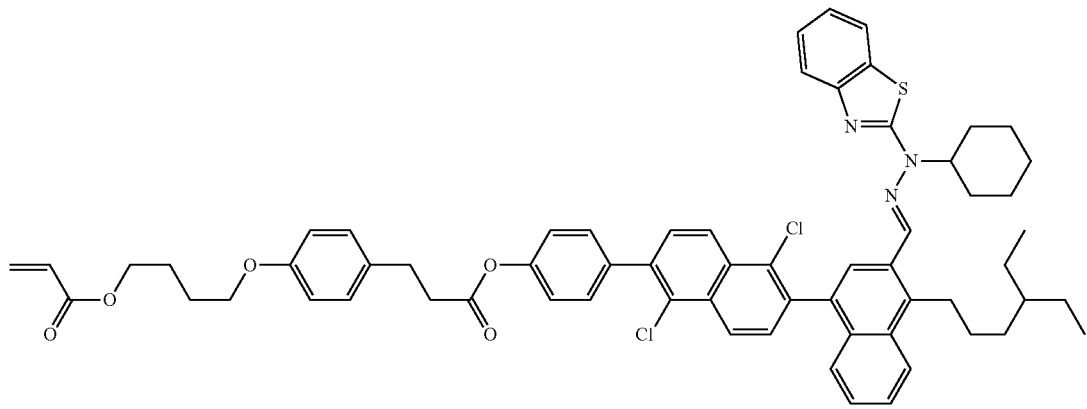
(I-85)
[Chem. 47]
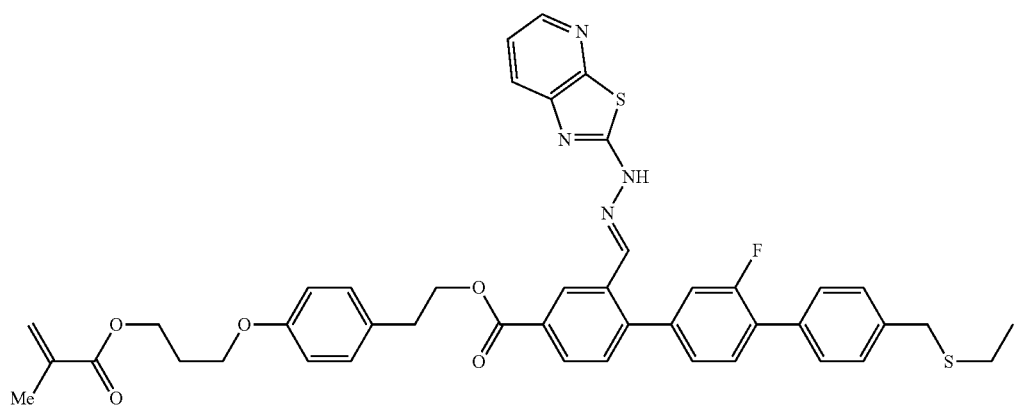
(I-86)
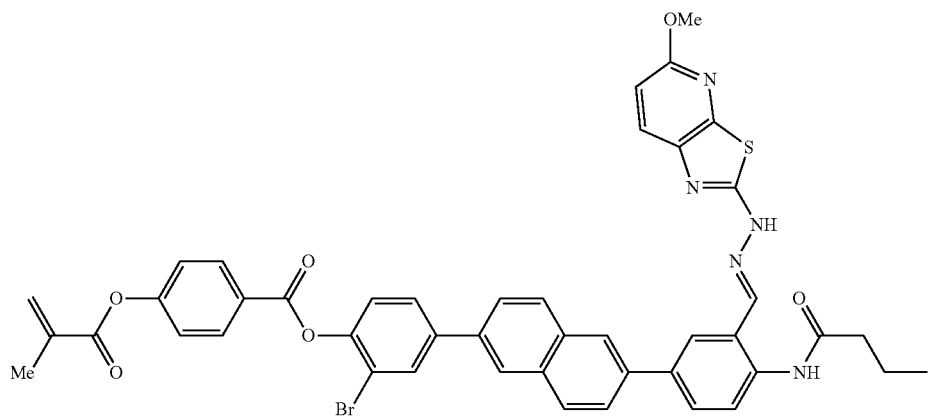
(I-87)

(I-88)
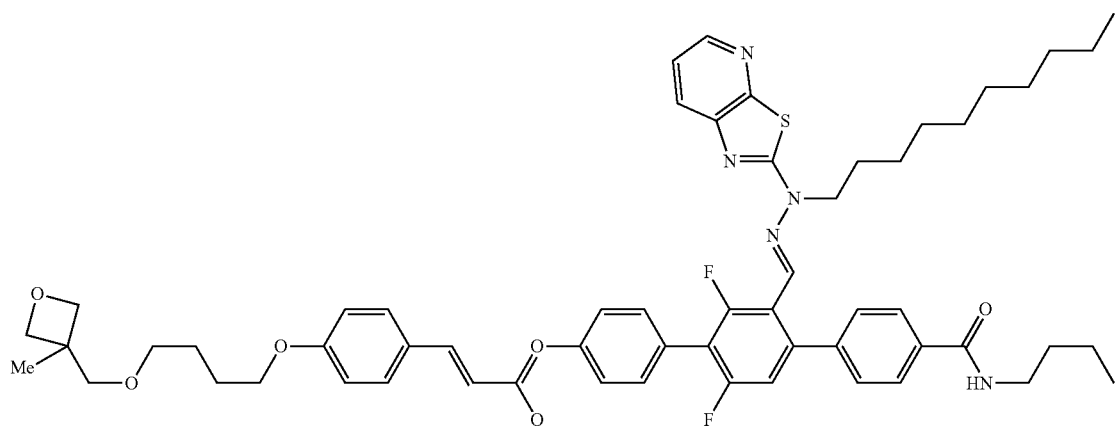
(I-89)
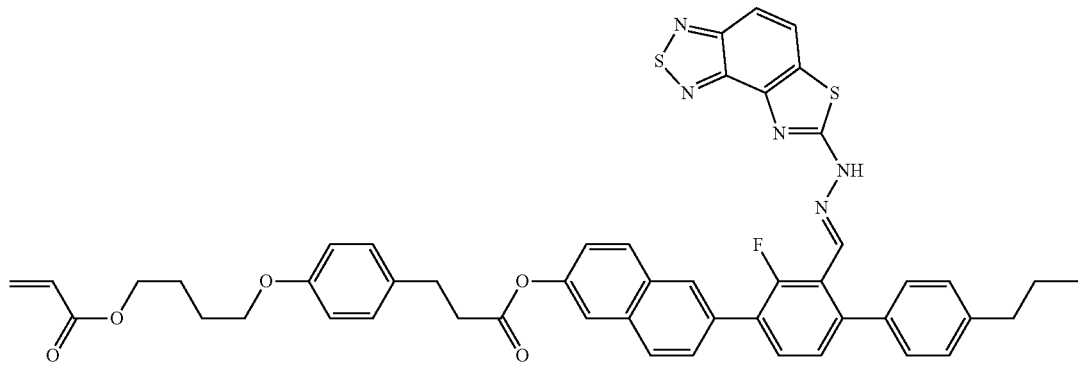
(I-90)
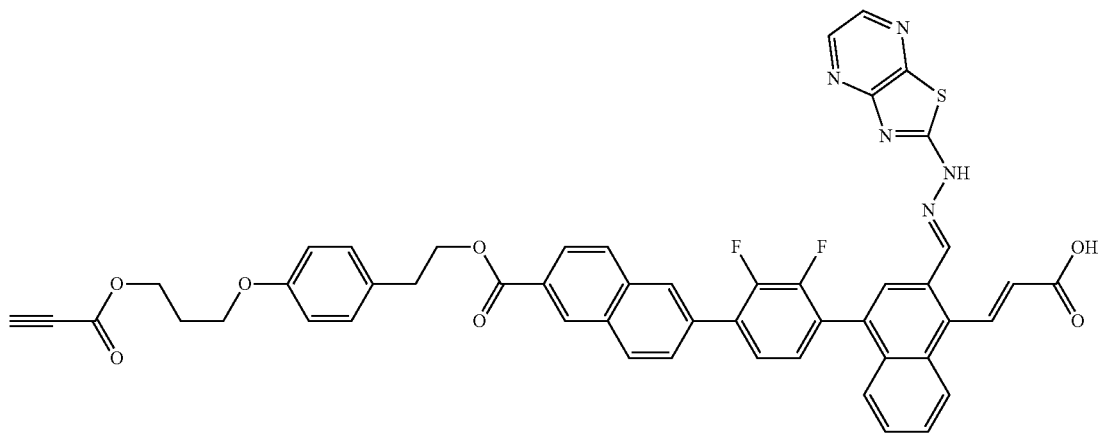

-continued
[Chem. 48]
(I-91)
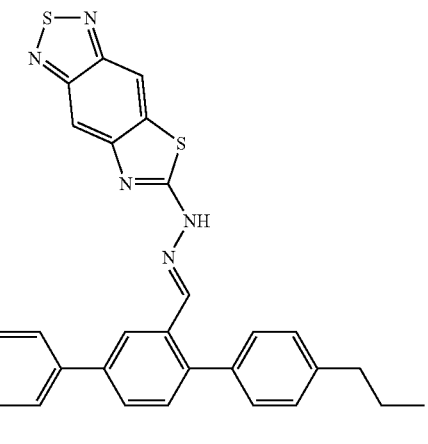
(I-92)
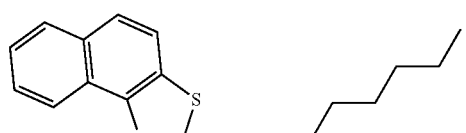
(I-93)
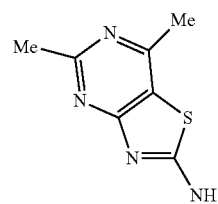
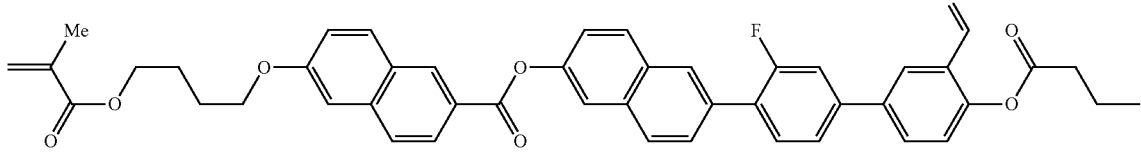
(I-94)
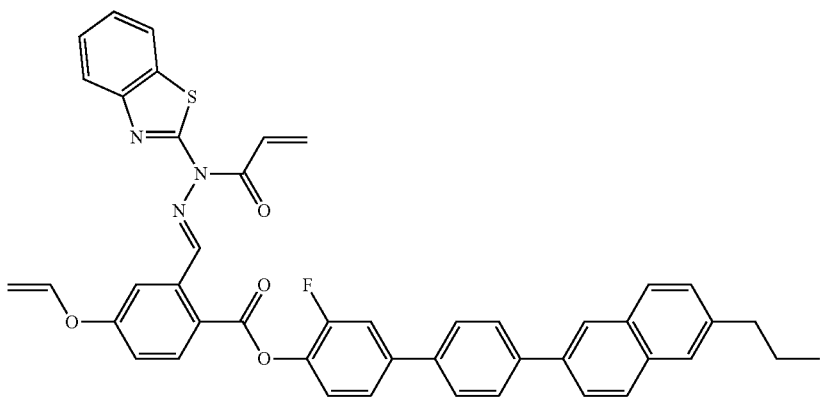

(I-95)
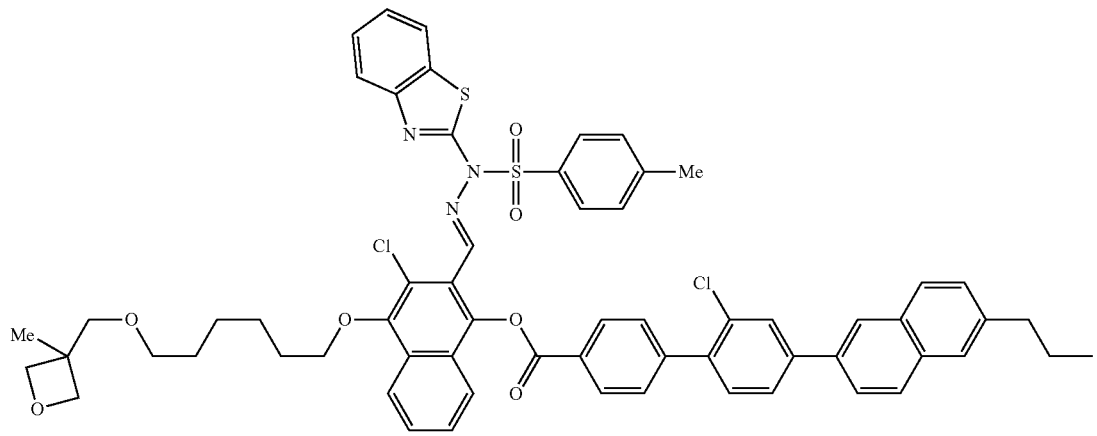
[Chem. 49]
(I-96)
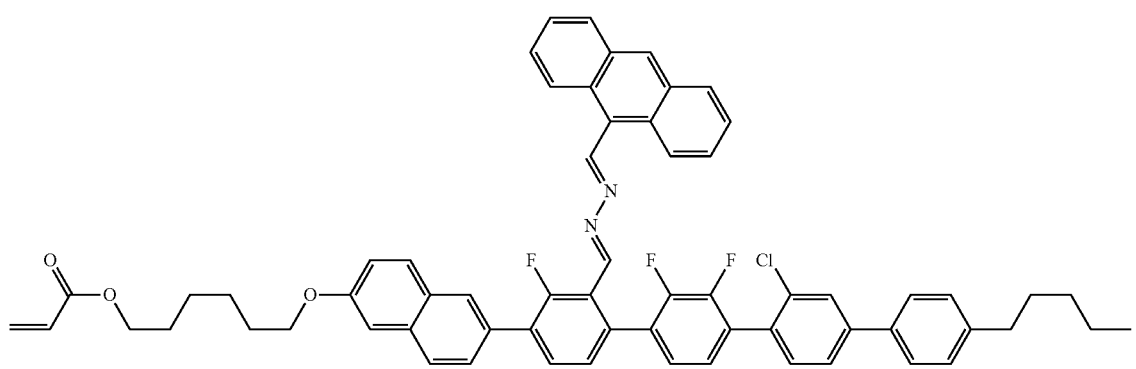
(I-97)
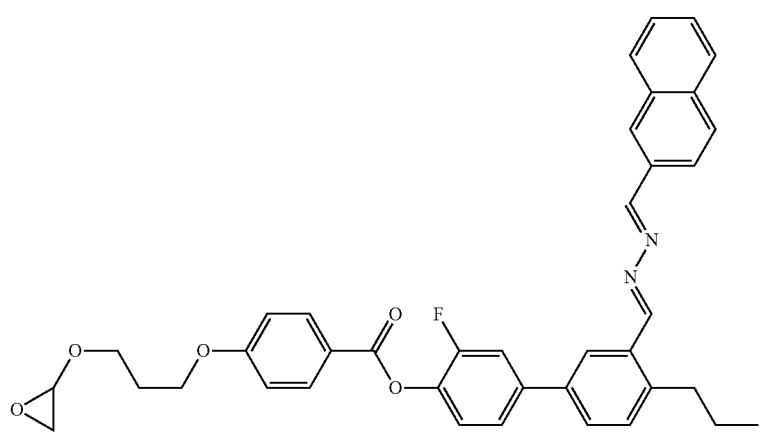

-continued
(I-98)
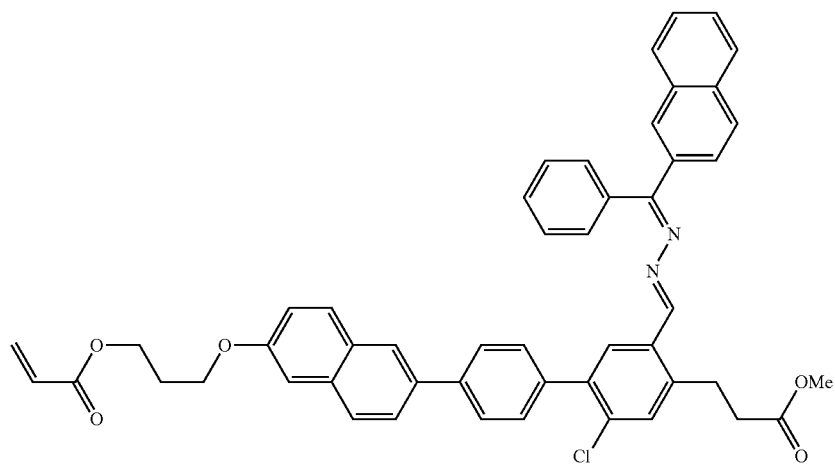
(I-99)
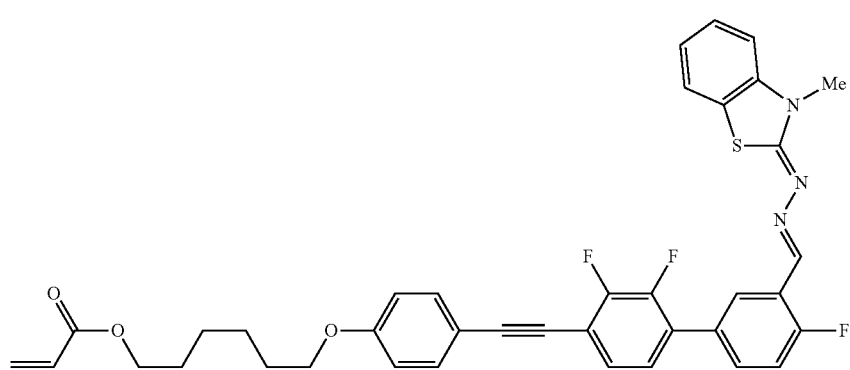
(I-100)
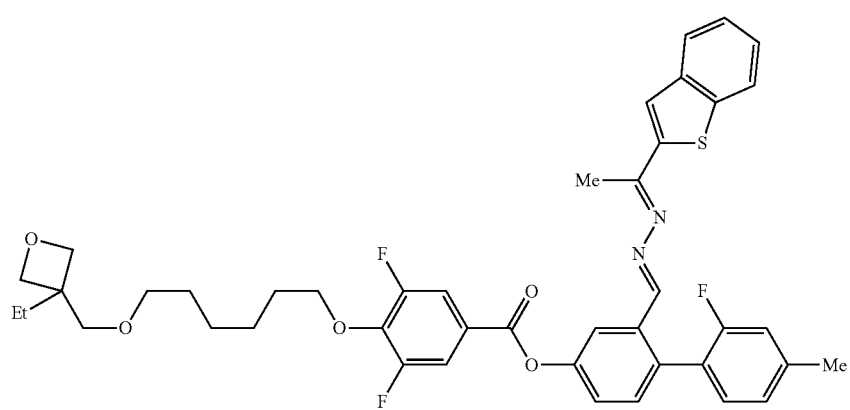

-continued
[Chem. 50]
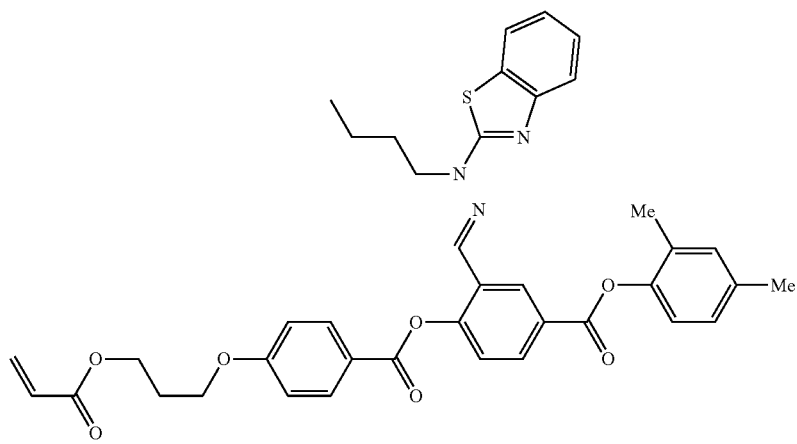
(I-101)
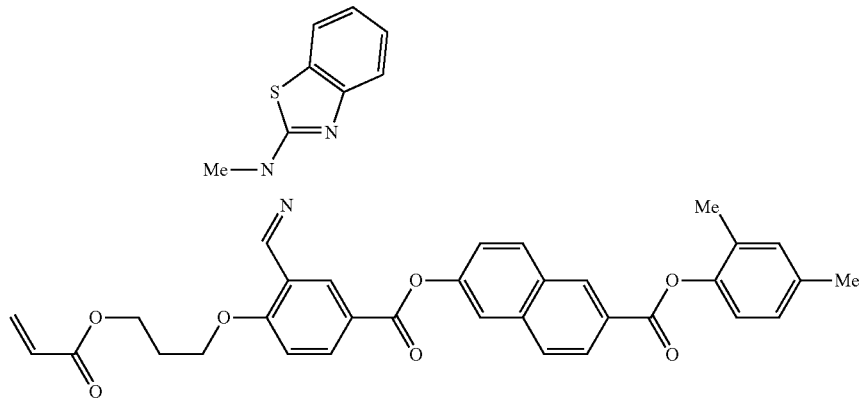
(I-102)
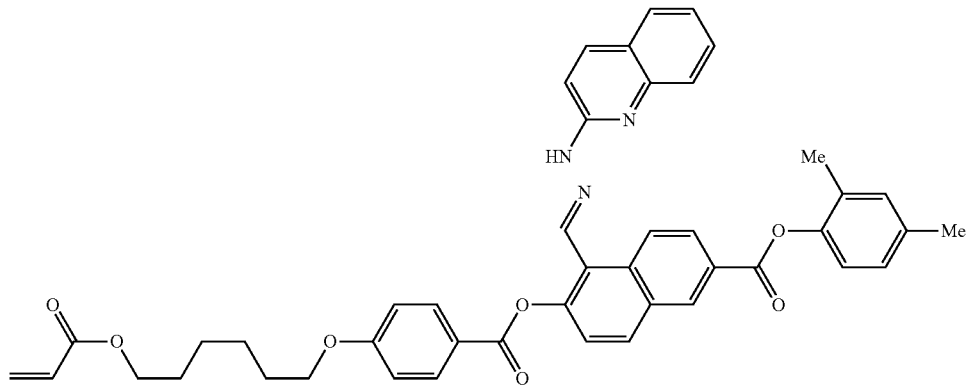
(I-103)
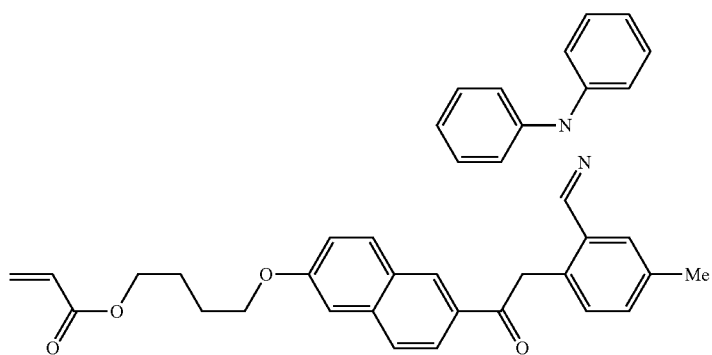
(I-104)

-continued
(I-105)
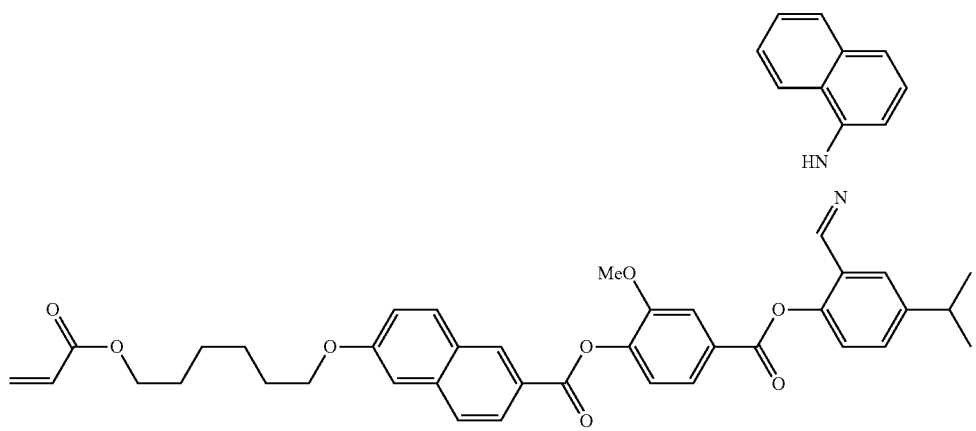
[Chem. 51]
(I-106)
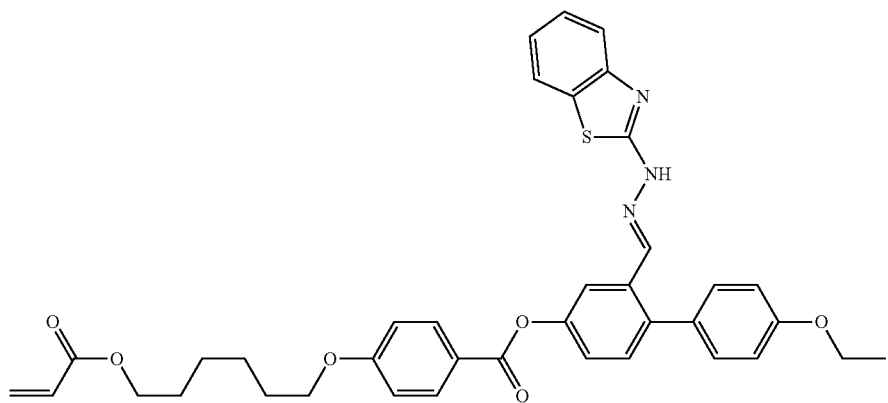
(I-107)
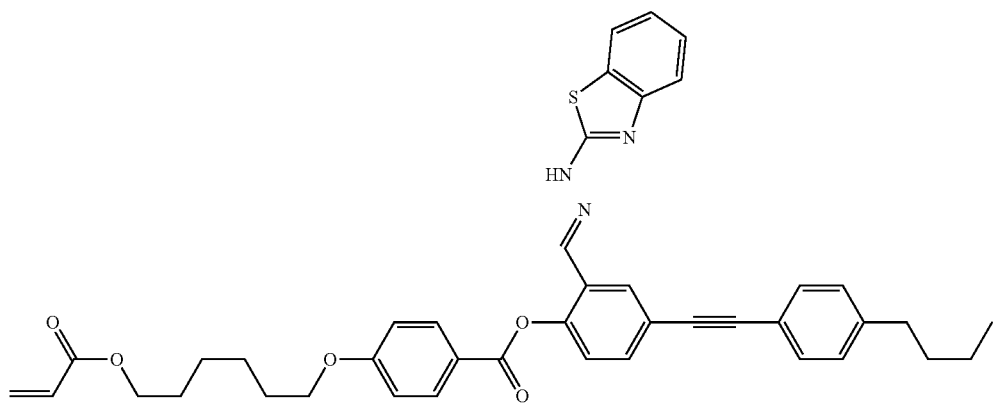

-continued
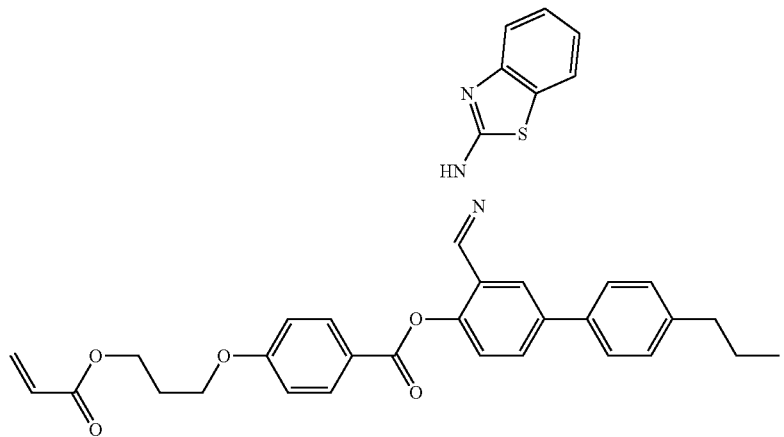
(I-108)
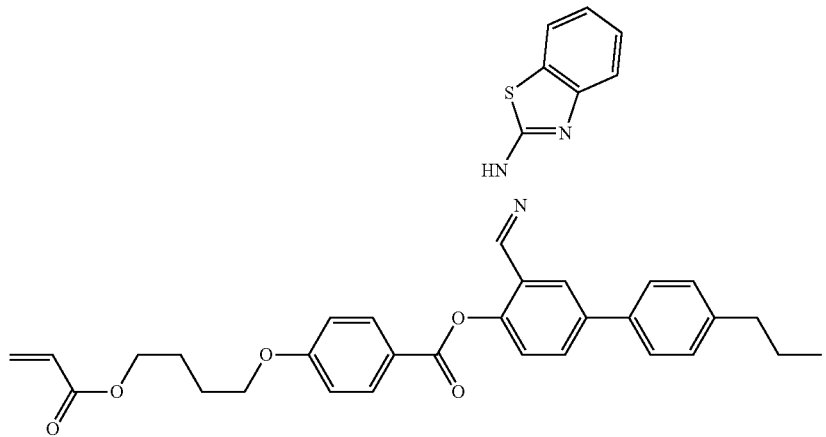
(I-109)
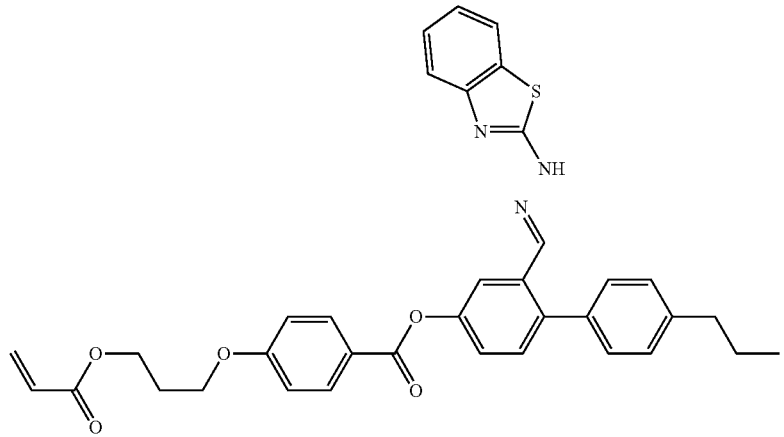
(I-110)

-continued
[Chem. 52]
(I-111)
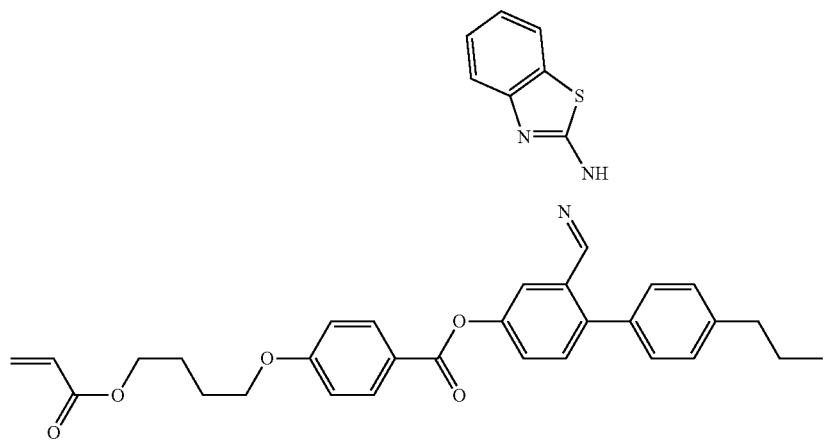
(I-112)
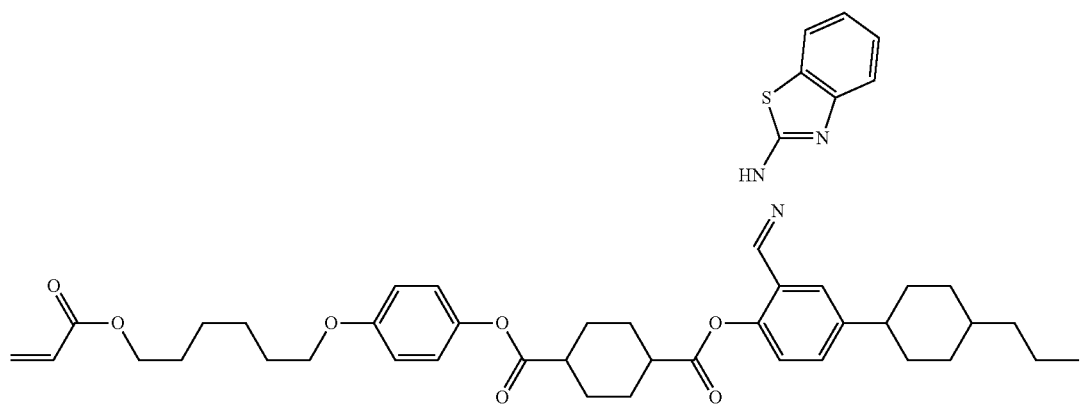
(I-113)
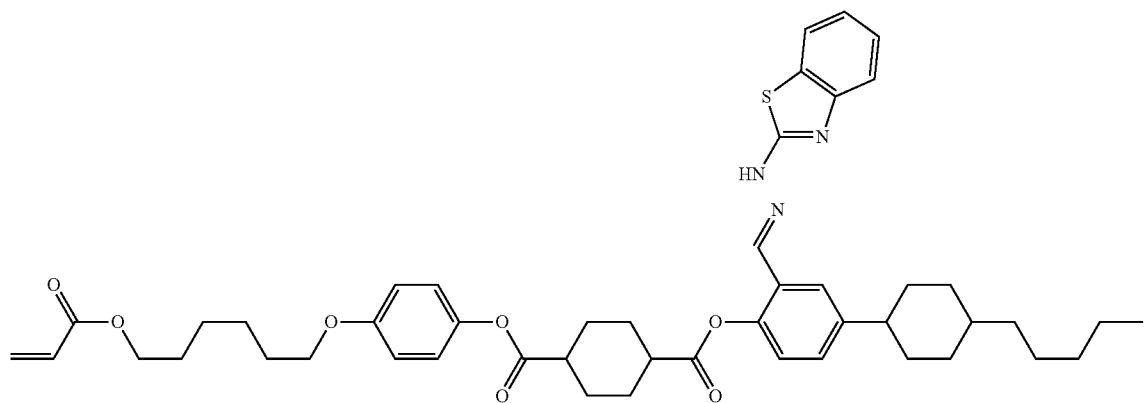

-continued
(I-114)
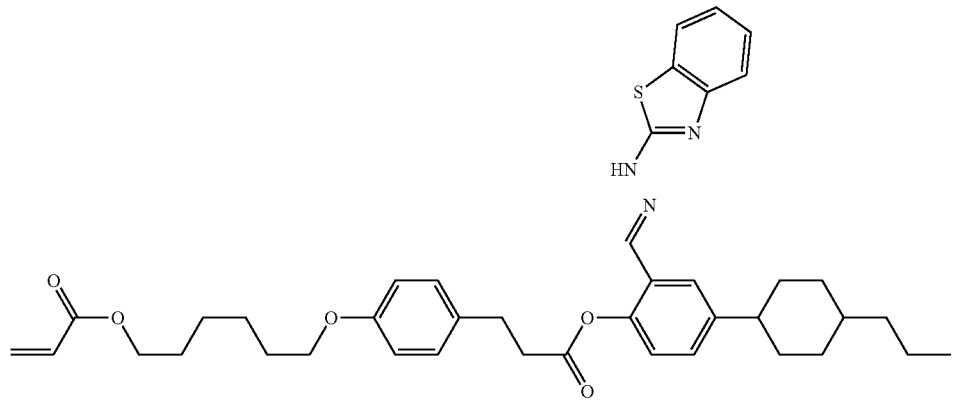
(I-115)
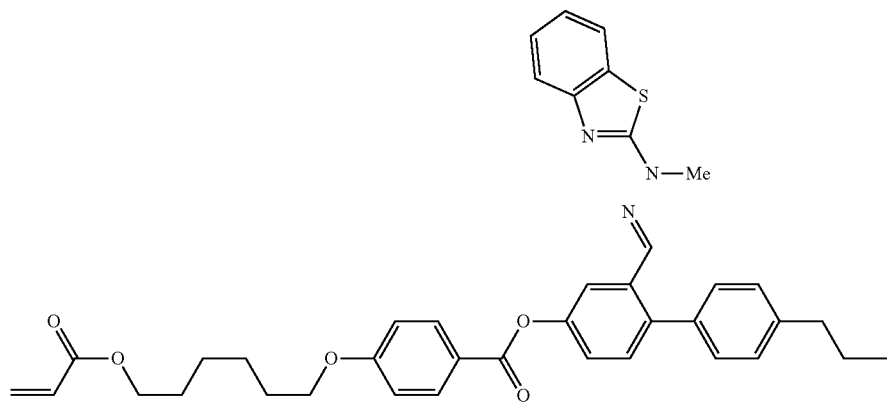
[Chem. 53]
(I-116)
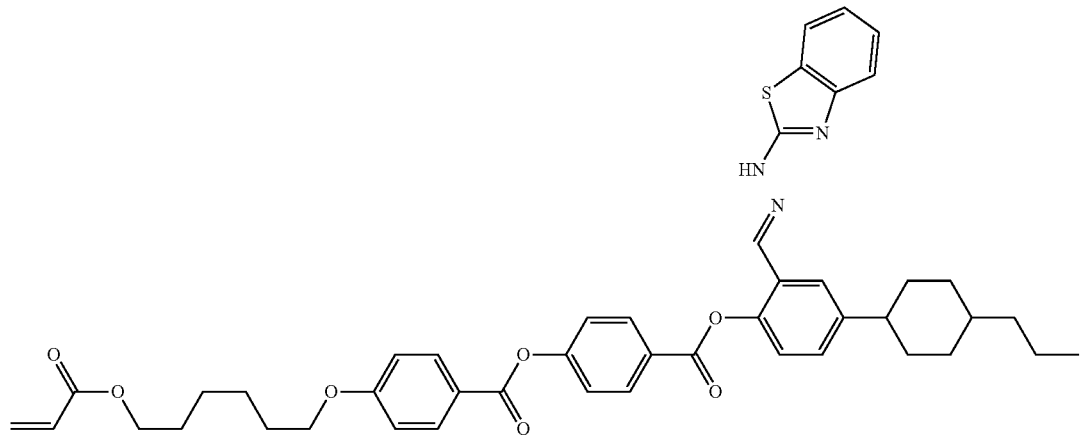

-continued
(I-117)
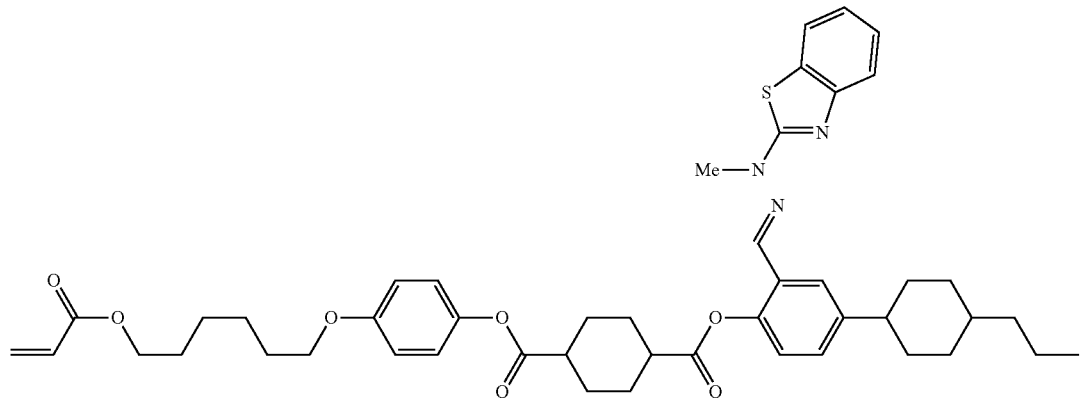
(I-118)
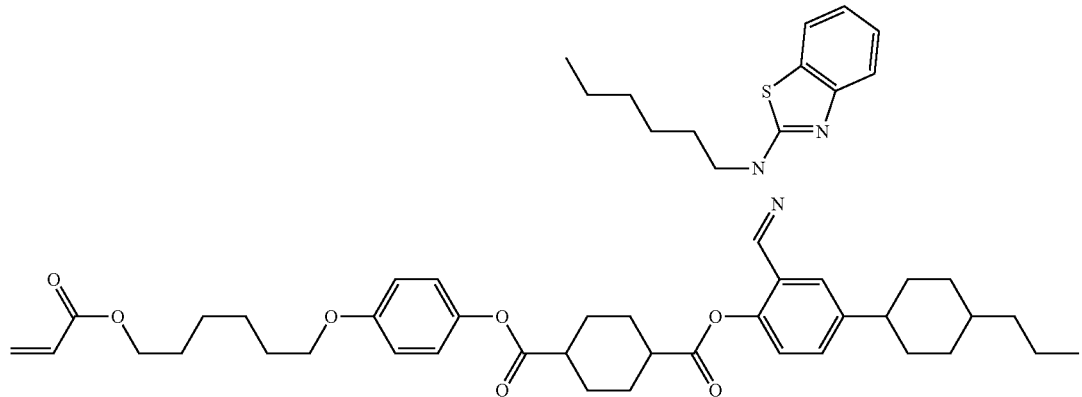
(I-119)
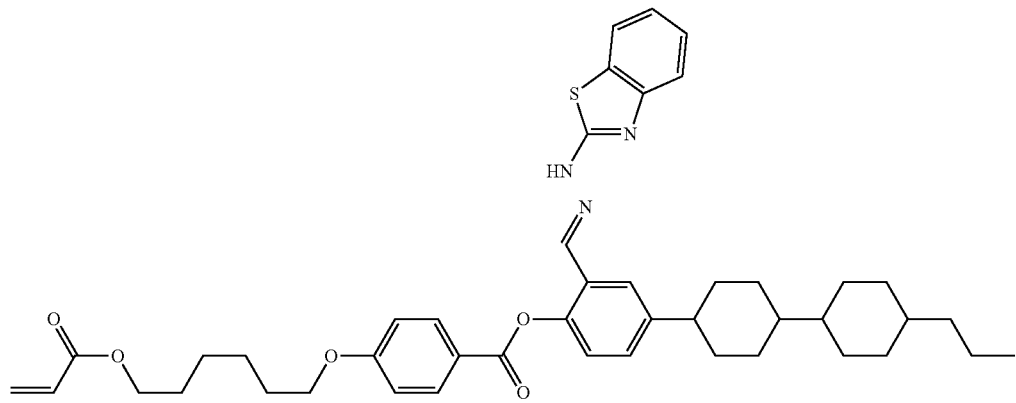
(I-120)
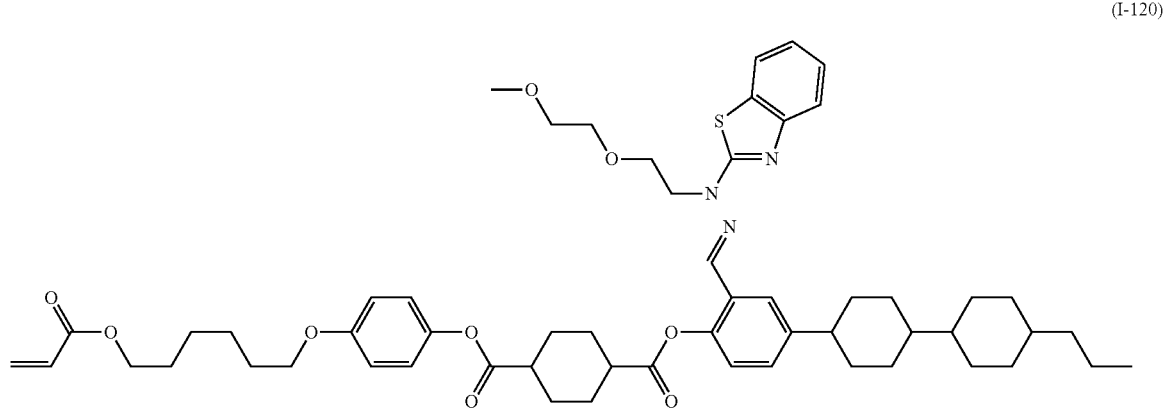

-continued
[Chem. 54]
(I-121)
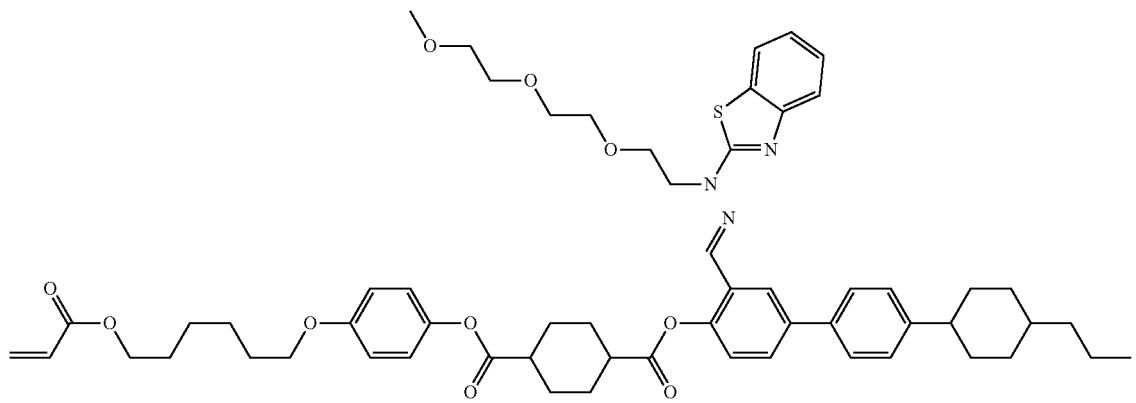
(I-122)
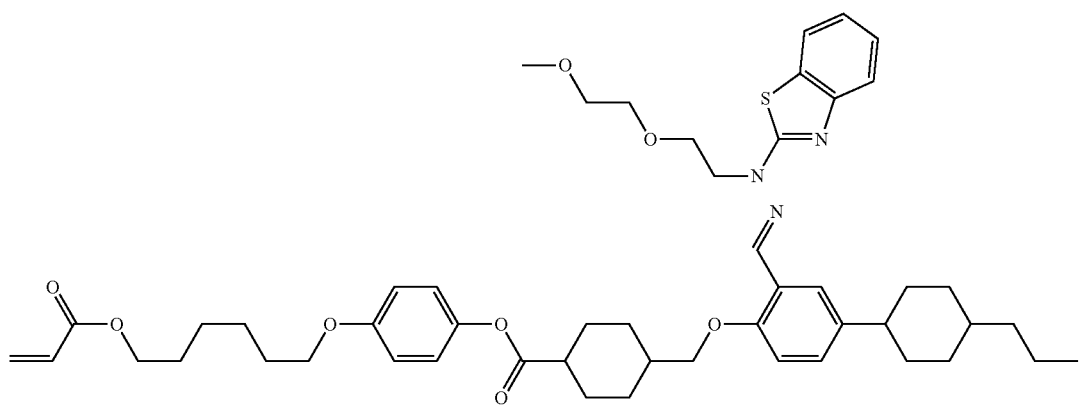
(I-123)
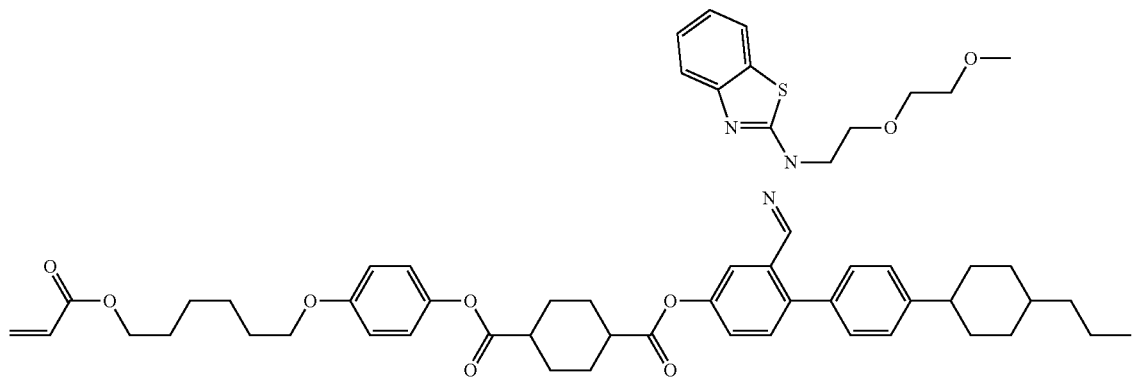

-continued
(I-124)
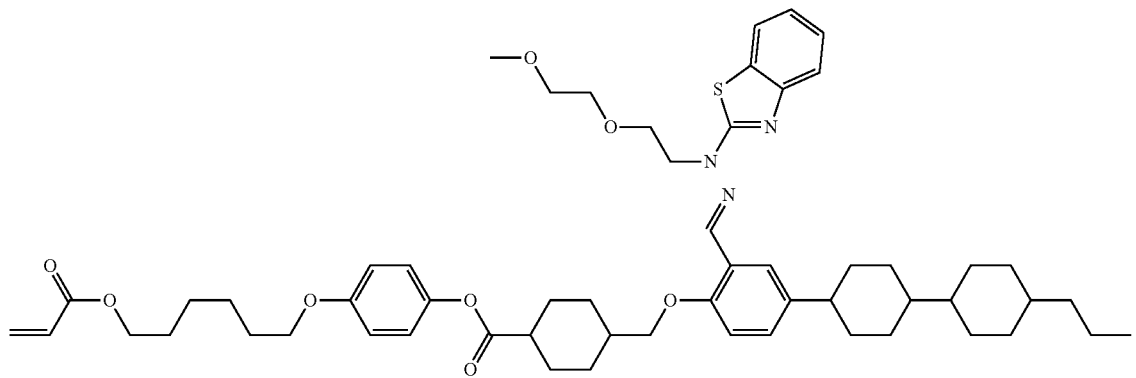
(I-125)
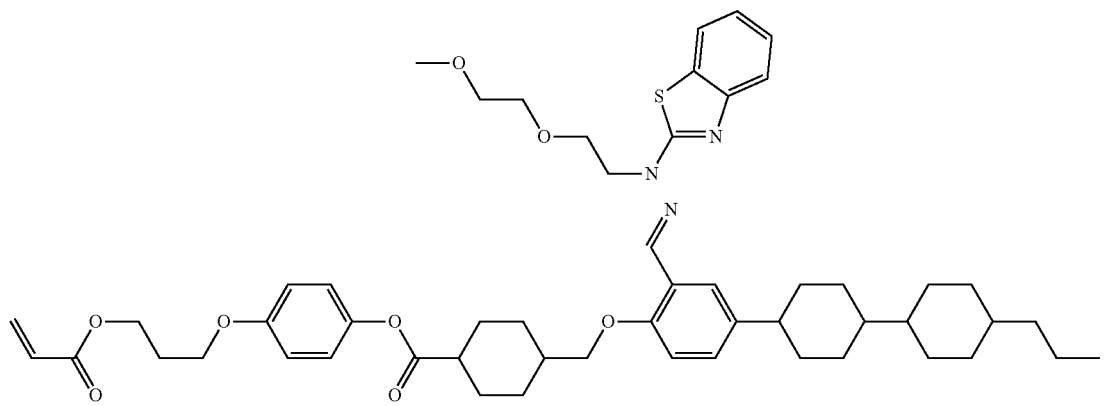
[Chem. 55]
(I-126)
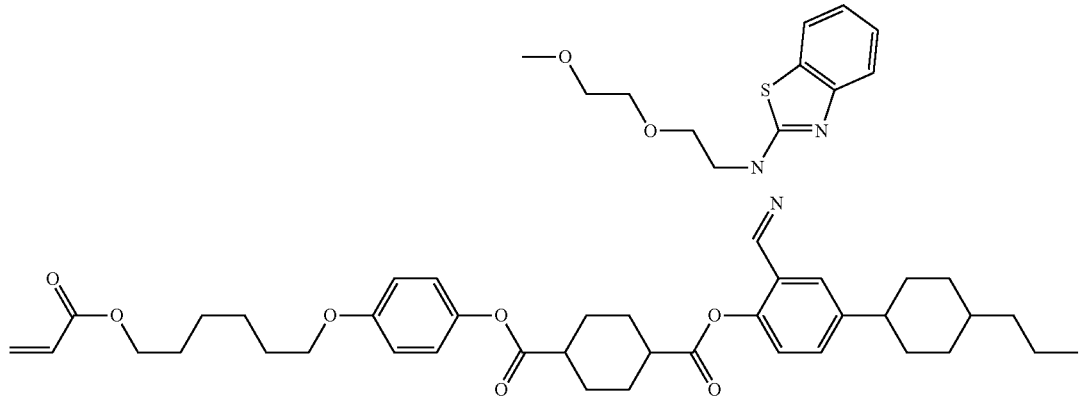

-continued
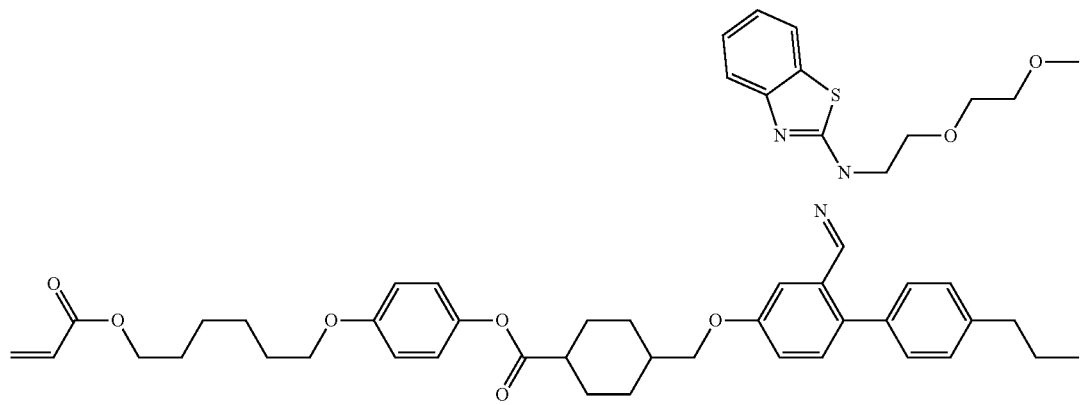
(I-127)
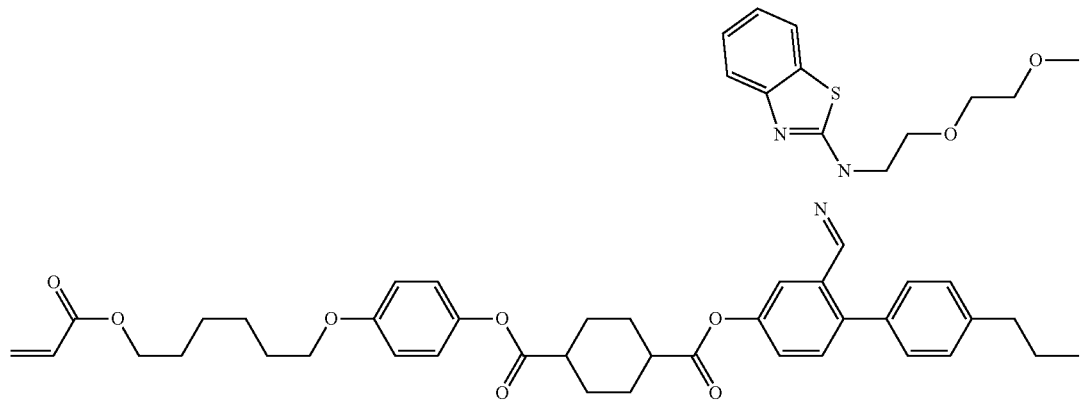
(I-128)
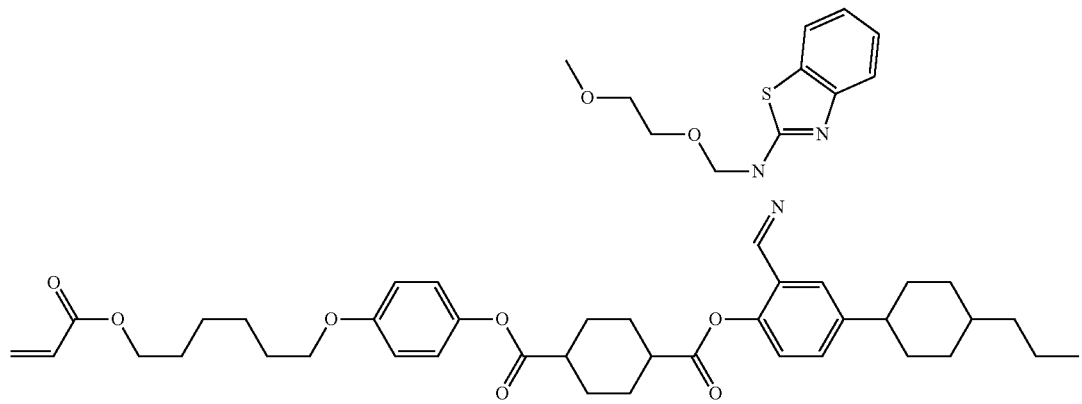
(I-129)
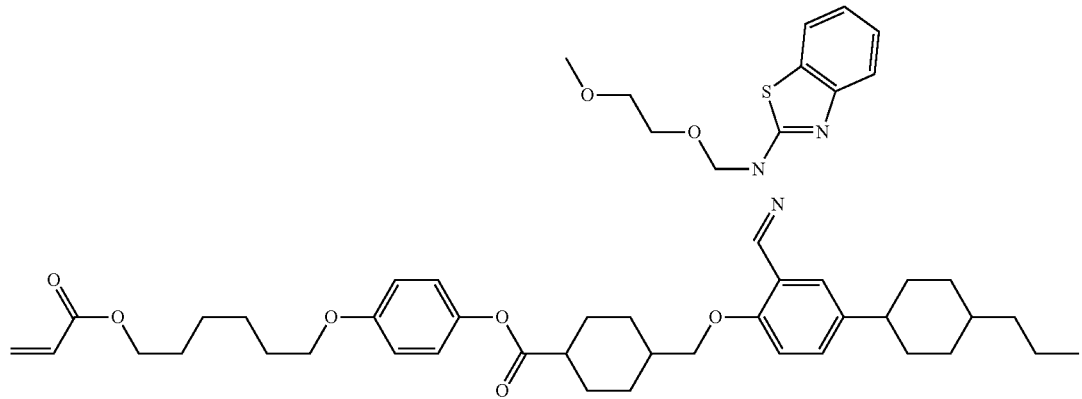
(I-130)

[Chem. 56]
(I-131)
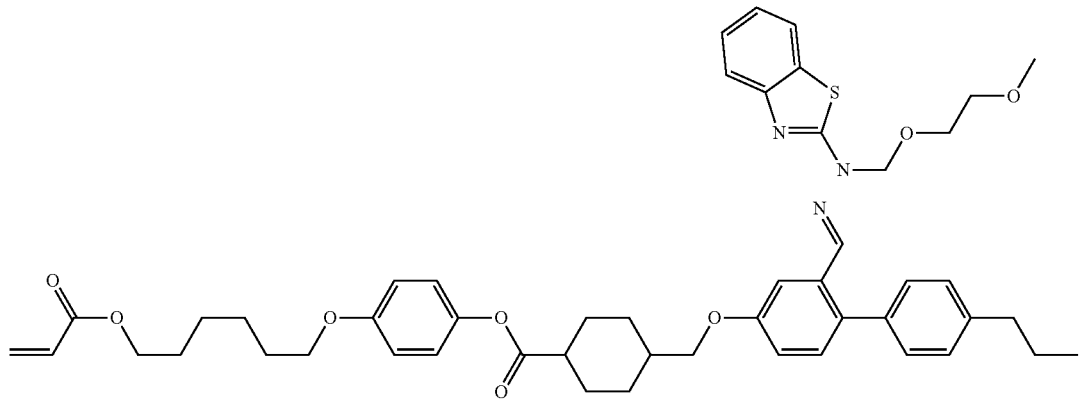
(I-132)
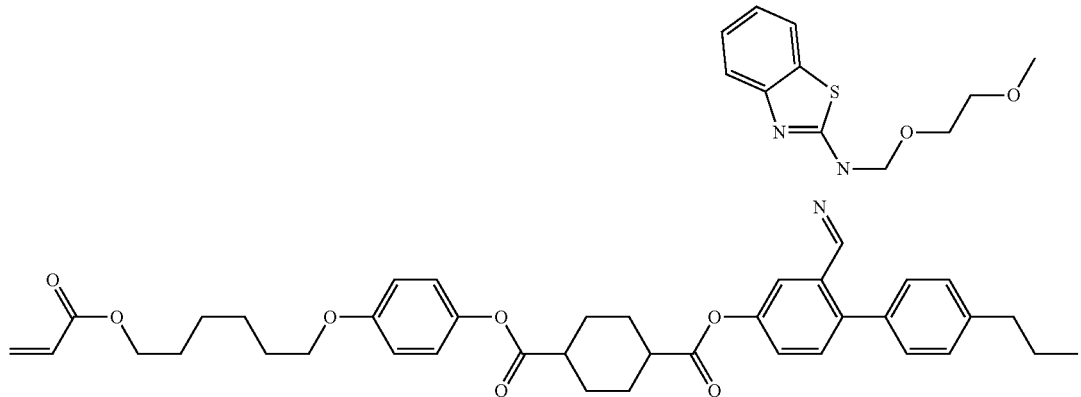
(I-133)
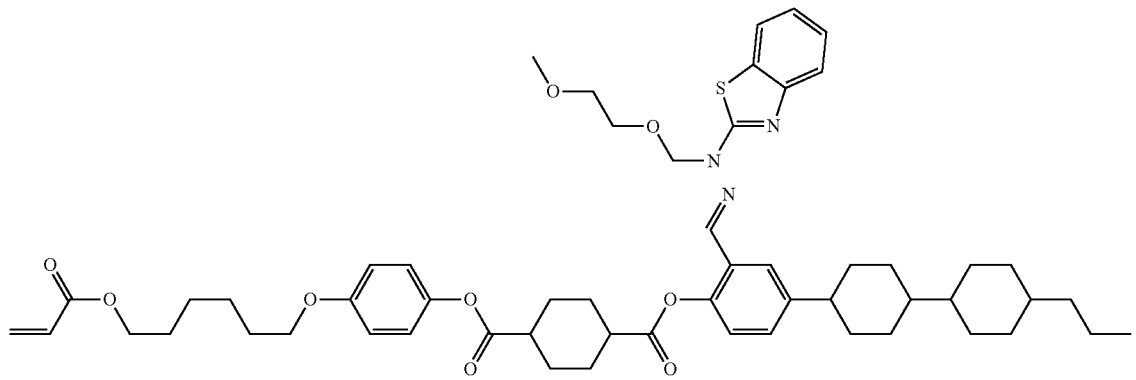

(I-134)

The compound according to the present invention can be produced by the following production method.

(Production Method 1) Production of Compound Represented by Formula (S-9) Below

[Chem. 57]

(S-9)

(in Formula (S-9), P, S, L, $R^1$, $W^1$, and $W^2$ each independently represent the same things as those defined in General Formula (I); s represents an integer of 0 to 4; t represents an integer of 0 to 3, and "halogen" represents a halogen atom or a halogen equivalent)

Formylation of the compound represented by Formula (S-1) gives the compound represented by Formula (S-2). An example of the reaction is conducted by a method in which the compound represented by Formula (S-1) is reacted with para-formaldehyde in the presence of magnesium chloride and a base. An example of the base is triethylamine.

The compound represented by Formula (S-2) is reacted with the compound represented by Formula (S-3) in the presence of a base to produce the compound represented by Formula (S-4). Examples of the base include potassium carbonate and cesium carbonate.

The compound represented by Formula (S-5) is reacted with, for example, hydrazine monohydrate to produce the compound represented by Formula (S-6).

The compound represented by Formula (S-6) is reacted with the compound represented by Formula (S-7) in the presence of a base to produce the compound represented by Formula (S-8). Examples of the base include potassium carbonate and cesium carbonate.

The compound represented by Formula (S-8) is reacted with the compound represented by Formula (S-4) in the presence of an acid catalyst to produce the compound represented by Formula (S-9). Examples of the acid include p-toluenesulfonic acid, pyridinium p-toluenesulfonate, and 10-camphorsulfonic acid.

(Production Method 2) Production of Compound Represented by Formula (S-15) Below

[Chem. 58]

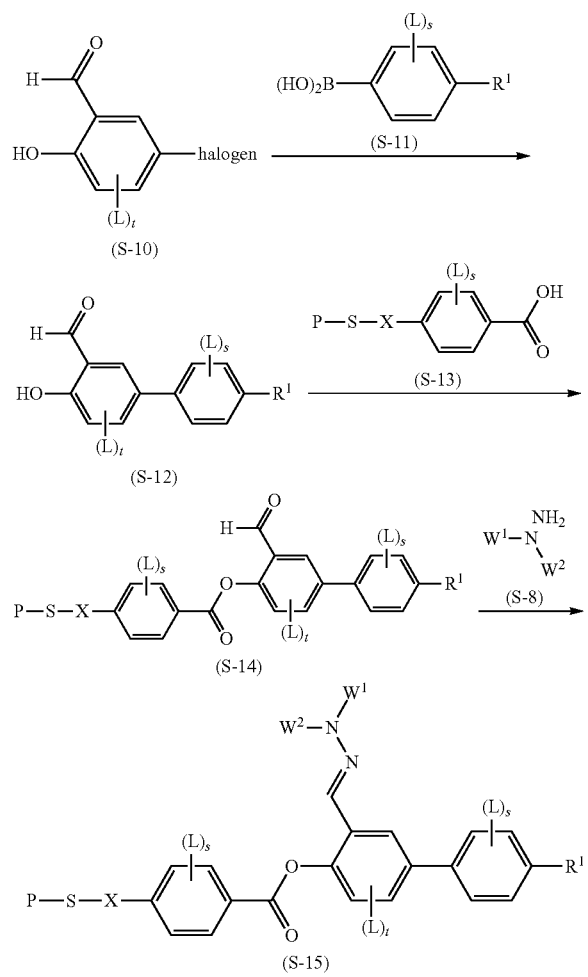

(in Formula (S-15), P, S, X, L, R¹, W¹, and W² each independently represent, the same things as those defined in General Formula (I); s each independently represents an integer of 0 to 4; t represents an integer of 0 to 3, and "halogen" represents a halogen atom or a halogen equivalent)

The compound represented by Formula (S-10) is reacted with the compound represented by Formula (S-11) to produce the compound represented by Formula (S-12). An example of the above reaction may be conducted by a method in which cross-coupling is performed in the presence of a metal catalyst and a base. Examples of the metal catalyst include [1,1'-bis(diphenylphosphino)ferrocene]palladium(II) dichloride, palladium acetate(II), and tetrakis(triphenylphosphine)palladium(0). An example of the base is triethylamine. The above reaction may be conducted under the conditions based on, for example, the methods described in the following literature: Metal-Catalyzed Cross-Coupling Reactions (Armin de Meijere and Francois Diedrich, Wiley-VCH), Palladium Reagents and Catalysts: New Perspectives for the 21st Century (Jiro Tsuji, Wiley & Sons, Ltd.), Cross-Coupling Reactions: A Practical Guide (Topics in Current Chemistry) (S. L. Buchwald, K. Fugami, T. Hiyama, M. Kosugi, M. Miura, N. Miyaura, A. R. Muci, M. Nomura, E. Shirakawa, and K. Tamao, Springer).

The compound represented by Formula (S-12) is reacted with the compound represented by Formula (S-13) to produce the compound represented by Formula (S-14). The above reaction may be conducted under conditions in which, for example, a condensing agent is used or in which the compound represented by Formula (S-13) is formed into an acid chloride, a mixed acid anhydride, or a carboxylic acid anhydride and subsequently reacted with the compound represented by General Formula (S-12) in the presence of a base. In the case where a condensing agent is used, examples of the condensing agent include N,N'-dicyclohexylcarbodiimide, N,N'-diisopropylcarbodiimide, and 1-ethyl-3-(3-dimethylaminopropyl)carbodiimide hydrochloride. Examples of the base include triethylamine and diisopropylethylamine.

The compound represented by Formula (S-14) is reacted with the compound represented by Formula (S-8) as in Production Method 1 to produce the compound represented by Formula (S-15).

(Production Method 3) Production of Compound Represented by Formula (S-25) Below

[Chem. 59]

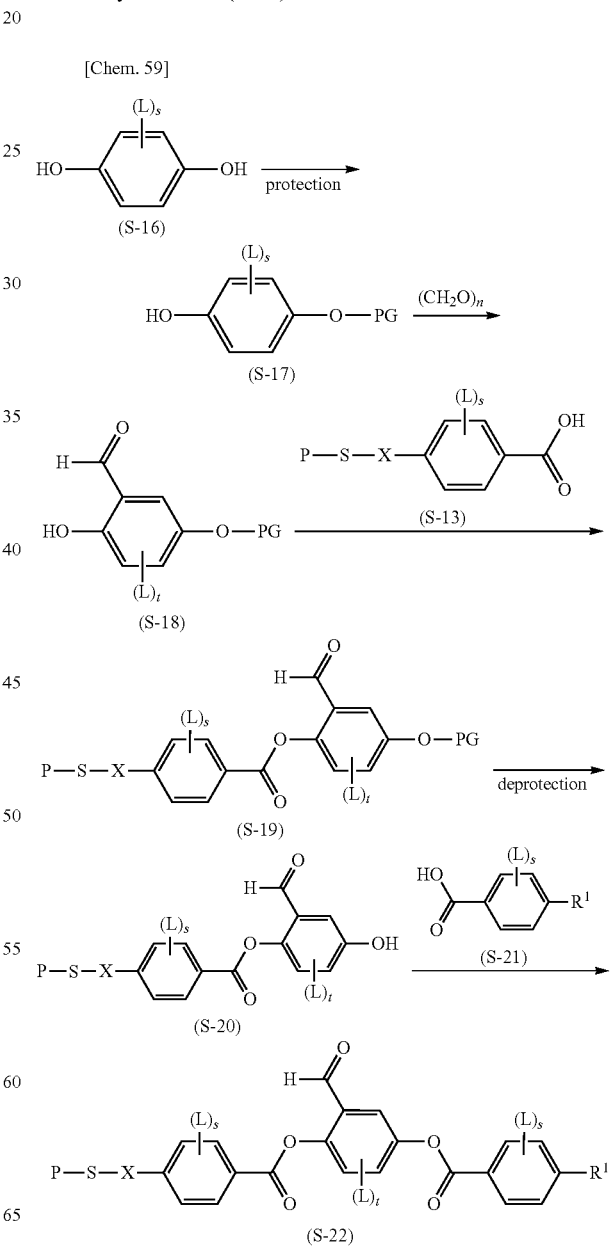

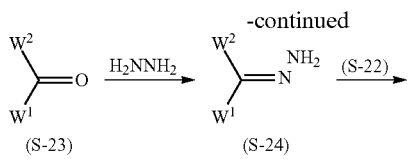

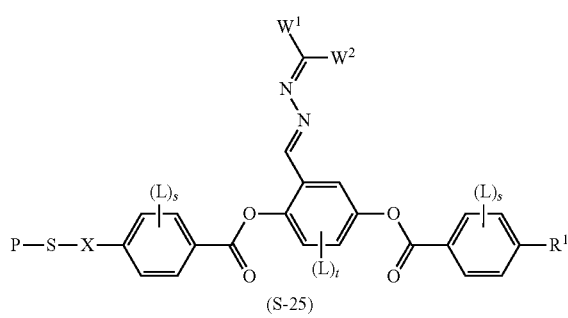

(in Formula (S-25), P, S, X, L, $R^1$, $W^1$, and $W^2$ each independently represent the same things as those defined in General Formula (I); s each independently represents an integer of 0 to 4; t represents an integer of 0 to 3; and PG represents a protecting group)

A hydroxyl group included in the compound represented by Formula (S-16) is protected with a protecting group (PG). The protecting group (PG) is not limited; any protecting group capable of performing protection consistently until a deprotection step is conducted may be used. Preferable examples of the protecting group (PG) include those described in GREENE'S PROTECTIVE GROUPS IN ORGANIC SYNTHESIS ((Fourth Edition), PETER G. M. WUTS and THEODORA W. GREENE, A John Wiley & Sons, Inc., Publication). A specific example of the protecting group is a tetrahydropyranyl group.

As in Production Method 1, formylation of the compound represented by Formula (S-17) gives the compound represented by Formula (S-18).

The compound represented by Formula (S-18) is reacted with the compound represented by Formula (S-13) as in Production Method 2 to produce the compound represented by Formula (S-19).

Subsequently, the protecting group (PG) included in the compound represented by Formula (S-19) is deprotected. The deprotection reaction may be conducted under any conditions that allow the compound represented by Formula (S-20) to be produced but is preferably conducted under the conditions described in the above literature.

The compound represented by Formula (S-20) is reacted with the compound represented by Formula (S-21) as in Production Method 2 to produce the compound represented by Formula (S-22).

The compound represented by Formula (S-23) is reacted with, for example, hydrazine monohydrate to produce the compound represented by Formula (S-24).

The compound represented by Formula (S-24) is reacted with the compound represented by Formula (S-22) as in Production Method 1 to produce the compound represented by Formula (S-25).

Examples of reaction conditions other than those described in the steps of Production Method 1 to 3 above include the reaction conditions described in the following literature: Jikken Kagaku Kouza ("Course on Experimental Chemistry", edited by The Chemical Society of Japan, printed by Maruzen Co., Ltd.), Organic Syntheses (A John Wiley & Sons, Inc.), Beilstein Handbook of Organic Chemistry (Beilstein-Institut fuer Literatur der Organischen Chemie, Springer-Verlag Berlin and Heidelberg GmbH & Co.K), and Fiesers' Reagents for Organic Synthesis (John Wiley & Sons, Inc.) and the conditions revealed through online search services such as SciFinder (Chemical Abstracts Service, American Chemical Society) and Reaxys (Elsevier Ltd.).

In each of the above steps, an appropriate reaction solvent may be used. The solvent is not limited; any solvent that enables a desired compound to be produced may be used. Examples of the solvent include tert-butyl alcohol, isobutyl alcohol, isopropyl alcohol, isopentyl alcohol, cyclohexanol, 1-butanol, 2-butanol, 1-octanol, 2-methoxyethanol, ethylene glycol, diethylene glycol, methanol, methylcyclohexanol, ethanol, propanol, chloroform, carbon tetrachloride, dichloromethane, 1,2-dichloroethane, 1,2-dichloroethylene, 1,1,2,2-tetrachloroethane, trichloroethylene, 1-chlorobutane, carbon disulfide, acetone, acetonitrile, benzonitrile, N,N-dimethylformamide, N,N-dimethylacetamide, dimethylsulfoxide, 1,3-dimethyl-2-imidazolidinone, diethyl ether, ethylene glycol monoethyl ether, ethylene glycol monoethyl ether acetate, ethylene glycol monobutyl ether, ethylene glycol monomethyl ether, diethylene glycol diethyl ether, o-dichlorobenzene, xylene, o-xylene, p-xylene, m-xylene, chlorobenzene, isobutyl acetate, isopropyl acetate, isoamyl acetate, ethyl acetate, butyl acetate, propyl acetate, pentyl acetate, methyl acetate, 2-methoxyethyl acetate, hexamethylphosphoric triamide, tris(dimethylamino)phosphine, cyclohexanone, 1,4-dioxane, dichloromethane, styrene, tetrachloroethylene, tetrahydrofuran, pyridine, 1-methyl-2-pyrrolidinone, 1,1,1-trichloroethane, toluene, hexane, pentane, cyclohexane, cyclopentane, heptane, benzene, methyl isobutyl ketone, tert-butyl methyl ether, methyl ethyl ketone, methylcyclohexanone, methyl butyl ketone, diethyl ketone, gasoline, coal tar naphtha, petroleum ether, petroleum naphtha, petroleum benzine, turpentine oil, and mineral spirit. In the case where the reaction is conducted under an organic: solvent-water two-phase system, a phase-transfer catalyst may be used. Examples of the phase-transfer catalyst include benzyltrimethylammonium chloride, polyoxyethylene(20) sorbitan monolaurate [Tween 20], and sorbitan monooleate [Span 80].

Purification may optionally be performed in each of the above steps. Examples of a purification method include chromatography, recrystallization, distillation, sublimation, reprecipitation, adsorption, and liquid separation. In the case where a purifying agent is used, examples of the purifying agent include silica gel, alumina, active carbon, active clay, Celite, zeolite, mesoporous silica, carbon nanotube, carbon nanohorn, white charcoal, charcoal, graphene, an ion-exchange resin, Japanese acid clay, silicon dioxide, diatomaceous earth, pearlite, cellulose, an organic polymer, and a porous gel.

The compound according to the present invention is preferably included in a nematic liquid crystal composition, a smectic liquid crystal composition, a chiral smectic liquid crystal composition, or a cholesteric liquid crystal composition. A liquid crystal composition including the reactive compound according to the present invention may further include a compound other than the compound according to the present invention.

Specifically, the other polymerizable compound that can be used together with the polymerizable compound according to the present invention in a mixture is preferably a compound represented by General Formula (II-1) below,

[Chem. 60]

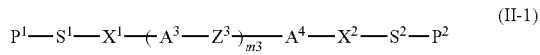
(II-1)

and/or a compound represented by General Formula (II-2) below,

[Chem. 61]

(II-2)

(in General Formulae (II-1) and (II-2), $P^1$, $P^2$, and $P^3$ each independently represent a polymerizable group; $S^1$, $S^2$, and $S^3$ each independently represent a single bond or an alkylene group having 1 to 20 carbon atoms in which one —$CH_2$— group or two or more —$CH_2$— groups that are not adjacent to one another may be each independently replaced with —O—, —COO—, —OCO—, or —OCOO—; $X^1$, $X^2$, and $X^3$ each independently represent —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —CF=CF—, —C≡C—, or a single bond; $Z^3$ and $Z^4$ each independently represent —O—, —S—, —$OCH_2$—, —$CH_2O$—, —COO—, —OCO—, —CO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —$CH_2CH_2$—, —$CH_2CF_2$—, —$CF_2CH_2$—, —$CF_2CF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —CF=CF—, —C≡C—, or a single bond; $A^3$, $A^4$, $A^5$, and $A^6$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, or a 1,3-dioxane-2,5-diyl group; $A^3$, $A^4$, $A^5$, and $A^6$ may optionally be each independently substituted with an alkyl group, a halogenated alkyl group, an alkoxy group, a halogenated alkoxy group, a halogen atom, a cyano group, or a nitro group; $R^5$ represents a hydrogen atom, a fluorine atom, a chlorine atom, a bromine atom, an iodine atom, a pentafluorosulfanyl group, a cyano group, a nitro group, an isocyano group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—; m3 and m4 represent 0, 1, 2, or 3; and, when m3 and/or m4 represents 2 or 3, the two or three $A^3$ groups, $A^5$ groups, $Z^3$ groups, and/or $Z^4$ groups may be each identical to or different from one another). It is particularly preferable that $P^1$, $P^2$, and $P^3$ be acrylic groups or methacrylic groups. Specifically, the compound represented by General Formula (II-1) is preferably a compound represented by General Formula (II-1A),

[Chem. 62]

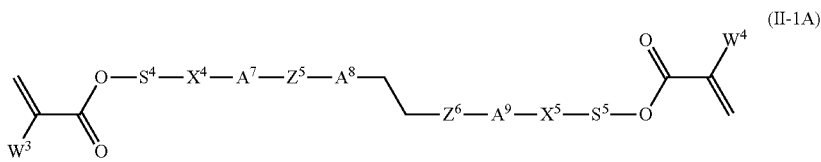
(II-1A)

(in General Formula (II-1A), $W^3$ and $W^4$ each independently represent hydrogen or a methyl group; $S^4$ and $S^5$ each independently represent an alkylene group having 2 to 18 carbon atoms; $X^4$ and $X^5$ each independently represent —O—, —COO—, —OCO—, or a single bond; $Z^5$ and $Z^6$ each independently represent —COO— or —OCO—; and $A^7$, $A^8$, and $A^9$ each independently represent a 1,4-phenylene group that may optionally be substituted with a fluorine atom, a chlorine atom, a linear or branched alkyl group having 1 to 4 carbon atoms, or a linear or branched alkoxy group having 1 to 4 carbon atoms). The compound represented by General Formula (II-1) is particularly preferably selected from compounds represented by Formulae (II-1A-1) to (II-1A-4) below,

[Chem. 63]

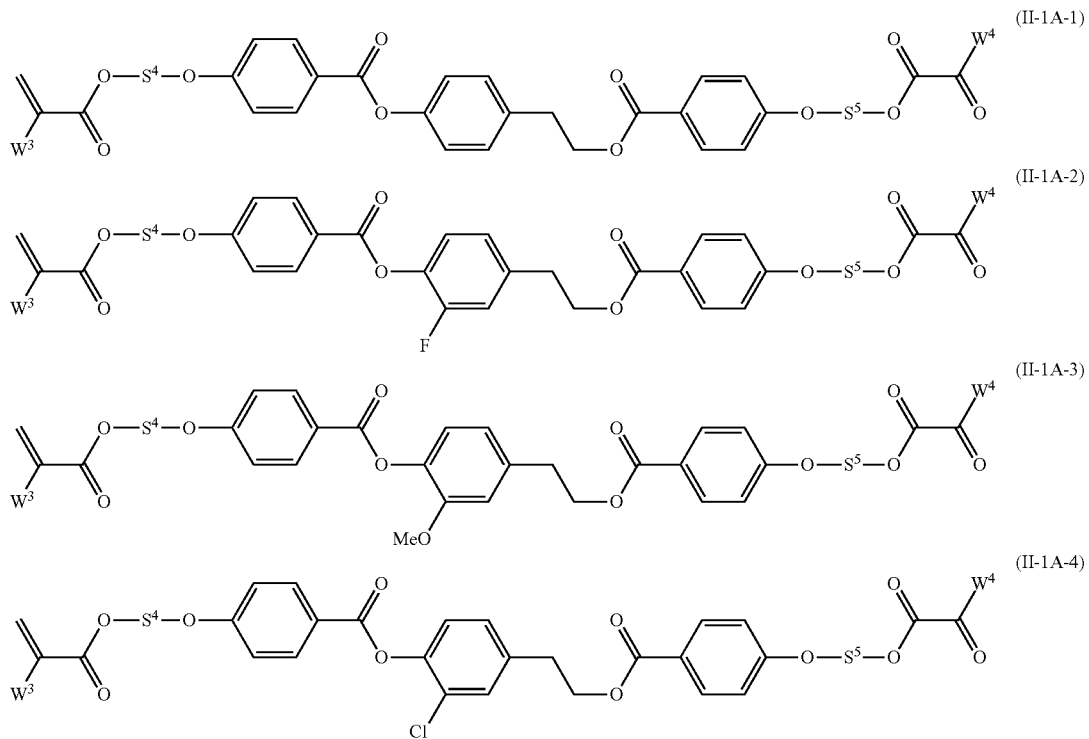

(in Formulae (II-1A-1) to (II-1A-4), $W^3$ and $W^4$ each independently represent hydrogen or a methyl group; $S^4$ represents the same thing as $S^4$ of General Formula (II-1A); and $S^5$ represents the same thing as $S^5$ of General Formula (II-1A)). Compounds represented by Formulae (II-1A-1) to (II-1A-4) in which $S^4$ and $S^5$ each independently represent an alkylene group having 2 to 8 carbon atoms are particularly preferable.

Other preferable examples of a difunctional polymerizable compound include the compounds represented by General Formulae (II-1B-1) to (II-1B-3) below,

[Chem. 64]

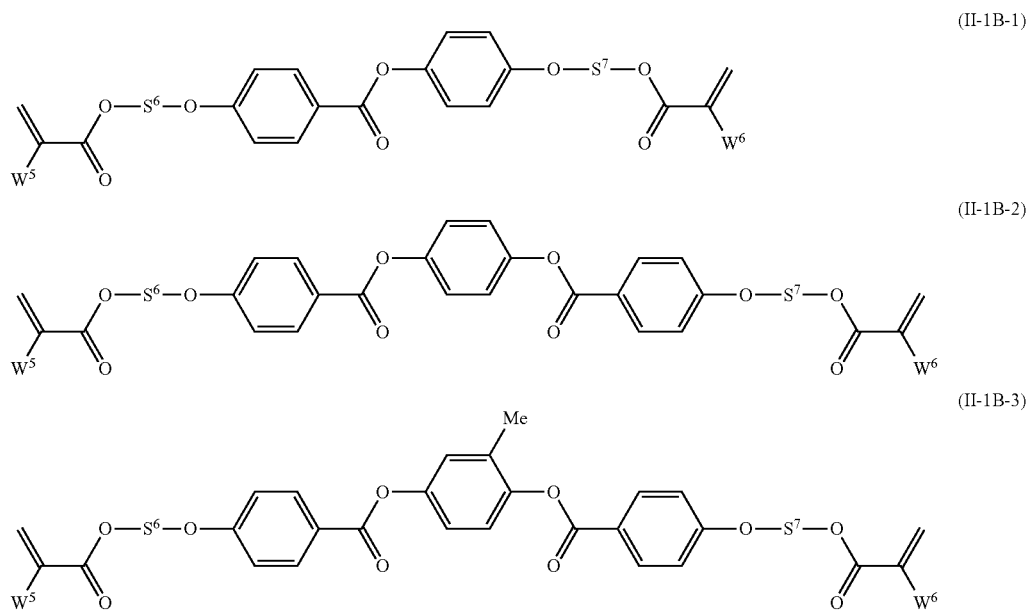

(in General Formulae (II-1B-1) to (II-1B-3), $W^5$ and $W^6$ each independently represent hydrogen or a methyl group; and $S^6$ and $S^7$ each independently represent an alkylene group having 2 to 18 carbon atoms). Compounds represented by Formulae (II-1B-1) to (II-1B-3) in which $S^6$ and $S^7$ each independently represent an alkylene group having 2 to 8 carbon atoms are particularly preferable.

Specific examples of the compound represented by General Formula (II-2) include compounds represented by General Formulae (II-2-1) to (II-2-7) below,

[Chem. 65]

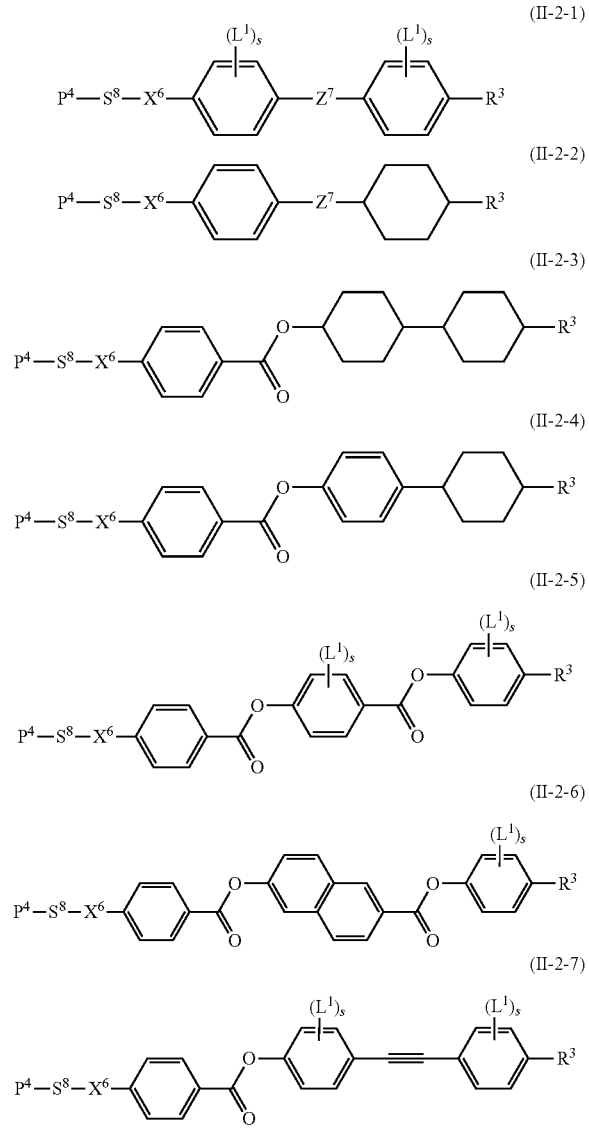

(in General Formulae (II-2-1) to (II-2-7), $P^4$ represents the same thing as P of General Formula (I); $S^8$ represents a single bond or an alkylene group having 1 to 20 carbon atoms in which one —$CH_2$— group or two or more —$CH_2$— groups that are not adjacent to one another may be each independently replaced with —O—, —COO—, —OCO—, or —O—CO—O—; $X^6$ represents a single bond, —O—, —COO—, or —OCO—; $Z^7$ represents a single bond, —COO—, or —OCO—; $L^1$ represents a fluorine atom, a chlorine atom, or a linear or branched alkyl group having 1 to 10 carbon atoms in which one —$CH_2$— group or two or more —$CH_2$— groups that are not adjacent to one another may be each independently replaced with —O—, —COO—, or —OCO—; s represents an integer of 0 to 4; $R^3$ represents a hydrogen atom, a fluorine atom, a chlorine atom, a cyano group, a nitro group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—).

The polymerizable liquid crystal composition including the compound according to the present invention may include a polymerizable compound that does not have liquid crystal properties in an amount such that the liquid crystal properties of the composition are not impaired significantly. Specifically, any compound known in the related art as a polymer-forming monomer or a polymer-forming oligomer may be used. Specific examples of such a compound include the compounds described in "Hikari Kouka Gijutsu Databook, Zairyou-hen ("Photo-curing Technology Databook, Material Section") (monomer, oligomer, photopolymerization initiator)" (supervised by Kunihiro Ichimura and Kiyomi Kato, edited by Technonet).

While the compound according to the present invention can be polymerized without using a photopolymerization initiator, a photopolymerization initiator may be used depending on the purpose. In such a case, the concentration of the photopolymerization initiator in the compound according to the present invention is preferably 0.1% to 15% by mass, is more preferably 0.2% to 10% by mass, and is further preferably 0.4% to 8% by mass. Examples of the photopolymerization initiator include benzoin ethers, benzophenones, acetophenones, benzyl ketals, and acylphosphine oxides. Specific examples of the photopolymerization initiator include 2-methyl-1-(4-methylthiophenyl)-2-morpholinopropan-1-one (IRGACURE 907) and benzoic acid [1-[4-(phenylthio)benzoyl]heptylidene]amino (IRGACURE OXE 01). Examples of thermal polymerization initiators include an azo compound and a peroxide. Specific examples of the thermal polymerization initiators include 2,2'-azobis (4-methoxy-2,4-dimethylvaleronitrile) and 2,2'-azobis (isobutyronitrile). The above polymerization initiators may be used alone or in combination of two or more.

The liquid crystal composition according to the present invention may optionally include a stabilizer in order to enhance preservation stability. Examples of the stabilizer include hydroquinones, hydroquinone monoalkyl ethers, tert-butylcatechols, pyrogallols, thiophenols, nitro compounds, β-naphthylamines, β-naphthols, and nitroso compounds. In the case where the stabilizer is used, the content of the stabilizer added to the composition is preferably 0.005% to 1% by mass, is more preferably 0.02% to 0.8% by mass, and is further preferably 0.03% to 0.5% by mass. The above stabilizers may be used alone or in combination of two or more. Specifieally, the stabilizer is preferably selected from the compounds represented by Formulae (III-1) to (III-35) below,

[Chem. 66]
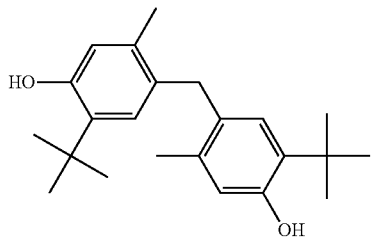
(III-1)
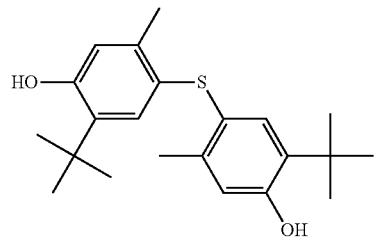
(III-2)
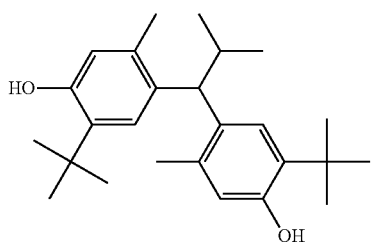
(III-3)
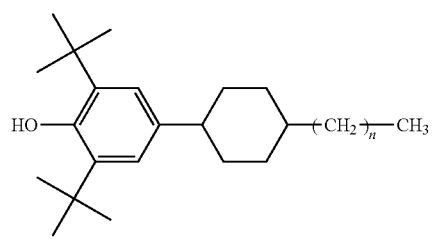
(III-4)
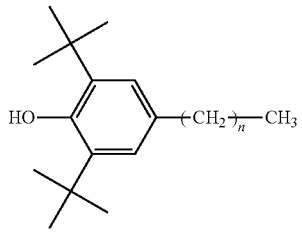
(III-5)
[Chem. 67]
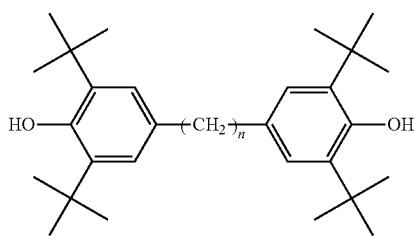
(III-6)
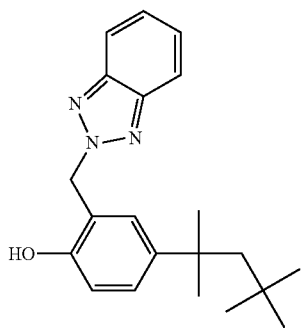
(III-8)
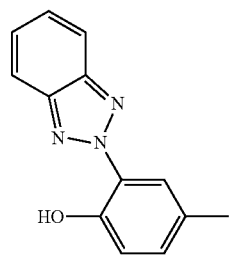
(III-7)
(III-9)

-continued
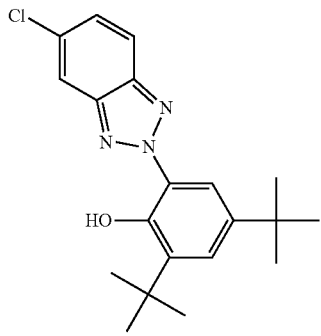
(III-10)
[Chem. 68]
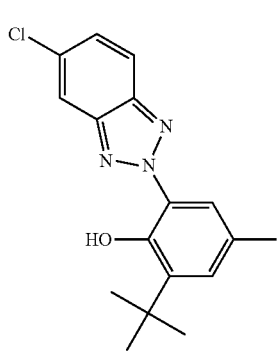
(III-11)
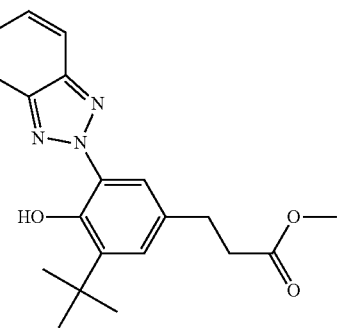
(III-12)
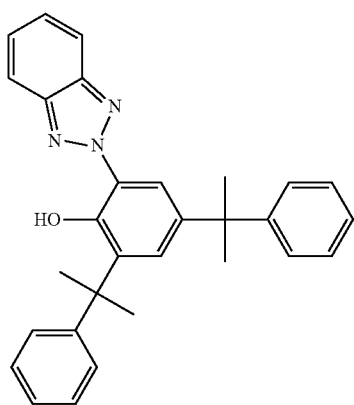
(III-13)
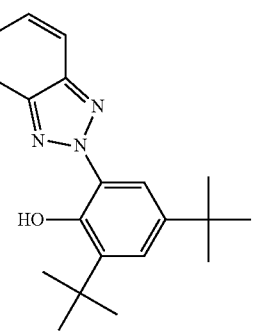
(III-14)
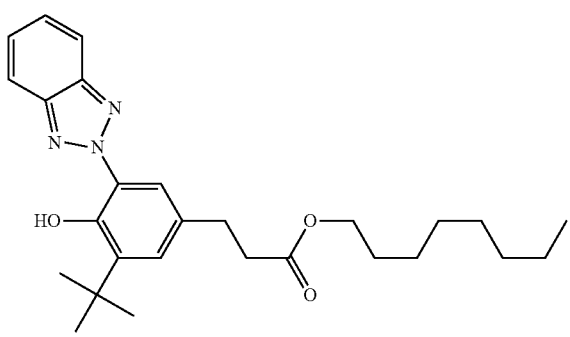
(III-15)

[Chem. 69]
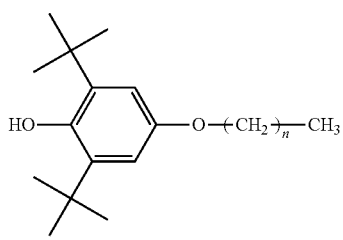 (III-16)
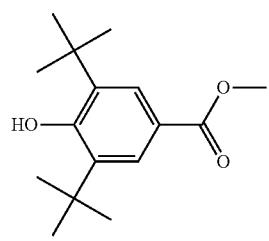 (III-17)
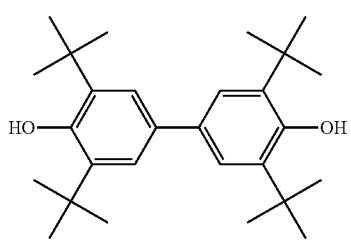 (III-18)
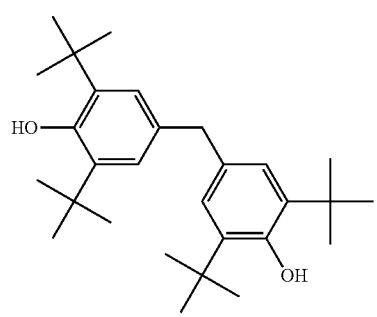 (III-19)
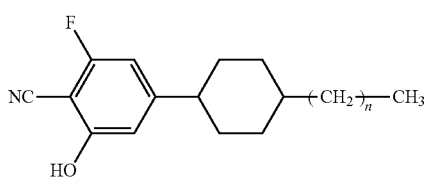 (III-20)
[Chem. 70]
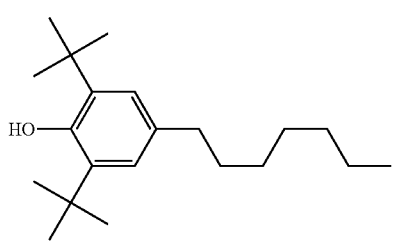 (III-21)
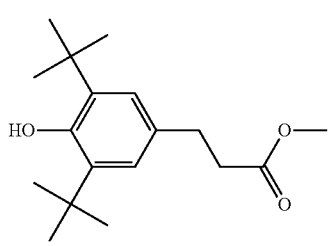 (III-22)
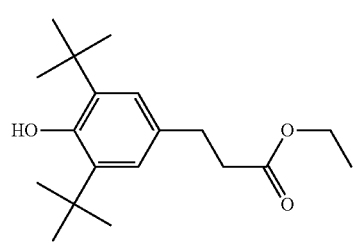 (III-23)
(III-24)

-continued
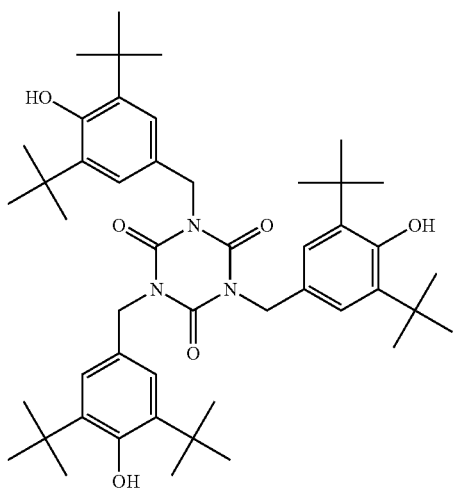
(III-25)
[Chem. 71]
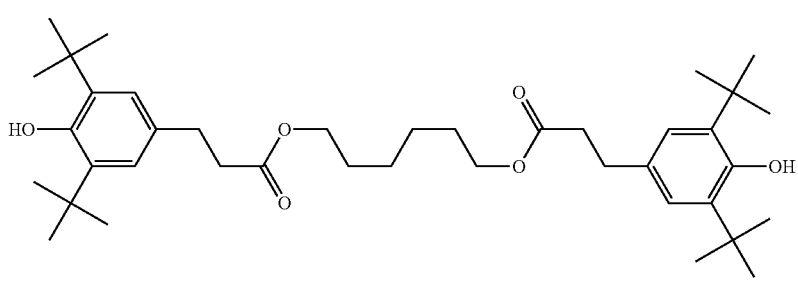
(III-26)
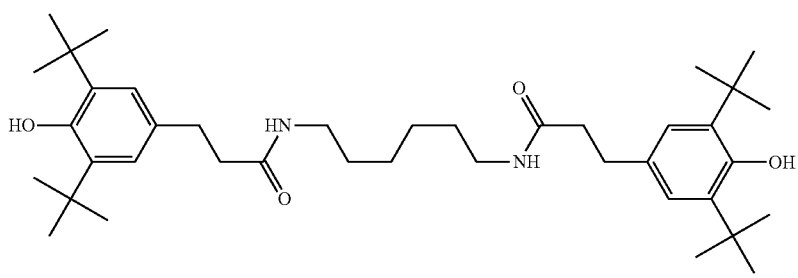
(III-27)
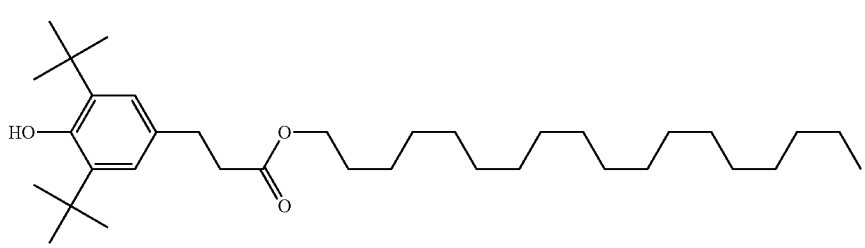
(III-28)
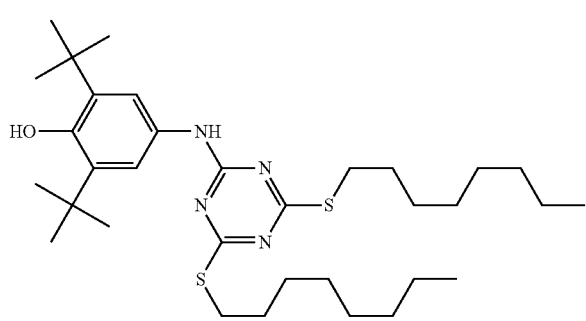
(III-29)

(III-30)
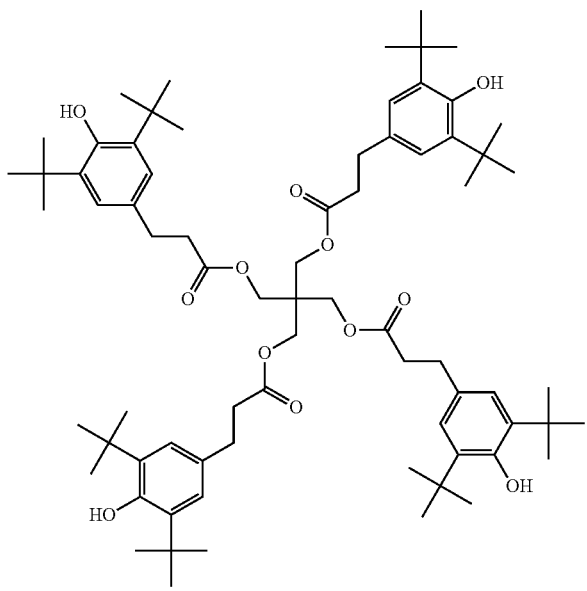
[Chem. 72]
(III-31)
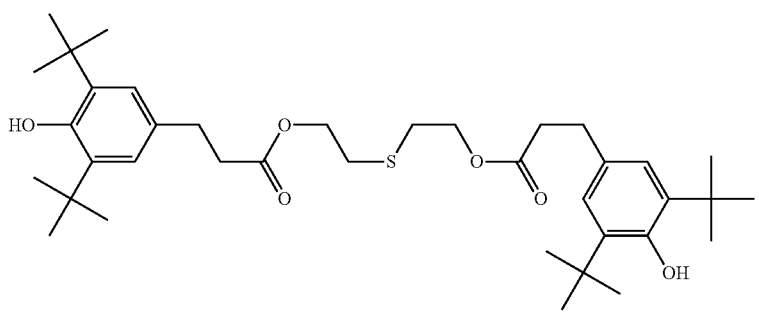
(III-32)
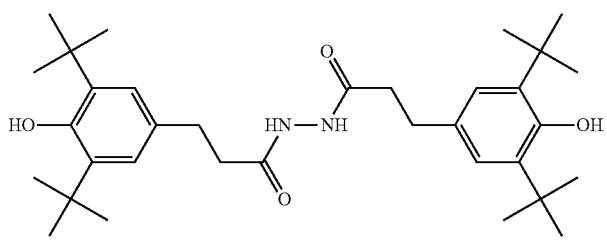
(III-33)
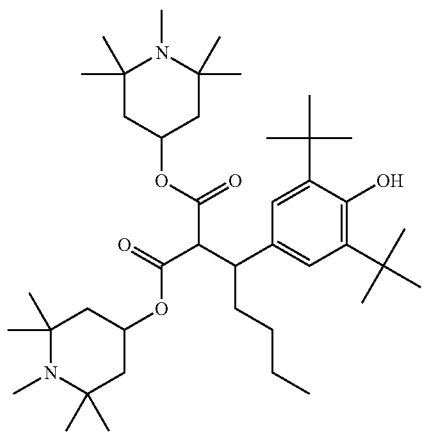

-continued

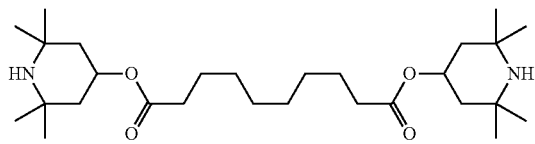
(III-34)

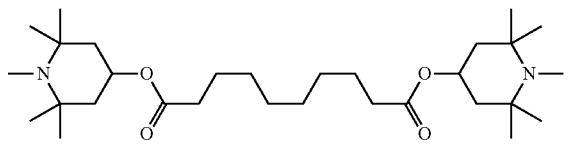
(III-35)

(in Formulae (III-1) to (III-35), n represents an integer of 0 to 20).

In the case where a polymerizable liquid crystal composition including the compound according to the present invention is used for producing films, optical devices, functional pigments, drugs, cosmetics, coating agents, synthetic resins, and the like, the polymerizable liquid crystal composition may include a metal, a metal complex, a dye, a pigment, a colorant, a fluorescent material, a phosphorescent material, a surfactant, a leveling agent, a thixotropic agent, a gelatinizing agent, a polysaccharide, an ultraviolet absorber, an infrared absorber, an anti-oxidizing agent, an ion-exchange resin, a metal oxide such as titanium oxide, and the like depending on the purpose.

A polymer produced by polymerizing a polymerizable liquid crystal composition including the compound according to the present invention may be used in various applications. For example, a polymer produced by polymerizing a polymerizable liquid crystal composition including the compound according to the present invention that has not been aligned may be used for producing a light-scattering plate, a depolarization plate, or a moiré fringe-prevention plate. On the other hand, a polymer produced by polymerizing a polymerizable liquid crystal composition that has been aligned advantageously has an optical anisotropy. Such an optically anisotropic body can be produced by, for example, depositing a polymerizable liquid crystal composition including the compound according to the present invention on a substrate rubbed with a cloth or the like, a substrate provided with an organic thin film formed thereon, or a substrate provided with an alignment film formed thereon by the oblique deposition of SiO$_2$ or interposing the polymerizable liquid crystal composition between substrates and polymerizing the polymerizable liquid crystal composition.

Examples of a method for depositing the polymerizable liquid crystal composition on a substrate include spin coating, die coating, extrusion coating, roll coating, wire bar coating, gravure coating, spray coating, dipping, and printing. When coating is employed, an organic solvent may be added to the polymerizable liquid crystal composition. Examples of the organic solvent include a hydrocarbon solvent, a halogenated hydrocarbon solvent, an ether solvent, an alcohol solvent, a ketone solvent, an ester solvent, and aprotic solvent. Examples of the hydrocarbon solvent include toluene and hexane. Examples of the halogenated hydrocarbon solvent include methylene chloride. Examples of the ether solvent include tetrahydrofuran, acetoxy-2-ethoxyethane, and propylene glycol monomethyl ether acetate. Examples of the alcohol solvent include methanol, ethanol, and isopropanol. Examples of the ketone solvent include acetone, methyl ethyl ketone, cyclohexanone, γ-butyrolactone, and N-methylpyrrolidones. Examples of the ester solvent include ethyl acetate and cellosolve. Examples of the aprotic solvent include dimethylformamide and acetonitrile. The above solvents may be used alone or in combination and selected appropriately with consideration of vapor pressure and solubility in the polymerizable liquid crystal composition. The organic solvent added to the polymerizable liquid crystal composition can be volatilized by air drying, heat drying, vacuum drying, or vacuum heat drying. It is possible to effectively increase ease of applying the polymerizable liquid crystal material to a substrate by forming an intermediate layer, such as a polyimide thin-film, on the substrate or by adding a leveling agent to the polymerizable liquid crystal material. Forming an intermediate layer, such as a polyimide thin-film, on a substrate effectively enhances the adhesion of a polymer produced by polymerizing the polymerizable liquid crystal material to the substrate.

Examples of an alignment treatment which are other than those described above include an alignment treatment in which the flow orientation of the liquid crystal material is used and an alignment treatment in which an electric field or a magnetic field is used. The above alignment methods may be used alone or in combination. A photo alignment method may also be used as an alignment method instead of rubbing. The shape of the substrate is not limited to planar; the substrate may include a portion having a curved surface. The substrate may be composed of an organic material or an inorganic material. Examples of the organic materials that can be used as a material for the substrate include polyethylene terephthalate, polycarbonate, polyimide, polyamide, polymethyl methacrylate, polystyrene, polyvinyl chloride, polytetrafluoroethylene, polychlorotrifluoroethylene, polyarylate, polysulfone, triacetylcellulose, cellulose, and polyether ether ketone. Examples of the inorganic materials that can be used as a material for the substrate include silicon, glass, and calcite.

The polymerization of a polymerizable liquid crystal composition including the compound according to the present invention is preferably performed by irradiating the polymerizable liquid crystal composition with an active energy ray, such as ultraviolet radiation or an electron beam, in order to perform polymerization in a short time. In the case where ultraviolet radiation is used, either of a polarized light source and an unpolarized light source may be used. In the case where the polymerization of the liquid crystal composition is performed while the liquid crystal composition is interposed between two substrates, at least one of the substrates which is irradiated with the active energy ray needs to be adequately permeable to the active energy ray. After a specific portion of the liquid crystal composition has been polymerized by using a mask when the liquid crystal composition is irradiated with the light, the conditions such as an electric field, a magnetic field, or a temperature may be changed in order to change the orientation of the other portion of the liquid crystal composition that has not yet been polymerized. In such a case, the other portion of the liquid crystal composition is subsequently polymerized by being irradiated with the active energy ray. The temperature at which the liquid crystal composition is irradiated with the active energy ray is preferably within the temperature range in which the polymerizable liquid crystal composition according to the present invention is present in a liquid crystal state. In particular, in the case where an optically anisotropic body is produced using photopolymerization, polymerization is preferably performed at a temperature closer to room temperature, that, is, typically, 25° C., in order not to induce unintended thermal polymerization. The intensity of the active energy ray is preferably 0.1 mW/cm$^2$ to 2 W/cm$^2$. If the intensity of the active energy ray is 0.1 mW/cm$^2$ or less, a large amount, of time may be required for the completion of photopolymerization, which degrades productivity. If the intensity of the active energy ray is 2 W/cm$^2$ or more, the polymerizable liquid crystal compound or the polymerizable liquid crystal composition may be degraded.

The optically anisotropic body produced by polymerizing the composition may be subjected to a heat treatment in order to reduce initial changes in the properties of the optically anisotropic body and increase the consistency in the properties of the optically anisotropic body. The temperature at which the heat treatment is performed is preferably 50° C. to 250° C. The amount of time during which the heat treatment is performed is preferably 30 seconds to 12 hours.

The optically anisotropic body produced by the above-described method may be used alone after being removed from the substrate. Alternatively, the optically anisotropic body may also be used without being removed from the substrate. A multilayer structure constituted by the optically anisotropic bodies may also be used. The optically anisotropic body may be bonded to another substrate.

EXAMPLES

The present invention is further described with reference to Examples below. The present invention is not limited by Example. When referring to a composition in Examples and Comparative Examples, "%" means "% by mass".

Example 1

Production of Compound Represented by Formula (I-1)

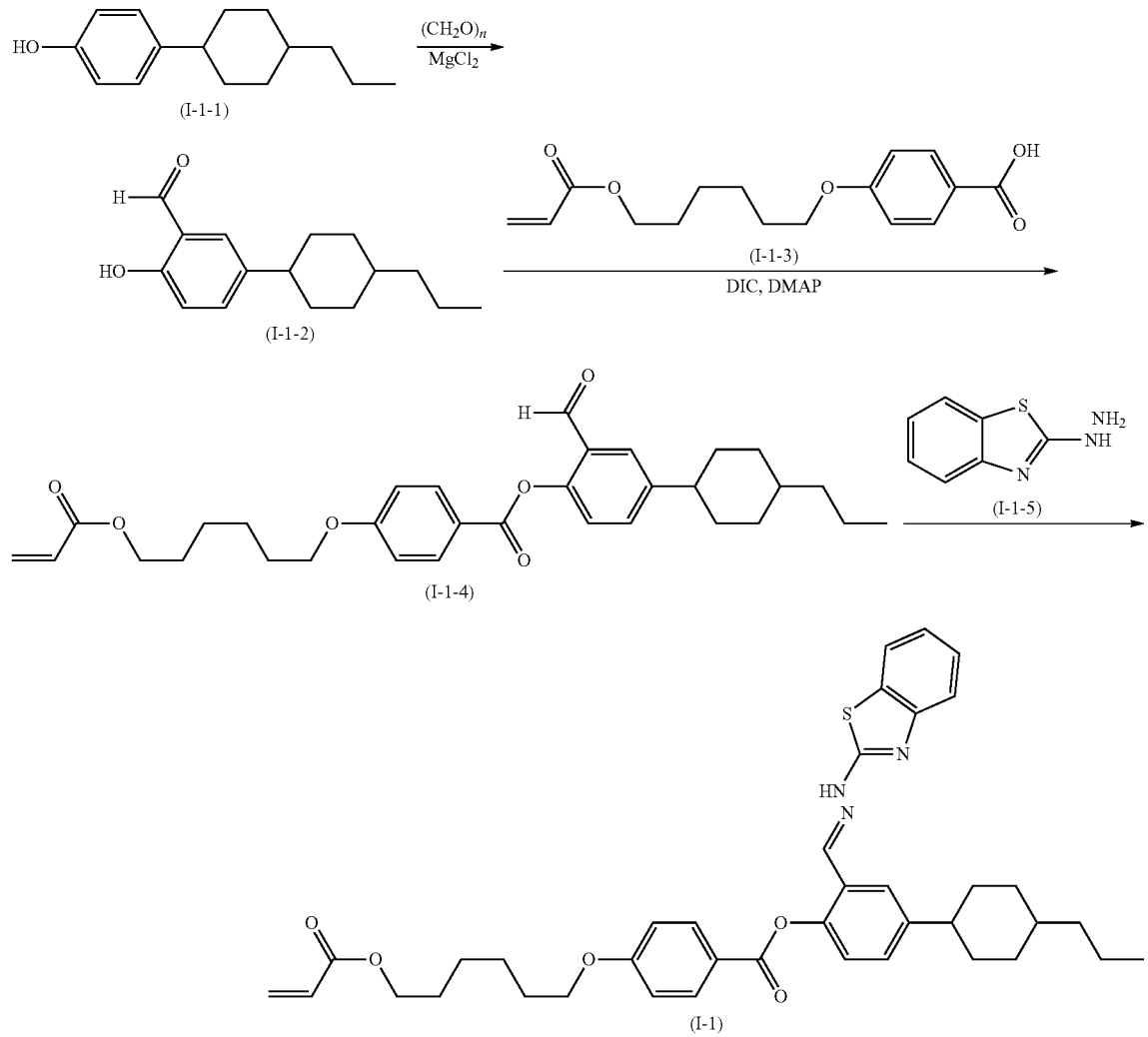

To a reaction container, 5,00 g of the compound represented by Formula (I-1-1), 3.27 g of magnesium chloride, 2.06 g of para-formaldehyde, 20 mL of triethylamine, and 80 mL of acetonitrile were added. While stirring was performed at 60° C., an adequate amount of para-formaldehyde was further added to the reaction container. After dilution had been performed with ethyl acetate, cleaning was performed with hydrochloric acid and a saline solution. Then, purification was performed by column chromatography. Hereby, 5.36 g of the compound represented by Formula (I-1-2) was prepared.

To a reaction container, 2.00 g of the compound represented by Formula (I-1-2), 2.37 g of the compound represented by Formula (I-1-3), 0.05 g of N,N-dimethylaminopyridine, and 30 mL of dichloromethane were added. To the reaction container, 1.23 g of diisopropylcarbodiimide was added dropwise. The resulting mixture was stirred at room temperature. After the resulting precipitate was removed by filtration, the filtrate was purified by column chromatography and recrystallization. Hereby, 3.17 g of the compound represented by Formula (I-1-4) was prepared.

To a reaction container, 2.00 g of the compound represented by Formula (I-1-4), 0.63 g of the compound represented by Formula (I-1-5), 0.05 g of (±)-10-camphorsulfonic acid, 10 mL of tetrahydrofuran, and 10 mL of ethanol were added. After stirring had been performed, the solvent was removed by distillation. Then, dispersion cleaning was performed using methanol. Subsequently, purification was performed by column chromatography and recrystallization. Hereby, 1.80 g of the compound represented by Formula (I-1) was prepared.

Transition temperature (temperature rise: 5° C./min): C 105 N 150 I $^1$H NMR (CDCl$_3$) δ 0.93 (t, 3H), 1.10 (q, 2H), 1.25 (m, 2H), 1.37 (m, 3H), 1.46-1.59 (m, 6H), 1.74 (quin, 2H), 1.81-1.98 (m, 6H), 2.56 (m, 1H), 4.03 (t, 2H), 4.19 (t, 2H), 5.83 (dd, 1H), 6.13 (dd, 1H), 6.41 (dd, 1H), 6.87 (d, 2H), 7.08 (t, 1H), 7.12 (d, 1H), 7.20 (t, 1H), 7.28 (dd, 1H), 7.45 (dd, 1H), 7.58 (d, 1H), 7.84 (s, 1H), 8.06 (m, 3H) ppm.

MS (m/z): 668 [M$^+$+1]

Example 2

Production of Compound Represented by Formula (I-2)

[Chem. 74]

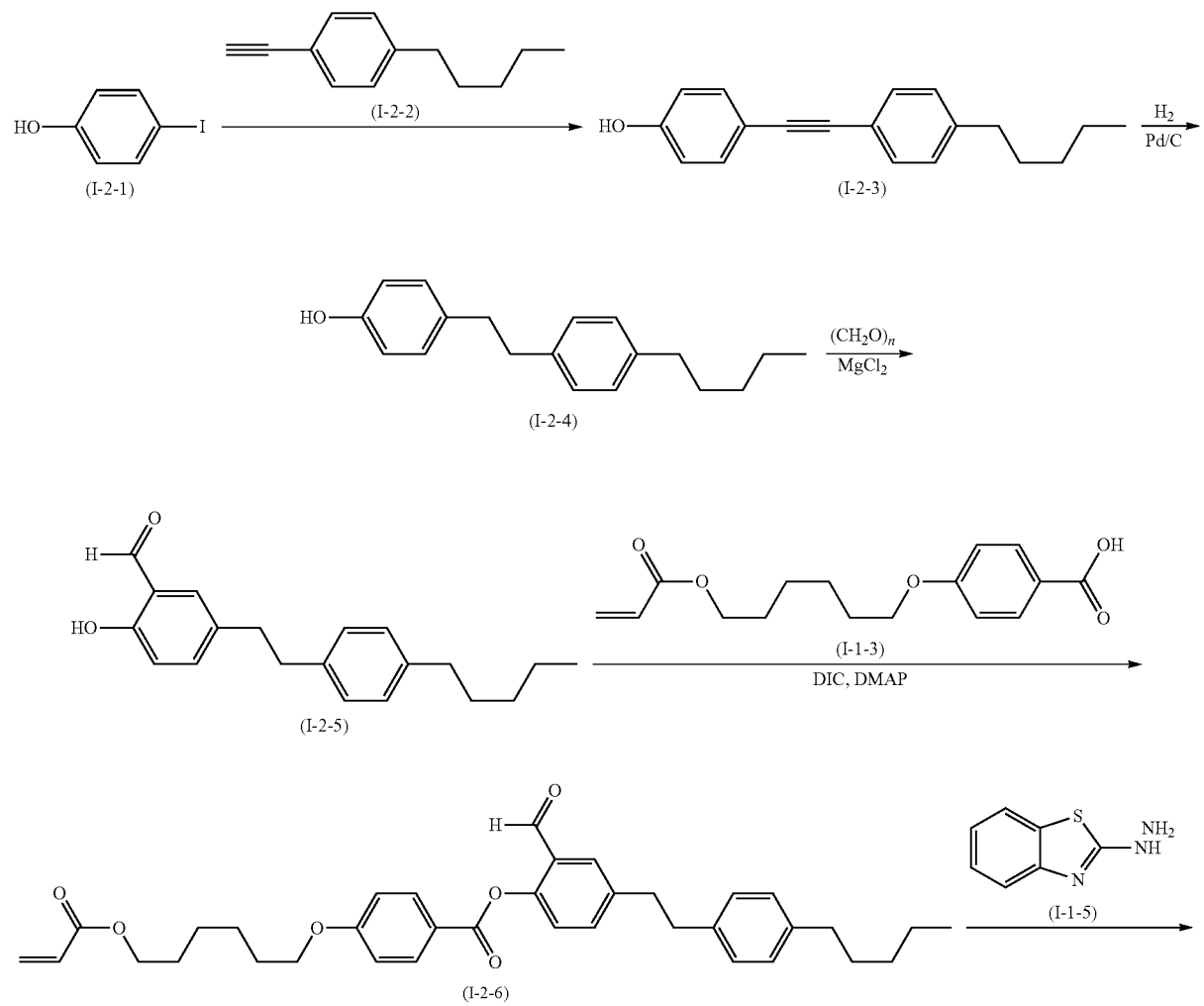

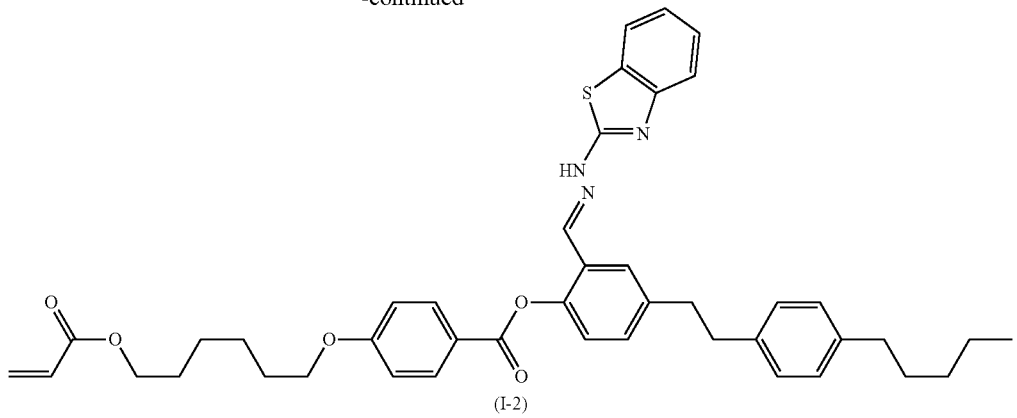

(I-2)

To a reaction container, 10.00 g of the compound represented by Formula (I-2-1), 15.66 g of the compound represented by Formula (I-2-2), 0.17 g of copper iodide(I), 30 mL of triethylamine, and 90 mL of N,N-dimethylformamide were added. After nitrogen purge had been performed, 0.53 g of tetrakis(triphenylphosphine)palladium(0) was added to the reaction container. The resulting mixture was stirred while being heated. After dilution had been performed with ethyl acetate, cleaning was performed using hydrochloric acid and a saline solution. Then, purification was performed by column chromatography and recrystallization. Hereby, 7.21 g of the compound represented by Formula (I-2-3) was prepared.

To an autoclave, 7.21 g of the compound represented by Formula (I-2-3), 1.40 g of palladium 5% on carbon, 30 mL of tetrahydrofuran, and 30 mL of ethanol were added. The resulting mixture was stirred with a hydrogen pressure of 0.5 MPa. After palladium on carbon had been removed by filtration and the filtrate had been concentrated, purification was performed by column chromatography and recrystallization. Hereby, 6.95 g of the compound represented by Formula (I-2-4) was prepared.

The compound represented by Formula (I-2) was prepared from the compound represented by Formula (I-2-4) as in Example 1.

Transition temperature (temperature rise: 5° C./min): C 62 N 95 poly $^1$H NMR (CDCl$_3$) δ 0.89 (t, 3H), 1.33 (m, 4H), 1.43-1.57 (m, 2H), 1.61 (quin, 2H), 1.73 (quin, 2H), 1.85 (quin, 2H), 2.59 (t, 2H), 2.97 (m, 4H), 4.03 (t, 2H), 4.19 (m, 2H), 5.83 (dd, 1H), 6.13 (dd, 1H), 6.41 (dd, 1H), 6.87 (d, 2H), 7.04-7.29 (m, 8H), 7.44 (d, 1H), 7.58 (d, 1H), 7.85 (s, 1H), 8.05 (m, 3H) ppm.

MS (m/z): 718 [M$^+$+1]

Example 3

Production of Compound Represented by Formula (I-3)

[Chem. 75]

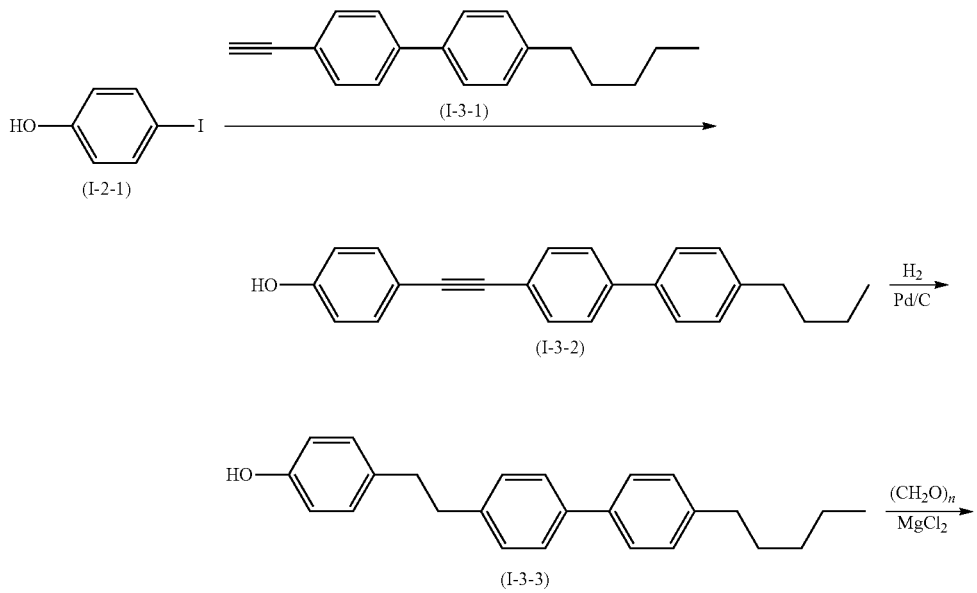

-continued
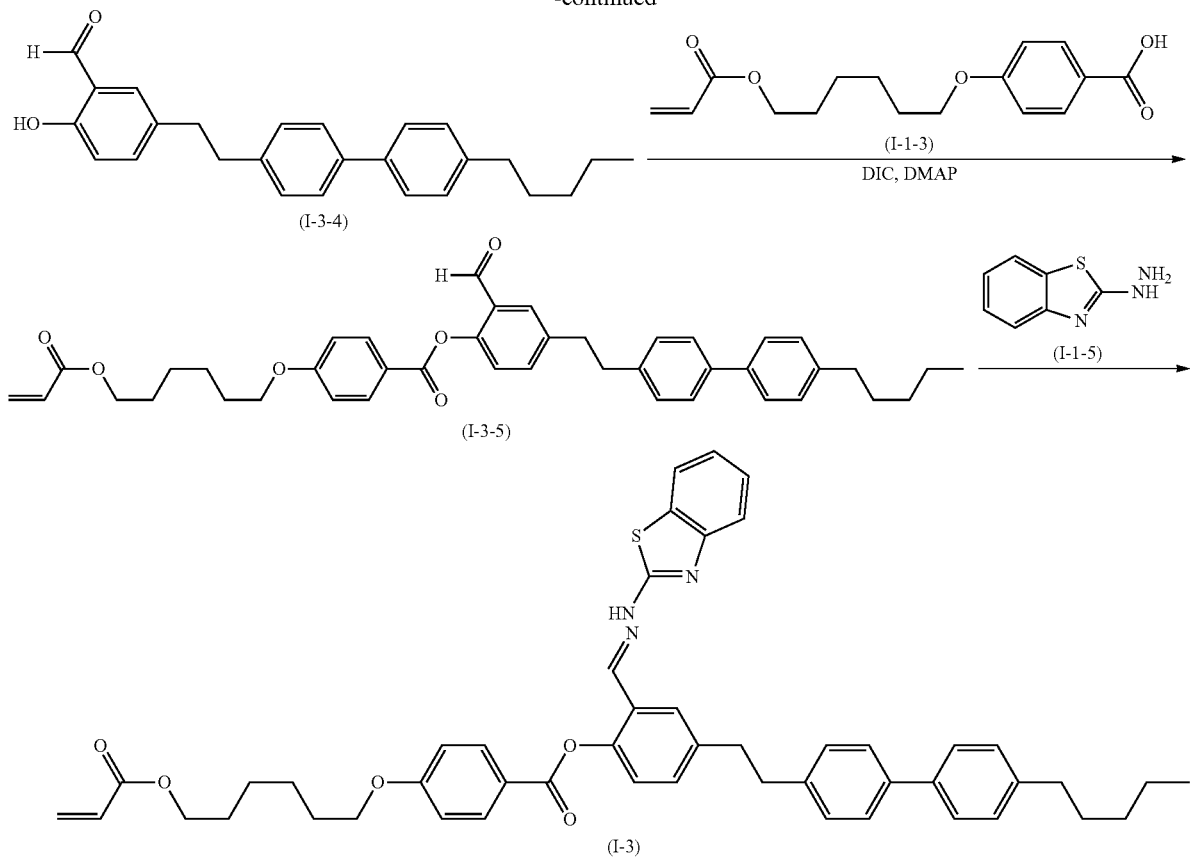
The compound represented by Formula (I-3) was prepared as in Example 2.
MS (m/z): 794 [M$^+$+1]
Example 4
Production of Compound Represented by Formula (I-4)
[Chem. 76]
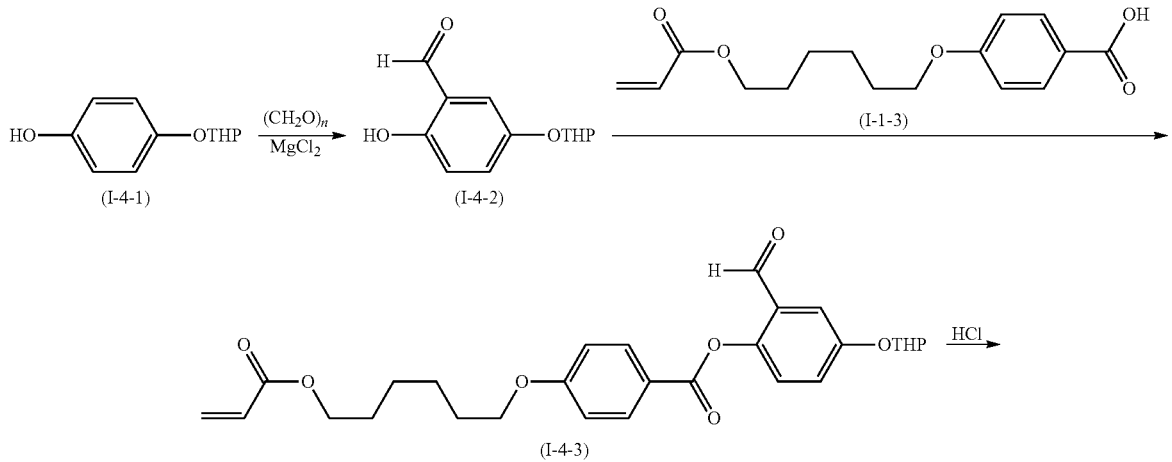

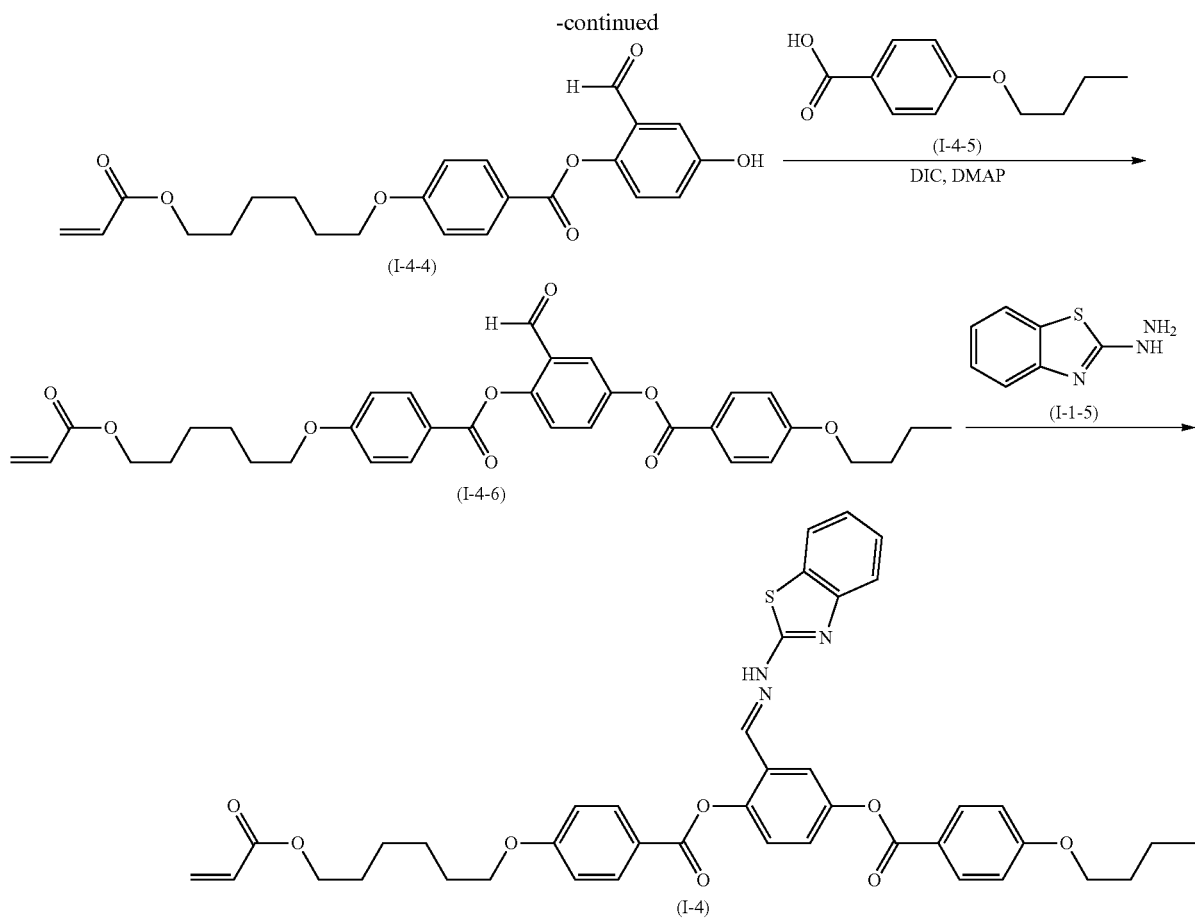

The compound represented by Formula (I-4-3) was prepared as in Example 1.

To a reaction container, 2.00 g of the compound represented by Formula (I-4-3), 10 mL of tetrahydrofuran, 10 mL of methanol, and 1 mL of concentrated hydrochloric acid were added. After the resulting mixture had been stirred, dilution was performed with ethyl acetate. Subsequently, cleaning was performed with a saline solution. Then, purification was performed by column chromatography. Hereby, 1.50 g of the compound represented by Formula (I-4-4) was prepared.

To a reaction container, 1.50 g of the compound represented by Formula (I-4-4), 0.70 g of the compound represented by Formula (I-4-5), 0.02 g of N,N-dimethylaminopyridine, and 20 mL of dichloromethane were added. To the reaction container, 0.69 g of diisopropylcarbodiimide was added dropwise. The resulting mixture was stirred. After the precipitate had been removed by filtration and the filtrate had been concentrated, purification was performed by column chromatography and recrystallization. Hereby, 1.49 g of the compound represented by Formula (I-4-6) was prepared.

The compound represented by Formula (I-4) was prepared as in Example 1.

Transition temperature (temperature rise: 5° C./min): C 156 N 173 I $^1$H NMR (CDCl$_3$) δ 1.02 (t, 3H), 1.40-1.92 (m, 12H), 4.00 (br, 2H), 4.09 (t, 2H), 4.18 (t, 2H), 5.82 (dd, 1H), 6.13 (dd, 1H), 6.41 (dd, 1H), 6.64-6.13 (m, 14H), 8.19 (d, 2H) ppm.

MS (m/z): 736 [M$^+$+1]

Example 5

Production of Compound Represented by Formula (I-5)

[Chem. 77]

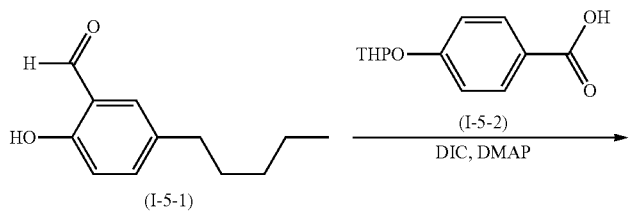

-continued

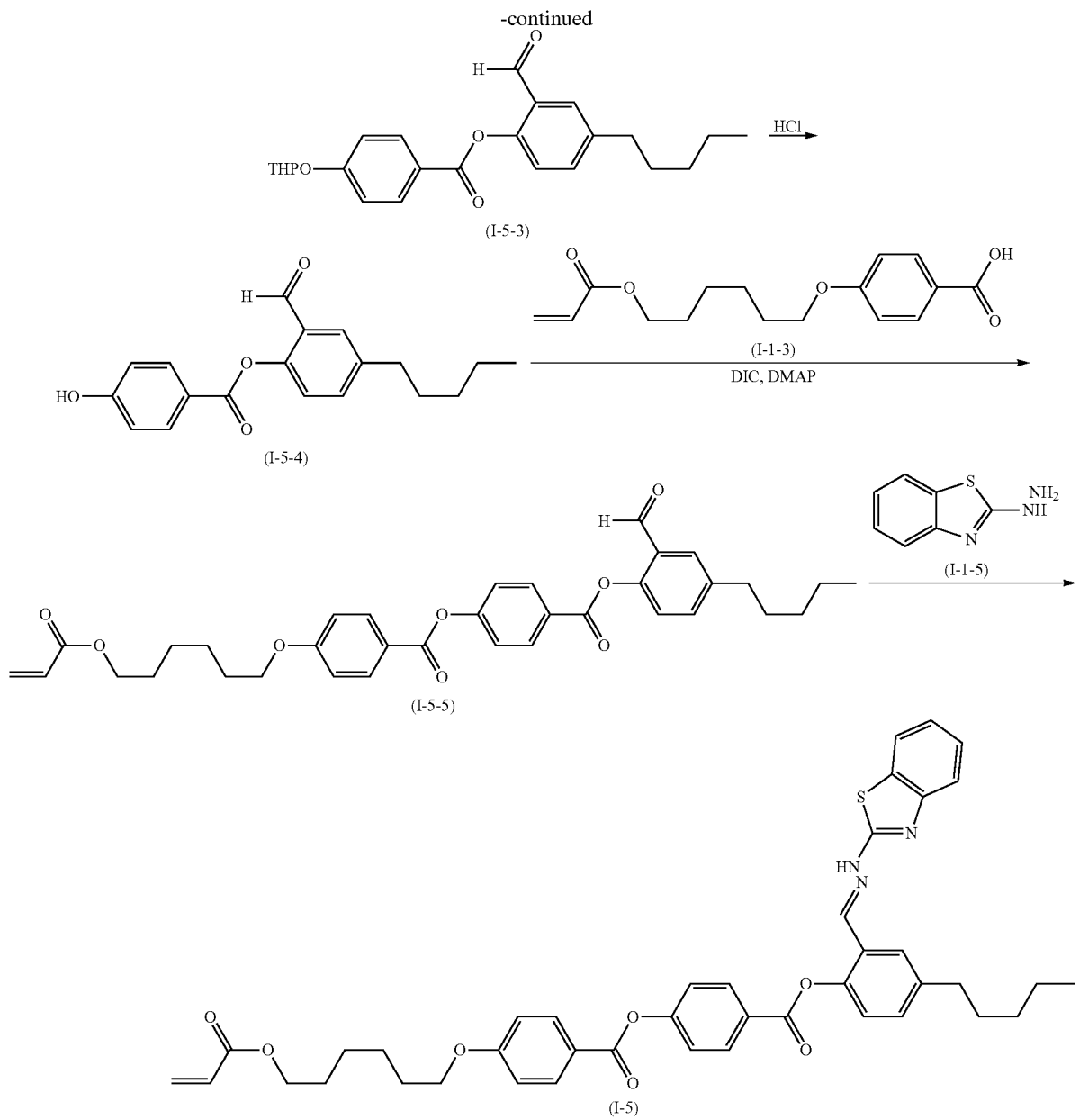

To a reaction container, 2.00 g of the compound represented by Formula (I-5-1), 2.31 g of the compound represented by Formula (I-5-2), 0.06 g of N,N-dimethylaminopyridine, and 20 mL of dichloromethane were added. To the reaction container, 1.97 g of diisopropylcarbodiimide was added dropwise. The resulting mixture was stirred. After the precipitate had been removed by filtration and the filtrate had been concentrated, purification was performed by column chromatography. Hereby, 2.89 g of the compound represented by Formula (I-5-3) was prepared.

To a reaction container, 2.89 g of the compound represented by Formula (I-5-3), 10 mL of tetrahydrofuran, 10 mL of methanol, and 1 mL of concentrated hydrochloric acid were added. After the resulting mixture had been stirred, dilution was performed with ethyl acetate. Then, cleaning was performed with a saline solution. Subsequently, purification was performed by column chromatography. Hereby, 2.16 g of the compound represented by Formula (I-5-4) was prepared.

The compound represented by Formula (I-5) was prepared as in Example 1.

Transition temperature (temperature rise: 5° C./min): C 147 N 153 I $^1$H NMR (CDCl$_3$) δ 0.93 (t, 3H), 1.37 (m, 4H), 1.46-1.59 (m, 4H), 1.63-1.78 (m, 4H), 1.86 (quin, 2H), 2.68 (t, 2H), 4.07 (t, 2H), 4.19 (t, 2H), 5.84 (dd, 1H), 6.14 (dd, 1H), 6.42 (dd, 1H), 7.00 (d, 2H), 7.09 (t, 1H), 7.12 (d, 1H), 7.19 (t, 1H), 7.23-7.33 (m, 3H), 7.45 (d, 1H), 7.61 (d, 1H), 7.80 (d, 1H), 8.07 (s, 1H), 8.14-8.23 (m, 4H) ppm.

MS (m/z): 734 [M++1]

Example 6

Production of Compound Represented by Formula (I-6)

[Chem. 78]

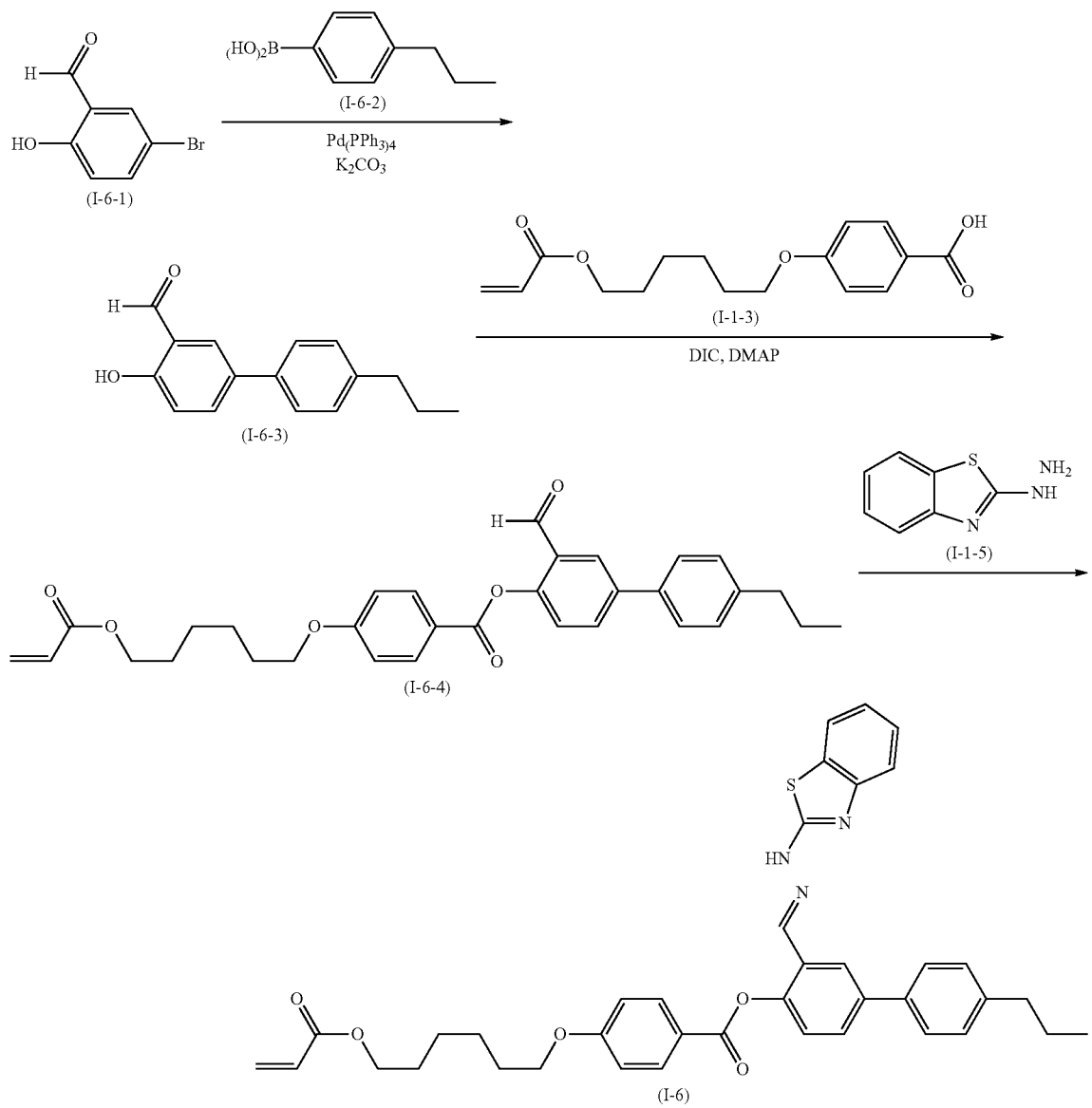

To a reaction container, 5.00 g of the compound represented by (I-6-1), 4.08 g of the compound represented by Formula (I-6-2), 5.16 g of potassium carbonate, 20 mL of ethanol, and 20 mL of water were added. After nitrogen purge had been performed, 0.29 g of tetrakis(triphenylphosphine)palladium(0) was added to the reaction container. The resulting mixture was stirred while being heated. After dilution with ethyl acetate and cleaning with hydrochloric acid and a saline solution had been performed, purification was performed by column chromatography. Hereby, 4.78 g of the compound represented by Formula (I-6-3) was prepared.

The compound represented by Formula (I-6) was prepared as in Example 1.

Transition temperature (temperature rise: 5° C./min): C 79 N 137 I $^1$H NMR (CDCl$_3$) δ 1.01 (t, 3H), 1.48 (m, 4H), 1.69-1.79 (m, 6H), 2.67 (t, 2H), 3.95 (m, 2H), 4.18 (t, 2H), 5.83 (dd, 1H), 6.13 (dd, 1H), 6.41 (dd, 1H), 6.83 (m, 2H), 7.03-7.68 (m, 10H), 7.97-8.30 (m, 4H) ppm.

MS (m/z): 662 [M$^+$+1]
Example 7
Production of Compound Represented by Formula (I-7)
[Chem. 79]
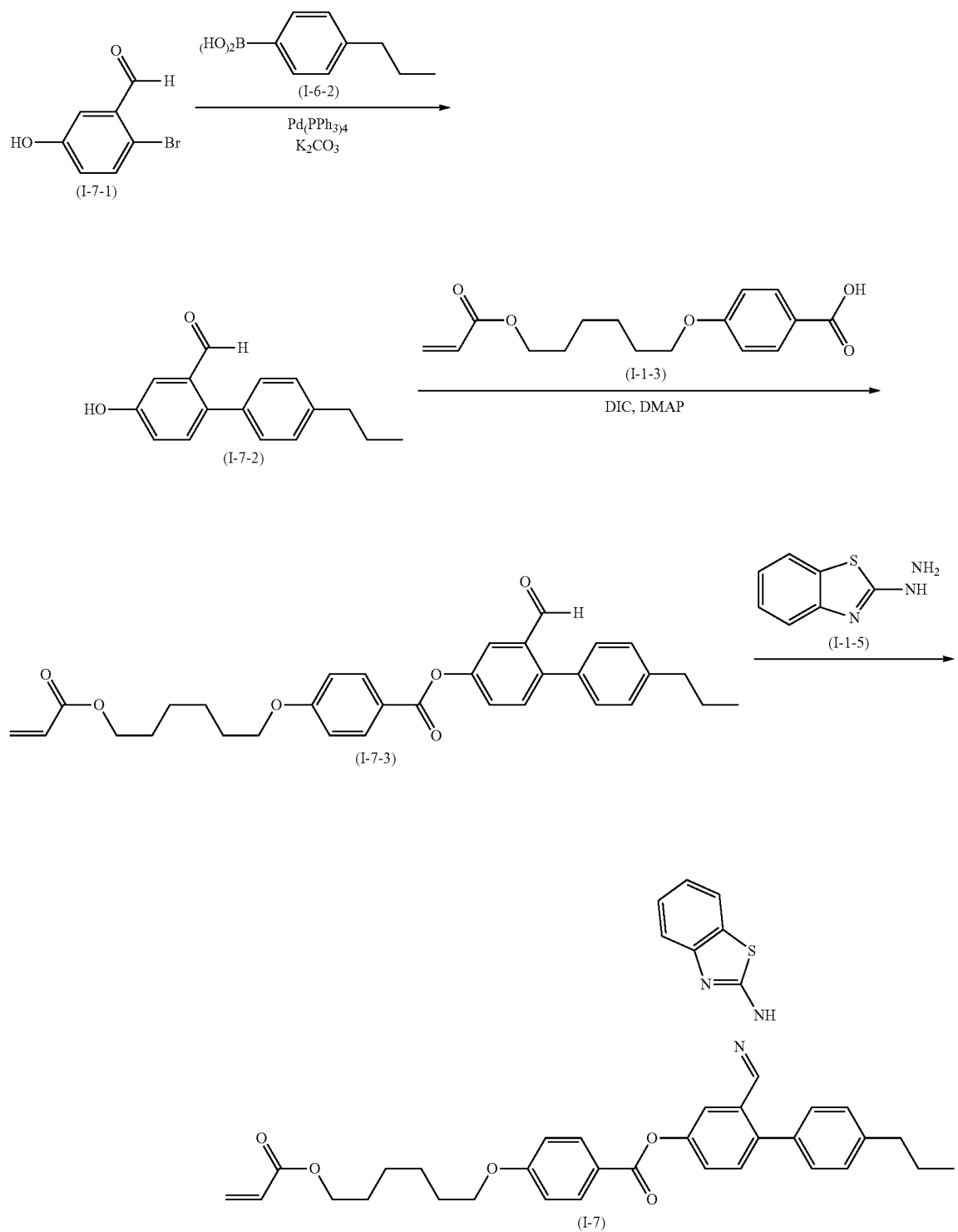

The compound represented by Formula (I-7) was prepared as in Example 6.
Transition temperature (temperature rise: 5° C./min): C 79 N 112 I
$^1$H NMR (CDCl$_3$) δ 0.96 (t, 3H), 1.43-1.78 (m, 8H), 1.87 (quin, 2H), 2.60 (t, 2H), 4.08 (t, 2H), 4.20 (t, 2H), 5.83 (dd, 1H), 6.13 (dd, 1H), 6.42 (dd, 1H), 7.01 (d, 2H), 7.09 (t, 1H), 7.17-7.29 (m, 7H), 7.37 (d, 1H), 7.60 (d, 1H), 7.91 (s, 2H), 8.21 (d, 2H) ppm.
MS (m/z): 662 [M$^+$+1]
Example 8
Production of Compound Represented by Formula (I-8)
[Chem. 80]
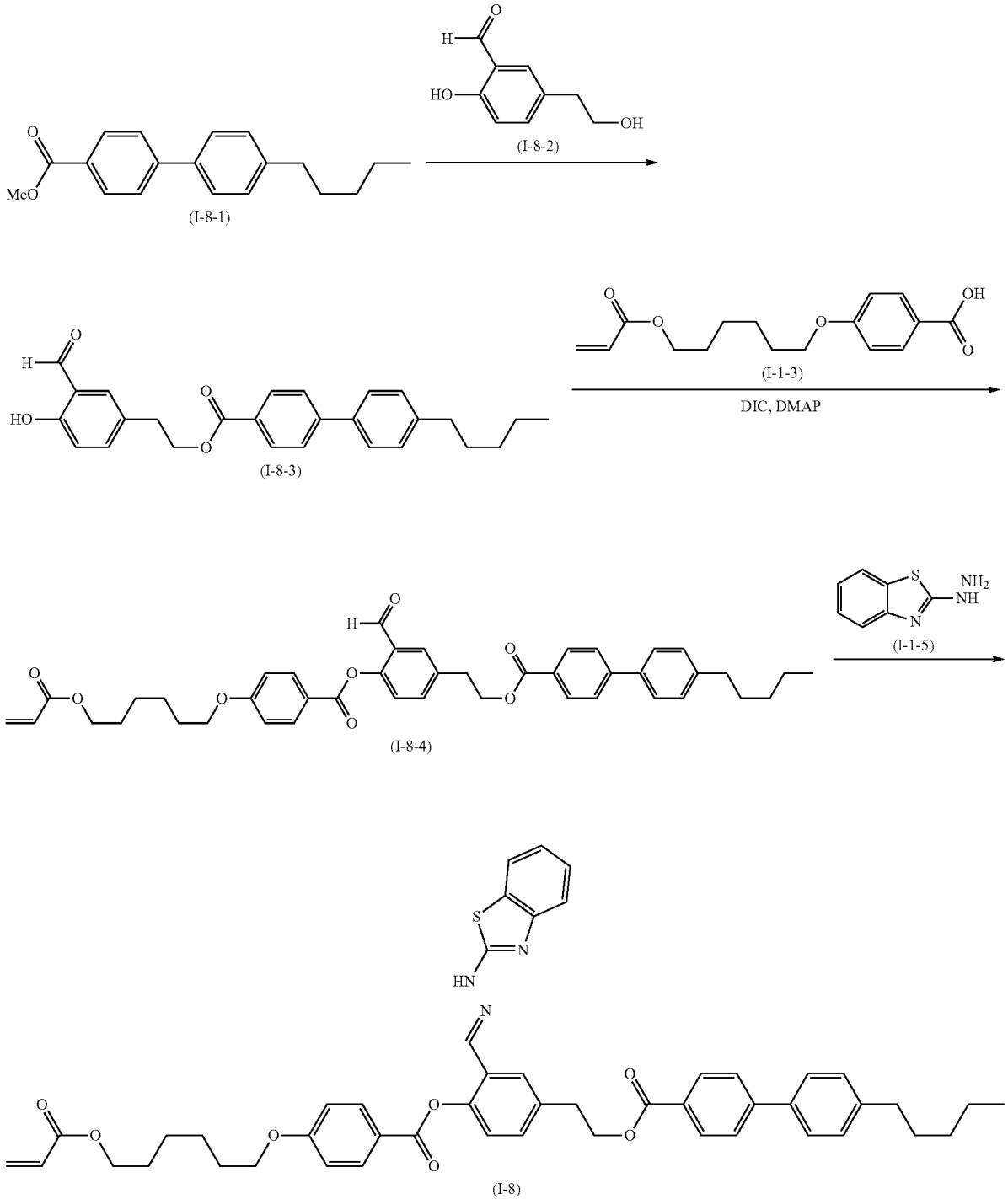

To a reaction container, 5.00 g of the compound represented by Formula (I-8-1), 2.94 g of the compound represented by Formula (I-8-2), 0.2 g of dibutyltin oxide, and 50 mL of toluene were added. The resulting mixture was heated to reflux while the solvent was replaced. Subsequently, purification was performed by column chromatography. Hereby, 5.90 g of the compound represented by Formula (I-8-3) was prepared.

The compound represented by Formula (I-8) was prepared as in Example 1.

MS (m/z): 838 [M$^+$+1]

Example 9

Production of Compound Represented by Formula (I-9)

[Chem. 81]

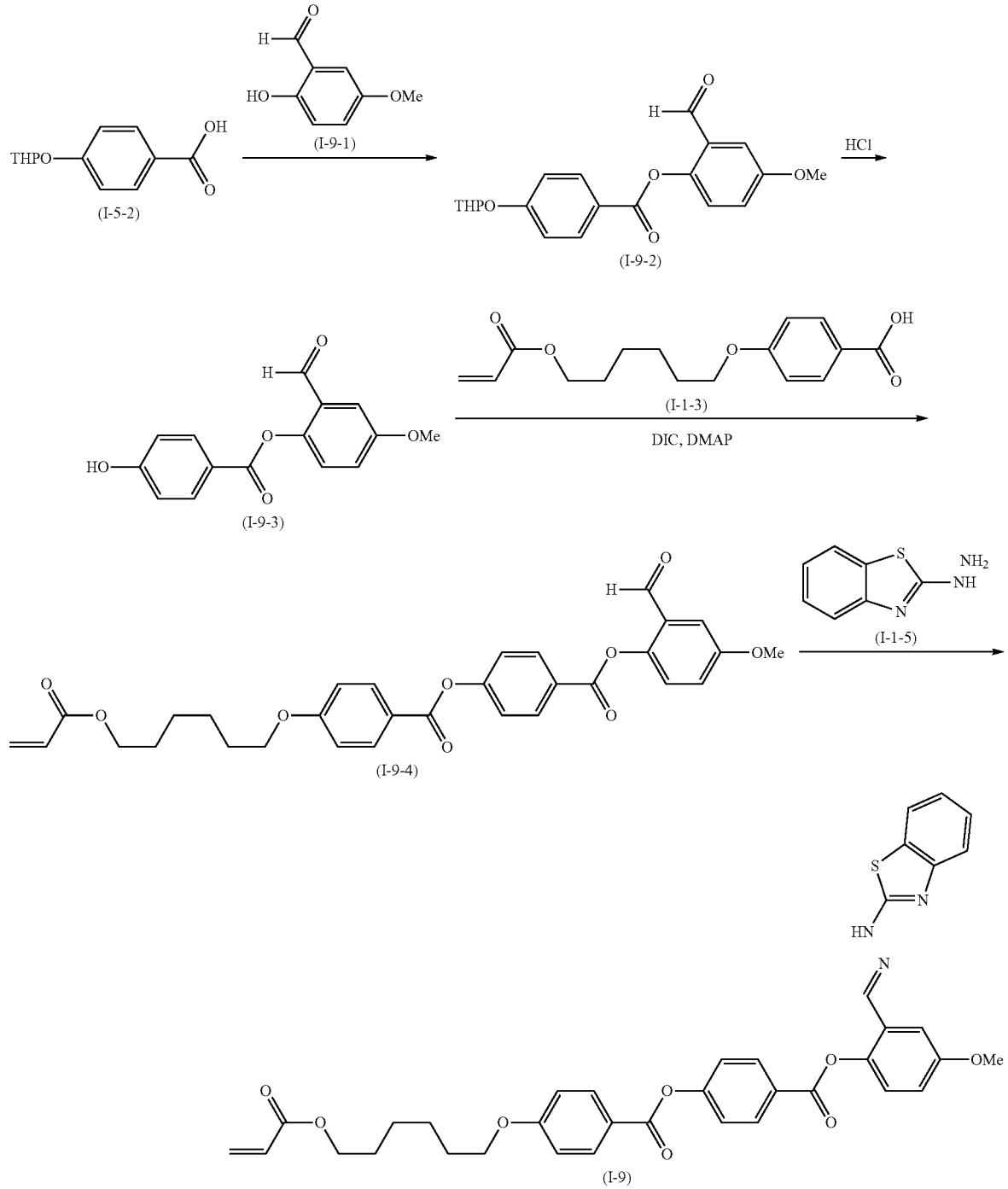

To a reaction container, 3.00 g of the compound represented by Formula (I-5-2), 2.05 g of the compound represented by Formula (I-9-1), 0.08 g of N,N-dimethylaminopyridine, and 20 mL of dichloromethane were added. To the reaction container, 2.56 g of diisopropylcarbodiimide was added dropwise. The resulting mixture was stirred. Subsequently, purification was performed by column chromatography. Hereby, 3.85 g of the compound represented by Formula (I-9-2) was prepared.

To a reaction container, 3.85 g of the compound represented by Formula (I-9-2), 20 mL of tetrahydrofuran, 20 mL of methanol, and 1 mL of concentrated hydrochloric acid were added. After the resulting mixture had been stirred, dilution was performed with ethyl acetate. Then, cleaning was performed with a saline solution. Subsequently, purification was performed by column chromatography. Hereby, 2.79 g of the compound represented by Formula (I-9-3) was prepared.

The compound represented by Formula (I-9) was prepared as in Example 1.

Transition temperature (temperature rise: 5° C./min): C 178 N 180 I $^1$H NMR (CDCl$_3$) δ 1.44-1.60 (m, 4H), 1.74 (quin, 2H), 1.86 (quin, 2H), 3.89 (s, 3H), 4.07 (t, 2H), 4.20 (t, 2H), 5.83 (dd, 1H), 6.14 (dd, 1H), 6.42 (dd, 1H), 6.99 (m, 3H), 7.09 (t, 1H), 7.13 (d, 1H), 7.19 (t, 1H), 7.27 (d, 2H), 7.44 (d, 1H), 7.54 (d, 1H), 7.60 (d, 1H), 8.03 (s, 1H), 8.17 (d, 4H) ppm.

MS (m/z): 694 [M$^+$+1]

Example 10

Production of Compound Represented by Formula (I-10)

[Chem. 82]

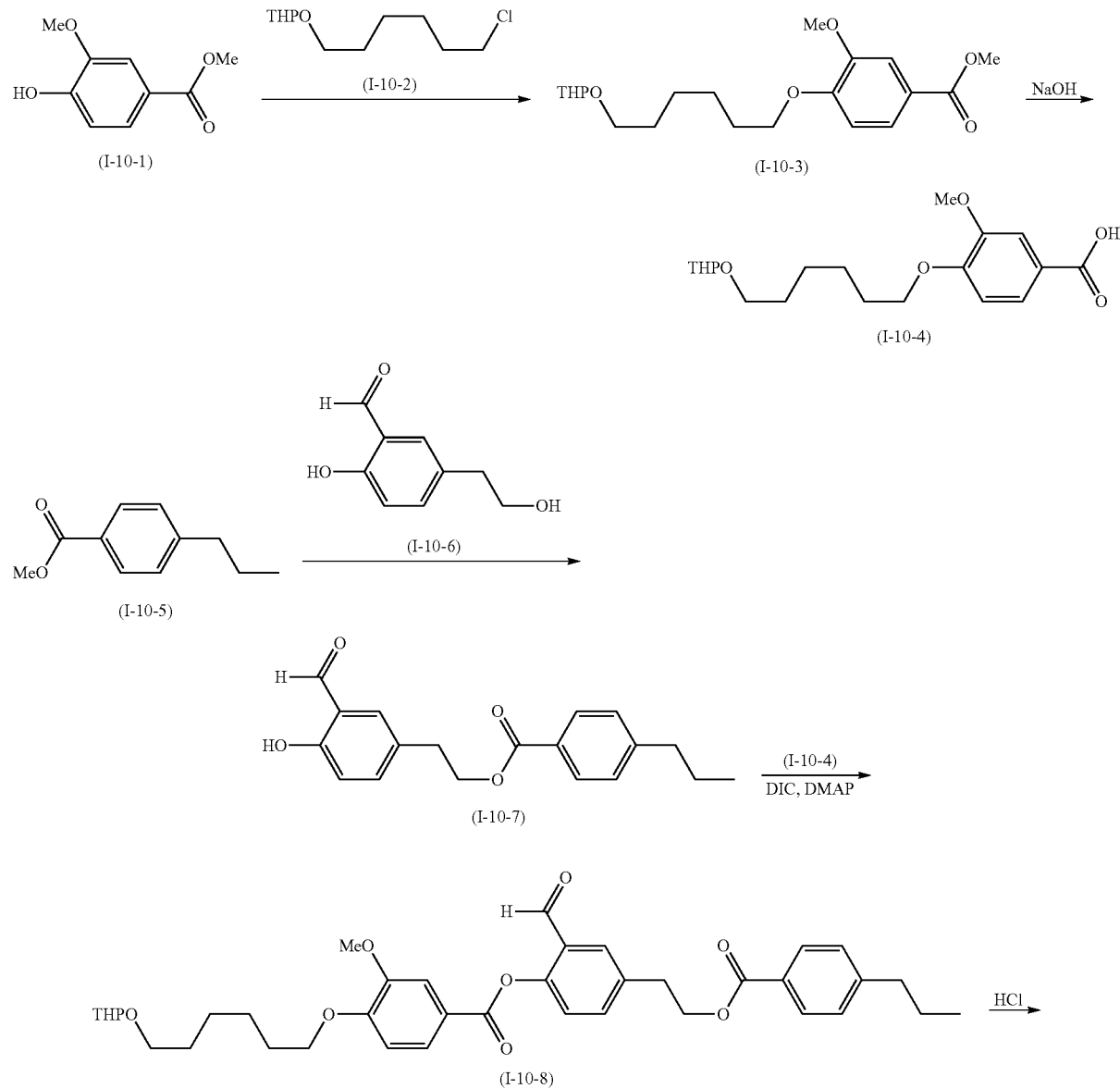

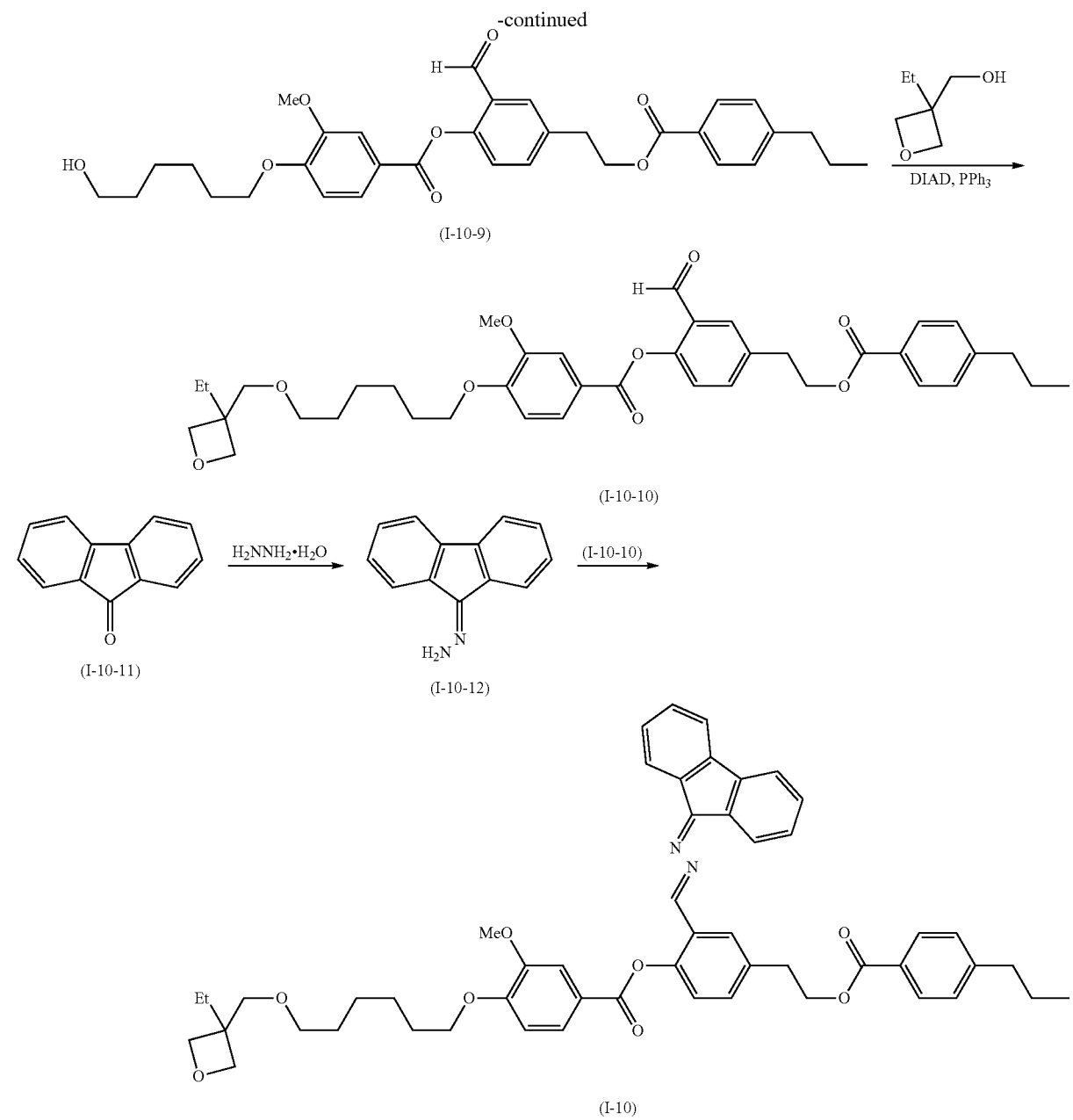

To a reaction container, 5.00 g of the compound represented by Formula (I-10-1), 9.09 g of the compound represented by Formula (I-10-2), 5.69 g of potassium carbonate, and 40 mL of N,N-dimethylformamide were added. After the resulting mixture had been stirred while being heated, dilution with toluene and cleaning with hydrochloric acid and a saline solution were performed. Then, purification was performed by column chromatography. Hereby, 8.05 g of the compound represented by Formula (I-10-3) was prepared.

To a reaction container, 8,05 g of the compound represented by Formula (I-10-3), 100 mL of methanol, and 20 mL of an aqueous sodium hydroxide solution were added. The resulting mixture was stirred while being heated. After neutralization had been performed, dilution with ethyl acetate and cleaning with a saline solution were performed.

Then, purification was performed by column chromatography. Hereby, 6.19 g of the compound represented by Formula (I-10-4) was prepared.

The compound represented by Formula (I-10-7) was prepared as in the preparation of the compound represented by Formula (I-8-3) in Example 8.

To a reaction container, 3.00 g of the compound represented by Formula (I-10-7), 3.38 g of the compound represented by Formula (I-10-4), 0.06 g of N,N-dimethylaminopyridine, and 30 mL of dichloromethane were added. To the reaction container, 1.82 g of diisopropylcarbodiimide was added dropwise. The resulting mixture was stirred. Subsequently, purification was performed by column chromatography. Hereby, 4.97 g of the compound represented by Formula (I-10-8) was prepared.

To a reaction container, 4.97 g of the compound represented by Formula (I-10-8), 20 mL of tetrahydrofuran, 20 mL of methanol, and 1 mL of concentrated hydrochloric acid were added. After the resulting mixture had been stirred, dilution was performed with ethyl acetate. Then, cleaning was performed with a saline solution. Subsequently, purification was performed by column chromatography. Hereby, 3.46 g of the compound represented by Formula (I-10-9) was prepared.

To a reaction container, 3.46 g of the compound represented by Formula (I-10-9), 0.86 g of 3-ethyl-3-oxetanemethanol, 1.93 g of triphenylphosphine, and 30 mL of tetrahydrofuran were added. While ice cooling was performed, 1.49 g of diisopropyl azodicarboxylate was added dropwise to the reaction container. The resulting mixture was stirred at room temperature. Then, purification was performed by column chromatography and recrystallization. Hereby, 3.25 g of the compound represented by Formula (I-10-10) was prepared.

The compound represented by Formula (I-10-12) was prepared by the method described in WO2012/141245A1.

The compound represented by Formula (I-10) was prepared as in Example 1.

MS (m/z): 837 [M$^+$+1]

Example 11

Production of Compound Represented by Formula (I-11)

[Chem. 83]

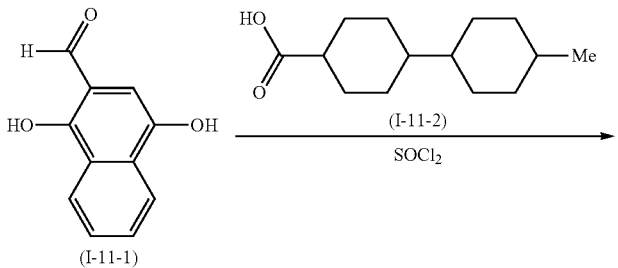

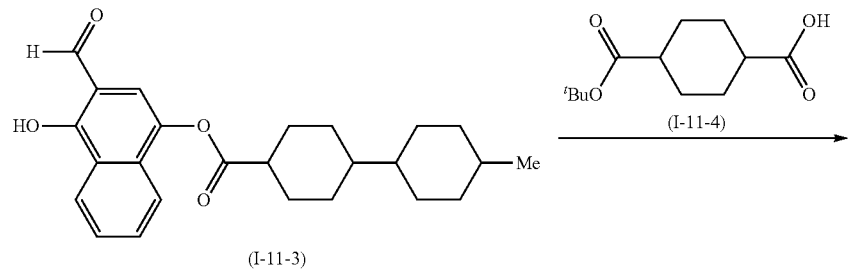

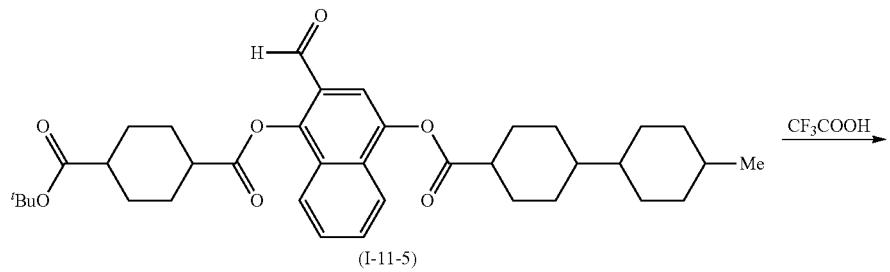

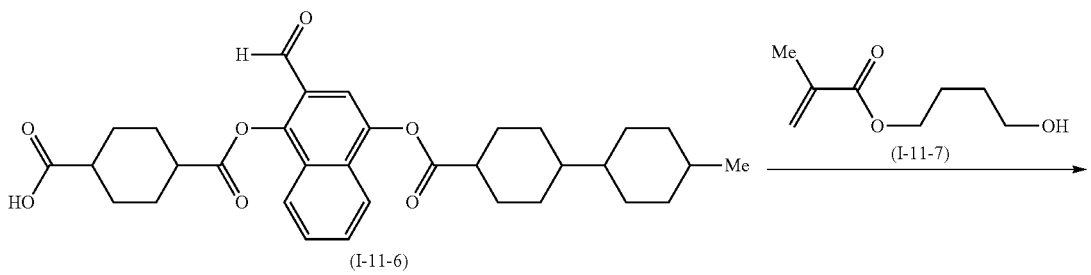

-continued

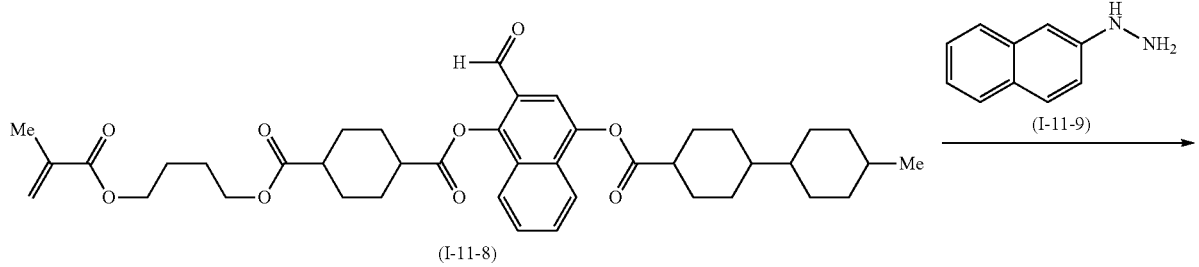

(I-11-8)            (I-11-9)

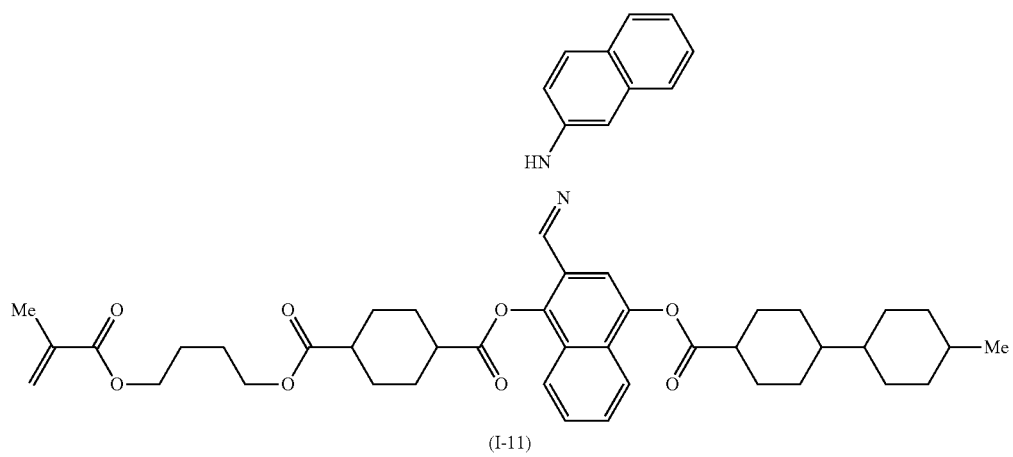

(I-11)

To a reaction container, 2.00 g of the compound represented by Formula (I-11-2) and 20 mL of thionyl chloride were added. After the resulting mixture had been stirred while being heated, thionyl chloride was removed by distillation to produce an acid chloride. To a reaction container, 1.68 g of the compound represented by Formula (I-11-1), 30 mL of tetrahydrofuran, and 2.70 g of triethylamine were added. While cooling was performed, a tetrahydrofuran solution of the acid chloride was added dropwise to the reaction container. After the resulting mixture had been stirred at room temperature, dilution with ethyl acetate and cleaning with hydrochloric acid and a saline solution were performed. Subsequently, purification was performed by column chromatography. Hereby, 1.41 g of the compound represented by Formula (I-11-3) was prepared.

To a reaction container, 1.41 g of the compound represented by Formula (I-11-3), 0.81 g of the compound represented by Formula (I-11-4), 0.02 g of N,N-dimethylaminopyridine, and 20 mL of dichloromethane were added. To the reaction container, 0.68 g of diisopropylcarbodiimide was added dropwise. After the resulting mixture had been stirred, purification was performed by column chromatography. Hereby, 1.73 g of the compound represented by Formula (I-11-5) was prepared.

To a reaction container, 1.73 g of the compound represented by Formula (I-11-5), 20 mL of dichloromethane, and 20 mL of trifluoroacetic acid were added. After the resulting mixture had been stirred, diisopropyl ether was added to the reaction container in order to cause precipitation. Subsequently, filtration and cleaning were performed. Hereby, 1.25 g of the compound represented by Formula (I-11-6) was prepared.

To a reaction container, 1.25 g of the compound represented by Formula (I-11-6), 0.43 g of the compound represented by Formula (I-11-7), 0.78 g of triphenylphosphine, and 10 mL of tetrahydrofuran were added. While ice cooling was performed, 0.60 g of diisopropyl azodicarboxylate was added dropwise to the reaction container. Subsequently, stirring was performed at room temperature. Then, purification was performed by column chromatography and recrystallization. Hereby, 1.10 g of the compound represented by Formula (I-11-8) was prepared.

The compound represented by Formula (I-11) was prepared as in Example 1.

IR: 3060-3030, 2975-2920, 1725, 1630, 1200, 1160, 1130, 750, 690 cm$^{-1}$.

MS (m/z): 82 9 [M$^+$+1]
Example 12
Production of Compound Represented by Formula (I-12)
[Chem. 84]
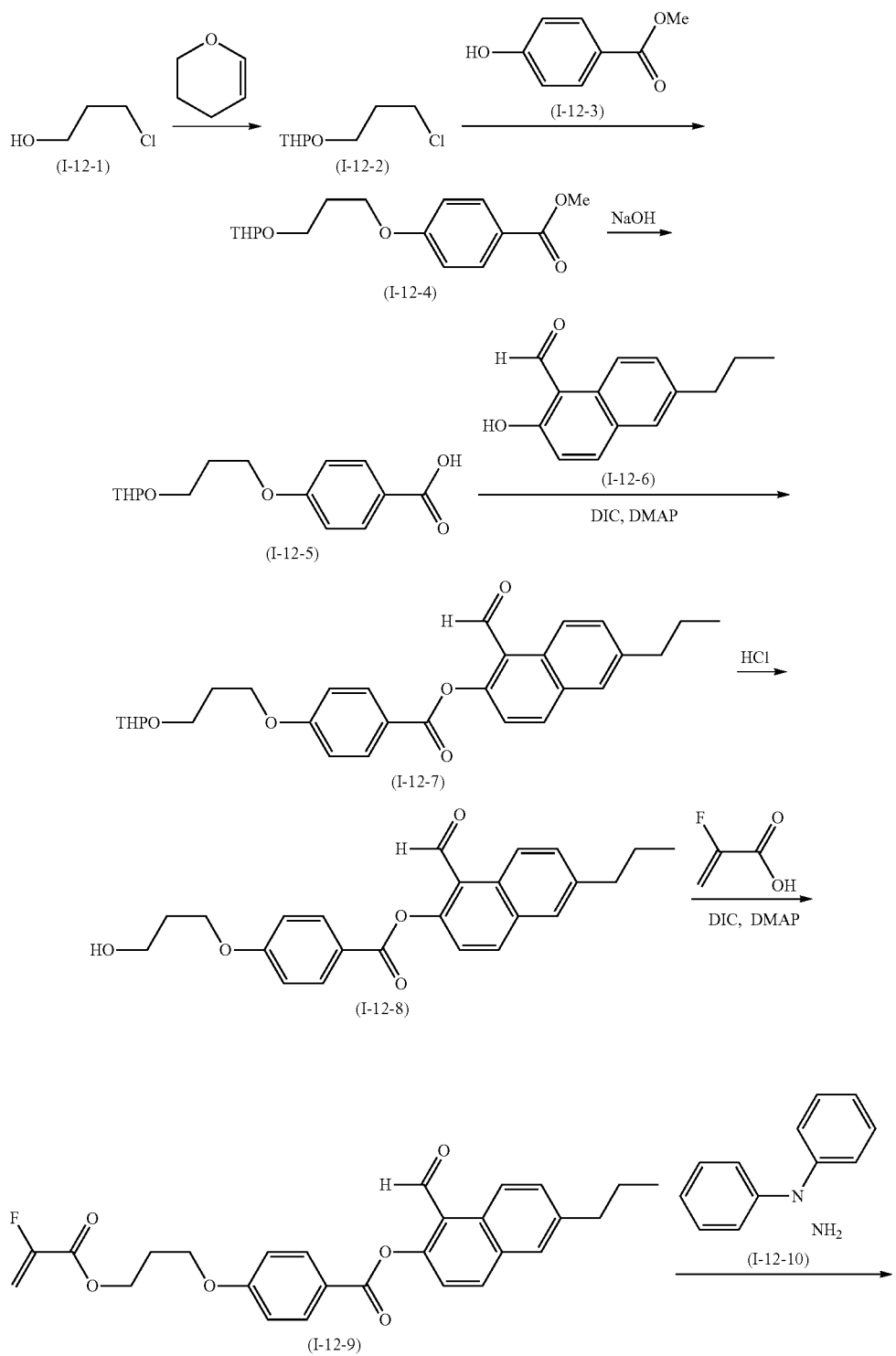

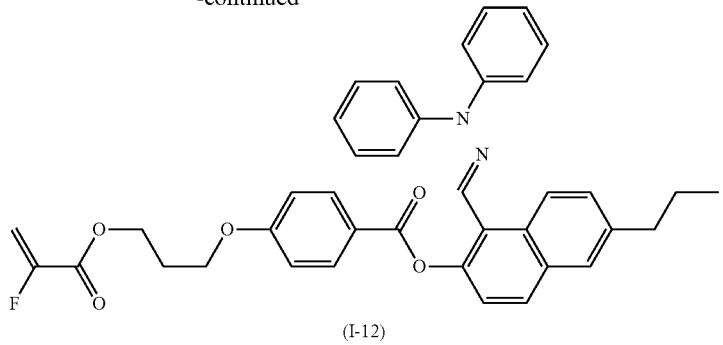

(I-12)

To a reaction container, 5.00 g of the compound represented by Formula (I-12-1), 0.25 g of pyridinium p-toluenesulfonate, and 20 mL of dichloromethane were added. To the reaction container, 6.67 g of 3,4-dihydro-2H-pyran was added dropwise. The resulting mixture was stirred. After cleaning had been performed with a saturated aqueous solution of sodium bicarbonate, purification was performed by column chromatography. Hereby, 8.50 g of the compound represented by Formula (I-12-2) was prepared.

To a reaction container, 4.00 g of the compound represented by Formula (I-12-2), 2.62 g of the compound represented by Formula (I-12-3), 8.42 g of cesium carbonate, and 40 mL of dimethyl sulfoxide were added. After the resulting mixture had been stirred while being heated, dilution with toluene and cleaning with water and a saline solution were performed. Then, purification was performed by column chromatography. Hereby, 4.06 g of the compound represented by Formula (I-12-4) was prepared.

To a reaction container, 4.06 g of the compound represented by Formula (I-12-4), 40 mL of methanol, and 20 mL of an aqueous sodium hydroxide solution were added. After the resulting mixture had been stirred while being heated, neutralization and extraction with ethyl acetate were performed. Subsequently, purification was performed by column chromatography. Hereby, 3.48 g of the compound represented by Formula (I-12-5) was prepared.

To a reaction container, 3.48 g of the compound represented by Formula (I-12-5), 2.66 g of the compound represented by Formula (I-12-6), 0.08 g of N,N-dimethylaminopyridine, and 40 mL of dichloromethane were added. To the reaction container, 1.88 g of diisopropylcarbodiimide was added dropwise. The resulting mixture was stirred. Subsequently, purification was performed by column chromatography. Hereby, 4.73 g of the compound represented by Formula (I-12-7) was prepared.

To a reaction container, 4.73 g of the compound represented by Formula (I-12-7), 20 mL of tetrahydrofuran, 20 mL of methanol, and 1 mL of concentrated hydrochloric acid were added. After the resulting mixture had been stirred, dilution with ethyl acetate and cleaning with a saline solution were performed. Subsequently, purification was performed by column chromatography. Hereby, 3.51 g of the compound represented by Formula (I-12-8) was prepared.

To a reaction container, 3.51 g of the compound represented by Formula (I-12-8), 0.05 g of N,N-dimethylaminopyridine, 0.97 g of 2-fluoroacrylic acid, and 20 mL of dichloromethane were added. To the reaction container, 1.47 g of diisopropylcarbodiimide was added dropwise. The resulting mixture was stirred. Subsequently, purification was performed by column chromatography and recrystallization. Hereby, 3.32 g of the compound represented by Formula (I-12-9) was prepared.

The compound represented by Formula (I-12) was prepared as in Example 1.

MS (m/s): 631 [M$^+$+1]

Example 13

Production of Compound Represented by Formula (I-13)

[Chem. 85]

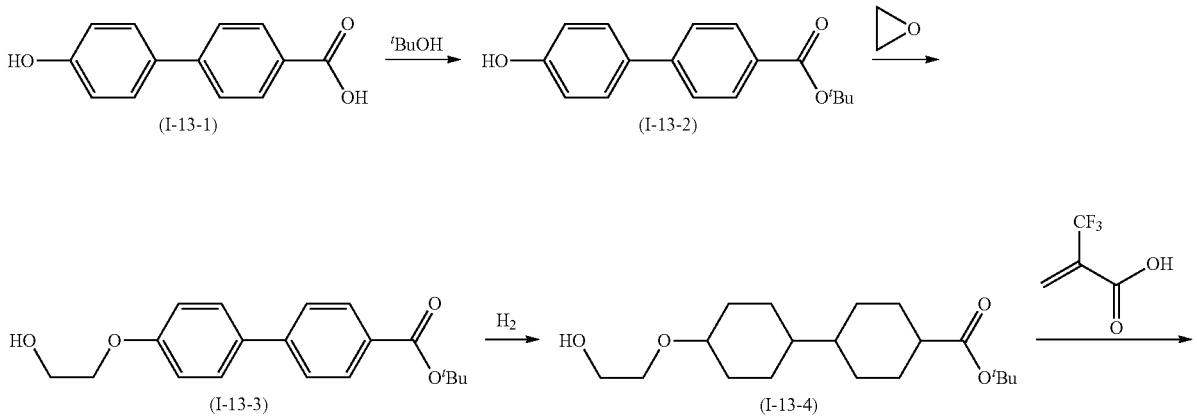

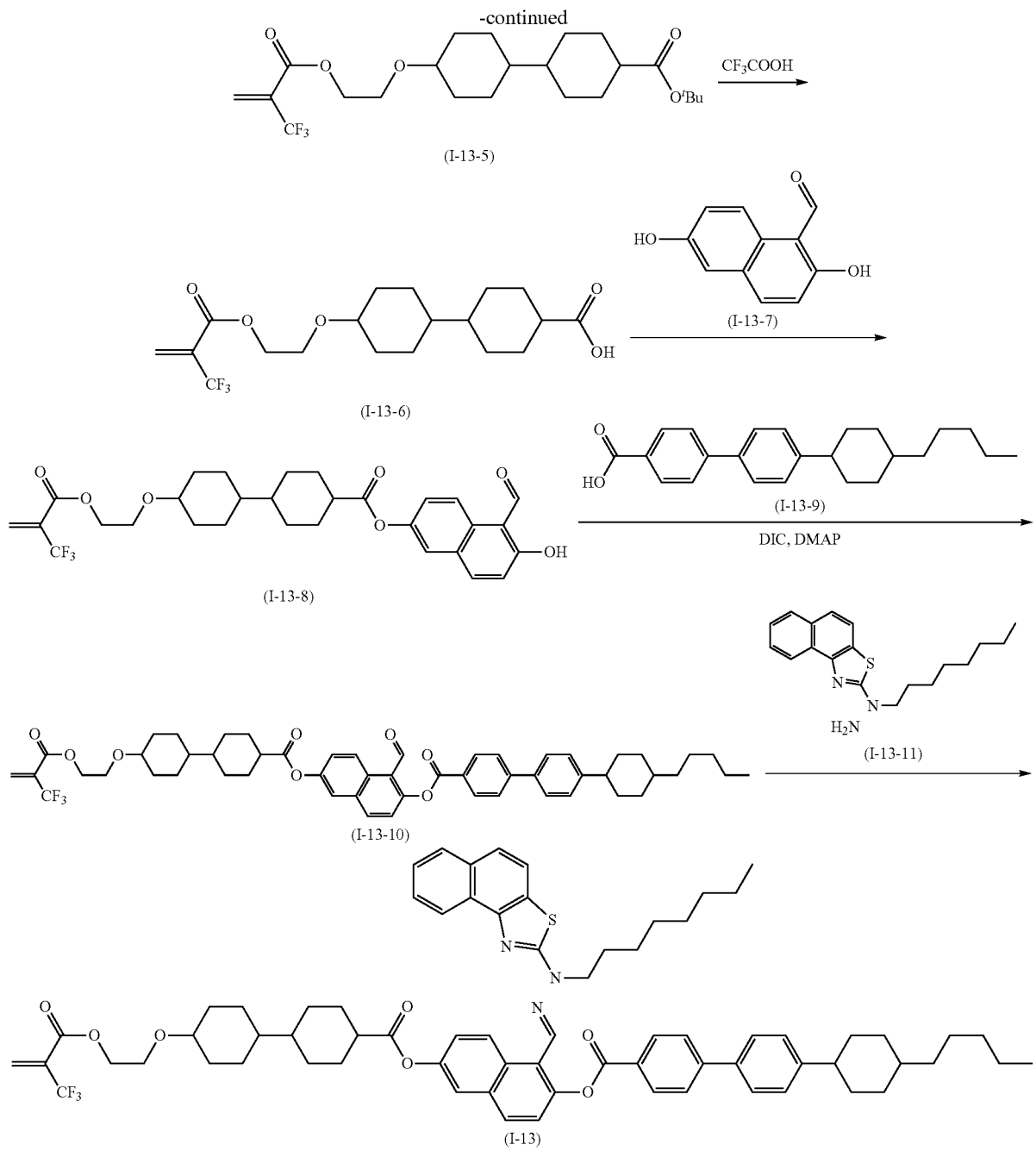

To a reaction container, 3.00 g of the compound represented by Formula (I-13-1), 0.09 g of N,N-dimethylaminopyridine, 60 mL of tert-butyl alcohol, and 90 mL of tetrahydrofuran were added. To the reaction container, a solution prepared by dissolving 4.33 g of N,N'-dicyclohexylcarbodiimide in 30 mL of tetrahydrofuran was added dropwise. After the resulting had been stirred, filtration and concentration were performed. Subsequently, purification was performed by column chromatography. Hereby, 1.89 g of the compound represented by Formula (I-13-2) was performed.

To a reaction container, 1.89 g of the compound represented by Formula (I-13-2), 1.45 g of potassium carbonate, and 20 mL of ethanol were added. To the reaction container, 10 mL of ethylene oxide was added at 0° C. The resulting mixture was stirred. After filtration and concentration had been performed, purification was performed by column chromatography. Hereby, 1.76 g of the compound represented by Formula (I-13-3) was prepared.

To an autoclave, 1.76 g of the compound represented by Formula (I-13-3), 30 mL of tetrahydrofuran, 30 mL of ethanol, and 5.0 mg of rhodium/alumina were added. After the resulting mixture had been stirred at 60° C. and 8.0 MPa, filtration and concentration were performed. Subsequently, purification was performed by column chromatography. Hereby, 1.10 g of the compound represented by Formula (I-13-4) was prepared.

To a reaction container, 1.10 g of the compound represented by Formula (I-13-4), 0.02 g of N,N-dimethylaminopyridine, 15 mL of dichloromethane, and 0.57 g of 2-(trifluoromethyl)acrylic acid were added. To the reaction container, 0.51 g of diisopropylcarbodiimide was added dropwise. After the resulting mixture had been stirred, purification was performed by column chromatography. Hereby, 1.21 g of the compound represented by Formula (I-13-5) was prepared.

To a reaction container, 1.21 g of the compound represented by Formula (I-13-5), 10 mL of dichloromethane, and 10 mL of trifluoroacetic acid were added. After the resulting mixture had been stirred, dilution with ethyl acetate and cleaning with a saline solution were performed. Subsequently, purification was performed by column chromatography and recrystallization. Hereby, 0.95 g of the compound represented by Formula (I-13-6) was prepared.

To a reaction container, 0.95 g of the compound represented by Formula (I-13-6), 0.46 g of the compound represented by Formula (I-13-7), 0.01 g of N,N-dimethylaminopyridine, and 10 mL of dichloromethane were added. While cooling was performed, 0.37 g of diisopropylcarbodiimide was added dropwise to the reaction container. The resulting mixture was stirred. Subsequently, purification was performed by column chromatography and recrystallization. Hereby, 0.55 g of the compound represented by Formula (I-13-8) was prepared.

To a reaction container, 0.55 g of the compound represented by Formula (I-13-8), 0.34 g of the compound represented by Formula (I-13-9), 0.01 g of N,N-dimethylaminopyridine, and 10 mL of dichloromethane were added. To the reaction container, 0.15 g of diisopropylcarbodiimide was added dropwise. The resulting mixture was stirred. Subsequently, purification was performed by column chromatography and recrystallization. Hereby, 0.69 g of the compound represented by Formula (I-13-10) was prepared.

The compound represented by Formula (I-13-11) was prepared as in Example 5 described in WO2014/010325A1. The compound represented by Formula (I-13) was prepared as in Example 1.

MS (m/z): 1204 [$M^+$+1]

Example 14

Production of Compound Represented by Formula (I-14)

[Chem. 86]

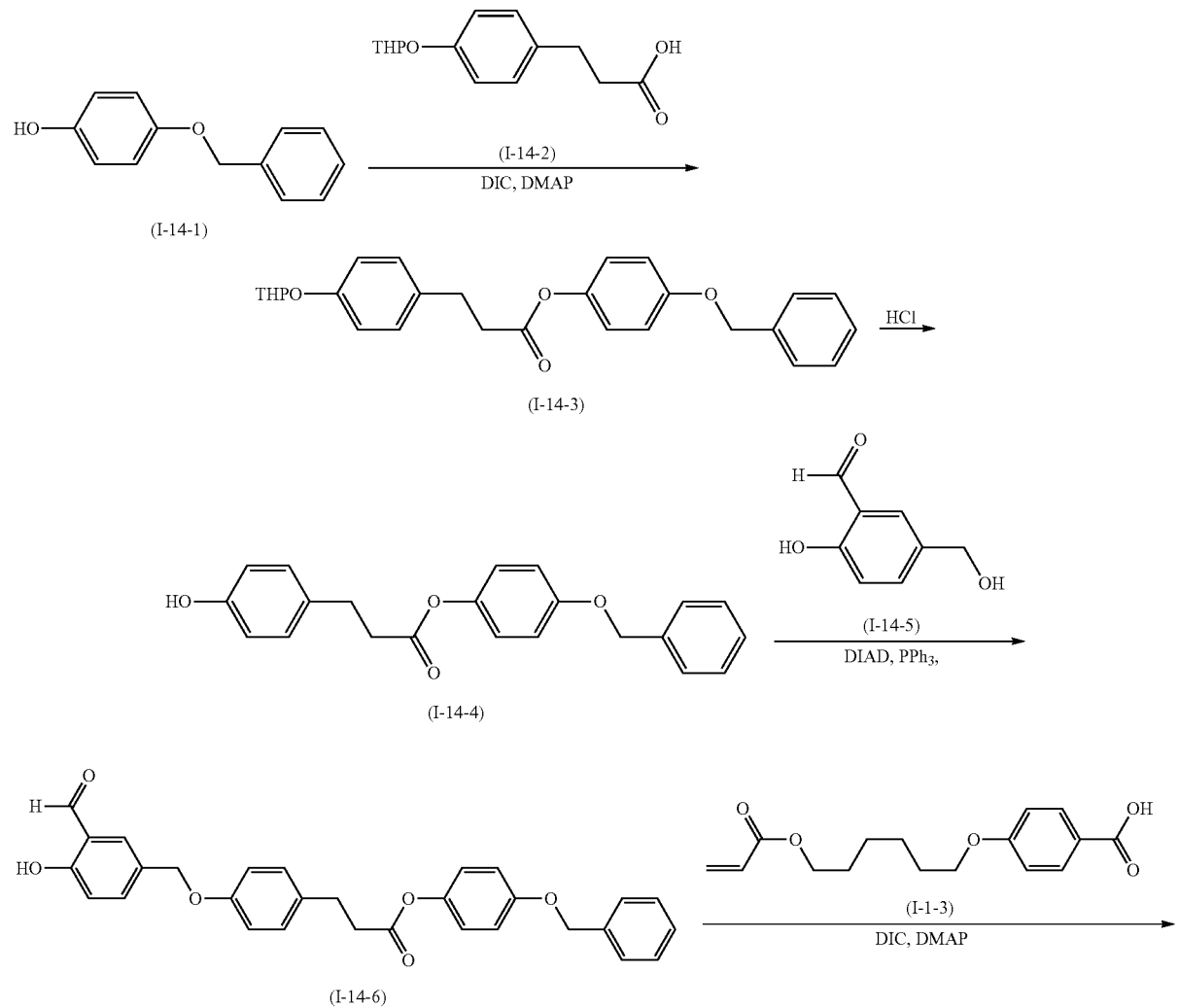

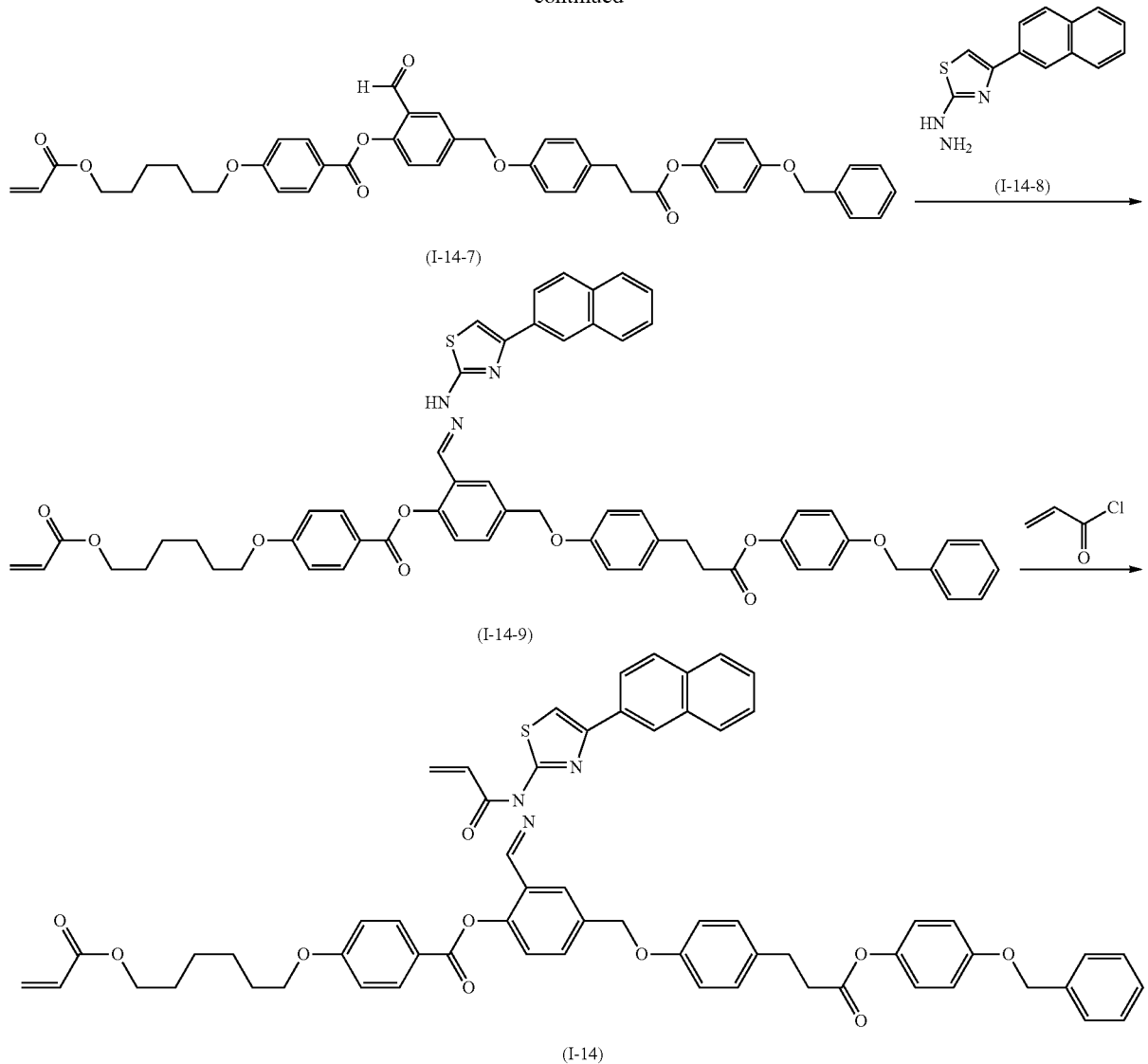

To a reaction container, 5.00 g of the compound represented by Formula (I-14-1), 6.25 g of the compound represented by Formula (I-14-2), 0.15 g of N,N-dimethylaminopyridine, and 40 mL of dichloromethane were added. To the reaction container, 3.78 g of diisopropylcarbodiimide was added dropwise. The resulting mixture was stirred. Subsequently, purification was performed by column chromatography. Hereby, 8.64 g of the compound represented by Formula (I-14-3) was prepared.

To a reaction container, 8.64 g of the compound represented by Formula (I-14-3), 30 mL of tetrahydrofuran, 30 mL of methanol, and 2 mL of concentrated hydrochloric acid were added. After the resulting mixture had been stirred, dilution with ethyl acetate and cleaning with a saline solution were performed. Then, purification was performed by column chromatography. Hereby, 6.26 g of the compound represented by Formula (I-14-4) was prepared.

To a reaction container, 6.26 g of the compound represented by Formula (I-14-4), 2.74 g of the compound represented by Formula (I-14-5), 5.66 g of triphenylphosphine, and 60 mL of tetrahydrofuran were added. While cooling was performed, 4.36 g of diisopropyl azodicarboxylate was added dropwise to the reaction container. The resulting mixture was stirred. Subsequently, purification was performed by column chromatography and recrystallization. Hereby, 2.43 g of the compound represented by Formula (I-14-6) was prepared.

To a reaction container, 2.43 g of the compound represented by Formula (I-14-6), 1.47 g of the compound represented by Formula (I-1-3), 0.03 g of N,N-dimethylaminopyridine, and 30 mL of dichloromethane were added. To the reaction container, 0.76 g of diisopropylcarbodiimide was added dropwise. The resulting mixture was stirred. Then, purification was performed by column chromatography and recrystallization. Hereby, 3.05 g of the compound represented by Formula (I-14-7) was prepared.

The compound represented by Formula (I-14-8) was prepared as in Example 1 described in WO2014/065176A1. The compound represented by Formula (I-14-9) was prepared as in Example 1.

To a reaction container, 2.76 g of the compound represented by Formula (I-14-9), 0.57 g of triethylamine, and 20 mL of dichloromethane were added. To the reaction container, 0.31 g of acryloyl chloride was added. After the resulting mixture had been stirred, cleaning was performed with hydrochloric acid and a saline solution. Then, purification was performed by column chromatography and recrystallization. Hereby, 1.75 g of the compound represented by Formula (I-14) was prepared.

MS (m/z): 1034 [M$^+$+1]

Example 15

Production of Compound Represented by Formula (I-15)

[Chem. 87]

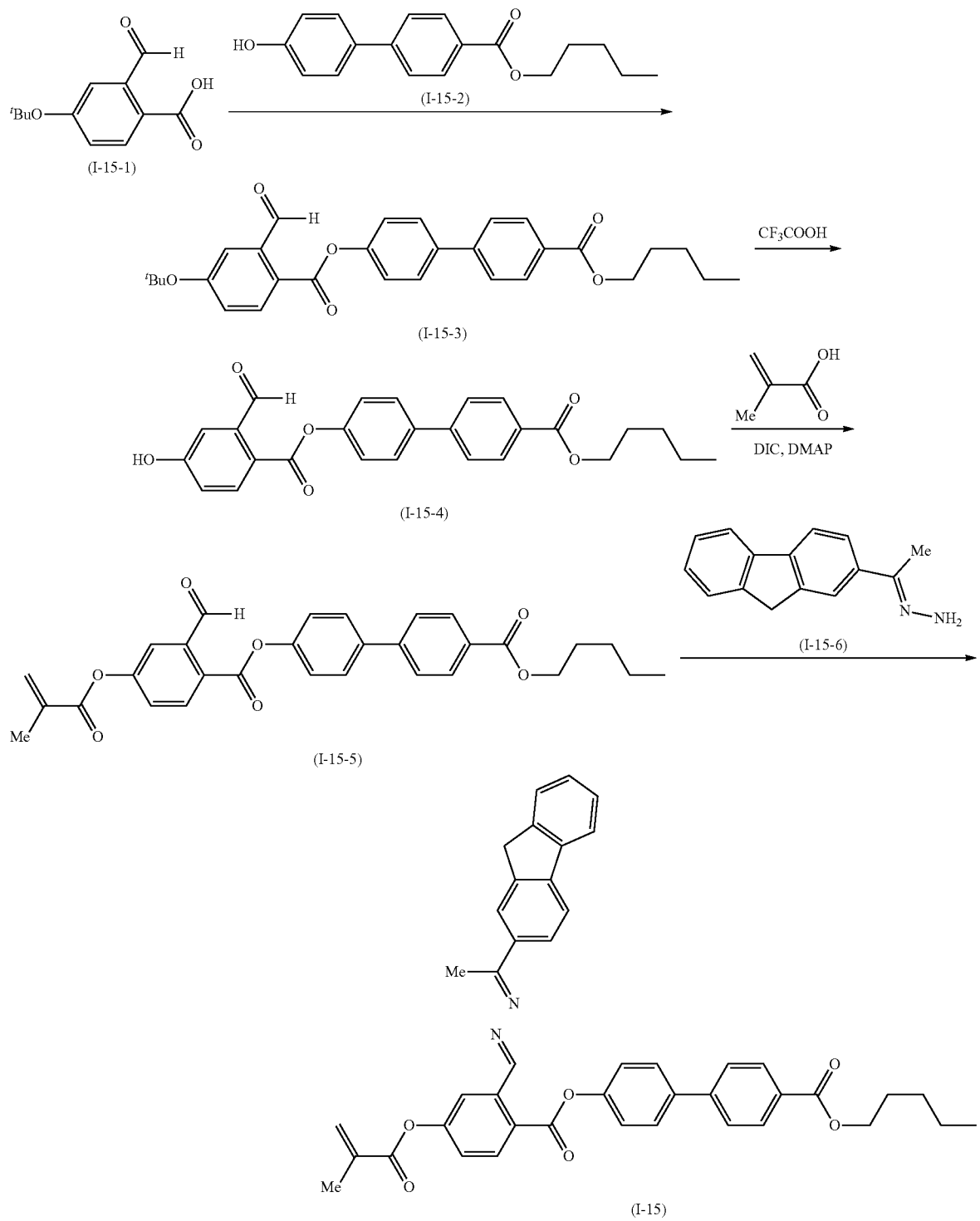

To a reaction container, 2.00 g of the compound represented by Formula (I-15-1), 2.56 g of the compound represented by Formula (I-15-2), 0.05 g of N,N-dimethylaminopyridine, and 20 mL of dichloromethane were added. To the reaction container, 1.36 g of diisopropylcarbodiimide was added dropwise. The resulting mixture was stirred. Then, purification was performed by column chromatography and recrystallization. Hereby, 3.52 g of the compound represented by Formula (I-15-3) was prepared.

To a reaction container, 3.52 g of the compound represented by Formula (I-15-3), 50 mL of dichloromethane, and 50 mL of trifluoroacetic acid were added. After the resulting mixture had been stirred, dilution with ethyl acetate and cleaning with a saline solution were performed. Then, purification was performed by column chromatography and recrystallization. Hereby, 2.49 g of the compound represented by Formula (I-15-4) was prepared.

To a reaction container, 2.49 g of the compound represented by Formula (I-15-4), 0.55 g of methacrylic acid, 0.04 g of N,N-dimethylaminopyridine, and 30 mL of dichloromethane were added. To the reaction container, 0.87 g of diisopropylcarbodiimide was added. The resulting mixture was stirred. Then, purification was performed by column chromatography and recrystallization. Hereby, 2.02 g of the compound represented by Formula (I-15-5) was prepared.

The compound represented by Formula (I-15-6) was prepared by the method described in WO2012/141254A1. The compound represented by Formula (I-15) was prepared as in Example 1.

MS (m/z): 705 [M$^+$+1]

Example 16

Production of Compound Represented by Formula (I-106)

[Chem. 88]

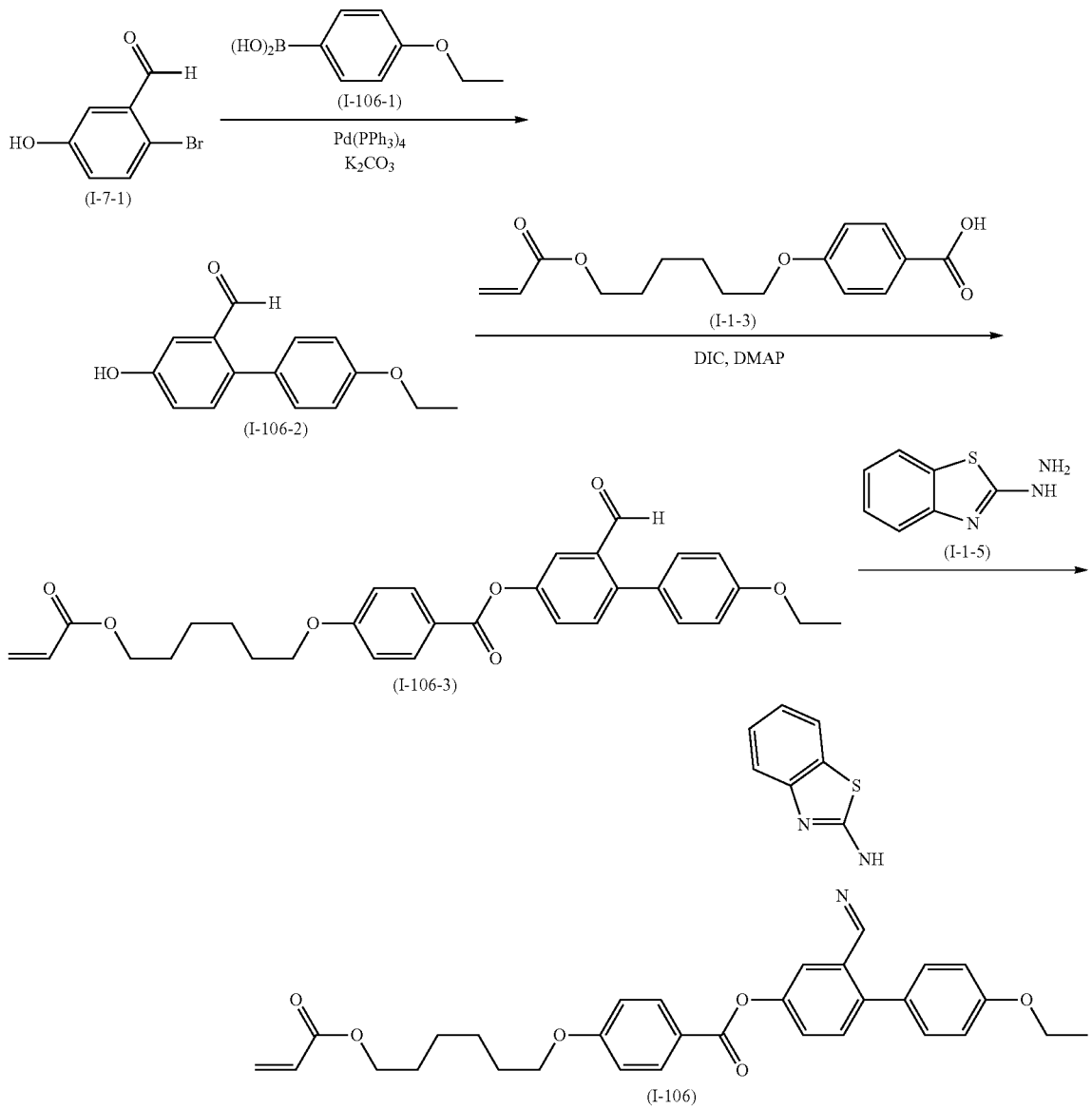

In a nitrogen atmosphere, 5.0 g of the compound represented by (I-7-1), 4.1 g of the compound represented by Formula (I-106-1), 5.2 g of potassium carbonate, 30 mL of ethanol, and 0.5 g of tetrakis(triphenylphosphine)palladium (0) were added to a reaction container. The resulting mixture was stirred while being heated at 70° C. After dilution with ethyl acetate and cleaning with hydrochloric acid and a saline solution had been performed, purification was performed by column chromatography (silica gel). Hereby, 3.6 g of the compound represented by Formula (I-106-2) was prepared.

The compound represented by Formula (I-106) was prepared as in Example 1.

Transition temperature (temperature rise: 5° C./min): C 169 N 178 I $^1$H NMR (CDCl$_3$) δ 1.43 (t, 3H), 1.47-1.60 (m, 4H), 1.75 (quin, 2H), 1.87 (m, 2H), 3.99 (q, 2H), 4.08 (t, 2H), 4.20 (t, 2H), 5.83 (dd, 1H), 6.14 (dd, 1H), 6.42 (dd, 1H), 6.85 (d, 2H), 7.01 (d, 2H), 7.08 (t, 1H), 7.14 (t, 1H), 7.20 (t, 3H), 7.25 (dd, 1H), 7.35 (d, 1H), 7.60 (d, 1H), 7.90 (d, 1H), 7.94 (s, 1H) 8.21 (d, 2H) ppm.

MS (m/z): 664 [M$^+$+1]

Example 17

Production of Compound Represented by Formula (I-107)

[Chem. 89]

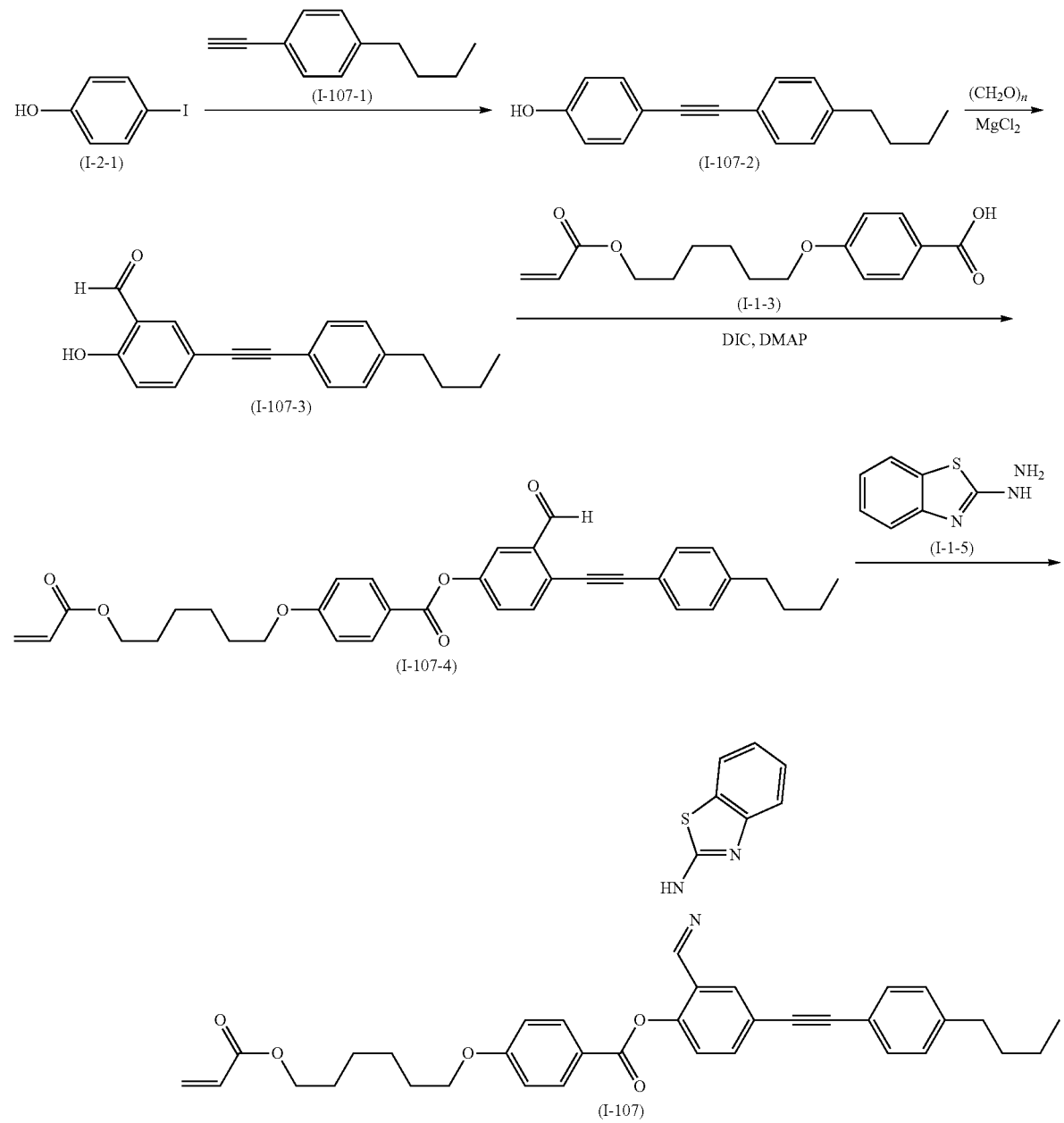

In a nitrogen atmosphere, 5.0 g of the compound represented by (I-2-1), 4.0 g of the compound represented by Formula (I-107-1), 0.2 g of copper iodide(I), 0.5 g of tetrakis(triphenylphosphine)palladium(0), 20 mL of triethylamine, and 60 mL of N,N-dimethylformamide were added to a reaction container. The resulting mixture was stirred while being heated at 90° C. After dilution with ethyl acetate and cleaning with hydrochloric acid and a saline solution had been performed, purification was performed by column chromatography (silica gel) and recrystallization. Hereby, 2.3 g of the compound represented by Formula (I-107-2) was prepared.

To a reaction container equipped with a cooling unit and a Dean and Stark device, 2,3 g of the compound represented by Formula (I-107-2), 1.3 g of magnesium chloride, 1.5 g of para-formaldehyde, 10 mL of triethylamine, and 20 mL of acetonitrile were added. The resulting mixture was heated to reflux while the solvent was replaced and an adequate amount of para-formaldehyde was added to the mixture. The resulting reaction liquid was added to hydrochloric acid. Subsequently, extraction with ethyl acetate and cleaning with water and a saline solution were performed. Then, purification was performed by column chromatography (silica gel). Hereby, 1.8 g of the compound represented by Formula (I-107-3) was prepared.

The compound represented by Formula (I-107) was prepared as in Example 1.

Transition temperature (temperature rise: 5° C./min): C 98 N 157 I $^1$H NMR (CDCl$_3$) δ 0.94 (t, 3H), 1.31-1.76 (m, 12H), 2.66 (t, 2H), 3.89 (t, 2H), 4.12 (t, 2H), 5.80 (dd, 1H), 6.13 (dd, 1H), 6.41 (dd, 1H), 6.50-8.20 (m, 16H) ppm.

MS (m/z): 700 [M$^+$+1]

Example 18

Production of Compound Represented by Formula (I-108)

[Chem. 90]

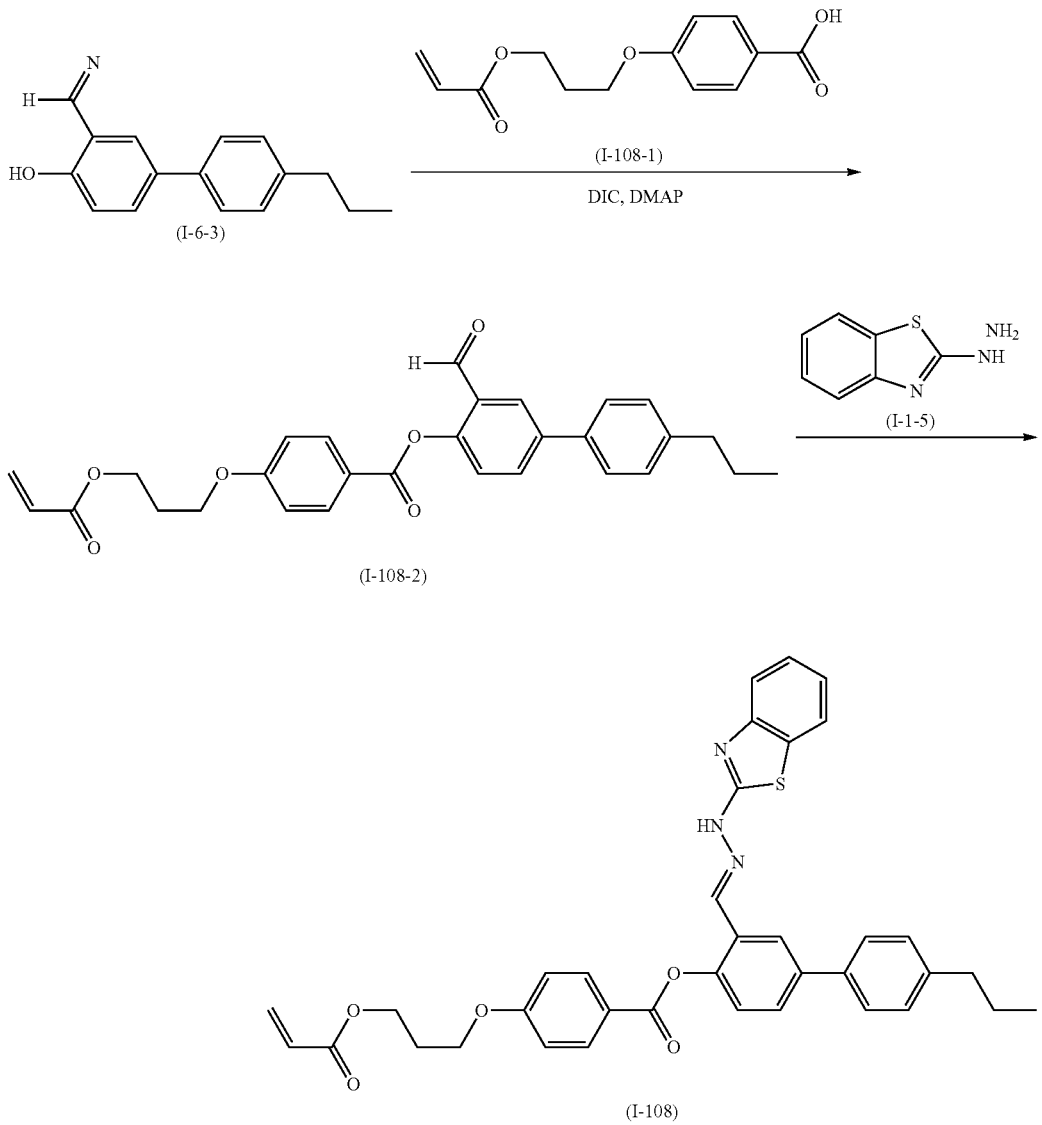

The compound represented by Formula (I-108) was prepared as in Example 6, except that the compound represented by Formula (I-1-3) was replaced with the compound represented by Formula (I-108-1).

Transition temperature (temperature rise: 5° C./min): C 5 164 I $^1$H NMR (DMSO-$d_6$) δ 0.94 (t, 3H), 1.65 (q, 2H), 2.15 (t, 2H), 2.63 (t, 2H), 4.22 (t, 2H), 4.30 (t, 2H), 5.96 (d, 1H), 6.20 (q, 1H), 6.36 (d, 1H), 7.10 (t, 1H), 7.18 (d, 2H), 7.28 (t, 1H), 7.35 (d, 2H), 7.52 (d, 2H), 7.63 (d, 2H), 7.23 (t, 2H), 8.15 (t, 3H), 8.25 (s, 1H) ppm.

MS (m/z): 620 [M$^+$+1]

Example 19

Production of Compound Represented by Formula (I-109)

[Chem. 91]

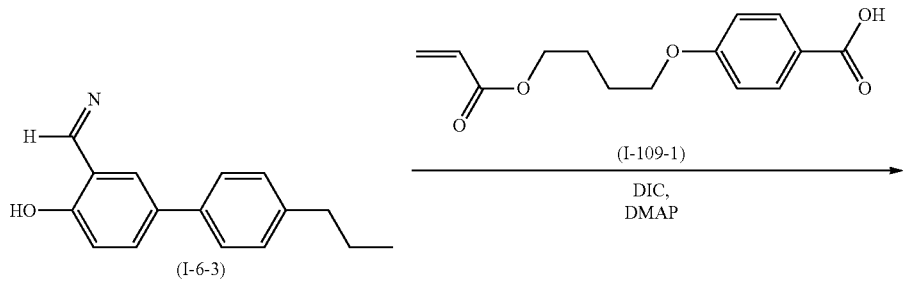

(I-6-3)     (I-109-1)
DIC, DMAP

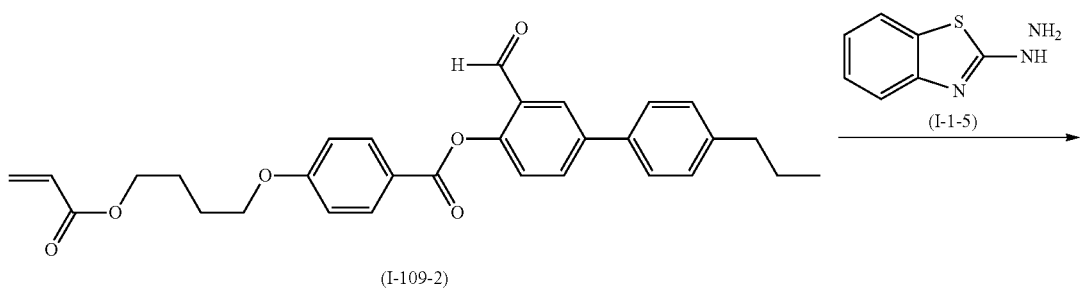

(I-109-2)     (I-1-5)

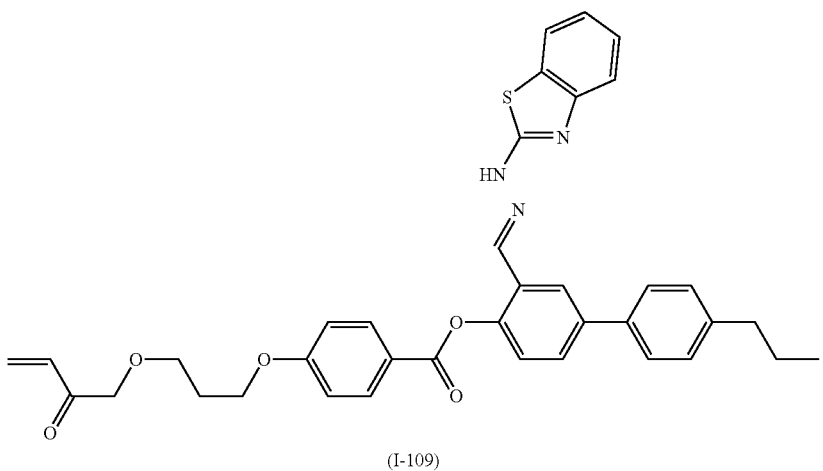

(I-109)

The compound represented by Formula (I-109) was prepared as in Example 6, except, that the compound represented by Formula (I-1-3) was replaced with the compound represented by Formula (I-109-1).
Transition temperature (temperature rise: 5° C./min): C 155 N 158 I
$^1$H NMR (CDCl$_3$) δ 1.02 (t, 3H), 1.73 (q, 3H), 1.86 (m, 4H), 2.68 (t, 2H), 3.96 (m, 2H), 4.24 (m, 2H), 5.85 (d, 1H), 6.14 (dd, 1H), 6.43 (d, 1H), 6.80 (m, 2H), 7.08-7.33 (m, 5H), 7.44 (m, 1H), 7.59 (m, 4H), 8.01 (m, 2H), 8.23 (m, 2H) ppm.
MS (m/z): 634 [M$^+$+1]
Example 20
Production of Compound Represented by Formula (I-110)
[Chem. 92]
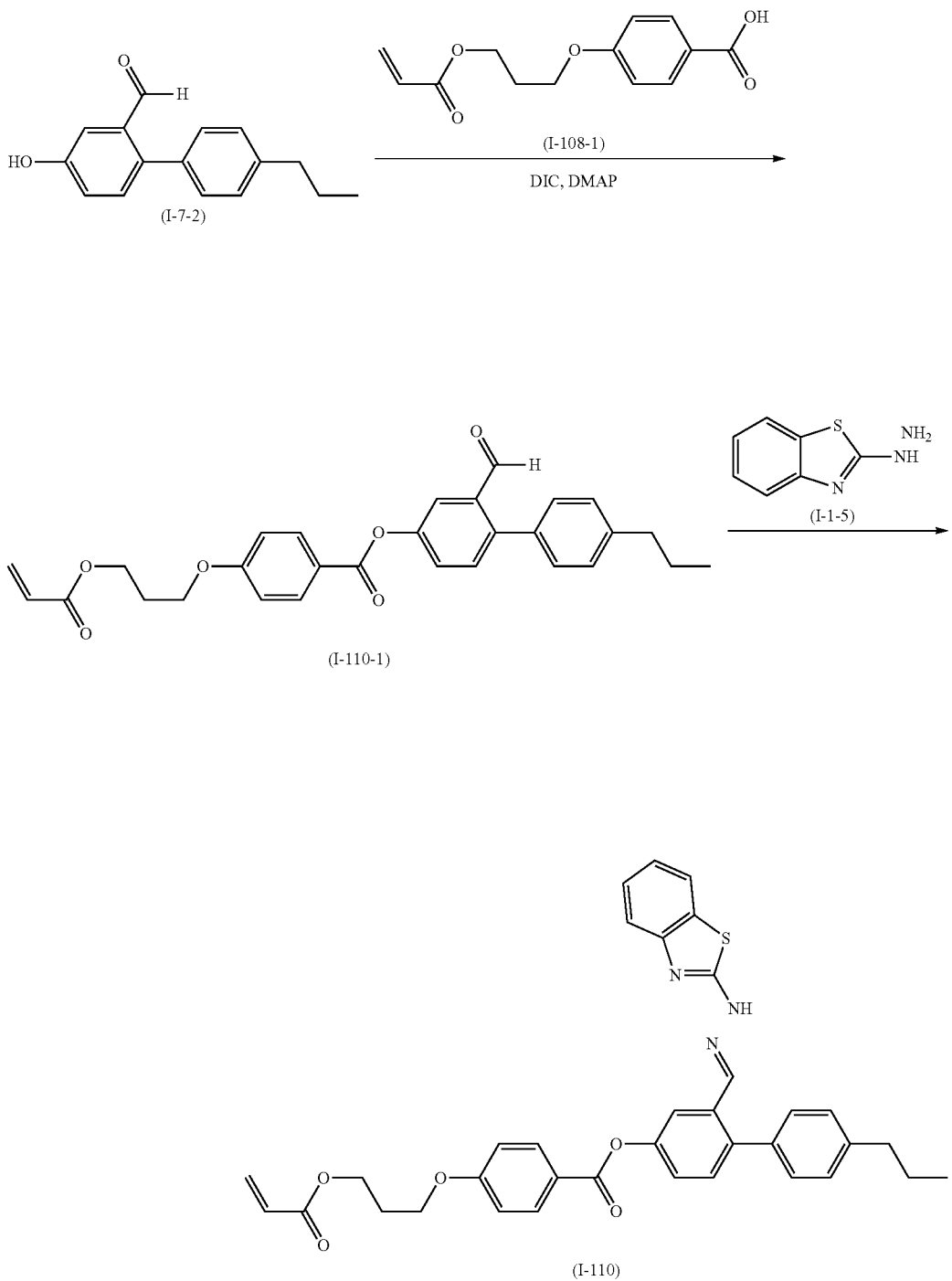

The compound represented by Formula (I-110) was prepared as in Example 7, except that the compound represented by Formula (I-1-3) was replaced with the compound represented by Formula (I-108-1).

Transition temperature (temperature rise: 5° C./min): C 5 154 I $^1$H NMR (CDCl$_3$) δ 0.95 (tt, 3H), 1.63 (m, 2H), 2.24 (quin, 2H), 2.59 (m, 2H), 4.19 (t, 2H), 4.41 (t, 2H), 5.85 (dd, 1H), 6.14 (dd, 1H), 6.43 (dd, 1H), 7.02 (d, 2H), 7.09-7.28 (m, 8H), 7.37 (d, 1H), 7.60 (d, 1H), 7.91 (m, 2H), 8.22 (d, 2H) ppm.

MS (m/z): 620 [M$^+$+1]

Example 21

Production of Compound Represented by Formula (I-111)

[Chem. 93]

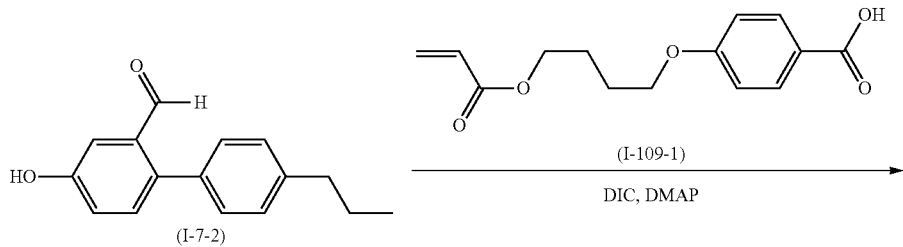

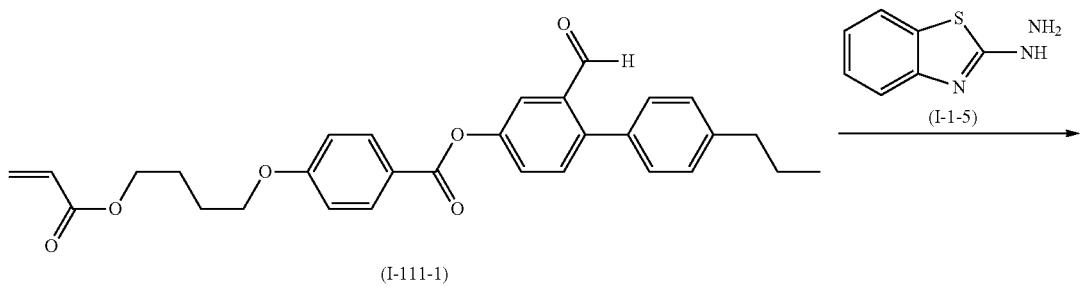

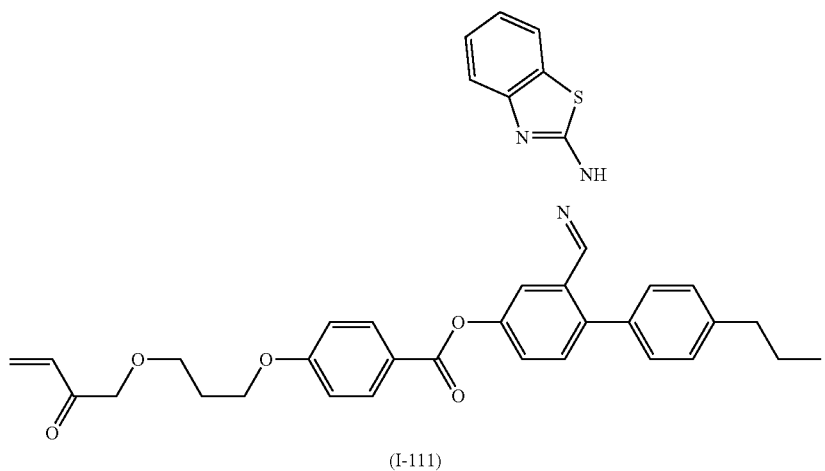

The compound represented by Formula (I-111) was prepared as in Example 7, except that the compound represented by Formula (I-1-3) was replaced with the compound represented by Formula (I-109-1).

Transition temperature (temperature rise: 5° C./min): C 146 N 149 I $^1$H NMR (CDCl$_3$) δ 0.95 (t, 3H), 1.63 (m, 2H), 1.93 (m, 4H), 2.58 (t, 2H), 4.12 (t, 2H), 4.28 (t, 2H), 5.85 (dd, 1H), 6.14 (dd, 1H), 6.43 (dd, 1H), 7.01 (d, 2H), 7.07-7.29 (m, 8H), 7.36 (d, 1H), 7.60 (d, 1H), 7.91 (m, 2H), 8.21 (d, 2H) ppm.

MS (m/z): 634 [M$^+$+1]

Example 22

Production of Compound Represented by Formula (I-112)

[Chem. 94]

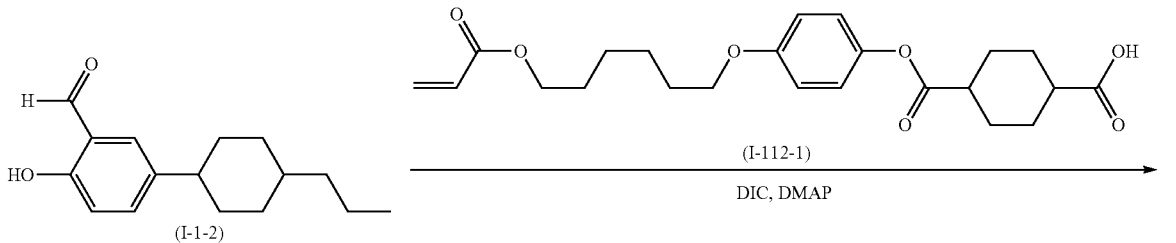

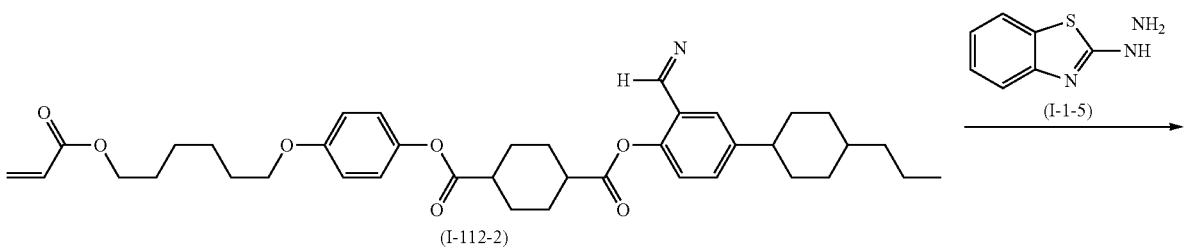

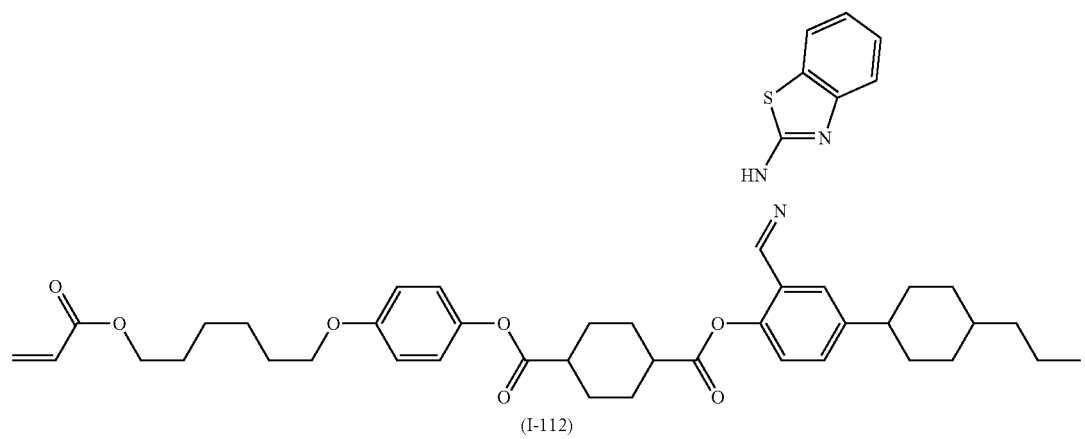

The compound represented by Formula (I-112-1) was prepared by the method described in Japanese Unexamined Patent Application Publication No. 2010-31223. To a reaction container, 2.0 g of the compound represented by Formula (I-1-2), 3.4 g of the compound represented by Formula (I-112-1), 0.4 g of N,N-dimethylaminopyridine, and 30 mL of dichloromethane were added. While ice cooling was performed, 1.3 g of diisopropylcarbodiimide was added dropwise to the reaction container. The resulting mixture was stirred at room temperature. After the precipitate had been removed by filtration, the filtrate was cleaned with hydrochloric acid, water, and a saline solution. Then, purification was performed by column chromatography (silica gel) and recrystallization. Hereby, 3.7 g of the compound represented by Formula (I-112-2) was prepared.

To a reaction container, 3.0 g of the compound represented by Formula (I-112-2), 0.8 g of the compound represented by Formula (I-1-5), 0.3 g of (±)-10-camphorsulfonic acid, 20 mL of tetrahydrofuran, and 20 mL of ethanol were added. After the resulting mixture had been stirred, the solvent was removed by distillation. Subsequently, dispersion cleaning was performed with methanol. Then, purification was performed by column chromatography (silica gel) and recrystallization (dichloromethane/methanol). Hereby, 2.2 g of the compound represented by Formula (I-112) was prepared.

Transition temperature (temperature rise: 5° C./min): C 117 N 220 I $^1$H NMR (CDCl$_3$) δ 0.92 (t, 3H), 1.07 (q, 2H), 1.24-2.06 (m, 27H), 2.35 (m, 2H), 2.55 (t, 1H), 3.95 (t, 2H), 4.18 (t, 2H), 5.83 (dd, 1H), 6.13 (dd, 1H), 6.42 (dd, 1H), 6.88 (d, 2H), 6.98 (m, 3H), 7.19-7.26 (m, 2H), 7.35 (m, 1H), 7.51 (m, 1H), 7.68 (m, 1H), 7.89 (m, 1H), 8.08 (m, 1H) ppm.

MS (m/z): 794 [M$^+$+1]

Example 23

Production of Compound Represented by Formula (I-113)

[Chem. 95]

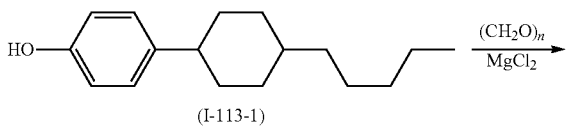

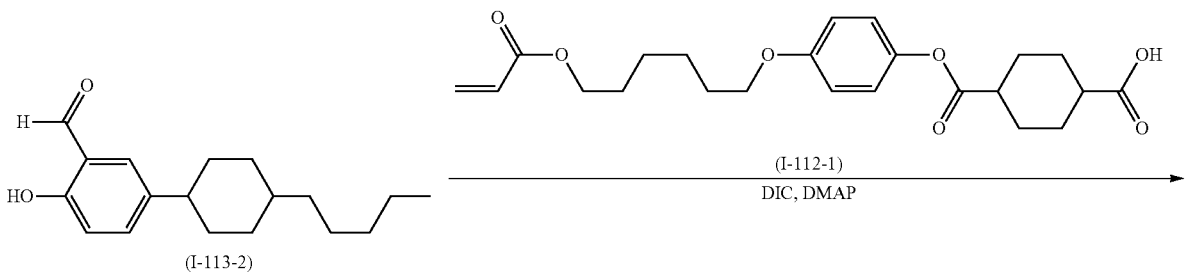

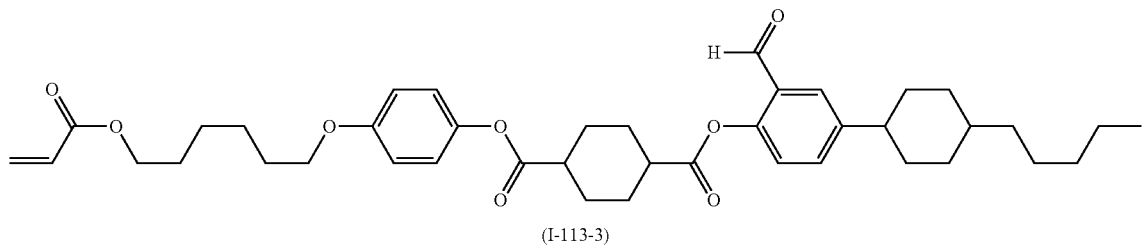

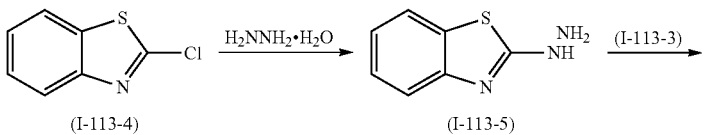

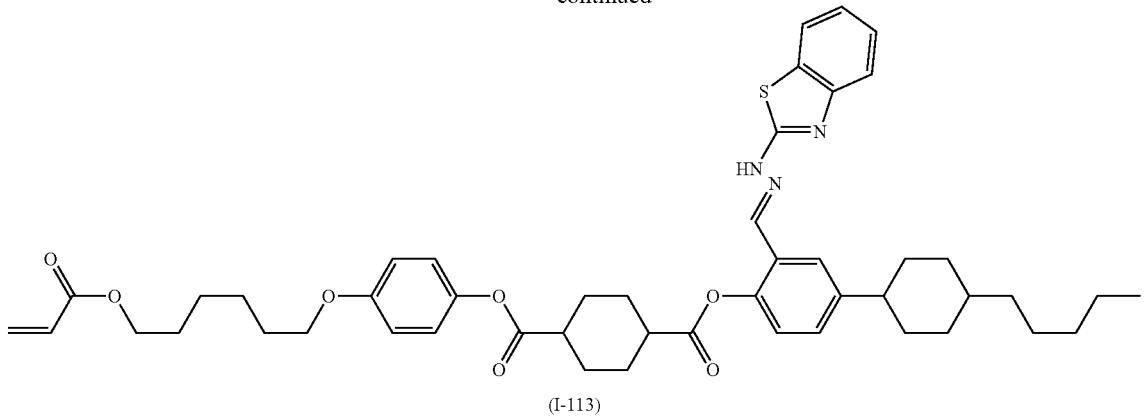

(I-113)

To a reaction container equipped with a cooling unit, 3.0 g of the compound represented by Formula (I-113-1), 1.7 g of magnesium chloride, 1.8 g of para-formaldehyde, 15 mL of triethylamine, and 50 mL of tetrahydrofuran were added. The resulting mixture was heated to reflux while an appropriate amount of para-formaldehyde was added to the reaction container. The resulting reaction liquid was added to hydrochloric acid. Subsequently, extraction with ethyl acetate and cleaning with water and a saline solution were performed. Then, purification was performed by column chromatography (silica gel). Hereby, 2.3 g of the compound represented by Formula (I-113-2) was prepared.

The compound represented by Formula (I-113) was prepared as in Example 22, except that the compound represented by Formula (I-1-2) was replaced with the compound represented by Formula (I-113-2).

Transition temperature (temperature rise: 5° C./min): C 90 S 156 N $^1$H NMR (CDCl$_3$) δ 0.92 (t, 3H), 1.09 (m, 2H), 1.31 (m, 13H), 1.48 (m, 6H), 1.74 (t, 3H), 1.81 (t, 3H), 1.93 (m, 6H), 2.54 (t, 1H), 2.72 (t, 1H), 3.94 (t, 2H), 4.18 (t, 2H), 5.81 (d, 1H), 6.13 (q, 1H), 6.41 (d, 1H), 6.41 (d, 1H), 6.88 (d, 2H), 6.96 (d, 2H), 7.20 (t, 1H), 7.26 (d, 1H), 7.45 (d, 1H), 7.57 (d, 1H), 7.84 (s, 1H), 8.07 (d, 3H) ppm.

MS (m/z): 822 [M$^+$+1]

Example 24

Production of Compound Represented by Formula (I-114)

[Chem. 96]

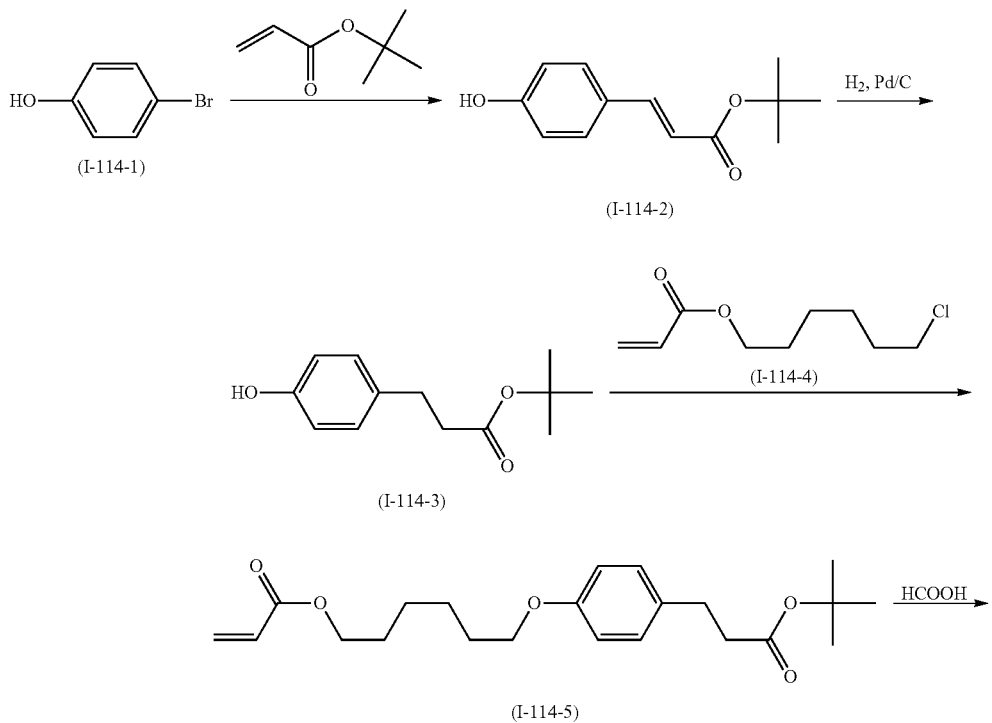

-continued

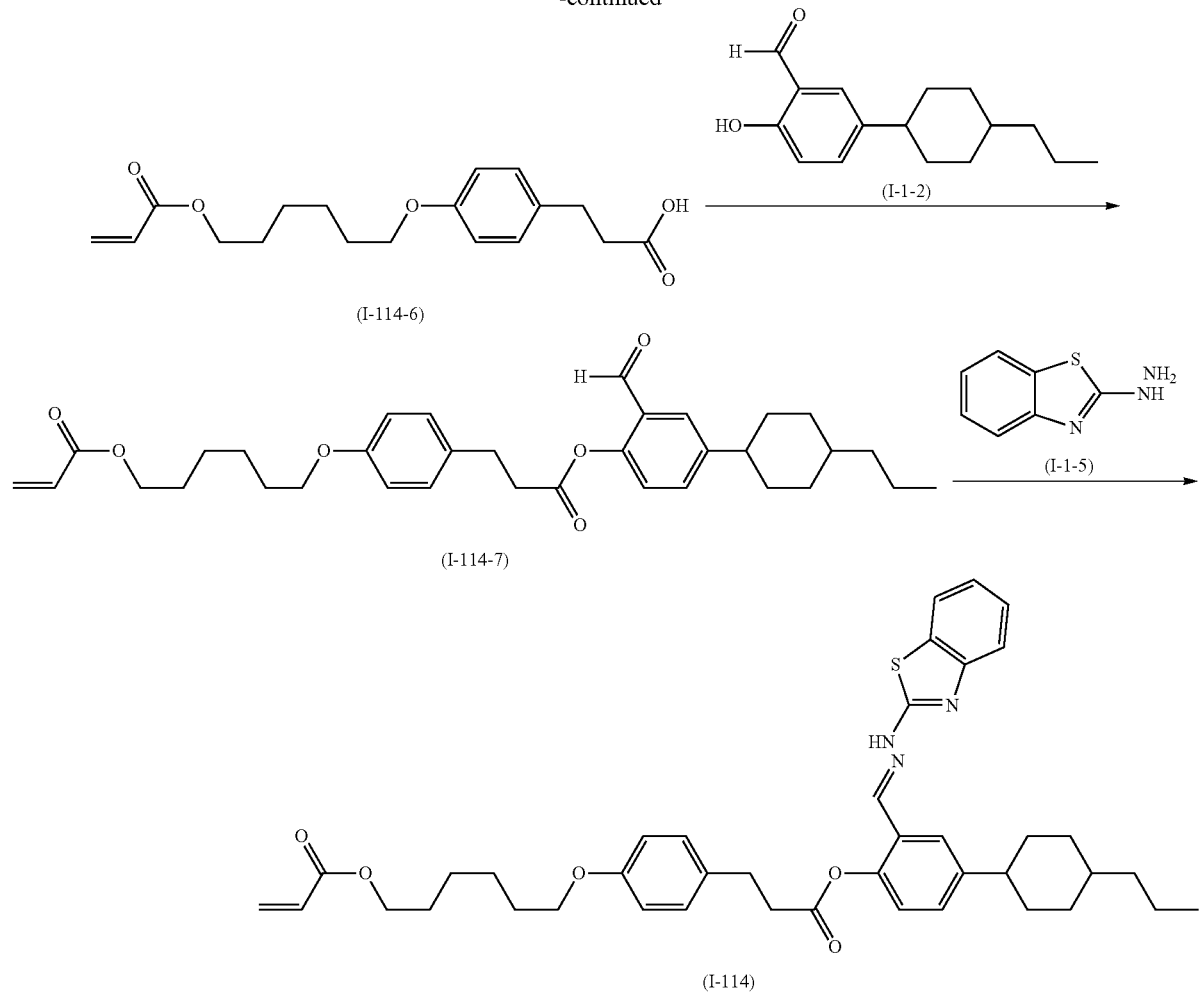

In a nitrogen atmosphere, 5.0 g of the compound represented by Formula (I-114-1), 4.4 g of tert-butyl acrylate, 6.0 g of potassium carbonate, 0.06 g of palladium acetate(II), and 50 mL of N,N-dimethylacetamide were added to a reaction container. The resulting mixture was stirred while being heated at 120° C. After cooling and dilution with ethyl acetate were performed, cleaning was performed with hydrochloric acid, water, and a saline solution. Subsequently, purification was performed by column chromatography (silica gel). Hereby, 5.1 g of the compound represented by Formula (I-114-2) was prepared.

To a reaction container, 5.1 g of the compound represented by Formula (I-114-2), 25 mL of tetrahydrofuran, 25 mL of ethanol, and 0.5 g of palladium 5% on carbon were added. The resulting mixture was stirred with a hydrogen pressure of 0.5 MPa. After the catalyst had been removed by filtration, purification was performed by column chromatography (silica gel). Hereby, 5.1 g of the compound represented by Formula (I-114-3) was prepared.

To a reaction container, 5.1 g of the compound represented by Formula (I-114-3), 4.5 g of the compound represented by Formula (I-114-4), 4.8 g of potassium carbonate, and 30 mL of N,N-dimethylformamide were added. The resulting mixture was stirred while being heated at 80° C. After the resulting mixture had been cooled, dilution with dichloromethane and cleaning with a saline solution were performed. Subsequently, purification was performed by column chromatography (silica gel). Hereby, 7.0 g of the compound represented by Formula (I-114-5) was prepared.

To a reaction container, 7.0 g of the compound represented by Formula (I-114-5), 30 mL of dichloromethane, and 30 mL of formic acid were added. The resulting mixture was stirred while being heated at 40° C. After the solvent had been removed by distillation, purification was performed by column chromatography (silica gel) and recrystallization (ethyl acetate/hexane). Hereby, 5.3 g of the compound represented by Formula (I-114-6) was prepared.

In a nitrogen atmosphere, 3.0 g of the compound represented by Formula (I-114-6), 2.3 g of the compound represented by Formula (I-1-2), 0.5 g of N,N-dimethylaminopyridine, and 30 mL of dichloromethane were added to a reaction container. While ice cooling was performed, 1.4 g of diisopropylcarbodiimide was added dropwise to the reaction container. The resulting mixture was stirred at room temperature. After the precipitate had been removed by filtration, the filtrate was cleaned with hydrochloric acid, water, and a saline solution. Subsequently, purification was performed by column chromatography (silica gel) and recrystallization (dichloromethane/methanol). Hereby, 3.6 g of the compound represented by Formula (I-114-7) was prepared.

To a reaction container, 3.6 g of the compound represented by Formula (I-114-7), 1.1 g of the compound represented by Formula (I-1-5), 0.5 g of (±)-10-camphorsulfonic acid, 20 mL of tetrahydrofuran, and 20 mL of ethanol were added. After the resulting mixture had been stirred, the solvent was removed by distillation and dispersion cleaning was performed with methanol. Subsequently, purification was performed by column chromatography (silica gel) (dichloromethane) and recrystallization (dichloromethane/methanol). Hereby, 2.7 g of the compound represented by Formula (I-114) was prepared.

Transition temperature (temperature rise and fall: 5° C./min): C 128 (N 80) I $^1$H NMR (CDCl$_3$) δ 0.92 (t, 3H), 1.07 (m, 2H), 1.20-1.50 (m, 11H), 1.66 (quin, 2H), 1.78 (quin, 2H), 1.89 (m, 4H), 2.51 (tt, 1H), 2.73 (t, 2H), 2.91 (t, 2H), 3.95 (t, 2H), 4.14 (t, 2H), 5.81 (dd, 1H), 6.12 (dd, 1H), 6.39 (dd, 1H), 6.85 (d, 2H), 6.93 (d, 1H), 7.09 (d, 2H), 7.14 (t, 1H), 7.21 (dd, 1H), 7.33 (t, 1H), 7.54 (d, 1H), 7.58 (s, 1H), 7.66 (d, 1H), 7.80 (d, 1H) ppm.

MS (m/z): 696 [M$^+$+1]

Example 25

Production of Compound Represented by Formula (I-115)

[Chem. 97]

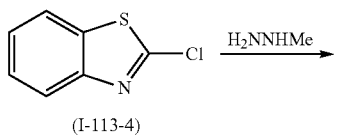

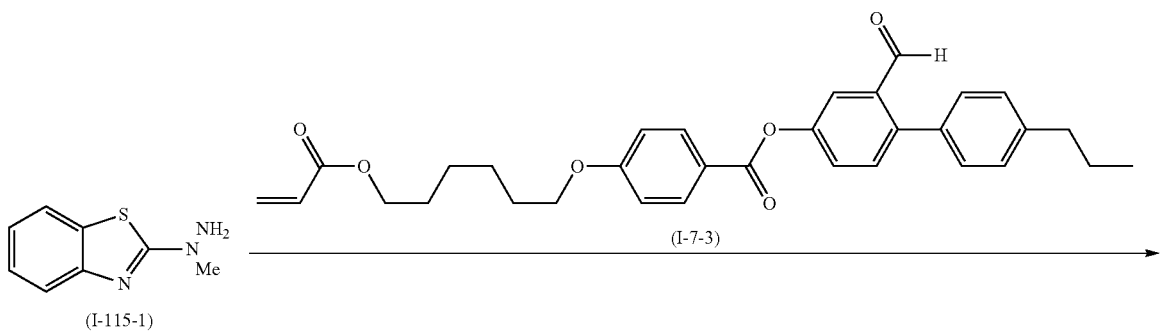

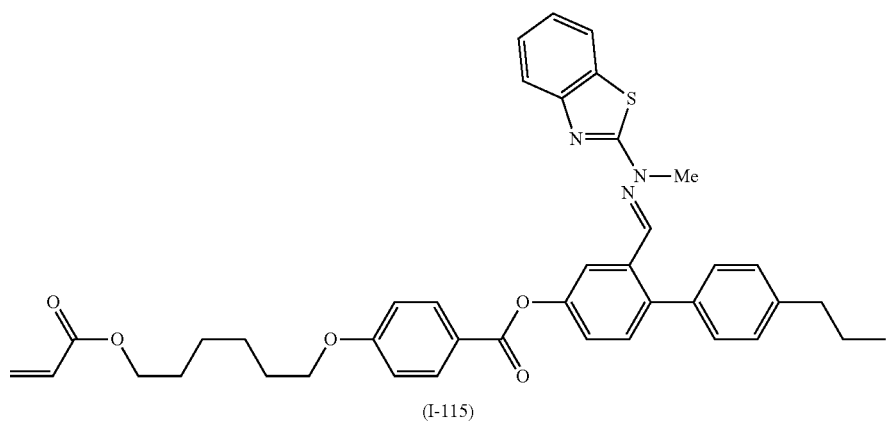

In a nitrogen atmosphere, 3.0 g of the compound represented by Formula (I-113-4), 20 mL of 1,2-dimethoxyethane, and 2.0 g of triethylamine were added to a reaction container. To the reaction container, 0.8 g of methyl hydrazine was added dropwise. The resulting mixture was stirred while being heated at 60° C. Then, dilution with dichloromethane and cleaning with a saline solution were performed. Subsequently, purification was performed by column chromatography (alumina). Hereby, 2,2 g of the compound represented by Formula (I-115-1) was prepared.

To a reaction container, 2.5 g of the compound represented by Formula (I-7-3), 0.9 g of the compound represented by Formula (I-115-1), 0.4 g of (±)-10-camphorsulfonic acid, 10 mL of tetrahydrofuran, and 10 mL of ethanol were added. After the resulting mixture had been stirred while being heated at 50° C., the solvent was removed by distillation and dispersion cleaning was performed with methanol. Subsequently, purification was performed by column chromatography (silica gel) and recrystallization (dichloromethane/methanol). Hereby, 1.9 g of the compound represented by Formula (I-114) was prepared.

Transition temperature (temperature rise and fail: 5° C./min): C 128 (N 80) I $^1$H NMR (CDCl$_3$) δ 1.00 (t, 3H), 1.47-1.60 (m, 4H), 1.73 (m, 4H), 1.87 (quin, 2H), 2.67 (t, 2H), 3.55 (s, 3H),4.08 (t, 2H), 4.20 (t, 2H), 5.84 (dd, 1H), 6.14 (dd, 1H), 6.42 (dd, 1H), 7.02 (d, 2H), 7.13 (t, 1H), 7.25-7.33 (m, 6H), 7.39 (d, 1H), 7.62 (dd, 2H), 7.69 (s, 1H), 7.93 (d, 1H), 8.22 (d, 2H) ppm.

MS (m/z): 696 [M$^+$+1]

Example 26

Production of Compound Represented by Formula (I-116)

[Chem. 98]

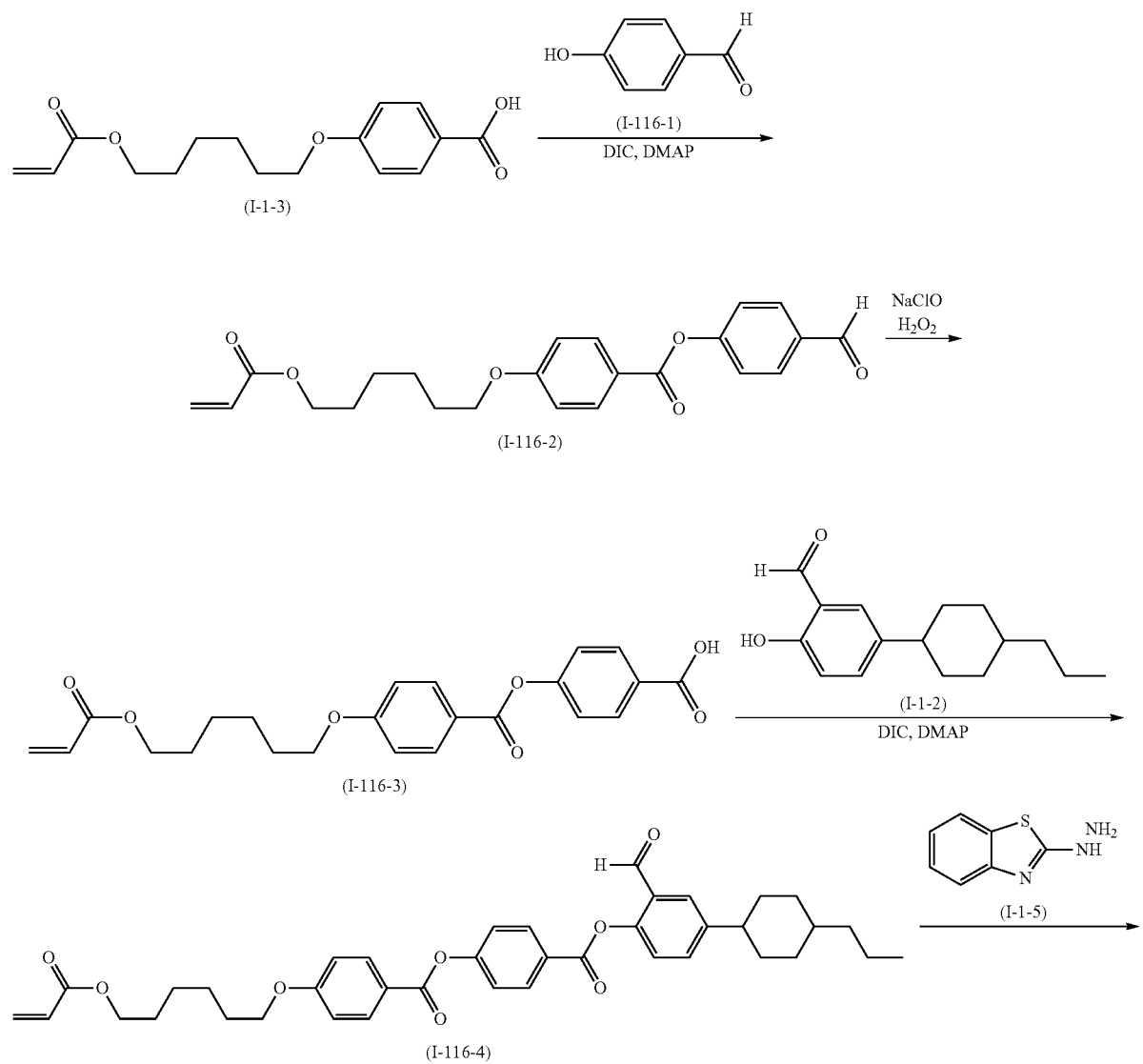

-continued

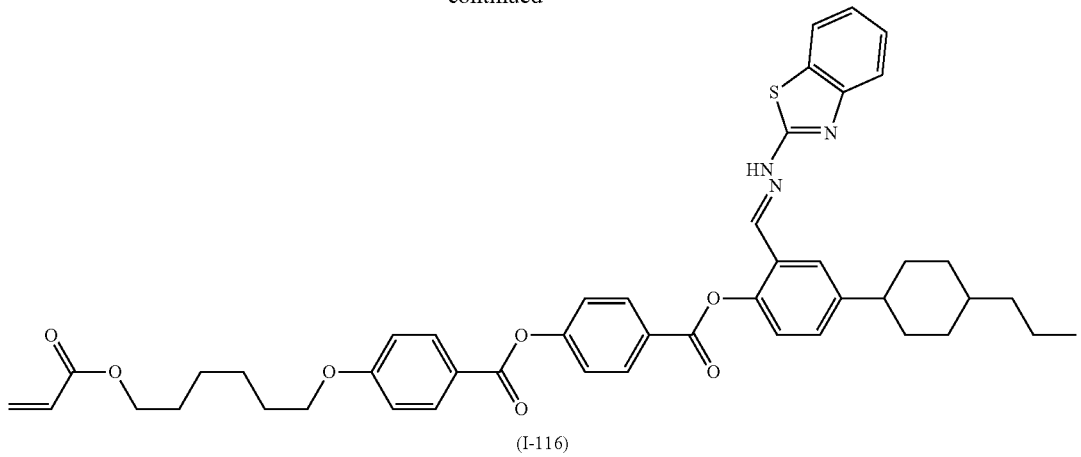

(I-116)

In a nitrogen atmosphere, 4.0 g of the compound represented by Formula (I-1-3), 1.7 g of the compound represented by Formula (I-116-1), 0.3 g of N,N-dimethylaminopyridine, and 30 mL of dichloromethane were added to a reaction container. While ice cooling was performed, 2.1 g of diisopropylcarbodiimide was added dropwise to the reaction container. The resulting mixture was stirred at room temperature. After the precipitate had been removed by filtration, the filtrate was cleaned with hydrochloric acid, water, and a saline solution. Subsequently, purification was performed by column chromatography (silica gel) and recrystallization (dichloromethane/methanol). Hereby, 4.3 g of the compound represented by Formula (I-116-2) was prepared.

To a reaction container, 4.3 g of the compound represented by Formula (I-116-2), 30 mL of methanol, 10 mL of water, 5.0 g of sodium dihydrogen phosphate dihydrate, and 30 mL of 30%-hydrogen peroxide water were added. An aqueous sodium chlorite solution was added dropwise to the reaction container. The resulting mixture was stirred while being heated at 40° C. Then, water was added to the reaction container and cooling was performed. The resulting solid was removed by filtration and cleaning was performed. Subsequently, drying was performed. Hereby, 4.1 g of the compound represented by Formula (I-116-3) was prepared.

In a nitrogen atmosphere, 4.1 g of the compound represented by Formula (I-116-3), 2.4 g of the compound represented by Formula (I-1-2), 0.2 g of N,N-dimethylaminopyridine, and 40 mL of dichloromethane were added to a reaction container. While ice cooling was performed, 1.5 g of diisopropylcarbodiimide was added dropwise to the reaction container. The resulting mixture was stirred at room temperature. After the precipitate had been removed by filtration, the filtrate was cleaned with hydrochloric acid, water, and a saline solution. Subsequently, purification was performed by column chromatography (silica gel) and recrystallization (dichloromethane/methanol). Hereby, 5.0 g of the compound represented by Formula (I-116-4) was prepared.

To a reaction container, 3.0 g of the compound represented by Formula (I-116-4), 0.8 g of the compound represented by Formula (I-1-5), 0.2 g of (±)-10-camphorsulfonic acid, 20 mL of tetrahydrofuran, and 10 mL of ethanol were added. After the resulting mixture had been stirred, the solvent was removed by distillation and dispersion cleaning was performed with methanol. Subsequently, purification was performed by column chromatography (silica gel) and recrystallization (dichloromethane/methanol). Hereby, 2.5 g of the compound represented by Formula (I-116) was prepared.

Transition temperature (temperature rise: 5° C./min): C 64-77 N>220 I $^1$H NMR (CDCl$_3$) δ 0.92 (t, 3H), 1.07 (q, 2H), 1.23 (m, 2H), 1.37 (m, 3H), 1.48-1.60 (m, 6H), 1.74 (quin, 2H), 1.33-1.90 (m, 4H), 1.97 (d, 2H), 2.56 (tt, 1H), 4.07 (t, 2H), 4.19 (t, 2H), 5.83 (dd, 1H), 6.13 (dd, 1H), 6.42 (dd, 1H), 7.00 (d, 2H), 7.11 (q, 1H), 7.12 (d, 1H), 7.19-7.31 (m, 4H), 7.46 (d, 1H), 7.61 (d, 1H), 7.85 (d, 1H), 8.09 (s, 1H), 8.17 (m, 4H) ppm.

MS (m/z): 788 [M$^+$+1]

Example 27

Production of Compound Represented by Formula (I-117)

[Chem. 99]

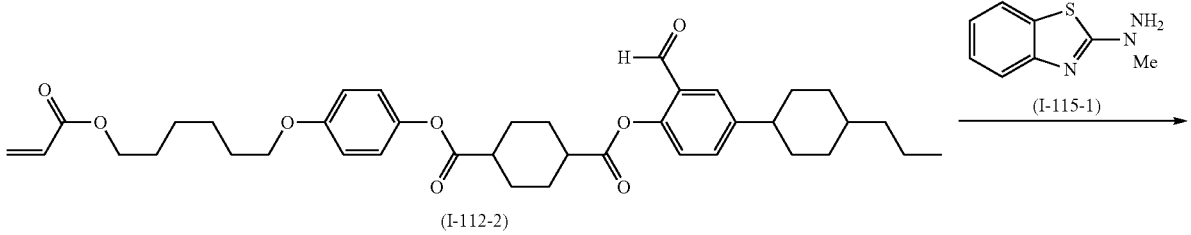

(I-112-2) (I-115-1)

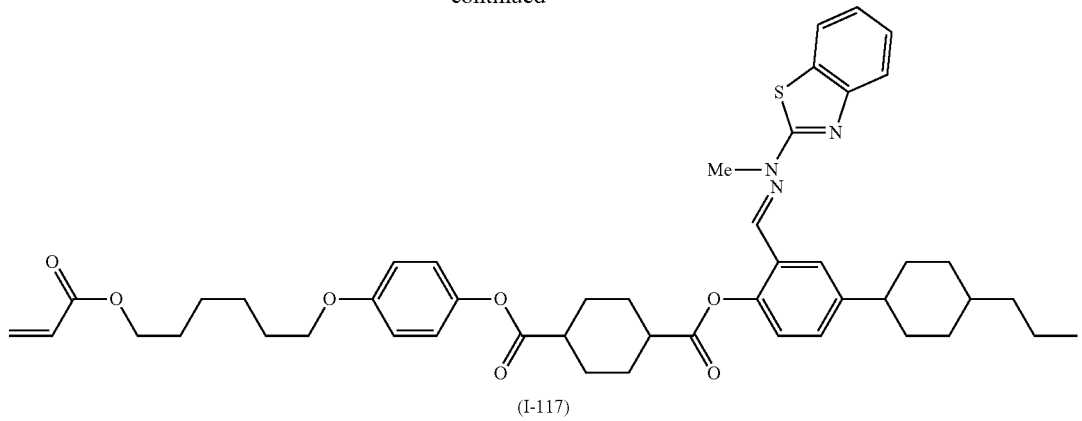

(I-117)

To a reaction container, 2.5 g of the compound represented by Formula (I-112-2), 0.7 g of the compound represented by Formula (I-115-1), 0.2 g of (±)-10-camphorsulfonic acid, 20 mL of tetrahydrofuran, and 10 mL of ethanol were added. After the resulting mixture had been stirred while being heated at 50° C., the solvent, was removed by distillation and dispersion cleaning was performed with methanol. Subsequently, purification was performed by column chromatography (silica gel) and recrystallization (dichloromethane/methanol). Hereby, 2.2 g of the compound represented by Formula (I-117) was prepared. Transition temperature (temperature rise: 5° C./min): C 147-156 N 173 I $^1$H NMR (CDCl$_3$) δ 0.92 (t, 3H), 1.11 (q, 2H), 1.25 (m, 2H), 1.37-1.55 (m, 9H), 1.71 (m, 6H), 1.78 (m, 2H), 1.94 (m, 4H), 2.33 (m, 4H), 2.56 (m, 2H), 2.70 (m, 1H), 3.72 (s, 3H), 3.94 (t, 2H), 4.17 (t, 2H), 5.82 (dd, 1H), 6.13 (dd, 1H), 6.40 (dd, 1H), 6.83 (d, 2H), 6.98 (m, 3H), 7.17 (t, 1H), 7.24 (dd, 1H), 7.35 (t, 1H), 7.66-7.72 (m, 3H), 7.88 (d, 1H) ppm.

MS (m/z): 808 [M$^+$+1]

Example 28

Production of Compound Represented by Formula (I-118)

[Chem. 100]

-continued

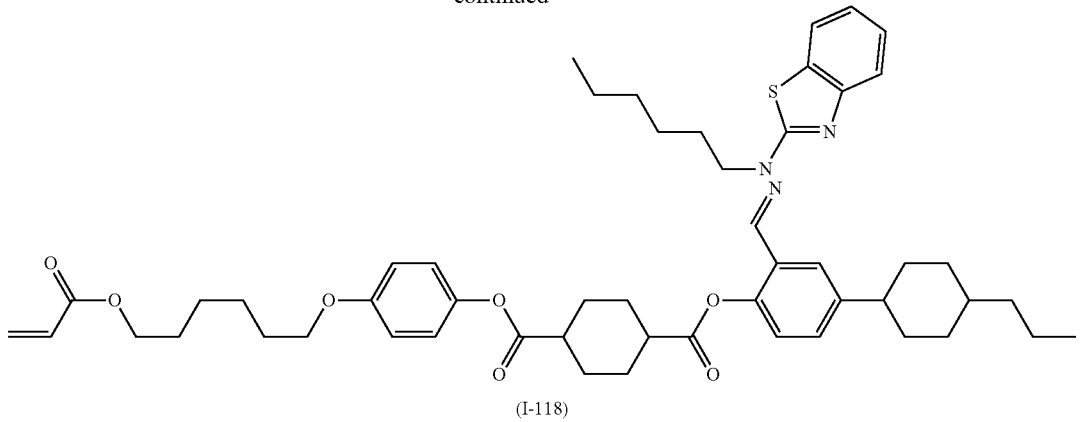

(I-118)

In a nitrogen atmosphere, 50 mL of hydrazine monohydrate and 50 mL of ethanol were added to a reaction container. To the reaction container, an ethanol solution containing 5.0 g of the compound represented by Formula (I-118-1) was added dropwise. The resulting mixture was stirred while being heated at 50° C. Then, dilution with dichloromethane and cleaning with water and a saline solution were performed. After drying had been performed with sodium sulfate, the solvent was removed by distillation. Hereby, 2.8 g of the compound represented by Formula (I-118-2) was prepared.

In a nitrogen atmosphere, 4.1 g of the compound represented by Formula (I-113-4), 20 mL of 1,2-dimethoxyethane, and 10 mL of triethylamine were added to a reaction container. To the reaction container, 2.8 g of the compound represented by Formula (I-113-2) was added dropwise. The resulting mixture was stirred while being heated at 50° C. The resulting reaction liquid was added to water, and the precipitated solid was cleaned with water and hexane. Hereby, 3.0 g of the compound represented by Formula (I-118-3) was prepared.

To a reaction container, 1.0 g of the compound represented by Formula (I-118-3), 2.6 g of the compound represented by Formula (I-112-2), 0.6 g of (±)-10-camphorsulfonic acid, 20 mL of tetrahydrofuran, and 10 mL of ethanol were added. After the resulting mixture had been stirred while being heated at 50° C., the solvent was removed by distillation and dispersion cleaning was performed with methanol. Subsequently, purification was performed by column chromatography (silica gel) and recrystallization (dichloromethane/methanol). Hereby, 2.5 g of the compound represented by Formula (I-118) was prepared. Transition temperature (temperature rise: 5° C./min): C 117-122 N 146 I $^1$H NMR (CDCl$_3$) δ 0.91 (m, 6H), 1.10 (q, 2H), 1.23-1.56 (m, 18H), 1.68-1.81 (m, 9H), 1.94 (t, 4H), 2.32 (m, 4H), 2.56-2.70 (m, 3H), 3.94 (t, 2H), 4.18 (t, 2H), 4.29 (t, 2H), 5.82 (dd, 1H), 6.13 (dd, 1H), 6.40 (dd, 1H), 6.89 (d, 2H), 6.99 (m, 3H), 7.16 (t, 1H), 7.23 (dd, 1H), 7.34 (t, 1H), 7.66-7.72 (m, 3H), 7.90 (d, 1H) ppm.

MS (m/z): 878 [M$^+$+1]

Example 29

Production of Compound Represented by Formula (I-119)

[Chem. 101]

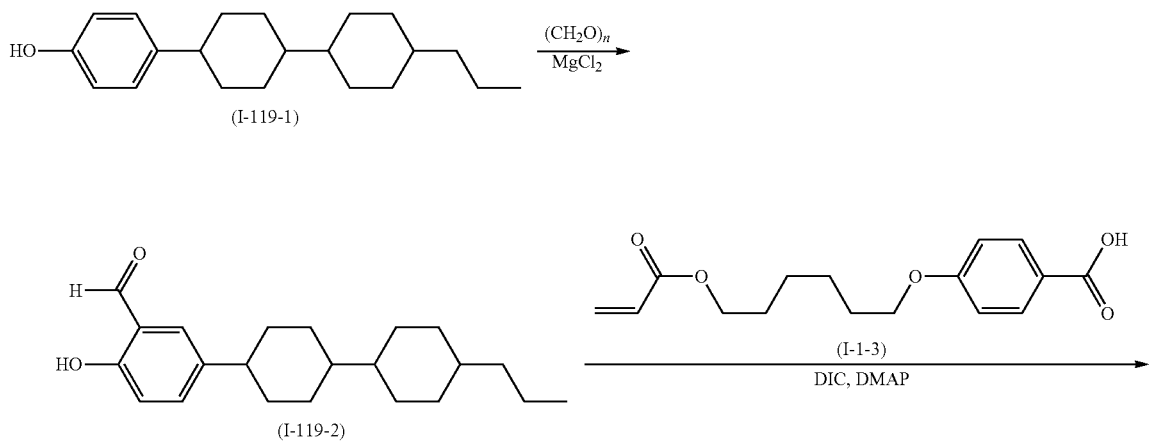

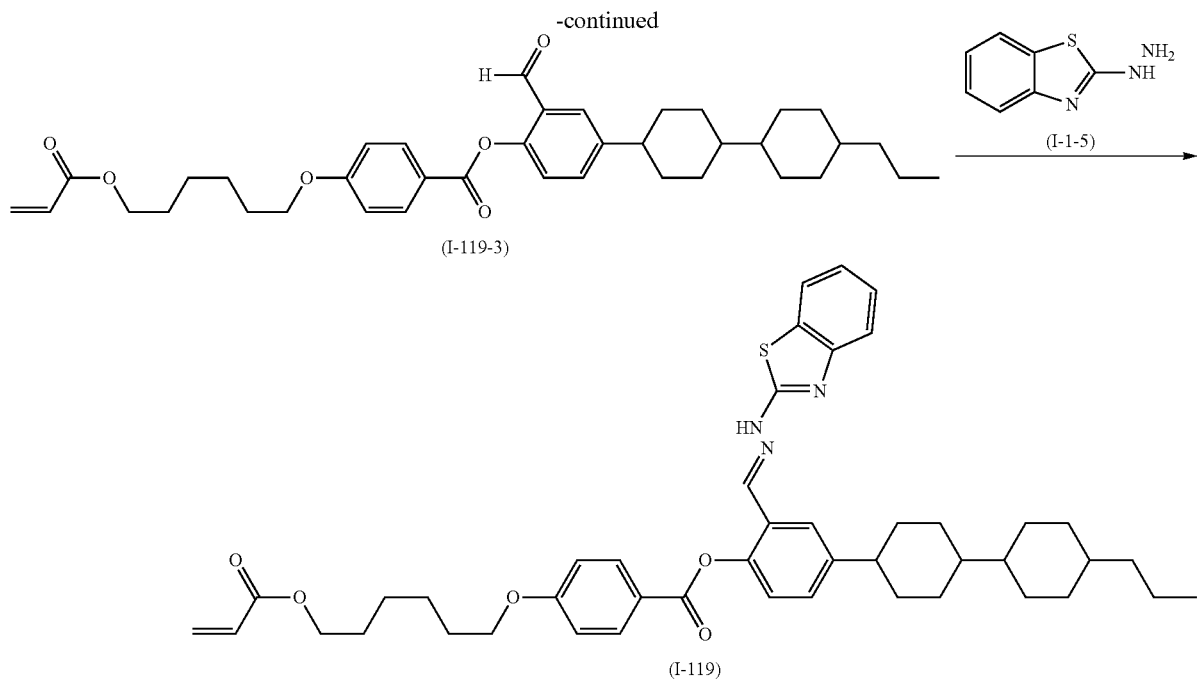

The compound represented by Formula (I-119) was prepared as in Example 1, except that the compound represented by Formula (I-1-1) was replaced with the compound represented by Formula (I-119-1).

Transition temperature (temperature rise: 5° C./min): C 190 N 260 I $^1$H NMR (CDCl$_3$) δ 0.89 (t, 1H), 1.05 (t, 2H), 1.31 (q, 2H), 1.50 (m, 6H), 1.74, (m, 15H), 2.54 (t, 1H), 4.03 (t, 2H), 4.19 (t, 2H), 5.81 (d, 1H), 6.13 (q, 1H), 6.41 (d, 1H), 6.43 (d, 1H), 7.09 (d, 2H), 7.11 (d, 2H), 7.20 (t, 1H), 7.26 (d, 1H), 7.45 (d, 1H), 7.57 (d, 1H), 7.84 (s, 1H), 8.07 (d, 3H) ppm.

MS (m/z): 750 [M$^+$+1]

Example 30

Production of Compound Represented by Formula (I-120)

[Chem. 102]

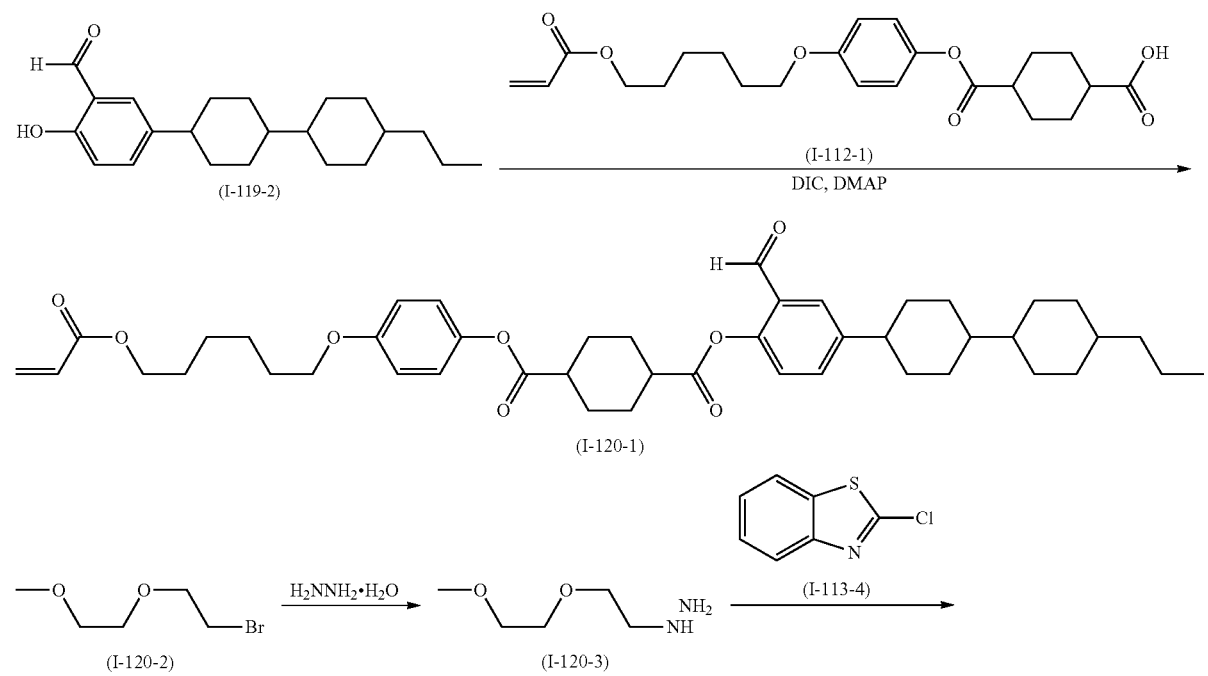

-continued

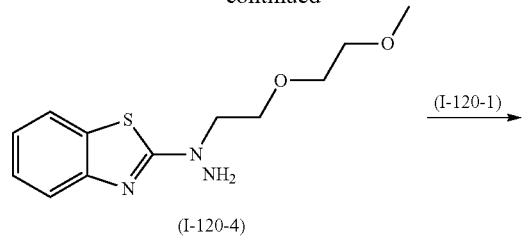
(I-120-4)

(I-120-1) →

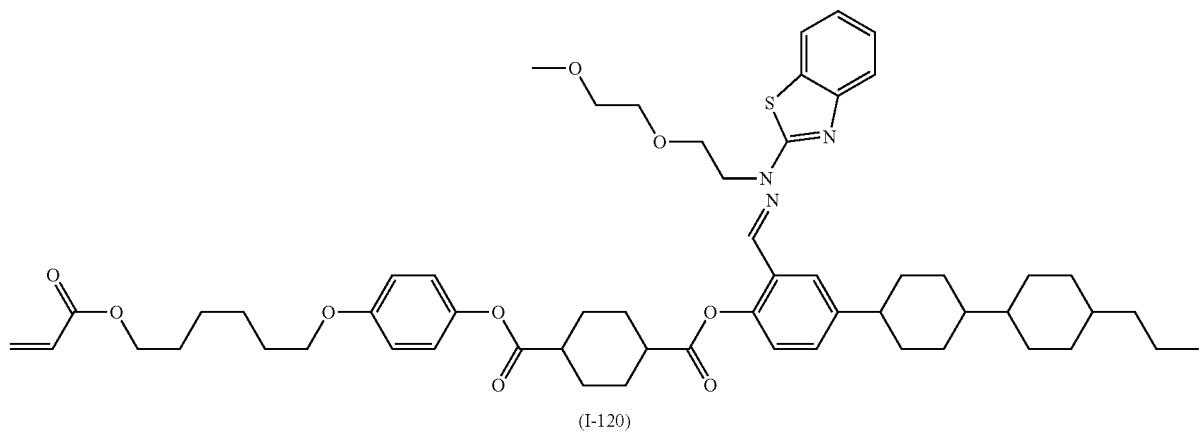
(I-120)

The compound represented by Formula (I-112-1) was prepared by the method described in Japanese Unexamined Patent Application Publication No. 2010-31223. To a reaction container, 2.0 g of the compound represented by Formula (I-119-2), 2.5 g of the compound represented by Formula (I-112-1), 0.4 g of N,N-dimethylaminopyridine, and 30 mL of dichloromethane were added. While ice cooling was performed, 0.9 g of diisopropylcarbodiimide was added dropwise to the reaction container. The resulting mixture was stirred at room temperature. After the precipitate had been removed by filtration, the filtrate was cleaned with hydrochloric acid, water, and a saline solution. Subsequently, purification was performed by column chromatography (silica gel) and recrystallization (dichloromethane/hexane). Hereby, 3.5 g of the compound represented by Formula (I-120-1) was prepared.

In a nitrogen atmosphere, 30 mL of hydrazine monohydrate and 30 mL of ethanol were added to a reaction container. To the reaction container, an ethanol solution containing 7.0 g of the compound represented by Formula (I-120-2) was added dropwise. The resulting mixture was stirred while being heated at 50° C. Then, the solvent was removed by distillation. Hereby, a mixture containing the compound represented by Formula (I-120-3) was prepared.

In a nitrogen atmosphere, 6.4 g of the compound represented by Formula (I-113-4), 30 mL of 1,2-dimethoxyethane, and 10 mL of triethylamine were added to a reaction container. To the resulting mixture, the mixture including the compound represented by Formula (I-120-3) was added. The resulting mixture was stirred while being heated at 50° C. The resulting reaction liquid was added to water, and the precipitated solid was cleaned with water and hexane. Hereby, 6.1 g of the compound represented by Formula (I-120-4) was prepared.

To a reaction container, 2.5 g of the compound represented by Formula (I-120-1), 0.9 g of the compound represented by Formula (I-120-4), 0.3 g of (±)-10-camphorsulfonic acid, 50 mL of tetrahydrofuran, and 20 mL of ethanol were added. After the resulting mixture had been stirred while being heated at 50° C., the solvent was removed by distillation and dispersion cleaning was performed with methanol. Subsequently, purification was performed by column chromatography (silica gel) and recrystallization (dichloromethane/methanol). Hereby, 2.0 g of the compound represented by Formula (I-120) was prepared.

$^1$H NMR (CDCl$_3$) δ 0.92 (t, 3H), 1.05-1.83 (m, 32H), 1.93 (t, 5H), 2.33 (m, 4H), 2.55 (m, 2H), 2.71 (m, 1H), 3.30 (s, 3H), 3.62 (m, 2H), 3.85 (t, 2H), 3.94 (t, 2H), 4.17 (t, 2H), 4.48 (t, 2H), 5.82 (dd, 1H), 6.12 (dd, 1H), 6.40 (dd, 1H), 6.88 (d, 2H), 6.99 (m, 3H), 7.17 (t, 1H), 7.23 (dd, 1H), 7.34 (t, 1H), 7.66 (d, 1H), 7.71 (d, 1H), 7.89 (d, 1H), 8.02 (s, 1H) ppm.

MS (m/z): 978 [M$^+$+1]
Example 31
Production of Compound Represented by Formula (I-122)
[Chem. 103]
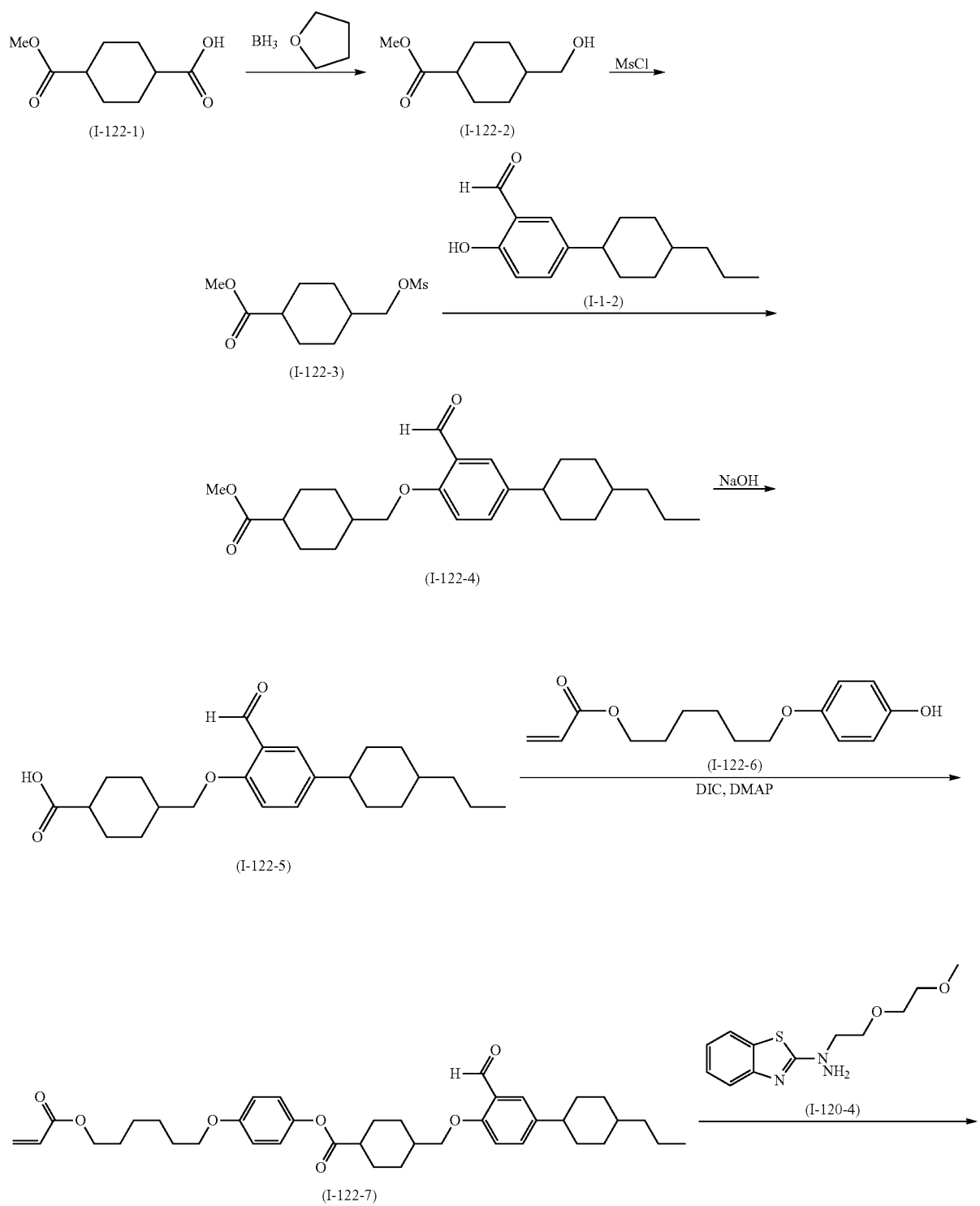

-continued

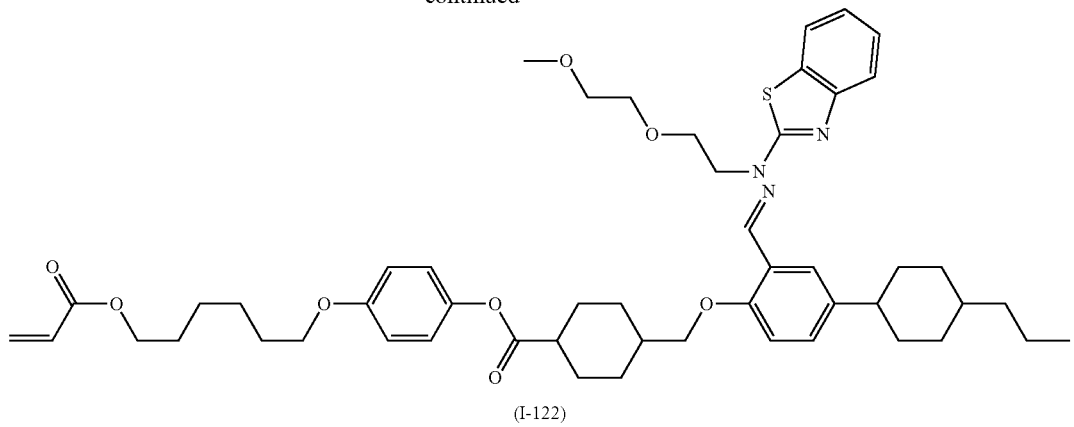

(I-122)

In a nitrogen atmosphere, 20.0 g of the compound represented by Formula (I-122-1) and 120 mL of tetrahydrofuran were added to a reaction container. While ice cooling was performed, 143 mL of borane-tetrahydrofuran complex (0.9 mol/L) was added dropwise to the reaction container. The resulting mixture was stirred for 2 hours. After the mixture had been added to 200 mL of 5%-hydrochloric acid, liquid separation was performed using 200 mL of ethyl acetate. Then, drying was performed with sodium sulfate and the solvent was subsequently removed by distillation. Hereby, 17.6 g of the compound represented by Formula (I-122-2) was prepared.

In a nitrogen atmosphere, 17.6 g of the compound represented by Formula (I-122-2), 12.1 g of pyridine, and 100 mL of dichloromethane were added to a reaction container. While ice cooling was performed, 12.9 g of methanesulfonyl chloride was added dropwise to the reaction container. The resulting mixture was stirred at room temperature for 8 hours. After the mixture had been added to 5%-hydrochloric acid, liquid separation was performed. Subsequently, purification was performed by column chromatography (silica gel). Hereby, 23.0 g of the compound represented by Formula (I-122-3) was prepared.

To a reaction container, 4.0 g of the compound represented by Formula (I-122-3), 3.9 g of the compound represented by Formula (I-1-2), 3.5 g of potassium carbonate, and 30 mL of N,N-dimethylformamide were added. The resulting mixture was stirred for 12 hours while being heated at 90° C. Then, dilution with dichloromethane and cleaning with water and a saline solution were performed. Subsequently, purification was performed by column chromatography (silica gel) and recrystallization. Hereby, 5.1 g of the compound represented by Formula (I-122-4) was prepared.

To a reaction container, 5.1 g of the compound represented by Formula (I-122-4), 30 mL of tetrahydrofuran, 30 mL of methanol, and 10 mL of a 25%-aqueous sodium hydroxide solution were added. The resulting mixture was stirred at 60° C. To the reaction container, hydrochloric acid was added. Subsequently, the solvent was removed by distillation. Then, cleaning with water and drying were performed. Hereby, 4.9 g of the compound represented by Formula (I-122-5) was prepared.

In a nitrogen atmosphere, 4.9 g of the compound represented by Formula (I-122-5), 3.4 g of the compound represented by Formula (I-122-6), 0.1 g of N,N-dimethylaminopyridine, and 40 mL of dichloromethane were added to a reaction container. While ice cooling was performed, 1.6 g of diisopropylcarbodiimide was added dropwise to the reaction container. The resulting mixture was stirred. Then, purification was performed by column chromatography (silica gel) and recrystallization. Hereby, 5.7 g of the compound represented by Formula (I-122-7) was prepared.

To a reaction container, 2.5 g of the compound represented by Formula (I-122-7), 1.1 g of the compound represented by Formula (I-120-4), 0.5 g of (±)-10-camphorsulfonic acid, 10 mL of tetrahydrofuran, and 10 mL of ethanol were added. After the resulting mixture had been stirred while being heated at 50° C., the solvent was removed by distillation and dispersion cleaning was performed with methanol. Then, purification was performed by column chromatography (silica gel) and recrystallization. Hereby, 2.1 g of the compound represented by Formula (I-122) was prepared.

Transition temperature (temperature rise: 5° C./min, temperature fall: 5° C./min): C 101-105 (N 82) I $^1$H NMR (CDCl$_3$) δ 0.92 (t, 3H), 1.08-1.91 (m, 26H), 2.06 (d, 2H), 2.24 (d, 2H), 2.51 (m, 2H), 3.30 (s, 3H), 3.51 (dd, 2H), 3.67 (dd, 2H), 3.87 (quin, 4H), 3.94 (t, 2H), 4.17 (t, 2H), 4.54 (t, 2H), 5.82 (dd, 1H), 6.12 (dd, 1H), 6.40 (dd, 1H), 6.86 (m, 3H), 6.97 (m, 2H), 7.16 (m, 2H), 7.32 (t, 1H), 7.65 (d, 1H), 7.70 (d, 1H), 7.82 (d, 1H), 8.36 (s, 1H) ppm.

Example 32

Production of Compound Represented by Formula (I-126)

[Chem. 104]

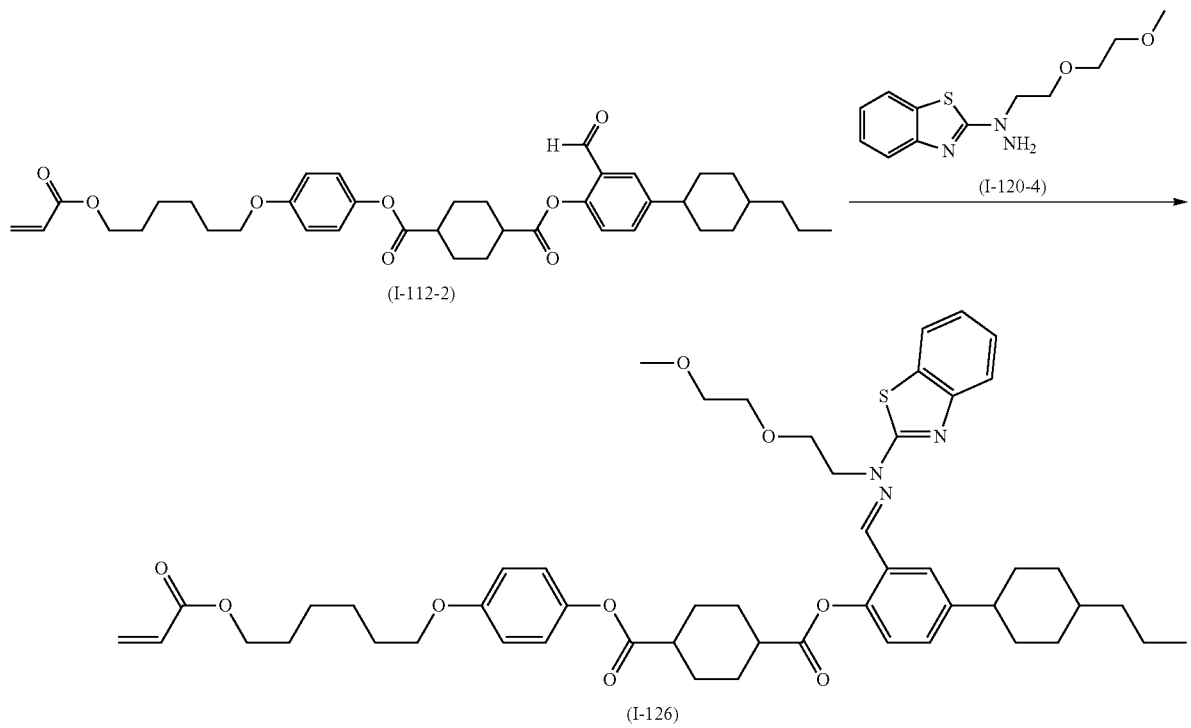

To a reaction container, 2.5 g of the compound represented by Formula (I-112-2), 1.0 g of the compound represented by Formula (I-120-4), 0.5 g of (±)-10-camphorsulfonic acid, 10 mL of tetrahydrofuran, and 10 mL of ethanol were added. After the resulting mixture had been stirred while being heated at 50° C., the solvent was removed by distillation and dispersion cleaning was performed with methanol. Subsequently, purification was performed by column chromatography (silica gel) and recrystallization. Hereby, 2.0 g of the compound represented by Formula (I-126) was prepared.

Transition temperature (temperature rise: 5° C./min): C 106 N 125 I $^1$H NMR (CDCl$_3$) δ 0.92 (t, 3H), 1.05-1.83 (m, 22H), 1.93 (t, 5H), 2.33 (m, 4H), 2.55 (m, 2H), 2.71 (m, 1H), 3.30 (s, 3H), 3.62 (m, 2H), 3.85 (t, 2H), 3.94 (t, 2H), 4.17 (t, 2H), 4.48 (t, 2H), 5.82 (dd, 1H), 6.12 (dd, 1H), 6.40 (dd, 1H), 6.88 (d, 2H), 6.99 (m, 3H), 7.17 (t, 1H), 7.23 (dd, 1H), 7.34 (t, 1H), 7.66 (d, 1H), 7.71 (d, 1H), 7.89 (d, 1H), 8.02 (s, 1H) ppm.

Example 33

Production of Compound Represented by Formula (I-127)

[Chem. 105]

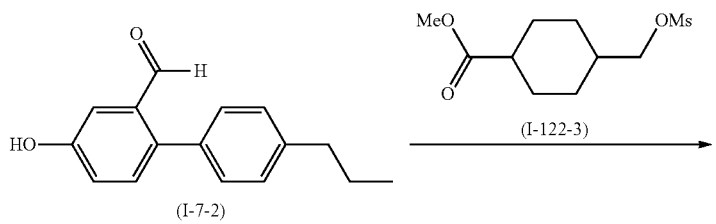

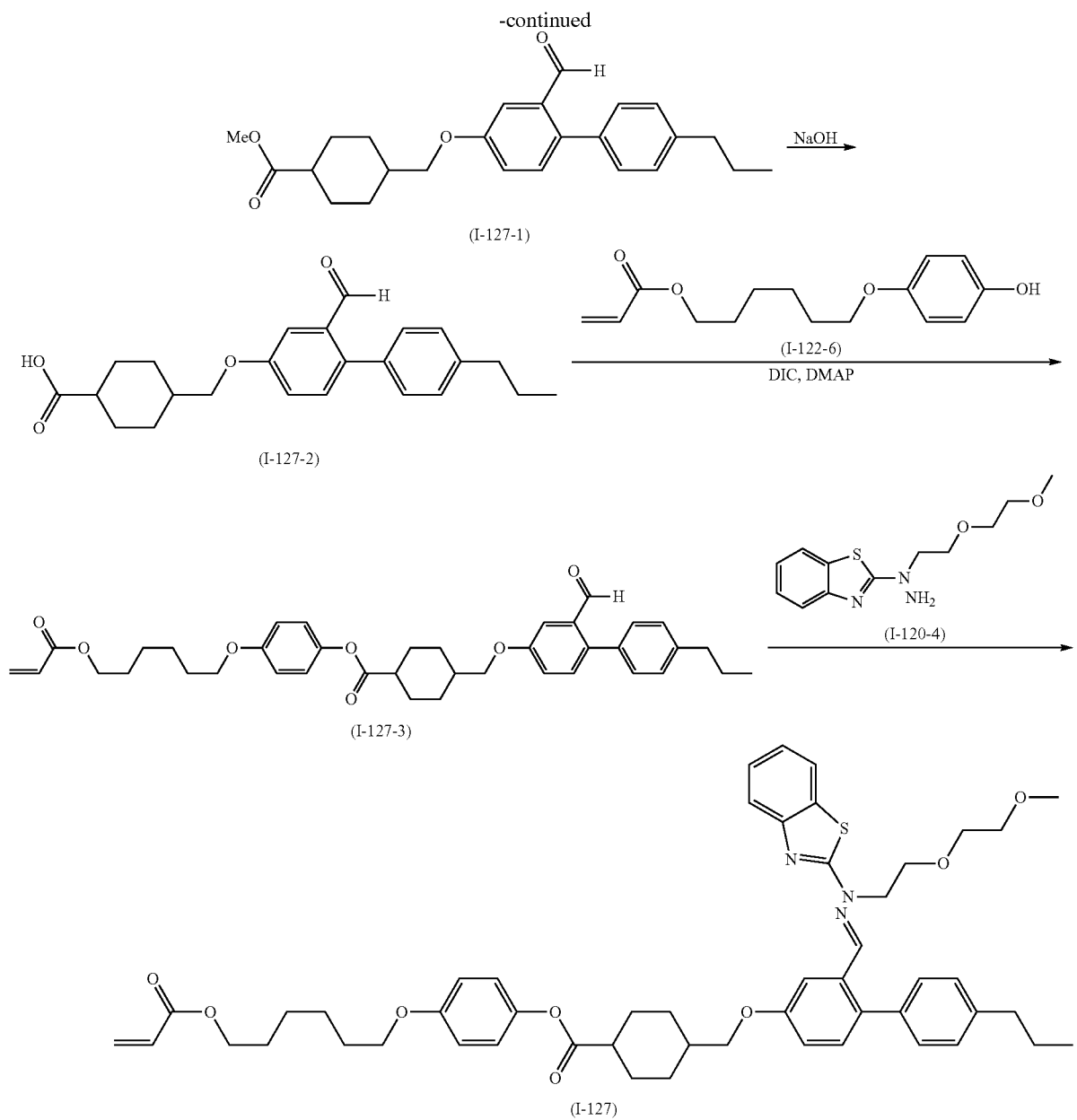

To a reaction container, 4.0 g of the compound represented by Formula (I-7-2), 4.2 g of the compound represented by Formula (I-122-3), 3.5 g of potassium carbonate, and 30 mL of N,N-dimethylformamide were added. The resulting mixture was stirred for 12 hours while being heated at 90° C. Then, dilution with dichloromethane and cleaning with water and a saline solution were performed. Subsequently, purification was performed by column chromatography (silica gel) and recrystallization. Hereby, 4.6 g of the compound represented by Formula (I-127-1) was prepared.

To a reaction container, 4.6 g of the compound represented by Formula (I-127-4), 30 mL of tetrahydrofuran, 30 mL of methanol, and 10 mL of a 25%-aqueous sodium hydroxide solution were added. The resulting mixture was stirred at 60° C. Hydrochloric acid was added to the reaction container, and the solvent was then removed by distillation. Subsequently, cleaning with water and drying were performed. Hereby, 4.4 g of the compound represented by Formula (I-127-2) was prepared.

In a nitrogen atmosphere, 4.4 g of the compound represented by Formula (I-127-2), 3.1 g of the compound represented by Formula (I-122-6), 0.1 g of N,N-dimethylaminopyridine, and 40 mL of dichloromethane were added to a reaction container. While ice cooling was performed, 1.8 g of diisopropylcarbodiimide was added dropwise to the reaction container. The resulting mixture was stirred. Subsequently, purification was performed by column chromatography (silica gel) and recrystallization. Hereby, 5.1 g of the compound represented by Formula (I-127-3) was prepared.

To a reaction container, 2.5 g of the compound represented by Formula (I-127-3), 1.1 g of the compound represented by Formula (I-120-4), 0.5 g of (±)-10-camphorsulfonic acid, 10 mL of tetrahydrofuran, and 10 mL of ethanol were added. After the resulting mixture had been stirred while being heated at 50° C., the solvent was removed by distillation and dispersion cleaning was performed with methanol. Subsequently, purification was performed by column chromatography (silica gel) and recrystallization. Hereby, 1.8 g of the compound represented by Formula (I-127) was prepared. Transition temperature (temperature rise: 5° C./min): C 67-100 I $^{1}$H NMR (CDCl$_{3}$) δ 1.00 (t, 3H), 1.28 (m, 2H), 1.45-1.81 (m, 12H), 1.97 (br, 1H), 2.13 (m, 2H), 2.26 (m, 2H), 2.57 (tt, 1H), 2.65 (t, 2H), 3.27 (s, 3H), 3.37 (m, 2H), 3.50 (m, 2H), 3.70 (t, 2H), 3.95 (q, 4H), 4.17 (t, 2H), 4.33 (t, 2H), 5.82 (dd, 1H), 6.12 (dd, 1H), 6.40 (dd, 1H), 6.87 (d, 2H), 6.98 (m, 3H), 7.15 (t, 1H), 7.25 (m, 5H), 7.32 (t, 1H), 7.64 (m, 2H), 7.69 (d, 1H), 7.91 (s, 1H) ppm.

The compounds represented by Formulae (I-16) to (I-105), (I-121), (I-123) to (I-125), and (I-128) were prepared as in Examples 1 to 33 and by methods conforming to the publicly known methods.

Examples 34 to 66 and Comparative Examples 1 to 3

Compounds used for evaluations were the compounds represented by Formulae (I-1) to (I-15), (I-106) to (I-120), (I-122), (I-126), and (I-127) described in Examples 1 to 33 and the compounds (R-1) to (R-3) described in PTL 1 to PTL 3, respectively.

[Chem. 106]

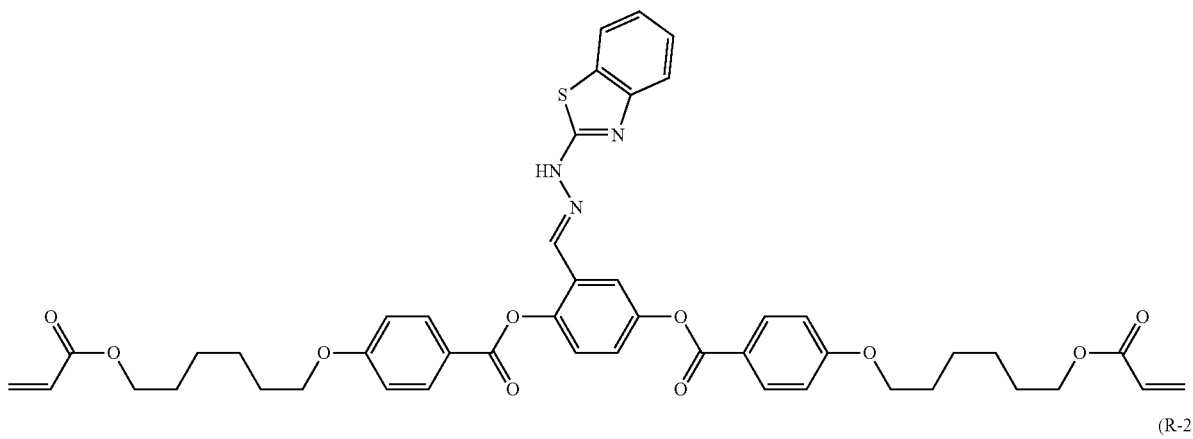

(R-1)

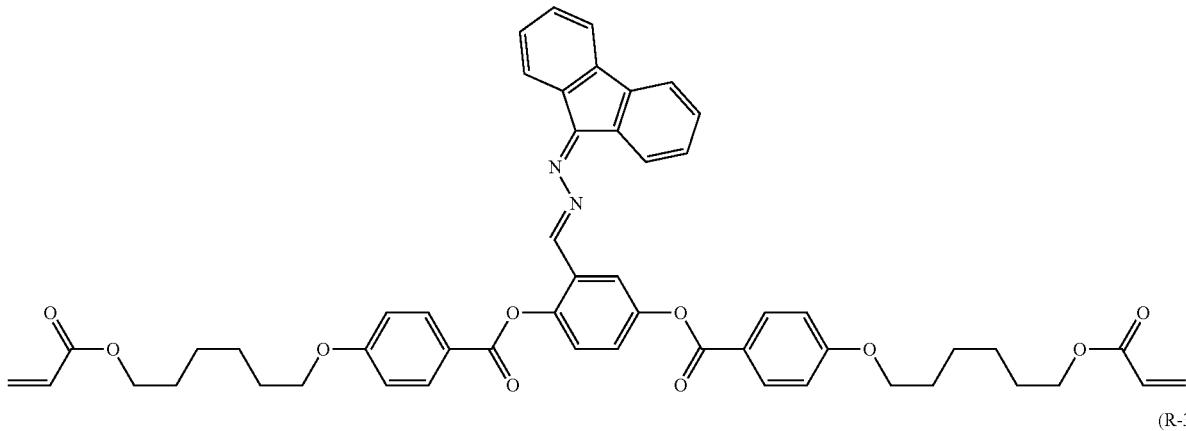

(R-2)

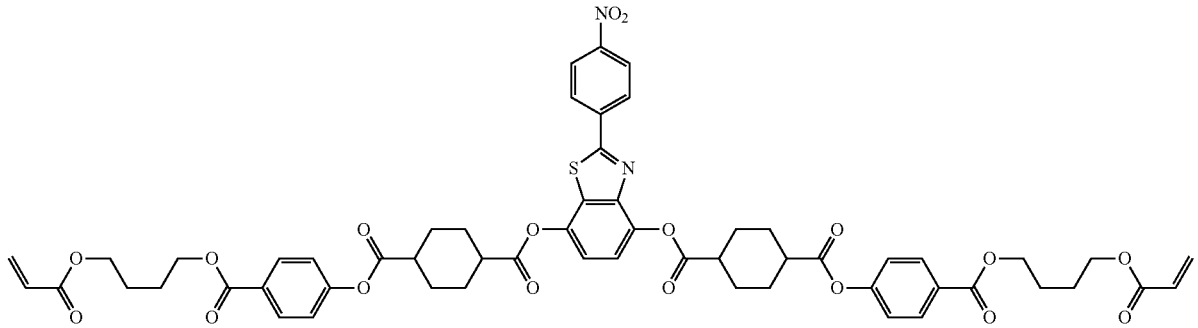

(R-3)

The stable-storage concentration of each of the evaluation compounds was measured in order to evaluate the preservation stability of the evaluation compound. The stable-storage concentration of an evaluation compound is the highest concentration of the evaluation compound in compositions prepared by adding the evaluation compound to a liquid crystal matrix at different concentrations that vary from 5% to 25% at intervals of 5% at which precipitation of crystals does not occur, even after the compositions are left to stand at 17.5° C. for 10 weeks. The higher the addition concentration of a compound, the higher the stable-storage concentration of the compound; that is, the lower the likelihood of crystals precipitating when the compound is stored over a prolonged period of time.

The liquid crystal matrix (X) used for measuring stable-storage concentration was a liquid crystal composition constituted by the following publicly known compound (X-1): 30%, compound (X-2): 30%, and compound (X-3): 40%. Table 1 shows the evaluation results.

[Chem. 107]

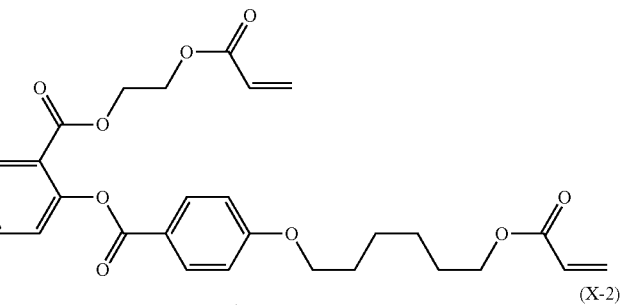
(X-1)

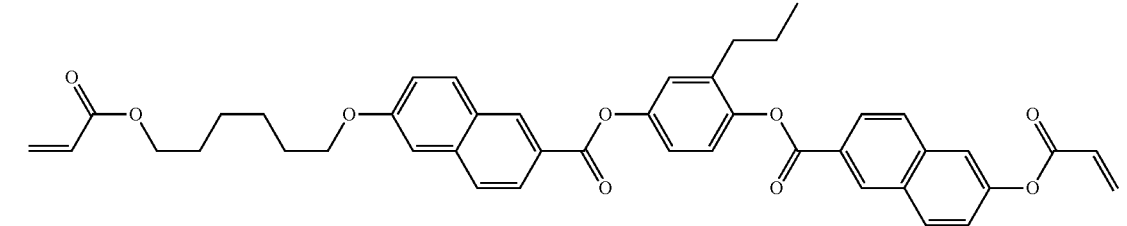
(X-2)

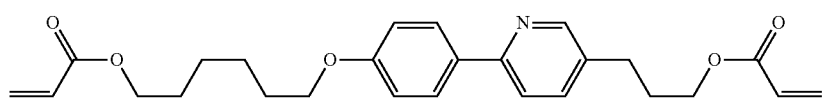
(X-3)

TABLE 1

| | Evaluation compound | Stable-storage concentration |
|---|---|---|
| Example 34 | Compound according to the present invention (I-1) | 25% |
| Example 35 | Compound according to the present invention (I-2) | 25% |
| Example 36 | Compound according to the present invention (I-3) | 20% |
| Example 37 | Compound according to the present invention (I-4) | 25% |
| Example 38 | Compound according to the present invention (I-5) | 20% |
| Example 39 | Compound according to the present invention (I-6) | 20% |
| Example 40 | Compound according to the present invention (I-7) | 25% |
| Example 41 | Compound according to the present invention (I-8) | 20% |
| Example 42 | Compound according to the present invention (I-9) | 20% |
| Example 43 | Compound according to the present invention (I-10) | 25% |
| Example 44 | Compound according to the present invention (I-11) | 20% |
| Example 45 | Compound according to the present invention (I-12) | 25% |
| Example 46 | Compound according to the present invention (I-13) | 15% |
| Example 47 | Compound according to the present invention (I-14) | 15% |
| Example 48 | Compound according to the present invention (I-15) | 15% |

TABLE 2

| | Evaluation compound | Stable-storage concentration |
|---|---|---|
| Example 49 | Compound according to the present invention (I-106) | 20% |
| Example 50 | Compound according to the present invention (I-107) | 20% |
| Example 51 | Compound according to the present invention (I-108) | 20% |
| Example 52 | Compound according to the present invention (I-109) | 20% |
| Example 53 | Compound according to the present invention (I-110) | 25% |
| Example 54 | Compound according to the present invention (I-111) | 25% |
| Example 55 | Compound according to the present invention (I-112) | 20% |

TABLE 2-continued

| Evaluation compound | | Stable-storage concentration |
|---|---|---|
| Example 56 | Compound according to the present invention (I-113) | 20% |
| Example 57 | Compound according to the present invention (I-114) | 25% |
| Example 58 | Compound according to the present invention (I-115) | 20% |
| Example 59 | Compound according to the present invention (I-116) | 15% |
| Example 60 | Compound according to the present invention (I-117) | 15% |
| Example 61 | Compound according to the present invention (I-118) | 20% |
| Example 62 | Compound according to the present invention (I-119) | 15% |
| Example 63 | Compound according to the present invention (I-120) | 15% |
| Example 64 | Compound according to the present invention (I-122) | 20% |
| Example 65 | Compound according to the present invention (I-126) | 20% |
| Example 66 | Compound according to the present invention (I-127) | 20% |
| Comparative example 1 | Comparative compound (R-1) | 20% |
| Comparative example 2 | Comparative compound (R-2) | 15% |
| Comparative example 3 | Comparative compound (R-3) | 5% |

The results shown in Tables 1 and 2 confirm that the highest addition concentration, at which the precipitation of crystals does not occur, of each of the compounds represented by Formulae (I-1) to (I-15), (I-106) to (I-120), (I-122), (I-126), and (I-127) according to the present invention, which were used in Examples 34 to 66 is substantially equal to or higher than that of a specific one of the compounds (R-1) to (R-3) used in Comparative Examples 1 to 3 which included the same number of rings in the direction of the long axis of the molecule as the evaluation compound, that is, the compositions according to the present invention had high preservation stability.

Examples 67 to 99 and Comparative Examples 4 to 6

A polyimide solution for alignment films was applied to a glass base material having a thickness of 0.7 mm by spin coating. The resulting film was dried at 100° C. for 10 minutes and subsequently fired at 200° C. for 60 minutes. Hereby, a coating film was formed. The coating film was rubbed with a commercially available rubbing device.

To compositions each prepared by adding a specific one of the evaluation compounds to the liquid crystal matrix (X) at a concentration of 25%, 1% of a photopolymerization initiator Irgacure 907 (produced by BASF SE), 0.1% of 4-methoxyphenol, and 80% of chloroform were added. Hereby, coating liquids were prepared. The coating liquids were each applied to the rubbed glass base material by spin coating. The resulting films were dried at 80° C. for 1 minute and at 120° C. for another 1 minute. Subsequently, the films were irradiated with ultraviolet radiation for 25 seconds at an intensity of 40 mW/cm² using a high-pressure mercury lamp. Hereby, evaluation films were prepared.

The polymers prepared above were inspected with a polarizing microscope in order to evaluate the degree of inconsistency. Ten films of each of the evaluation compounds were prepared, and the number of inconsistencies present in each film was counted. The total number of inconsistencies present in the ten films of each evaluation compound was calculated. An evaluation grade of "A" was given when the number of inconsistencies was 0. An evaluation grade of "B" was given when the number of inconsistencies was 1. An evaluation grade of "C" was given when the number of inconsistencies was 5 or less. An evaluation grade of "D" was given when the number of inconsistencies was 6 to 10. An evaluation grade of "E" was given when the number of inconsistencies was 11 to 20. An evaluation grade of "F" was given when the number of inconsistencies was 21 or more. Tables 3 and 4 show the evaluation results.

TABLE 3

| | Evaluation compound | Inconsistency |
|---|---|---|
| Example 67 | Compound according to the present invention (I-1) | A |
| Example 68 | Compound according to the present invention (I-2) | A |
| Example 69 | Compound according to the present invention (I-3) | A |
| Example 70 | Compound according to the present invention (I-4) | A |
| Example 71 | Compound according to the present invention (I-5) | B |
| Example 72 | Compound according to the present invention (I-6) | B |
| Example 73 | Compound according to the present invention (I-7) | B |
| Example 74 | Compound according to the present invention (I-8) | B |
| Example 75 | Compound according to the present invention (I-9) | C |
| Example 76 | Compound according to the present invention (I-10) | C |
| Example 77 | Compound according to the present invention (I-11) | D |
| Example 78 | Compound according to the present invention (I-12) | D |
| Example 79 | Compound according to the present invention (I-13) | D |
| Example 80 | Compound according to the present invention (I-14) | D |
| Example 81 | Compound according to the present invention (I-15) | D |

TABLE 4

| | Evaluation compound | Inconsistency |
|---|---|---|
| Example 82 | Compound according to the present invention (I-106) | B |
| Example 83 | Compound according to the present invention (I-107) | B |
| Example 84 | Compound according to the present invention (I-108) | B |
| Example 85 | Compound according to the present invention (I-109) | B |
| Example 86 | Compound according to the present invention (I-110) | B |
| Example 87 | Compound according to the present invention (I-111) | B |
| Example 88 | Compound according to the present invention (I-112) | A |
| Example 89 | Compound according to the present invention (I-113) | A |
| Example 90 | Compound according to the present invention (I-114) | B |
| Example 91 | Compound according to the present invention (I-115) | C |
| Example 92 | Compound according to the present invention (I-116) | B |
| Example 93 | Compound according to the present invention (I-117) | C |

TABLE 4-continued

| | Evaluation compound | Inconsistency |
|---|---|---|
| Example 94 | Compound according to the present invention (I-118) | A |
| Example 95 | Compound according to the present invention (I-119) | B |
| Example 96 | Compound according to the present invention (I-120) | B |
| Example 97 | Compound according to the present invention (I-122) | B |
| Example 98 | Compound according to the present invention (I-126) | A |
| Example 99 | Compound according to the present invention (I-127) | B |
| Comparative example 4 | Comparative compound (R-1) | E |
| Comparative example 5 | Comparative compound (R-2) | F |
| Comparative example 6 | Comparative compound (R-3) | F |

The results shown in Tables 3 and 4 confirm that the compounds represented by Formulae (I-1) to (I-15), (I-106) to (I-120), (I-122), (I-126), and (I-127) according to the present invention, which were used in Examples 67 to 99, each had a smaller number of inconsistencies than the compounds (R-1) to (R-3) used in Comparative Examples 4 to 6.

The above results confirm that the compounds represented by Formulae (I-1) to (I-15), (I-106) to (I-120), (I-122), (I-126), and (I-127) according to the present invention, which are described in Examples 1 to 33, are capable of forming a polymerizable composition having high preservation stability and that an optically anisotropic body including the compound according to the present invention reduces the occurrence of inconsistencies. Thus, the compound according to the present invention may be suitably used as a component of a polymerizable composition. An optically anisotropic body produced using a polymerizable liquid crystal composition including the compound according to the present invention may be suitably used for producing optical films or the like.

The invention claimed is:

1. A compound represented by General Formula (I) below,

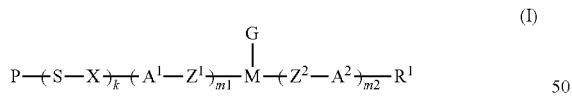

(I)

wherein, P represents a polymerizable group selected from the group consisting of groups represented by Formulae (P-1) to (P-20) below,

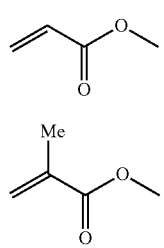
(P-1)

(P-2)

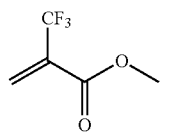
(P-3)

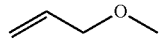
(P-4)

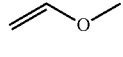
(P-5)

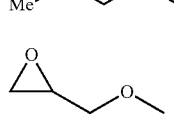
(P-6)

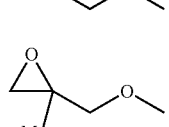
(P-7)

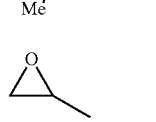
(P-8)

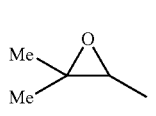
(P-9)

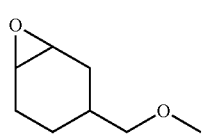
(P-10)

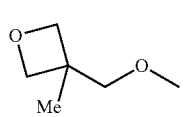
(P-11)

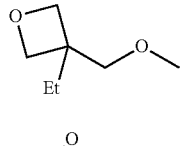
(P-12)

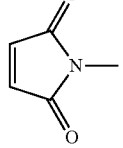
(P-13)

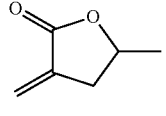
(P-14)

HS—
(P-15)

(P-16)

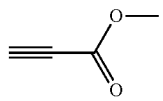
(P-17)

-continued (P-18)
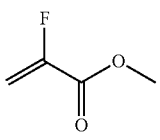

(P-19)
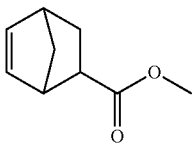

(P-20)
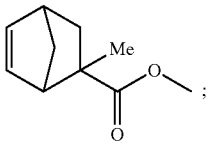

S represents an alkylene group having 1 to 20 carbon atoms and in which one —CH$_2$— group or two or more —CH$_2$— groups that are not adjacent to one another may be each independently replaced with —COO—, —OCO—, —OCO—O—, —CO—NH— or —NH—CO;

X represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —N=N—, —CH=N—N=CH—, or a single bond and, when a plurality of X groups are present, they may be identical to or different from one another in which P—(S—X)$_k$— does not include an —O—O— bond;

A$^1$ and A$^2$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, the above groups may be optionally substituted with one or more L substituents, and, when a plurality of A$^1$ groups and/or a plurality of A$^2$ groups are present, they may be identical to or different from one another;

L represents a fluorine atom, a chlorine atom, a bromine atom, an iodine atom, a pentafluorosulfanyl group, a nitro group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, when a plurality of L substituents are present, they may be identical to or different from one another, and some hydrogen atoms included in the alkyl group may be replaced with fluorine atoms;

Z$^1$ and Z$^2$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —N=N—, —CH=N—, —N=CH—, —CH=N—N=CH—, or a single bond, and, when a plurality of Z$^1$ groups and/or a plurality of Z$^2$ groups are present, they may be identical to or different from one another;

M represents a group selected from Formulae (M-1) to (M-8) below, (M-1)
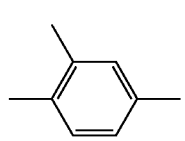

(M-2)
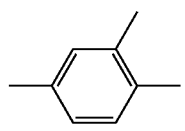

(M-3)
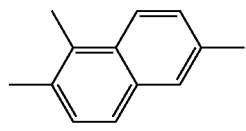

(M-4)
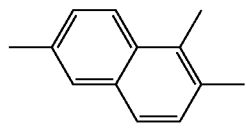

(M-5)
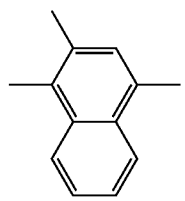

(M-6)
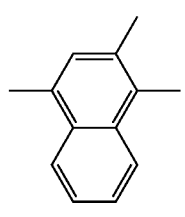

(M-7)
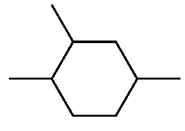

(M-8)

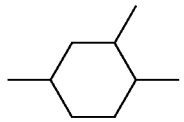

the above groups may be optionally substituted with one or more $L^M$ substituents, $L^M$ represents a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, some hydrogen atoms included in the alkyl group may be replaced with fluorine atoms, and, when a plurality of $L^M$ substituents are present, they may be identical to or different from one another;

$R^1$ represents a hydrogen atom, a fluorine atom, a chlorine atom, a bromine atom, an iodine atom, a pentafluorosulfanyl group, a cyano group, a nitro group, an isocyano group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, and some hydrogen atoms included in the alkyl group may be replaced with fluorine atoms;

G represents a group selected from Formulae (G-1) and (G-2) below,

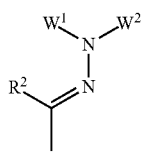
(G-1)

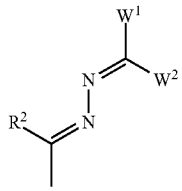
(G-2)

wherein, $R^2$ represents a hydrogen atom or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, or —NH—CO—, and some hydrogen atoms included in the alkyl group may be replaced with fluorine atoms;

$W^1$ represents a group having 2 to 30 carbon atoms, the group including at least one aromatic group, the group may be optionally substituted with one or more $L^W$ substituents, $L^W$ represents a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— group or two or more —$CH_2$— groups that are not adjacent to one another may be each independently replaced with —S—, —CO—, —COO—, —OCO—, —CO—S—, —S—CO—, —O—CO—O—, —CO—NH—, or —NH—CO—, some hydrogen atoms included in the alkyl group may be replaced with fluorine atoms, and, when a plurality of $L^W$ substituents are present, they may be identical to or different from one another;

$W^2$ represents a linear or branched alkyl group having 1 to 20 carbon atoms, the group may be optionally substituted with one or more $L^W$ substituents; and k represents an integer of 0 or 1, m1 and m2 each independently represent an integer of 0 to 4, and m1+m2 is an integer of 1 to 5.

2. The compound according to claim 1, wherein, in General Formula (I), S independently represents an alkylene group having 1 to 20 carbon atoms in which one —$CH_2$— group or two or more —$CH_2$— groups that are not adjacent to one another may be each independently replaced with —O—, —COO—, —OCO—, —OCO—O—, —CO—NH—, —NH—CO—, or —C≡C—.

3. The compound according to claim 1, wherein, in General Formula (I), a total number of π electrons included in $W^1$ and $W^2$ is 4 to 24.

4. The compound according to claim 1, wherein, in General Formula (I), the group represented by $W^1$ is a group represented by any one of Formulae (W-1) to (W-19) below,

(W-1)

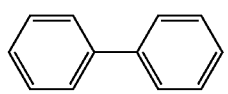
(W-2)

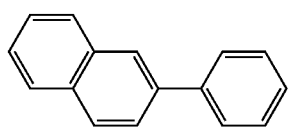
(W-3)

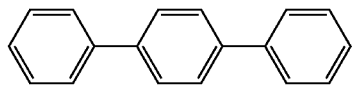
(W-4)

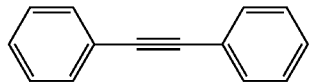
(W-5)

(W-6) 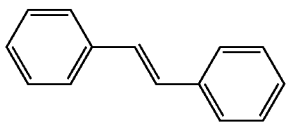

(W-7) 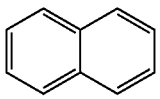

(W-8) 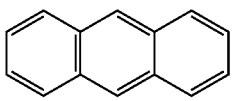

(W-9) 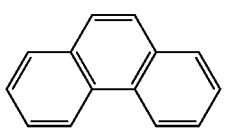

(W-10) 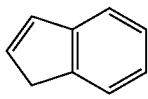

(W-11) 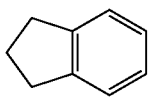

(W-12) 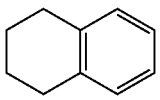

(W-13) 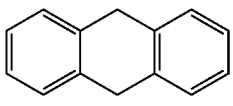

(W-14) 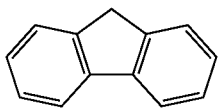

(W-15) 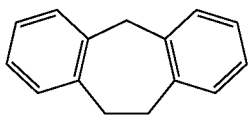

(W-16) 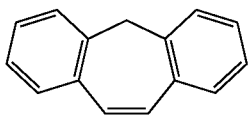

(W-17) 

(W-18) 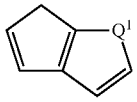

(W-19) 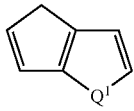

wherein, the above groups may have a bond at any position;

$Q^1$ represents —O—, —S—, —NR$^3$— (where R$^3$ represents a hydrogen atom or an alkyl group having 1 to 8 carbon atoms), or —CO—; —CH= groups included in the aromatic groups may be each independently replaced with an —N= group;

—CH$_2$— groups included in the aromatic groups may be each independently replaced with —O—, —S—, —NR$^4$— (where R$^4$ represents a hydrogen atom or an alkyl group having 1 to 8 carbon atoms), or —CO— providing that an —O—O— bond is not included; the above groups may be optionally substituted with one or more $L^W$ substituents; two or more groups selected from the above groups may be linked to one another with a single bond to form another group; and the above groups may form a ring structure constituted by $W^1$ and $W^2$.

5. The compound according to claim 1 selected from General Formulae (I-A) to (I-D) below,

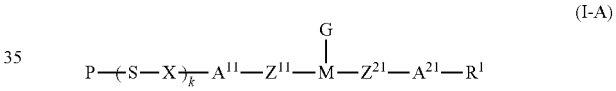  (I-A)

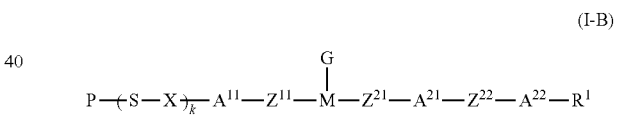  (I-B)

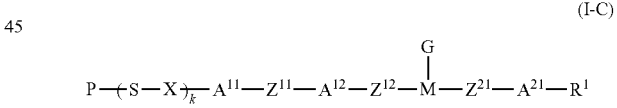  (I-C)

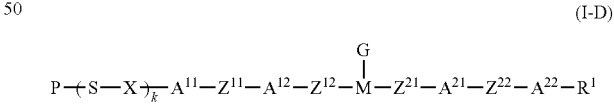  (I-D)

wherein, P, S, X, k, M, G, and $R^1$ represent the same things as those defined in General Formula (I); $A^{11}$ and $A^{12}$ each independently represent the same things as $A^1$ of General Formula (I); $Z^{11}$ and $Z^{12}$ each independently represent the same things as $Z^1$ of General Formula (I); $A^{21}$ and $A^{22}$ each independently represent the same things as $A^2$ of General Formula (I); and $Z^{21}$ and $Z^{22}$ each independently represent the same things as $Z^2$ of General Formula (I).

6. A composition comprising the compound according to claim 1.

7. A liquid crystal composition comprising the compound according to claim 1.

8. A polymer produced by polymerizing the composition according to claim 6.

9. An optically anisotropic body comprising the polymer according to claim 8.

10. A resin comprising the compound according to claim 1.

11. The compound represented by General Formula (I) according to claim 1 selected from the group consisting of the compounds represented by Formulae (I-13), (I-15), (I-19), (I-21), (I-22), (I-23), (I-26), (I-27), (I-31), (I-37), (I-41), (I-42), (I-52), (I-54), (I-56), (I-65), (I-66), (I-67), (I-70), (I-76), (I-77), (I-80), (I-81), (I-83), (I-88), (I-92), (I-101), (I-102), (I-115), (I-117) and (I-118).

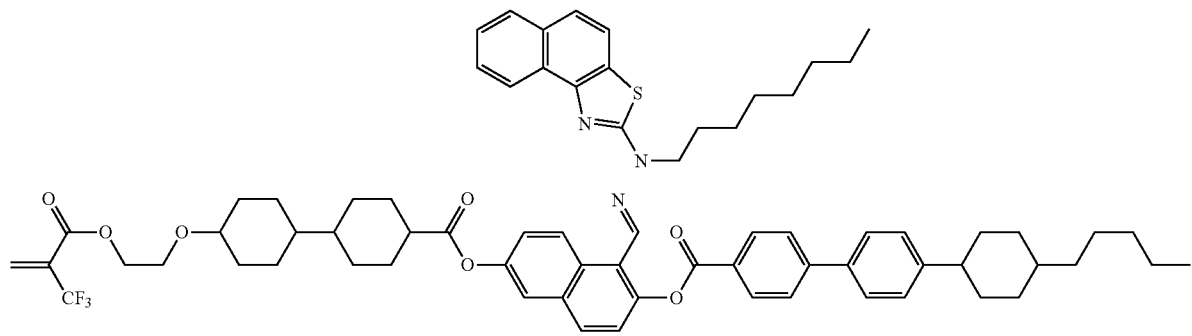

(I-13)

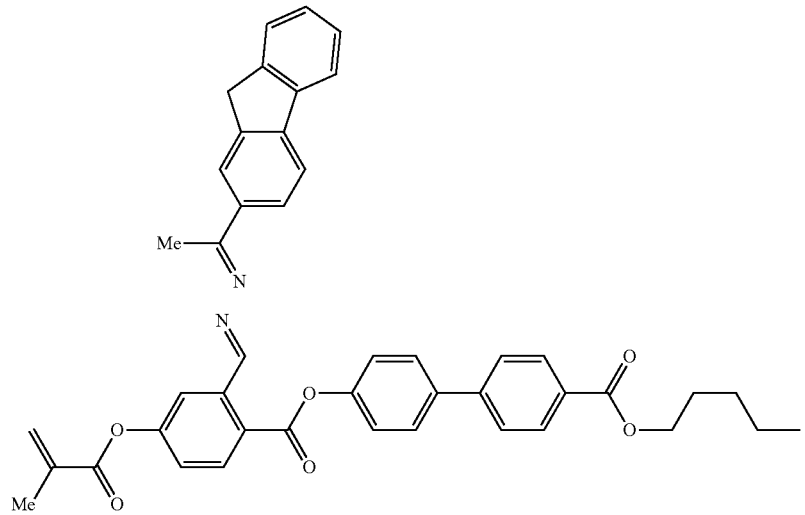

(I-15)

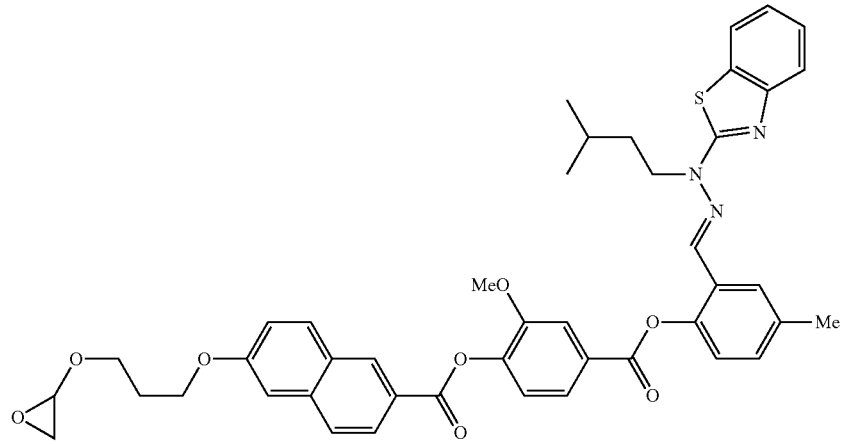

(I-19)

(I-21)
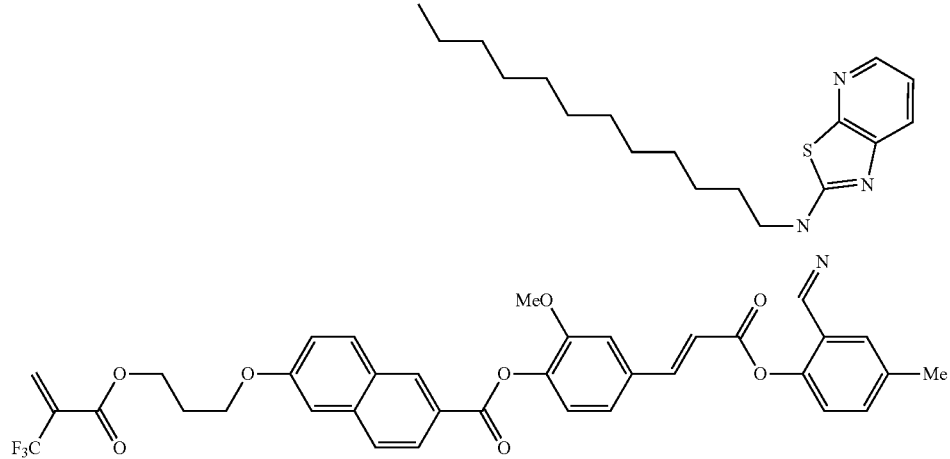
(I-22)
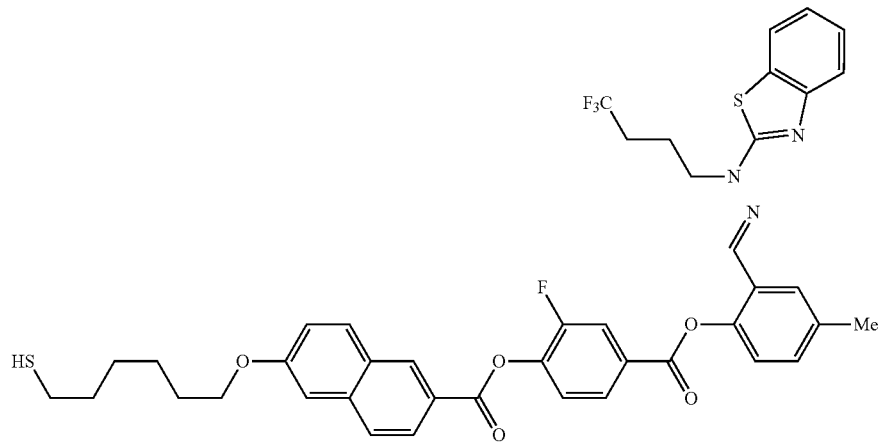
(I-23)
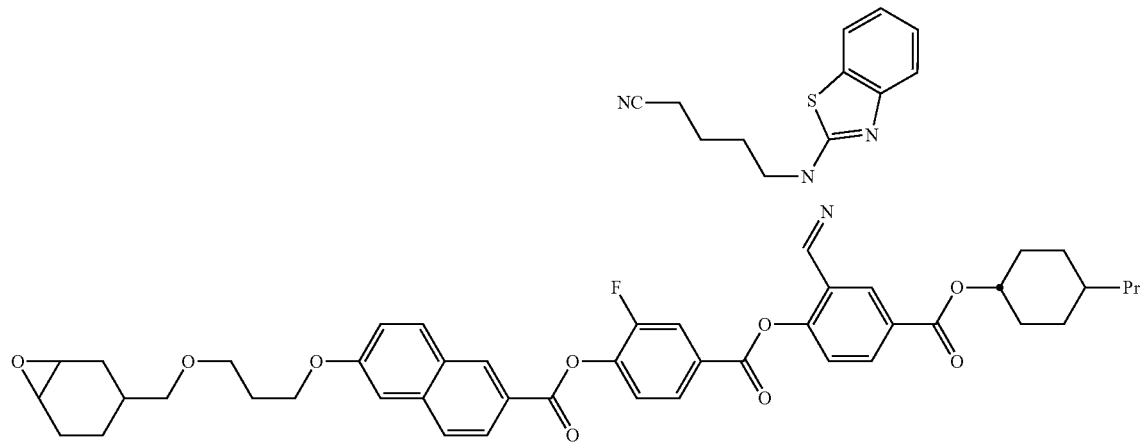

-continued
(I-26)
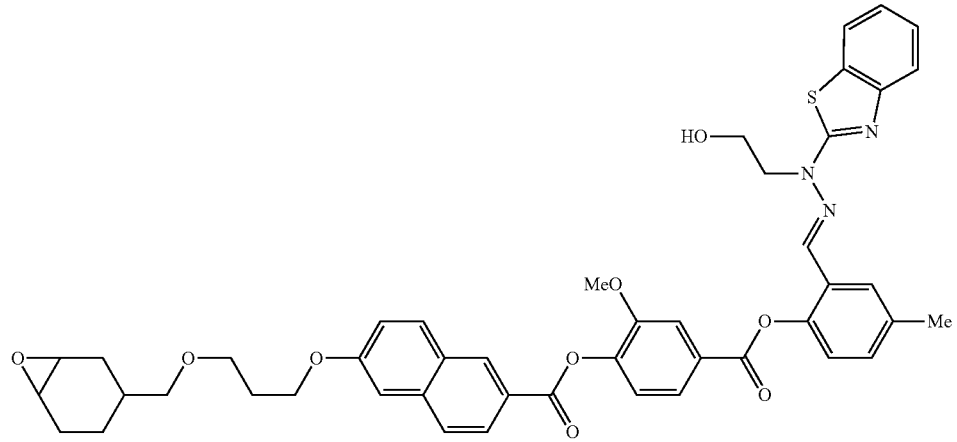
(I-27)
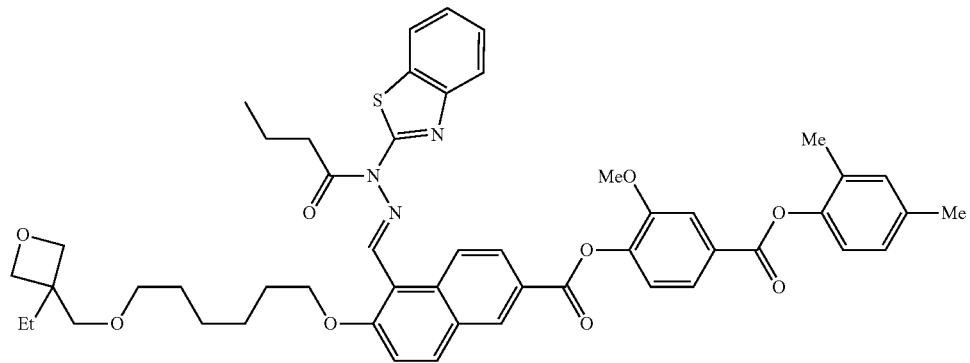
(I-31)
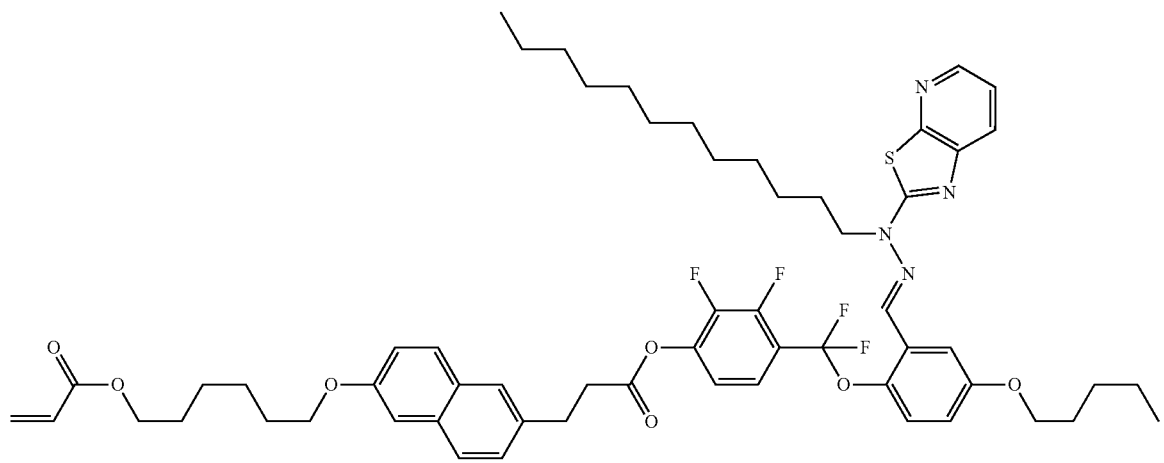

-continued
(I-37)
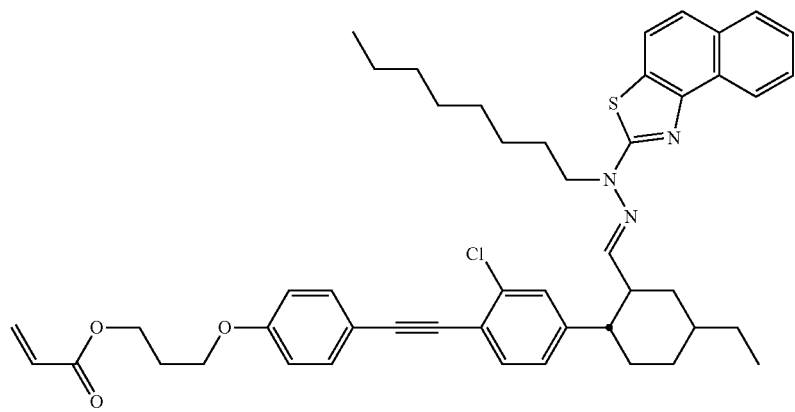
(I-41)
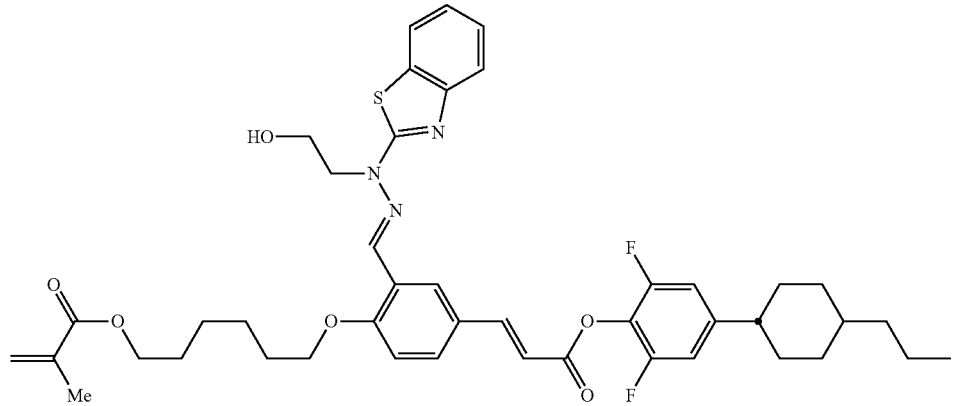
(I-42)
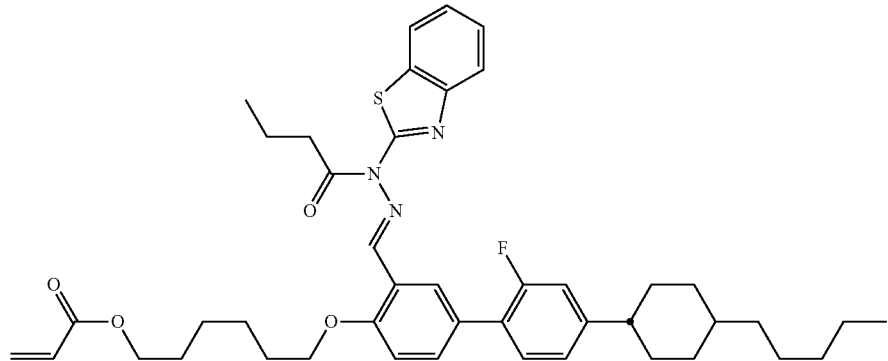
(I-52)
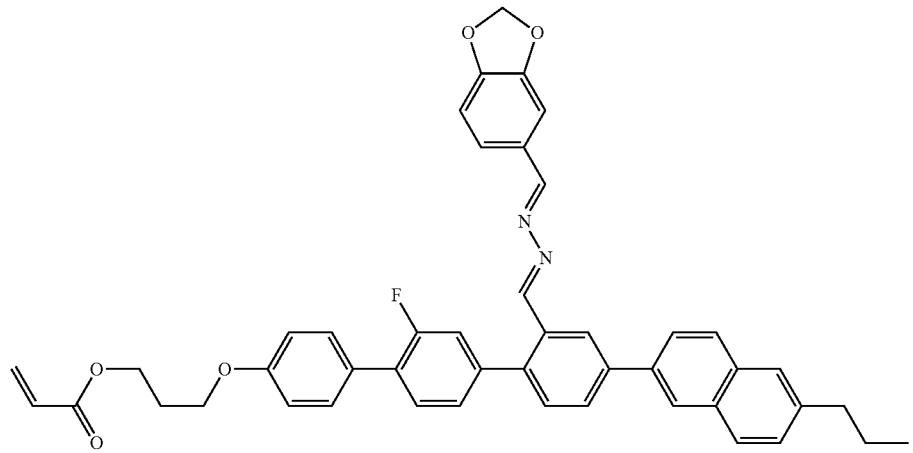

-continued
(I-54)
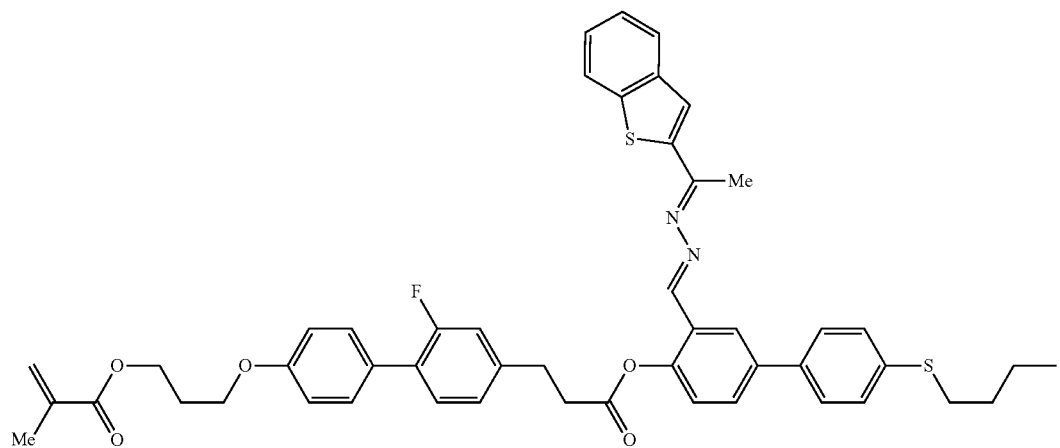
(I-56)
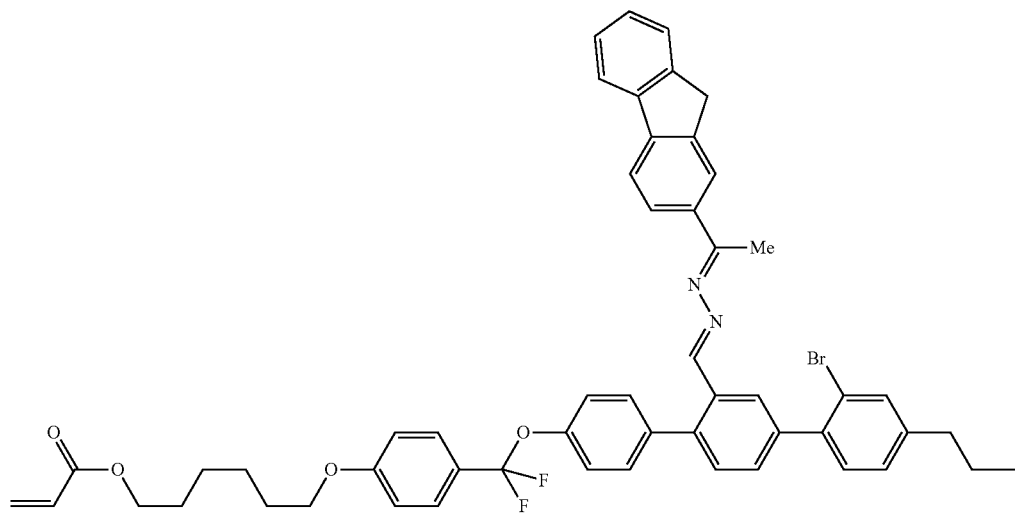
(I-65)
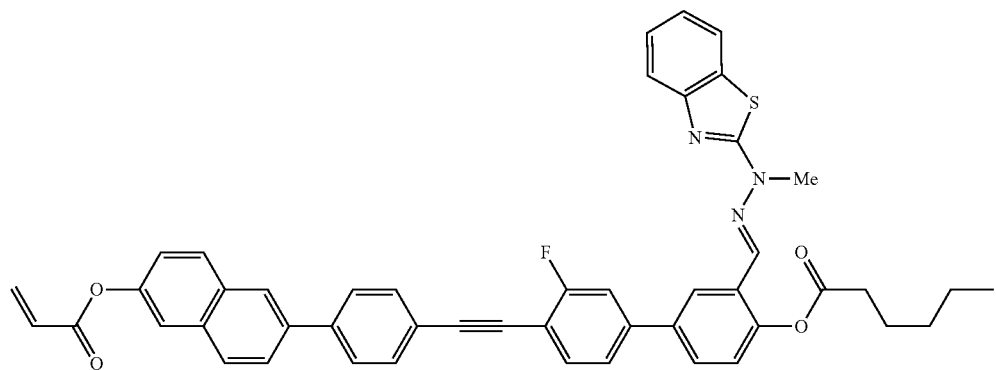

-continued
(I-66)
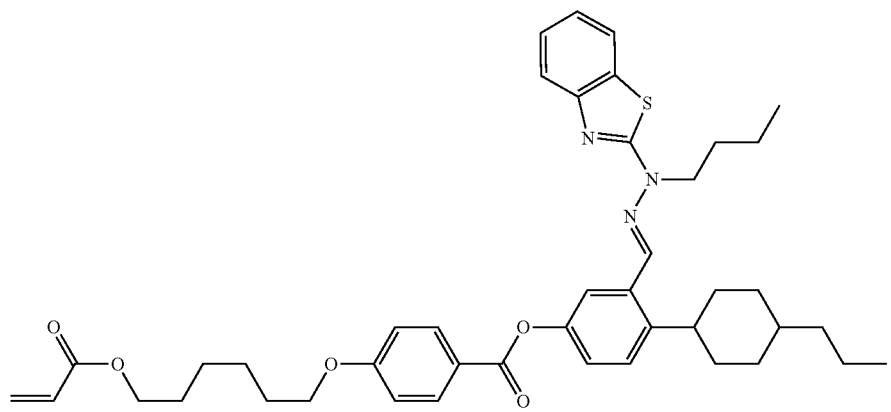
(I-67)
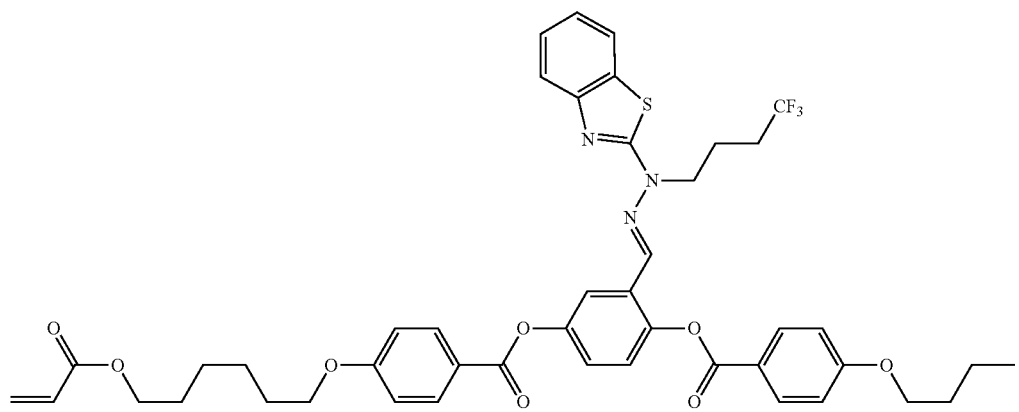
(I-70)
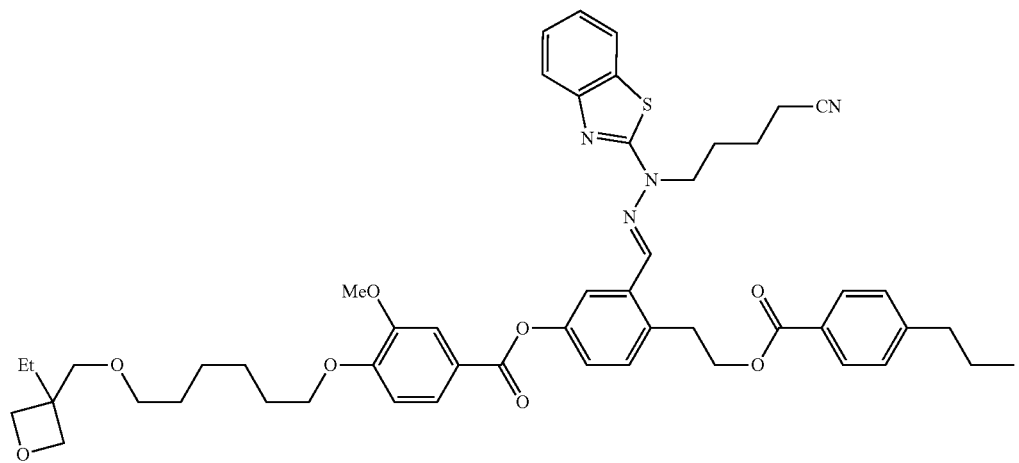

-continued
(I-76)
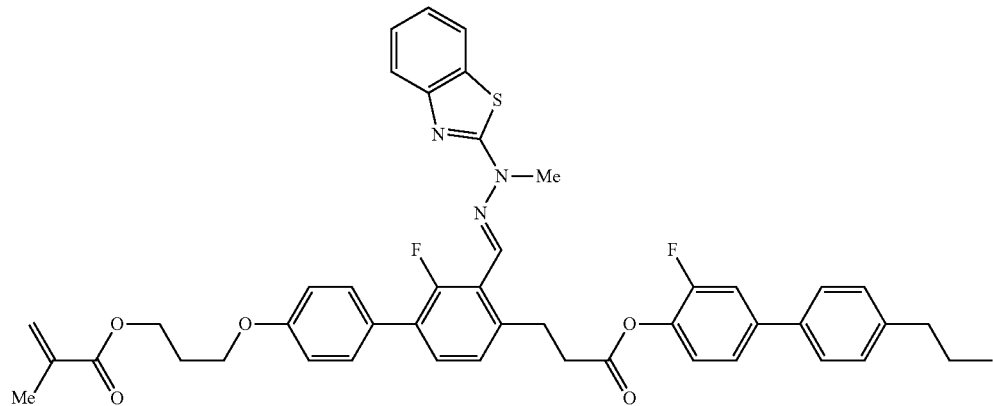
(I-77)
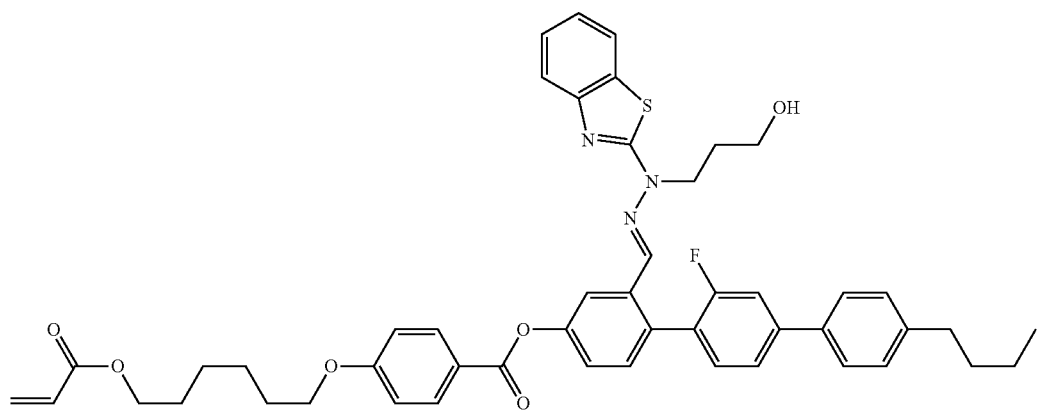
(I-80)
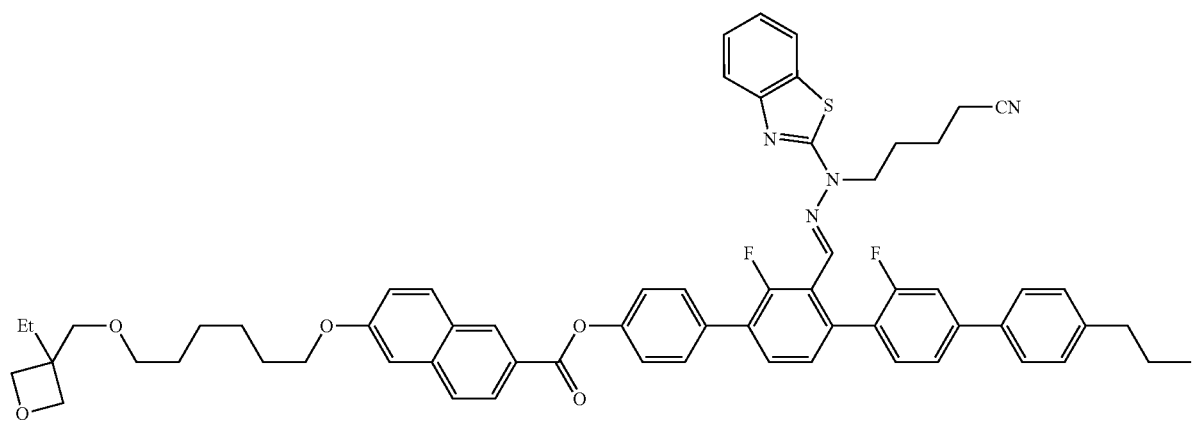

(I-81)
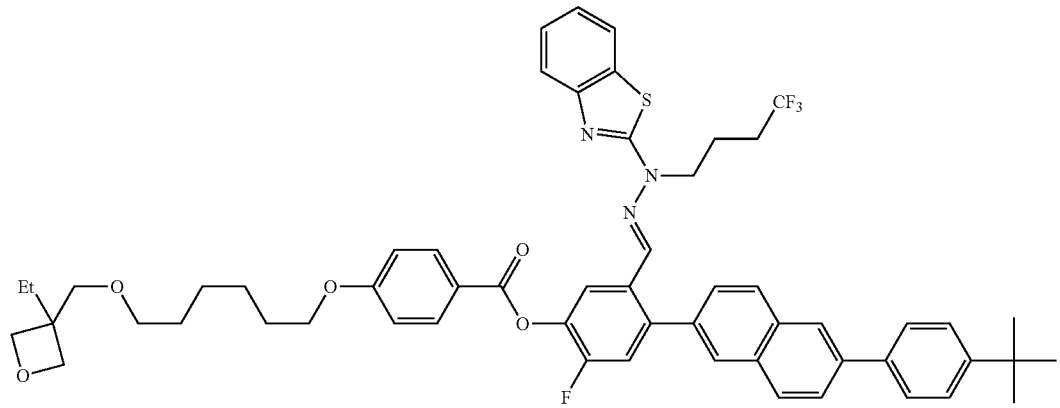
(I-83)
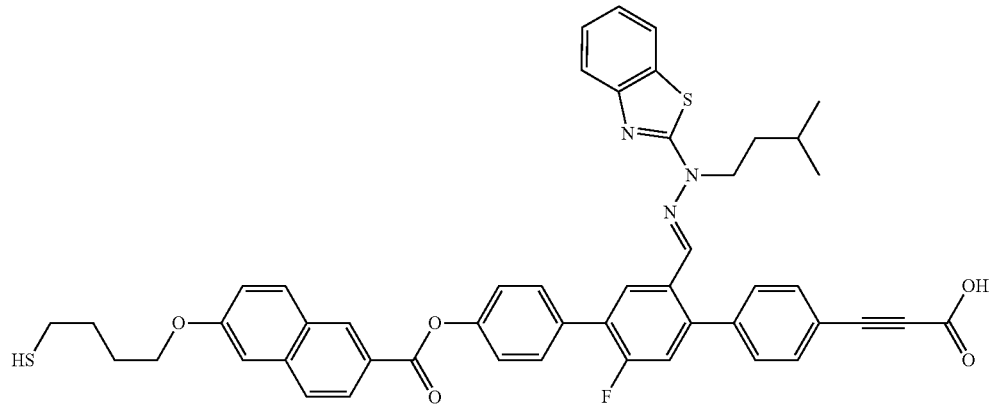
(I-88)
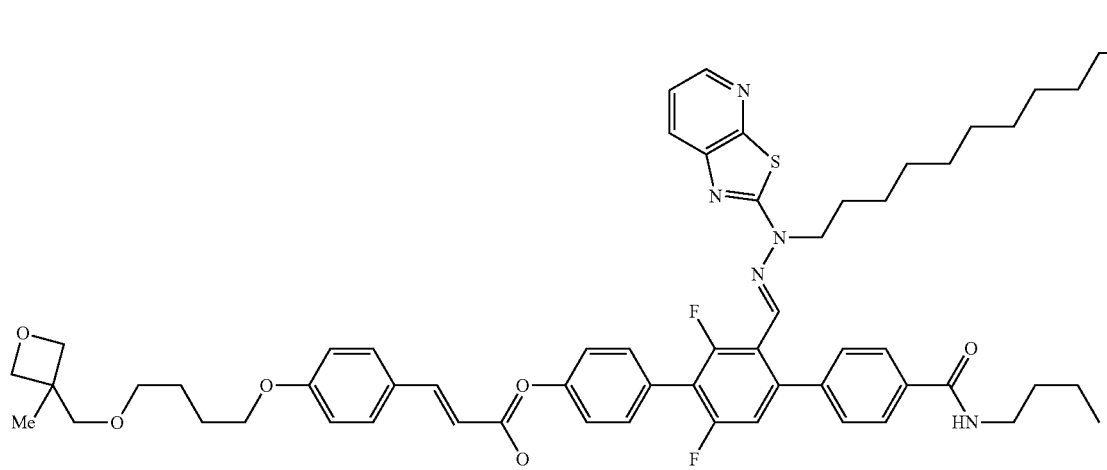

-continued
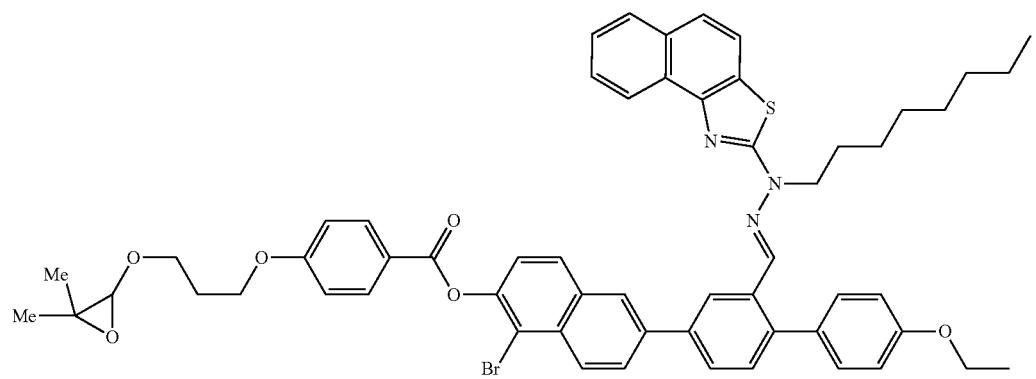
(I-92)
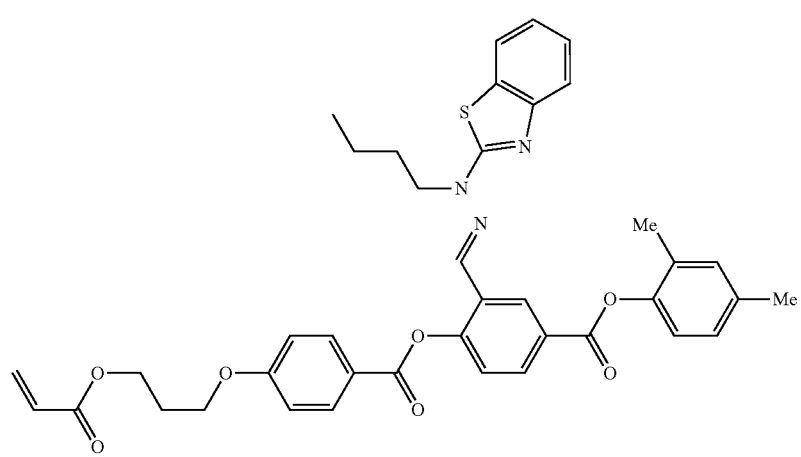
(I-101)
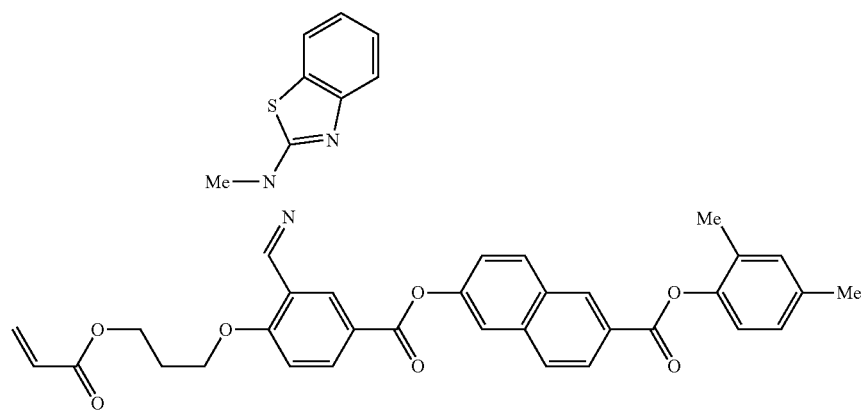
(I-102)
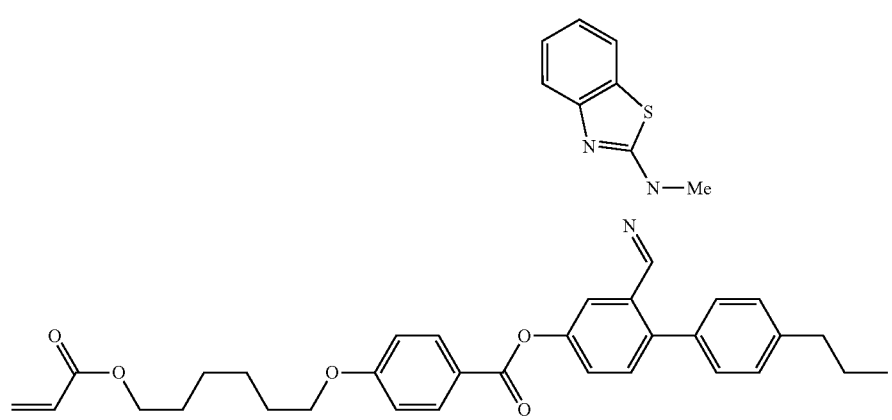
(I-115)

-continued
(I-117)
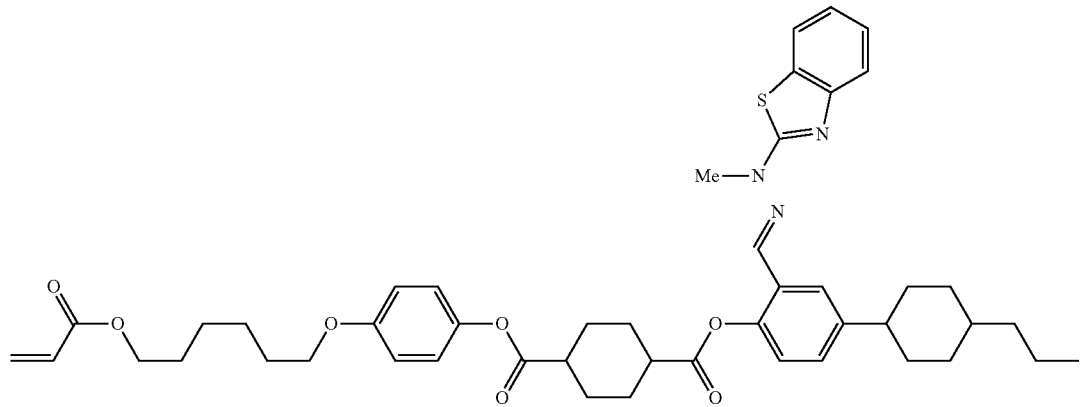
(I-118)
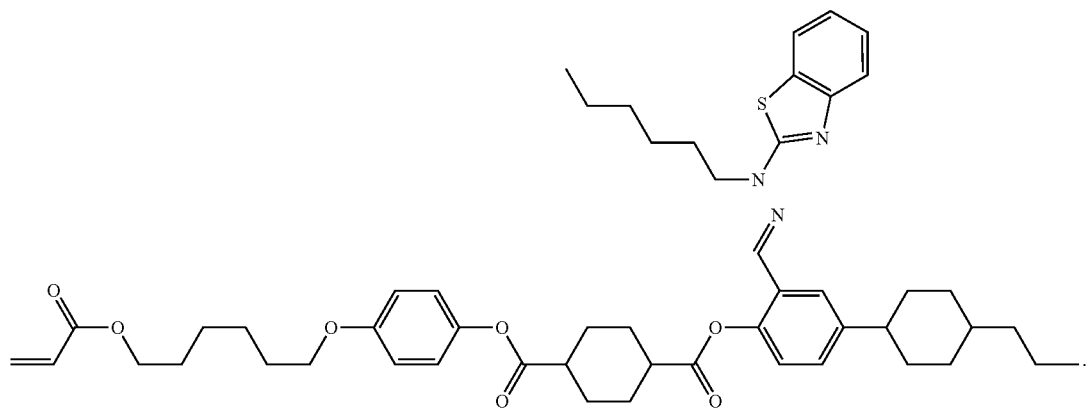
12. The compound represented by General Formula (I) according to claim 11 selected from the group consisting of the compounds represented by Formulae (I-117) and (I-118).
* * * * * ical

EX PARTE REEXAMINATION CERTIFICATE (12128th)
United States Patent
Horiguchi et al.

(10) Number: US 10,723,952 C1
(45) Certificate Issued: Aug. 24, 2022

(54) POLYMERIZABLE COMPOUND AND OPTICALLY ANISOTROPIC BODY

(71) Applicant: DIC Corporation, Tokyo (JP)

(72) Inventors: Masahiro Horiguchi, Kita-adachi-gun (JP); Yutaka Kadomoto, Kita-adachi-gun (JP); Tetsuo Kusumoto, Kita-adachi-gun (JP)

(73) Assignee: DIC CORPORATION, Tokyo (JP)

Reexamination Request:
No. 90/014,554, Jul. 29, 2020

Reexamination Certificate for:
Patent No.: 10,723,952
Issued: Jul. 28, 2020
Appl. No.: 15/517,441
PCT Filed: Oct. 6, 2015
PCT No.: PCT/JP2015/078322
§ 371 (c)(1),
(2) Date: Apr. 6, 2017
PCT Pub. No.: WO2016/056542
PCT Pub. Date: Apr. 14, 2016

(30) Foreign Application Priority Data

Oct. 9, 2014 (JP) .................. 2014-208048

(51) Int. Cl.
| | | |
|---|---|---|
| C09K 19/38 | (2006.01) | |
| A61K 8/37 | (2006.01) | |
| A61K 8/40 | (2006.01) | |
| A61K 8/46 | (2006.01) | |
| A61K 8/49 | (2006.01) | |
| A61K 8/69 | (2006.01) | |
| A61Q 19/00 | (2006.01) | |
| C07C 255/55 | (2006.01) | |
| C07C 323/52 | (2006.01) | |
| C07D 277/50 | (2006.01) | |
| C07D 277/84 | (2006.01) | |
| C07D 303/22 | (2006.01) | |
| C07D 303/48 | (2006.01) | |
| C07D 305/06 | (2006.01) | |
| C07D 417/12 | (2006.01) | |
| C07D 513/04 | (2006.01) | |
| C08F 20/18 | (2006.01) | |
| C08G 59/20 | (2006.01) | |
| C09K 19/34 | (2006.01) | |
| C09K 19/54 | (2006.01) | |
| C07D 277/82 | (2006.01) | |
| C07D 277/66 | (2006.01) | |
| C07C 251/86 | (2006.01) | |
| C07C 251/88 | (2006.01) | |
| C07D 339/06 | (2006.01) | |
| C07D 409/04 | (2006.01) | |
| C07D 417/04 | (2006.01) | |
| C08F 20/30 | (2006.01) | |
| C08G 65/18 | (2006.01) | |
| C08G 65/26 | (2006.01) | |
| C09K 19/32 | (2006.01) | |
| C09K 19/04 | (2006.01) | |
| A61K 47/22 | (2006.01) | |
| G02F 1/13363 | (2006.01) | |

(52) U.S. Cl.
CPC ............... *C09K 19/38* (2013.01); *A61K 8/37* (2013.01); *A61K 8/40* (2013.01); *A61K 8/46* (2013.01); *A61K 8/49* (2013.01); *A61K 8/4966* (2013.01); *A61K 8/69* (2013.01); *A61Q 19/00* (2013.01); *C07C 251/86* (2013.01); *C07C 251/88* (2013.01); *C07C 255/55* (2013.01); *C07C 323/52* (2013.01); *C07D 277/50* (2013.01); *C07D 277/66* (2013.01); *C07D 277/82* (2013.01); *C07D 277/84* (2013.01); *C07D 303/22* (2013.01); *C07D 303/48* (2013.01); *C07D 305/06* (2013.01); *C07D 339/06* (2013.01); *C07D 409/04* (2013.01); *C07D 417/04* (2013.01); *C07D 417/12* (2013.01); *C07D 513/04* (2013.01); *C08F 20/18* (2013.01); *C08F 20/30* (2013.01); *C08G 59/20* (2013.01); *C08G 65/18* (2013.01); *C08G 65/2612* (2013.01); *C09K 19/32* (2013.01); *C09K 19/34* (2013.01); *C09K 19/3486* (2013.01); *C09K 19/3497* (2013.01); *C09K 19/54* (2013.01); *A61K 47/22* (2013.01); *A61K 2800/10* (2013.01); *C07C 2601/14* (2017.05); *C07C 2603/18* (2017.05); *C07C 2603/24* (2017.05); *C07C 2603/32* (2017.05); *C09K 2019/0448* (2013.01); *G02F 1/13363* (2013.01)

(58) Field of Classification Search
None
See application file for complete search history.

(56) References Cited

To view the complete listing of prior art documents cited during the proceeding for Reexamination Control Number 90/014,554, please refer to the USPTO's public Patent Application Information Retrieval (PAIR) system under the Display References tab.

*Primary Examiner* — Jerry D Johnson

(57) ABSTRACT

The present invention provides a polymerizable compound that reduces, for example, the likelihood of crystals precipitating in a polymerizable composition including the polymerizable compound and enables the polymerizable composition to have high preservation stability and a polymerizable composition including the polymerizable compound which reduces the likelihood of inconsistencies being formed in a film-like polymer produced by polymerizing the polymerizable composition. Also provided are a polymer produced by polymerizing the polymerizable composition and an optically anisotropic body including the polymer. The present invention provides the compound represented by General Formula (I), a composition including the compound, a polymer produced by polymerizing the composition, and an optically anisotropic body including the polymer.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-7 and 10-12 are determined to be patentable as amended.

Claims 8 and 9, dependent on an amended claim, are determined to be patentable.

New claims 13-18 are added and determined to be patentable.

1. A *polymerizable* compound *for producing an optical film, the polymerizable compound* represented by General Formula (I) below, (I)

wherein, P represents a polymerizable group selected from the group consisting of groups represented by Formulae (P-1) *to (P-3), (P-7) to (P-11), (P-14) and (P-16) to (P-18)* [to (P-20)] below,

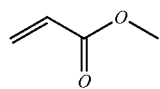
(P-1)

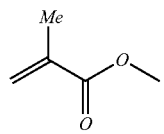
(P-2)

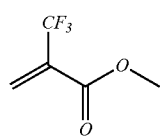
(P-3)

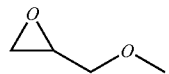
(P-7)

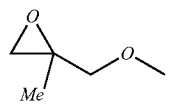
(P-8)

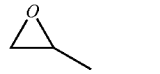
(P-9)

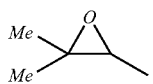
(P-10)

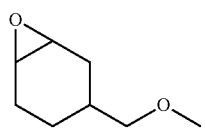
(P-11)

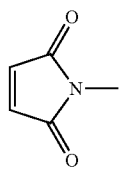
(P-14)

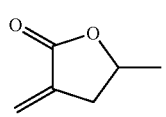
(P-16)

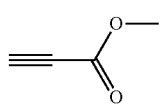
(P-17)

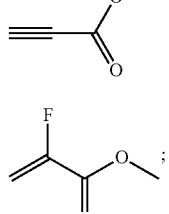
(P-18)

[

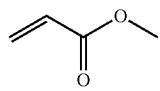
(P-1)

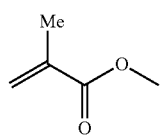
(P-2)

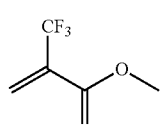
(P-3)

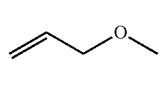
(P-4)

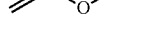
(P-5)

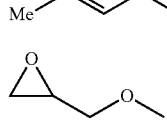
(P-6)

(P-7)

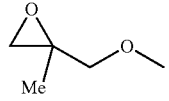
(P-8)

-continued

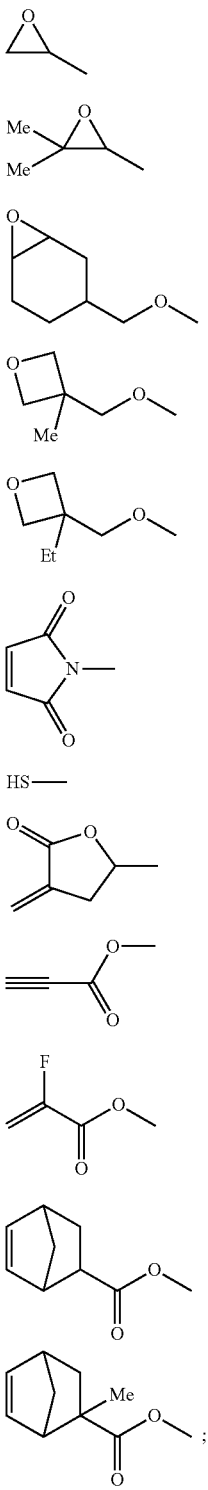

S represents an alkylene group having 1 to 20 carbon atoms and in which one -CH$_2$- group or two or more —CH$_2$— groups that are not adjacent to one another may be each independently replaced with —COO—, —OCO—, —OCO—O—, —CO—NH— or —NH—CO—;

X represents —O—, —S—, —OCH$_2$—, —CH$_2$O—, —CO—, —COO—, —OCO—, —CO—S—, —CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —COO—CH$_2$CH$_2$—, —OCO—CH$_2$CH$_2$—, —CH$_2$CH$_2$—COO—, —CH$_2$CH$_2$—OCO—, —COO-CH$_2$—, —OCO—CH$_2$—, —CH$_2$—COO—, -CH$_2$—OCO—, —N=N—, —CH=N—N=CH—, or a single bond and, when a plurality of X groups are present, they may be identical to or different from one another in which P—(S-X)$_k$— does not include an —O—O— bond;

A$^1$ and A$^2$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, the above groups may be optionally substituted with one or more L substituents, and, when a plurality of A$^1$ groups and/or a plurality of A$^2$ groups are present, they may be identical to or different from one another;

L represents a fluorine atom, a chlorine atom, a bromine atom, an iodine atom, a pentafluorosulfanyl group, a nitro group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —CH$_2$— group or two or more —CH2— groups that are not adjacent to one another may be each independently replaced with —O—, —S—, —CO—, —COO—, —OCO—, —CO—S—, —S—CO—, —O—CO—O—, —CO—NH—, 13 NH—CO—, when a plurality of L substituents are present, they may be identical to or different from one another, and some hydrogen atoms included in the alkyl group may be replaced with fluorine atoms;

Z$^1$ and Z$^2$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —COO—CH$_2$CH$_2$—, —OCO—CH$_2$CH$_2$—, —CH$_2$CH$_2$—COO—, —CH$_2$CH$_2$—OCO—, —COO-CH$_2$—, —OCO—CH$_2$—, —CH$_2$—COO—, —CH$_2$—OCO—, —N=N—, —CH=N—, —N=CH—, —CH=N-N=CH—, or a single bond, and, when a plurality of Z$^1$ groups and/or a plurality of Z$^2$ groups are present, they may be identical to or different from one another;

M represents a group selected from Formulae (M-1) to (M-8) below,

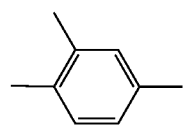

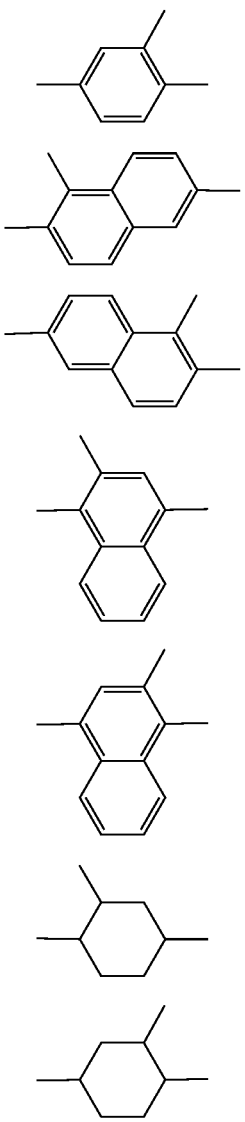

(M-2)

(M-3)

(M-4)

(M-5)

(M-6)

(M-7)

(M-8)

the above groups may be optionally substituted with one or more $L^M$ substituents, $L^M$ represents a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one -CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, some hydrogen atoms included in the alkyl group may be replaced with fluorine atoms, and, when a plurality of $L^M$ substituents are present, they may be identical to or different from one another;

$R^1$ represents a hydrogen atom, a fluorine atom, a chlorine atom, a bromine atom, an iodine atom, a pentafluorosulfanyl group, a cyano group, a nitro group, an isocyano group, a thioisocyano group, or a linear or branched alkyl group having 1 to 20 carbon atoms in which one —CH$_2$— group or two or more —CH2— groups that are not adjacent to one another may be each independently replaced with —O—, —S—, —CO—, —COO—, —OCO—, —CO—S—, —S—CO—, —O—CO—O—, —CO—NH—, —NH—CO—, and some hydrogen atoms included in the alkyl group may be replaced with fluorine atoms;

G represents [a group selected from Formulae] *Formula* (G-1) [and (G-2)] below,

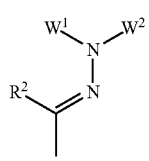

(G-1)

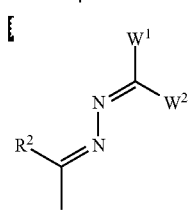

(G-2)

wherein, $R^2$ represents a hydrogen atom or a linear or branched alkyl group having 1 to 20 carbon atoms in which one —CH$^2$— group or two or more -CH2- groups that are not adjacent to one another may be each independently replaced with —O—, —S—, —CO—, —COO—, —OCO—, —CO—S—, —S—CO—, —O—CO—O—, —CO—NH—, or —NH—CO—, and some hydrogen atoms included in the alkyl group may be replaced with fluorine atoms;

$W^1$ represents a group having 2 to 30 carbon atoms, the group including at least one aromatic group, the group may be optionally substituted with one or more $L^w$ substituents, $L^w$ represents a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —CH$_2$— group or two or more —CH$_2$— groups that are not adjacent to one another may be each independently replaced with —S—, —CO—, —COO—, —OCO—, —CO—S—, —S—CO—, —O—CO—O—, —CO—NH—, or —NH—CO—, some hydrogen atoms included in the alkyl group may be replaced with fluorine atoms, and, when a plurality of $L^w$ substituents are present, they may be identical to or different from one another;

$W^2$ represents a linear or branched alkyl group having 1 to 20 carbon atoms, the group may be optionally substituted with one or more $L^W$ substituents; and k represents an integer of 0 or 1, m 1 and m2 each independently represent an integer of 0 to 4, and ml +m2 is an integer of 1 to 5.

2. The *polymerizable* compound according to claim 1, wherein, in General Formula (I), S independently represents an alkylene group having 1 to 20 carbon atoms in which one —CH$_2$— group or two or more —CH$_2$— groups that are not adjacent to one another may be each independently replaced with [—O—,] —COO—, —OCO—, —OCO—O—, —CO—NH—, *or* —NH-CO—, [, or —C≡C—.].

3. The *polymerizable* compound according to claim 1, wherein, in General Formula (I), total number of π electrons included in W$^1$ and W$^2$ is 4 to 24.

4. The *polymerizable* compound according to claim 1, wherein, in General Formula (I), the group represented by W$^1$ is a group represented by any one of Formulae (W-1) to (W-19) below,

(W-1)

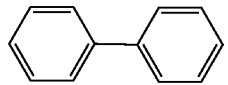
(W-2)

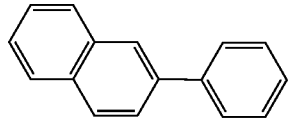
(W-3)

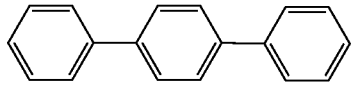
(W-4)

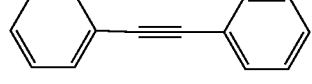
(W-5)

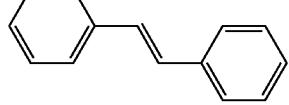
(W-6)

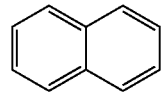
(W-7)

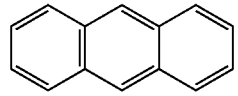
(W-8)

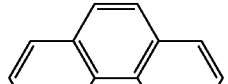
(W-9)

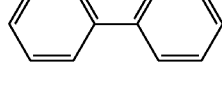
(W-10)

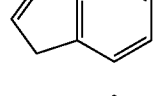
(W-11)

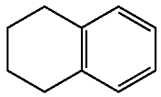
(W-12)

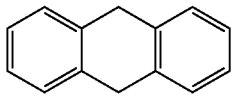
(W-13)

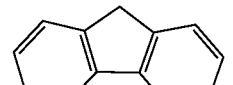
(W-14)

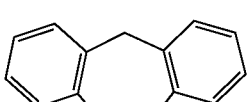
(W-15)

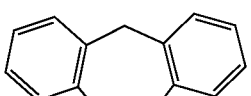
(W-16)

(W-17)

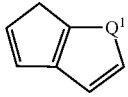
(W-18)

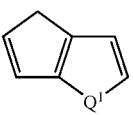
(W-19)

wherein, the above groups may have a bond at any position;

Q$^1$ represents —O—, —S—, —NR$^3$—(where R$^3$ represents a hydrogen atom or an alkyl group having 1 to 8 carbon atoms), or —CO—; —CH= groups included in the aromatic groups may be each independently replaced with an —N= group;

—CH$_2$— groups included in the aromatic groups may be each independently replaced with —O—, —S—, —NR$^4$—(where R$^4$ represents a hydrogen atom or an alkyl group having 1 to 8 carbon atoms), or 13 CO— providing that an —O—O— bond is not included; the above groups may be optionally substituted with one or more L$^W$ substituents; two or more groups selected from the above groups may be linked to one another with a single bond to form another group; and the above groups may form a ring structure constituted by W$^1$ and W$^2$.

5. The *polymerizable* compound according to claim 1 selected from General Formulae (I-A) to (I-D) below,

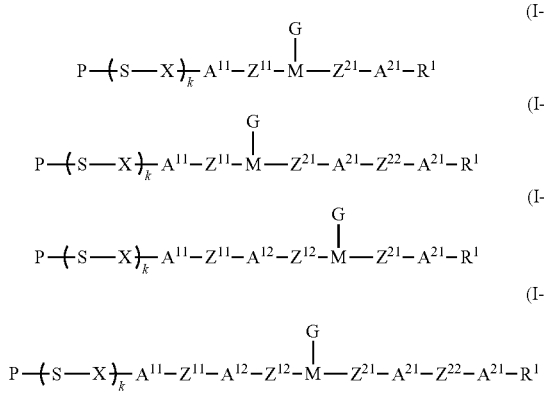

wherein, P, S, X, k, M, G, and $R^1$ represent the same things as those defined in General Formula (I); $A^{11}$ and $A^{12}$ each independently represent the same things as $A^1$ of General Formula (I); $Z^{11}$ and $Z^{12}$ each independently represent the same things as $Z^1$ of General Formula (I); $A^{21}$ and $A^{22}$ each independently represent the same things as $A^2$ of General Formula (I); and $Z^{21}$ and $Z^{22}$ each independently represent the same things as $Z^2$ of General Formula (I).

6. A composition comprising the *polymerizable* compound according to claim 1.

7. A liquid crystal composition comprising the *polymerizable* compound according to claim 1.

10. A resin comprising the *polymerizable* compound according to claim 1.

11. The *polymerizable* compound represented by General Formula (I) according to claim 1 selected from the group consisting of the compounds represented by Formulae (I-13), [(I-15),] (I-19), (I-21), I-22), (I-23), (I-26), (I-27), (I-31), [(I-37),] (I-41), (I-42), [(I-52), (I-54), (I-56), (I-65),] (I-66), (I-67), (I-70), (I-76), (I-77), (I-80), (I-81), (I-83), [(I-88),] (I-92), (I-101), (I-102), (I- 115), (I-117) and (I-118) [.].

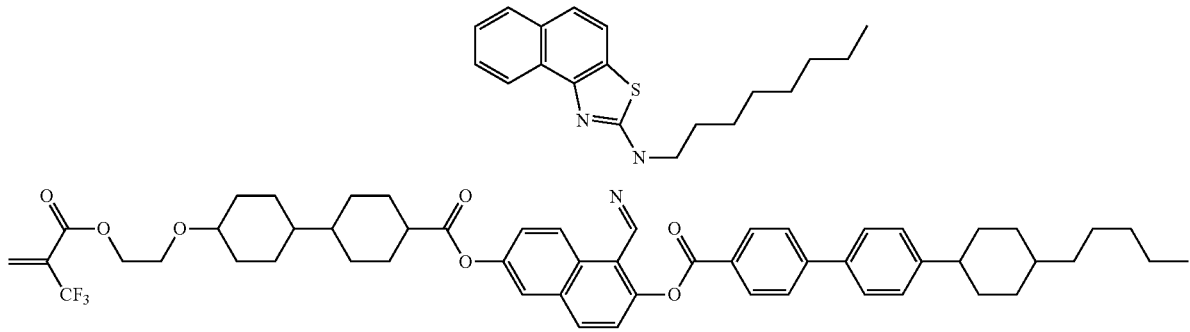

(I-13)

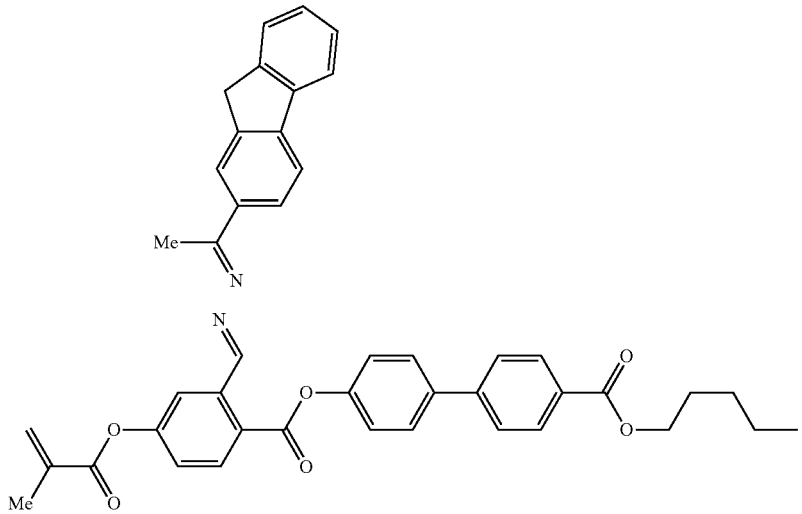

(I-15)

-continued
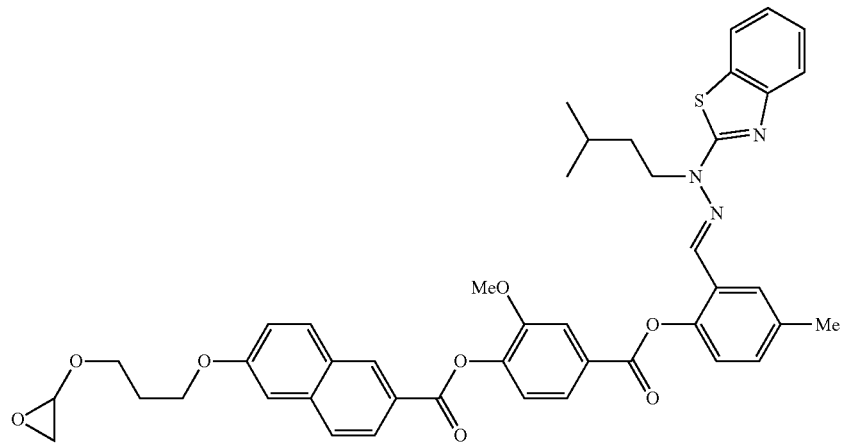
(I-19)
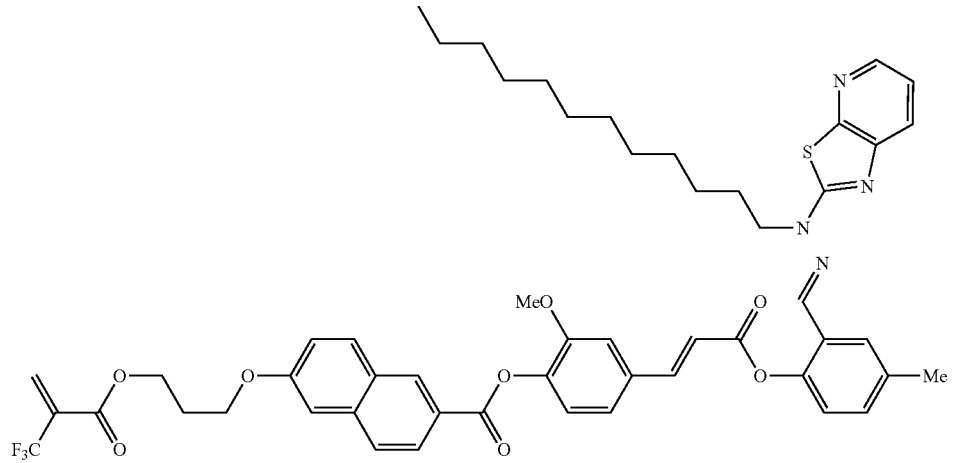
(I-21)
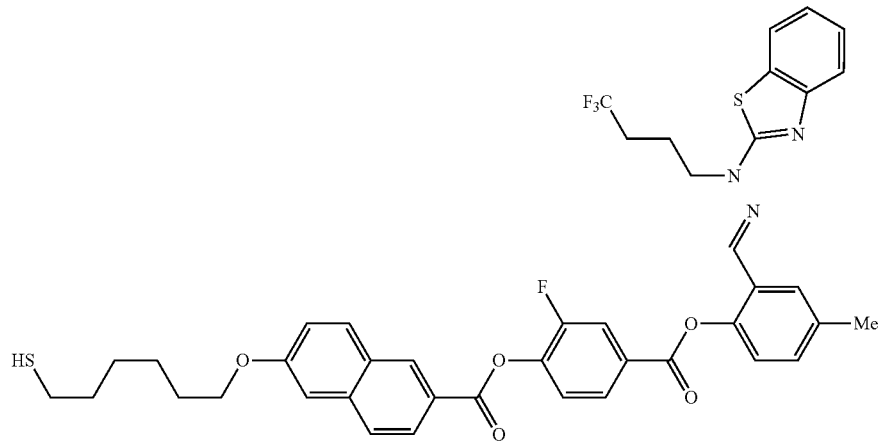
(I-22)

(I-23)
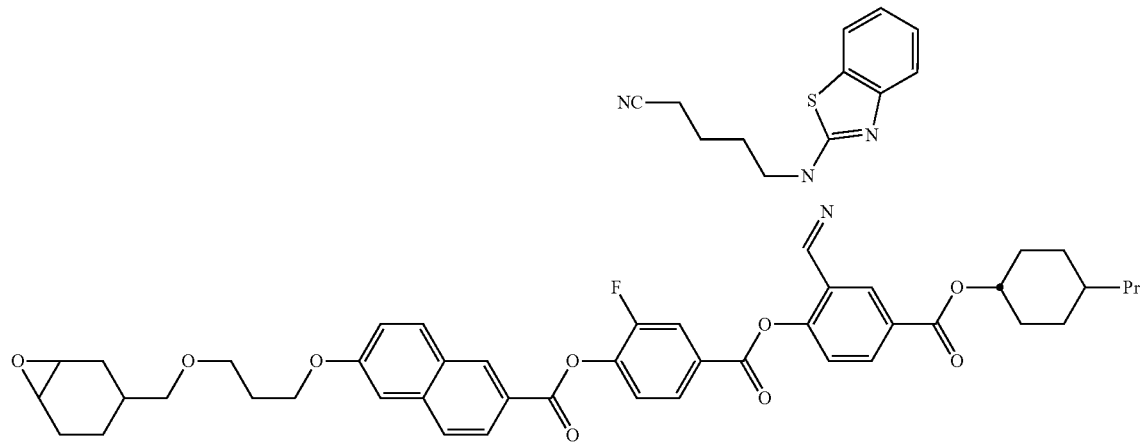
(I-26)
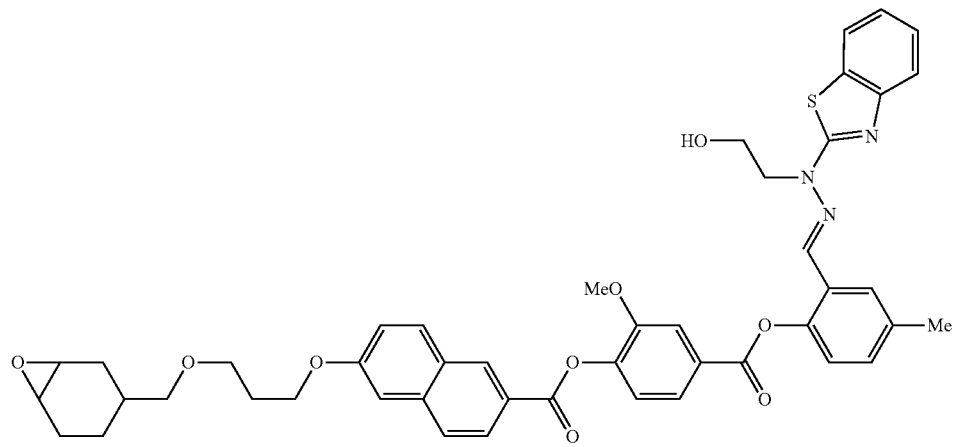
(I-27)
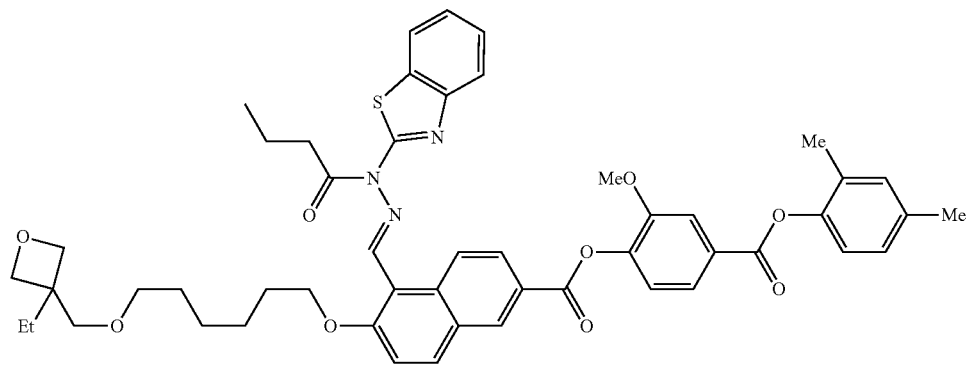

(I-31)
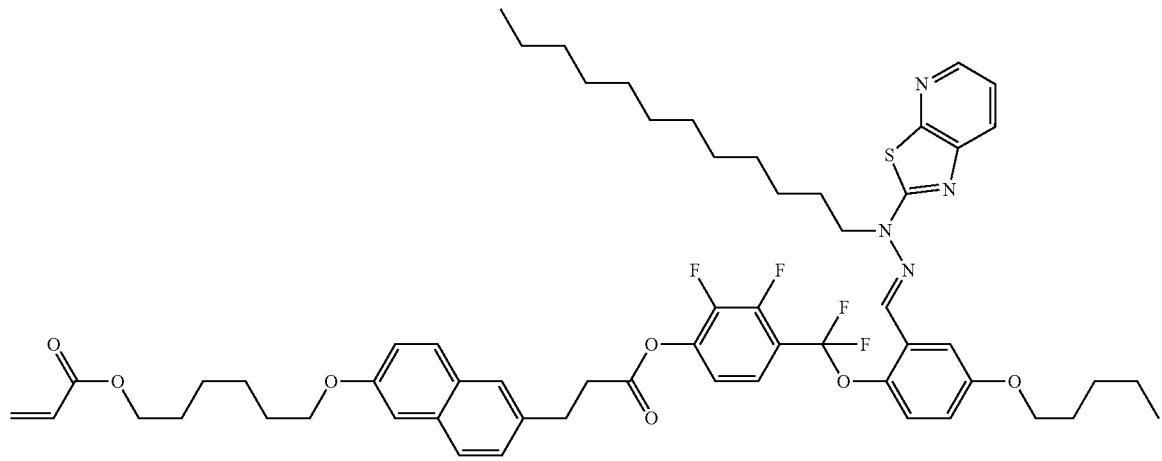
(I-37)
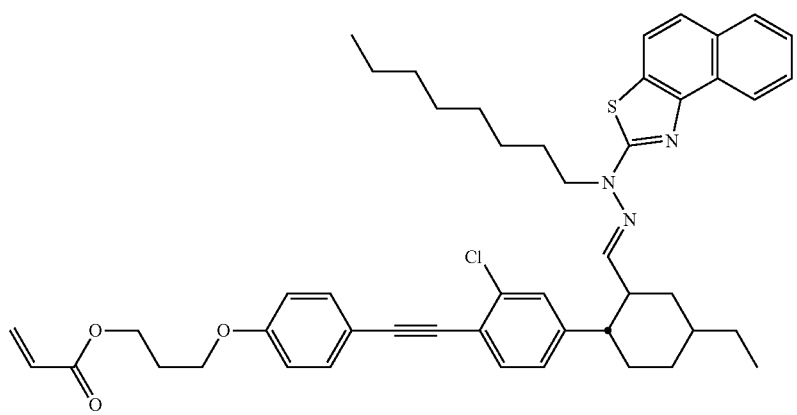
(I-41)
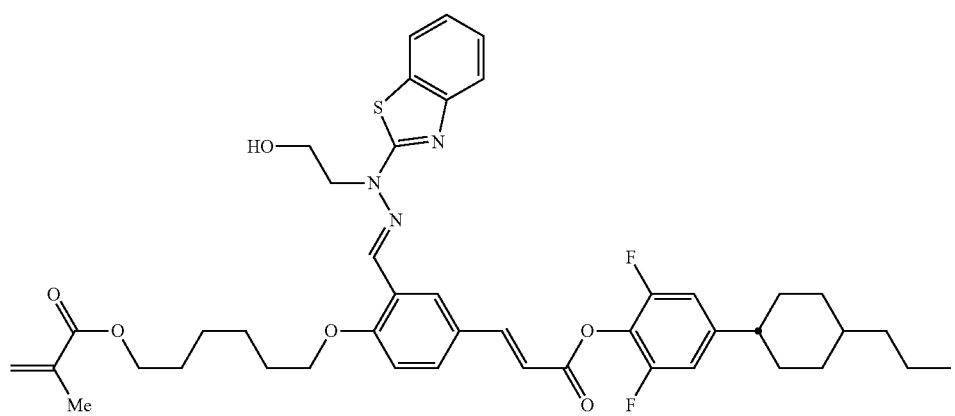

-continued
(I-42)
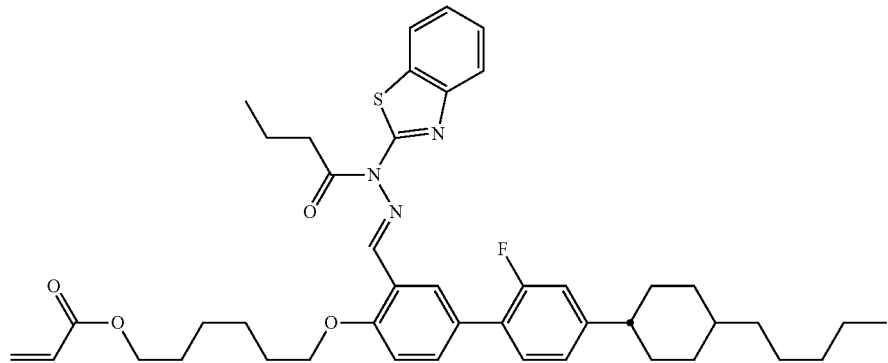
(I-52)
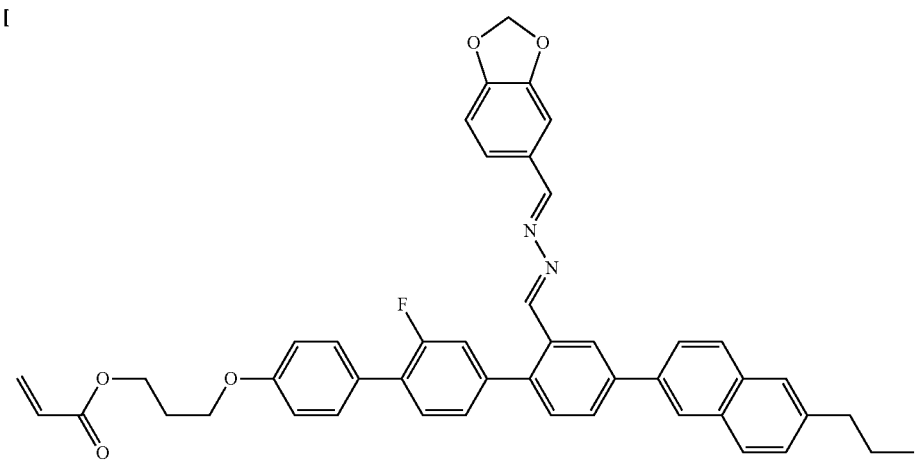
(I-54)
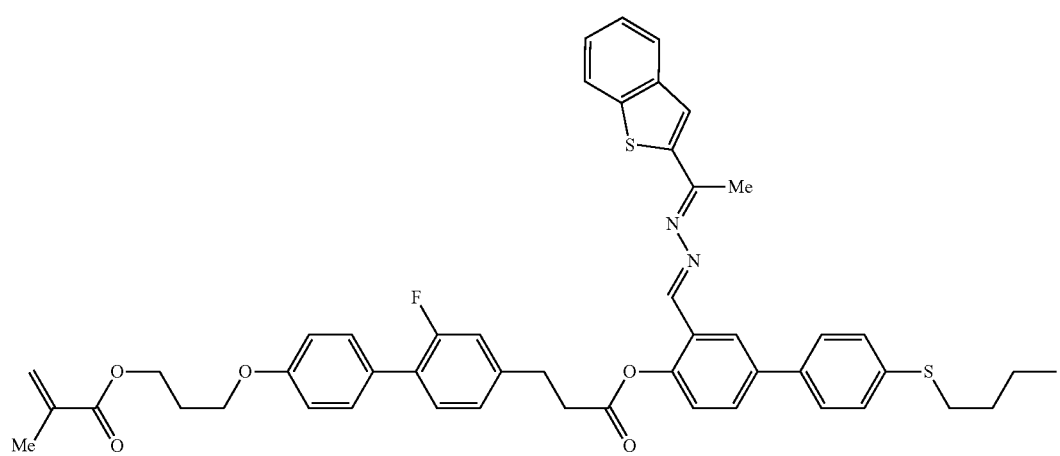

-continued
(I-56)
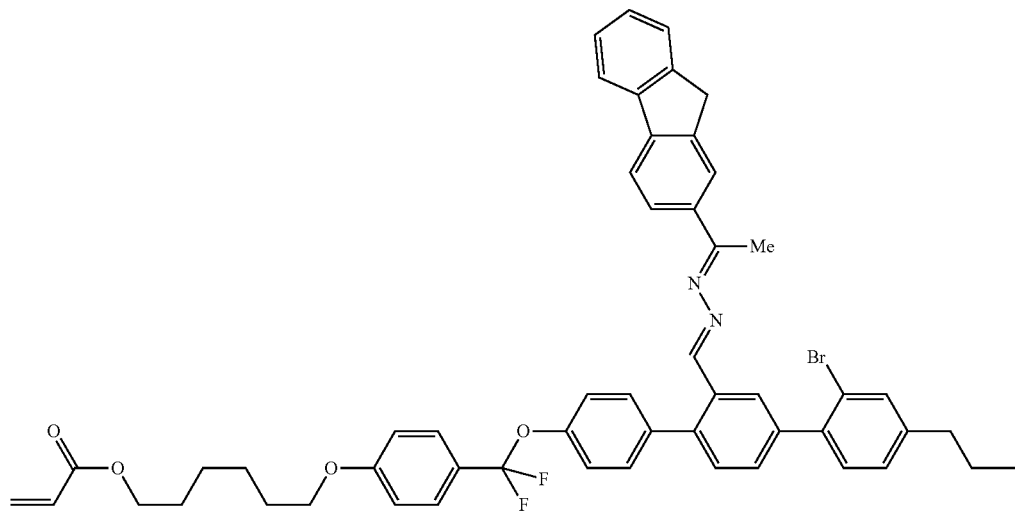
(I-65)
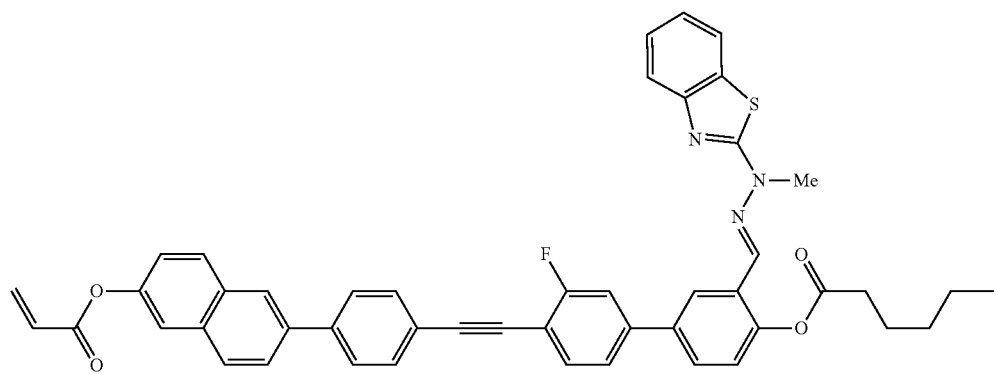
(I-66)
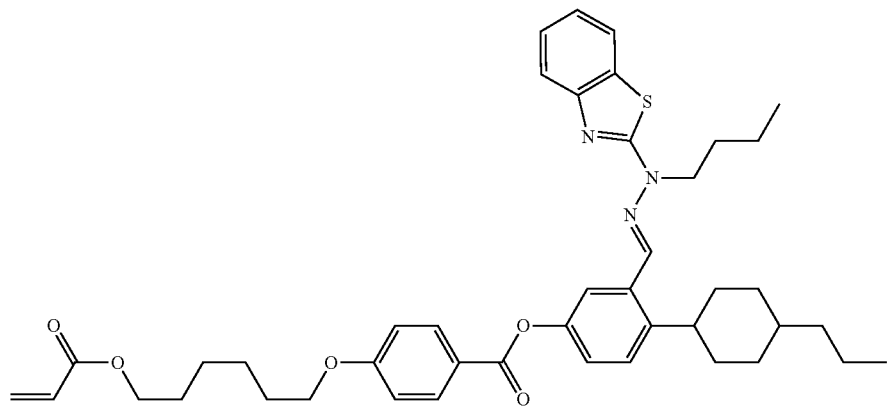

-continued
(I-67)
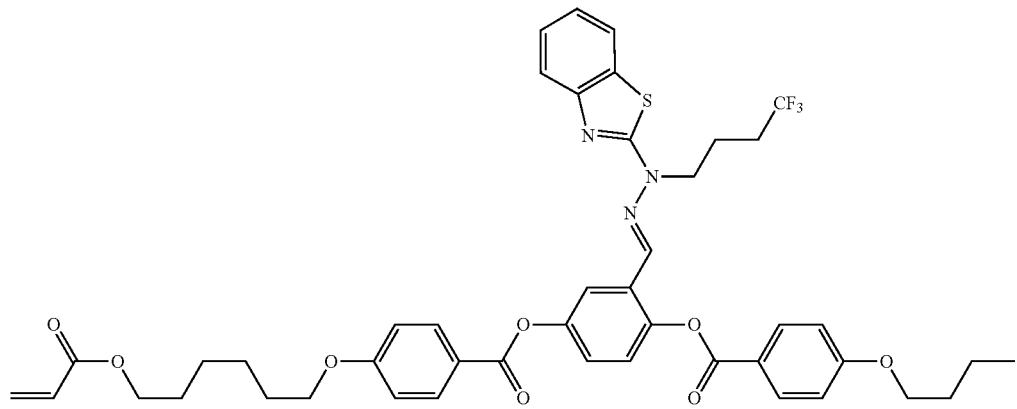
(I-70)
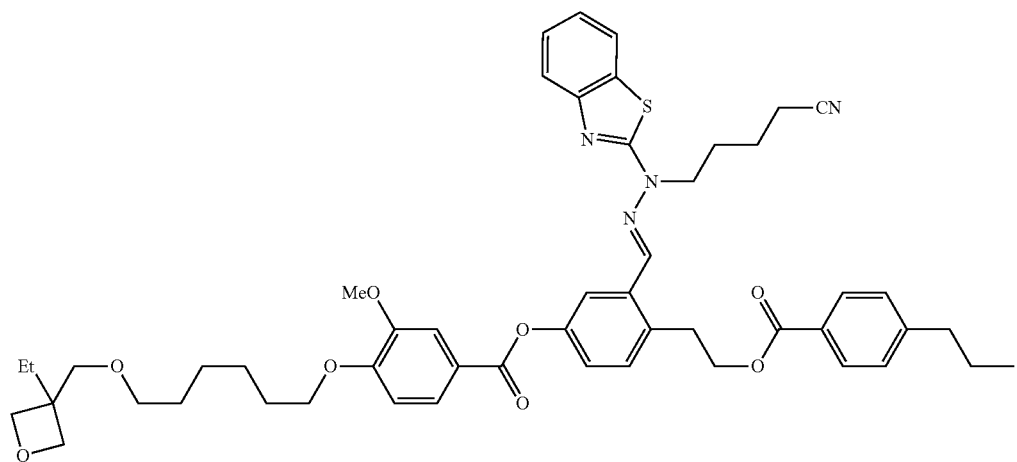
(I-76)
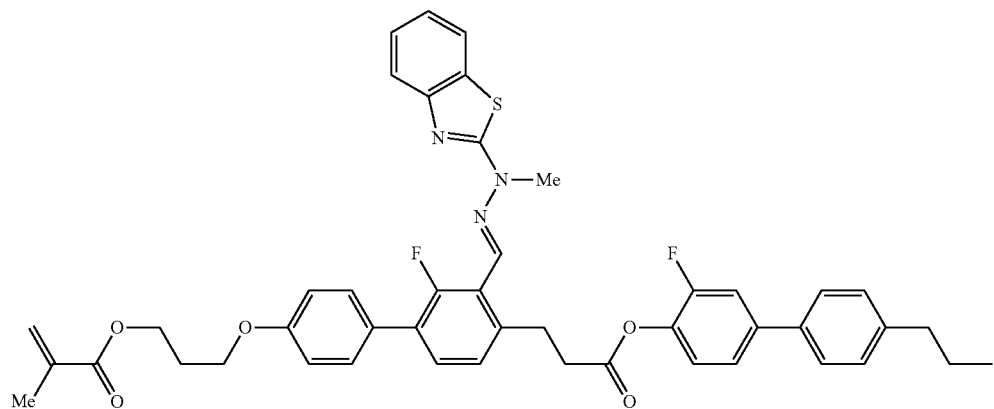

-continued
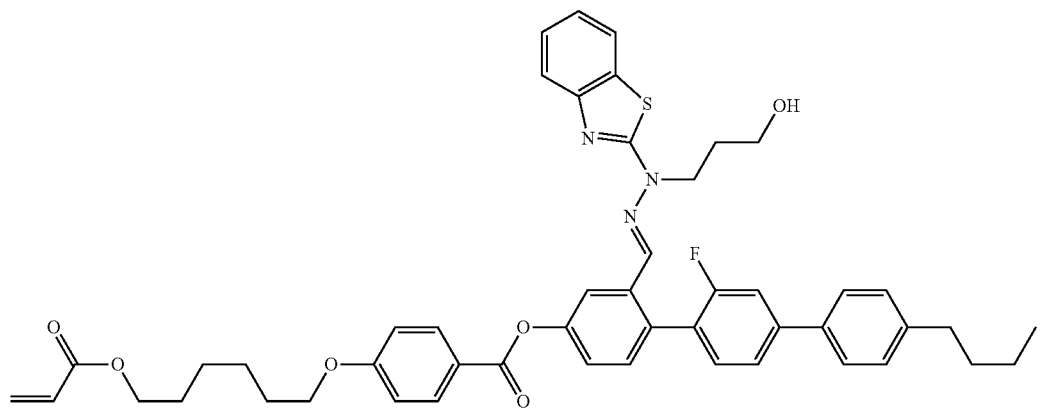
(I-77)
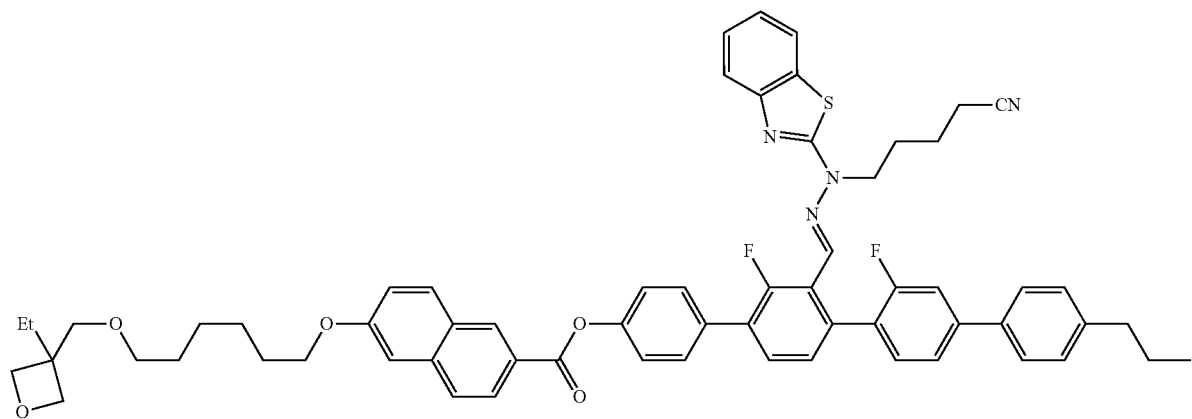
(I-80)
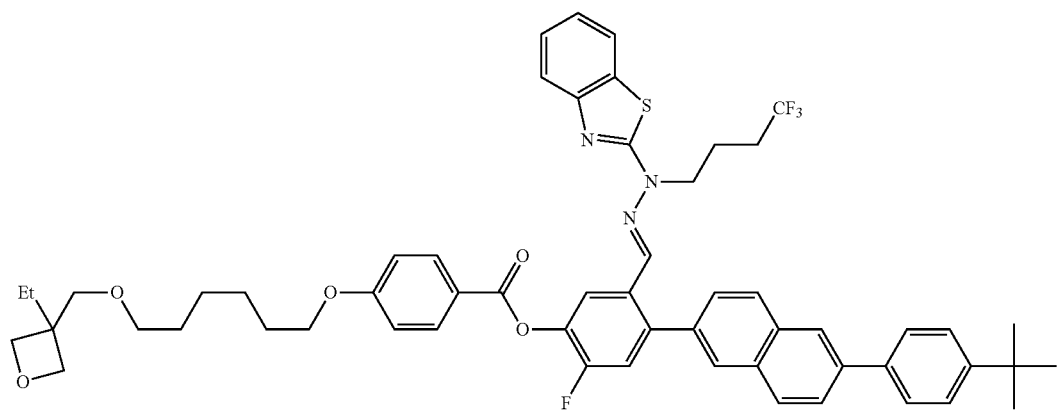
(I-81)

-continued
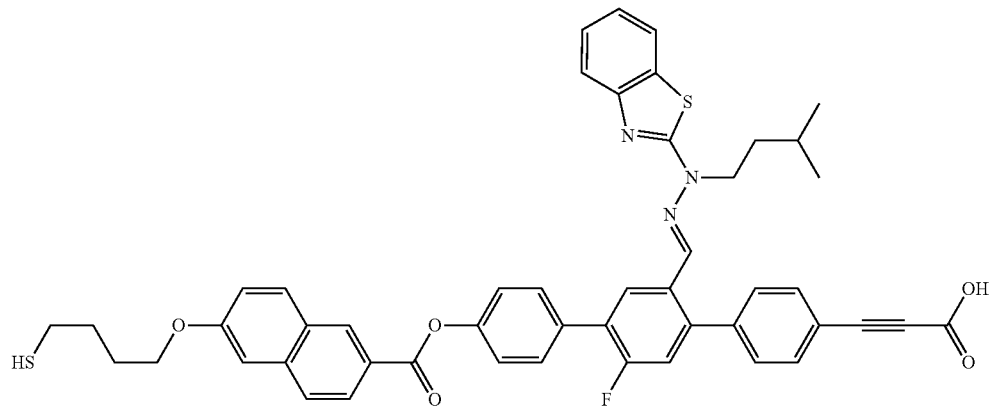
(I-83)
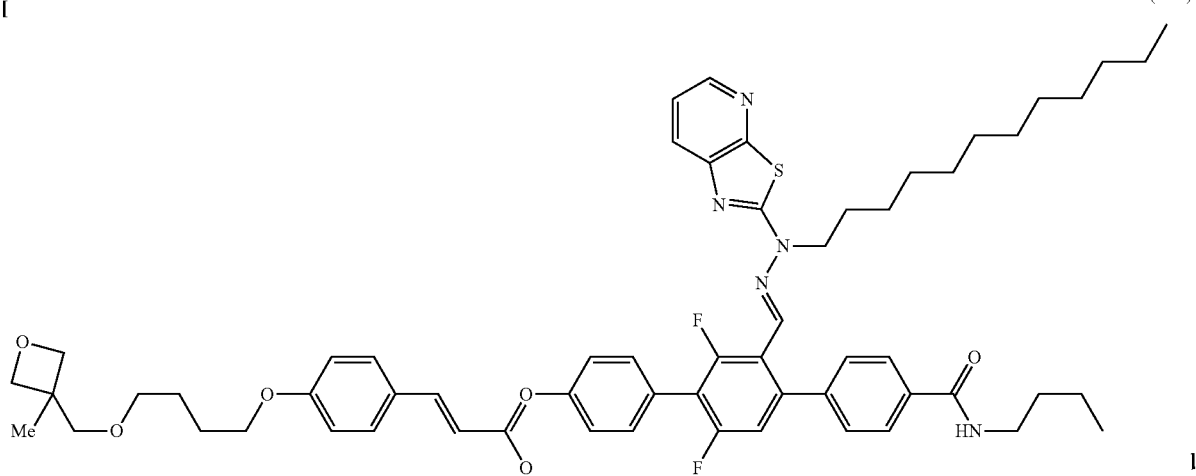
(I-88)
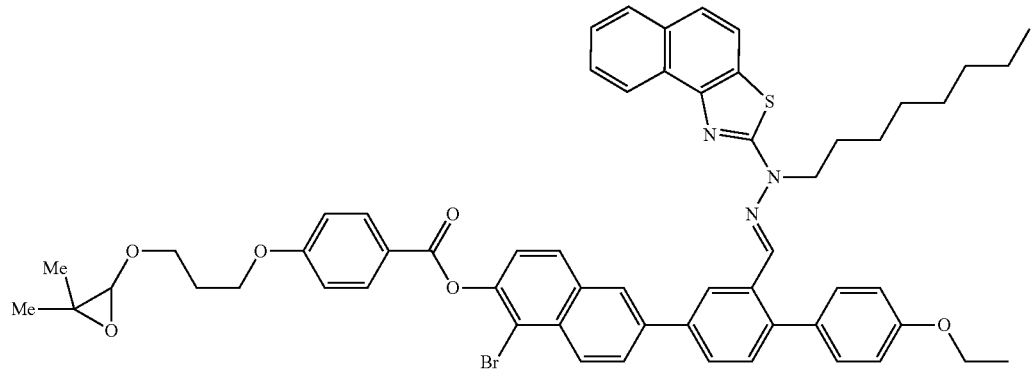
(I-92)

-continued
(I-101)
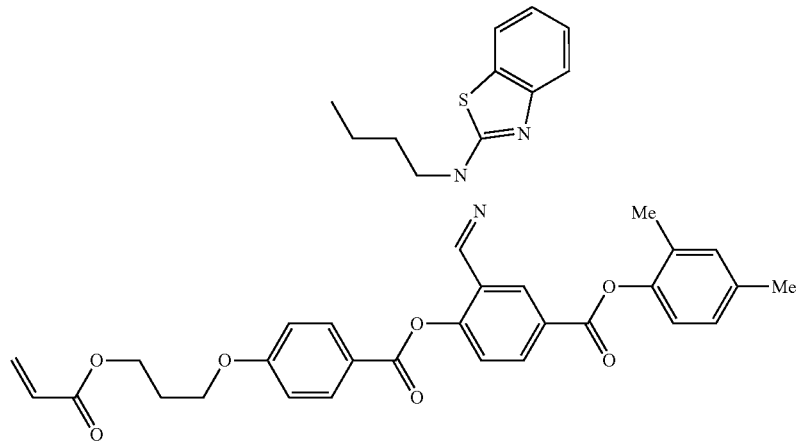
(I-102)
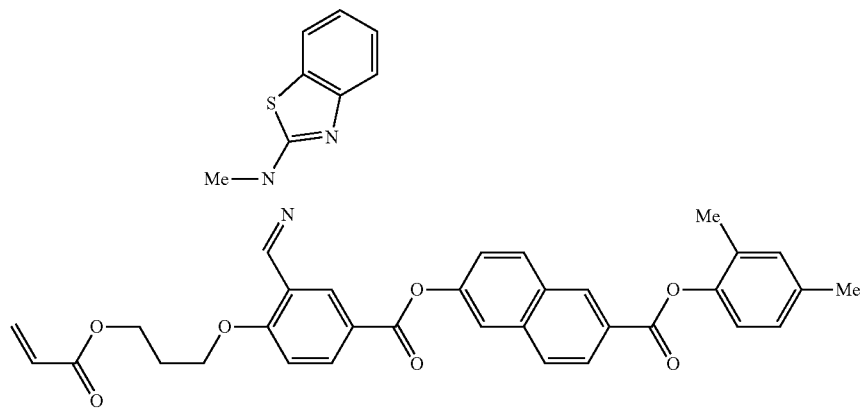
(I-115)
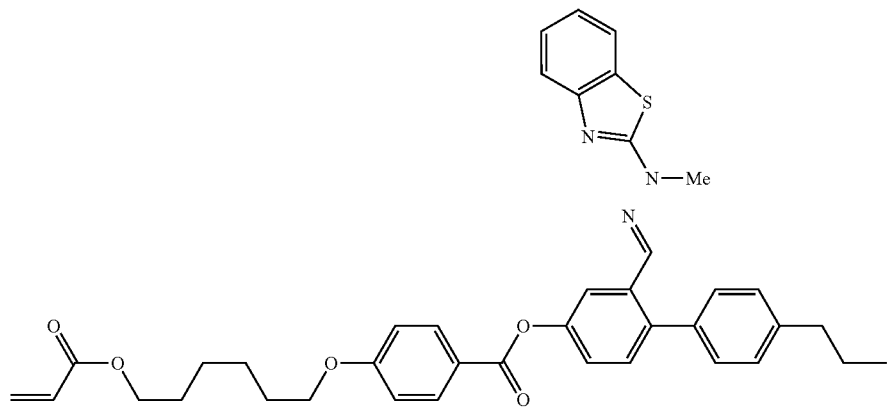

-continued

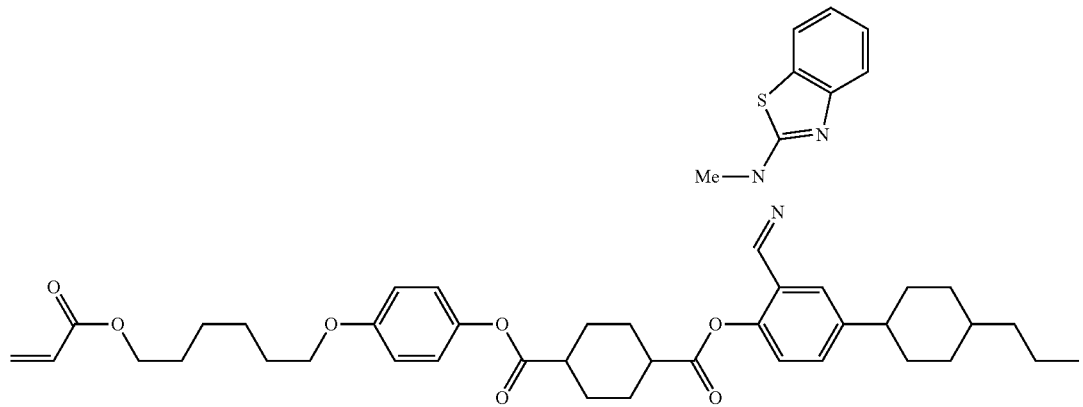
(I-117)

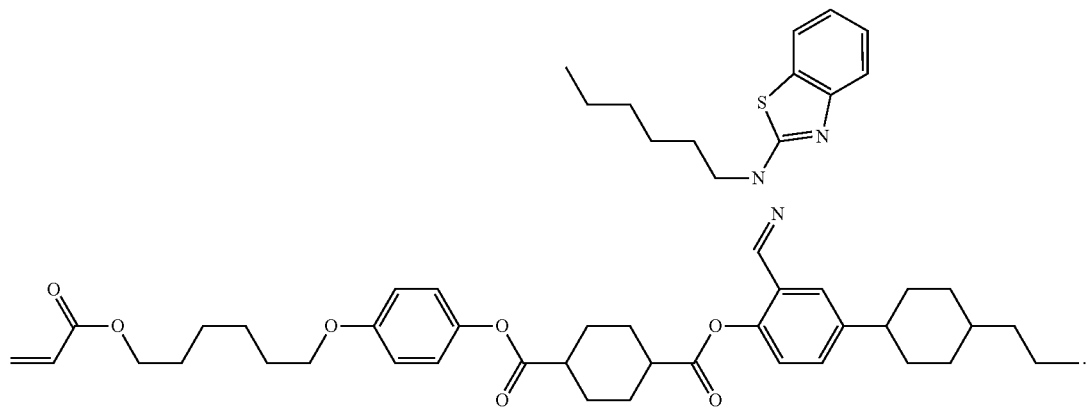
(I-118)

12. The *polymerizable* compound represented by General Formula (I) according to claim 11 selected from the group consisting of the compounds represented by Formulae (I-117) and (I-118).

13. *A polymerizable compound for producing an optical film, the polymerizable compound represented by General Formula (I) below,*

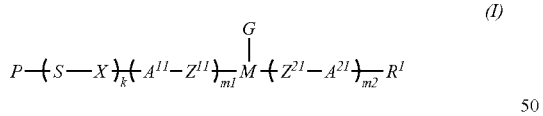
(I)

wherein, P represents a polymerizable group selected from the group consisting of groups represented by Formulae (P-1) to (P-20) below,

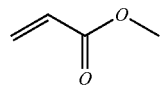
(P-1)

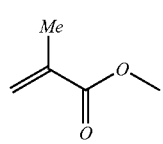
(P-2)

-continued

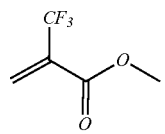
(P-3)

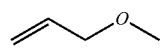
(P-4)

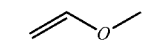
(P-5)

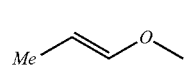
(P-6)

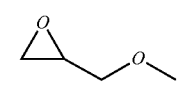
(P-7)

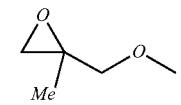
(P-8)

(P-9)

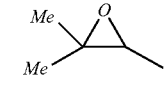
(P-10)

-continued

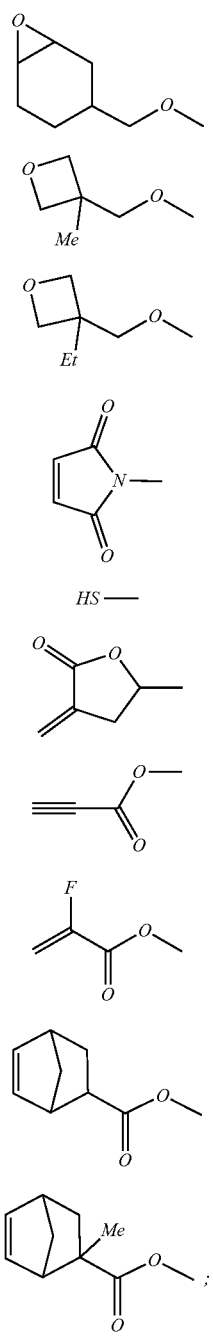

(P-11)
(P-12)
(P-13)
(P-14)
(P-15)
(P-16)
(P-17)
(P-18)
(P-19)
(P-20)

S represents an alkylene group having 1 to 20 carbon atoms and in which one —CH$_2$— group or two or more —CH$_2$— groups that are not adjacent to one another may be each independently replaced with —COO—, —OCO—, —OCO—O—, —CO—NH— or —NH—CO—;

X represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —N=N—, —CH=N—, N=CH—, or a single bond and, when a plurality of X groups are present, they may be identical to or different from one another in which P—(S—X)$_k$— does not include an —O—O— bond;

A$^1$ and A$^2$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, the above groups may be optionally substituted with one or more L substituents, and, when a plurality of A$^1$ groups and/or a plurality of A$^2$ groups are present, they may be identical to or different from one another;

L represents a fluorine atom, a chlorine atom, a bromine atom, an iodine atom, a pentafluorosulfanyl group, a nitro group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, when a plurality of L substituents are present, they may be identical to or different from one another, and some hydrogen atoms included in the alkyl group may be replaced with fluorine atoms;

Z$^1$ and Z$^2$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —N=N—, —CH=N—, —N=CH—, —CH=N=N=CH—, or a single bond, provided that one of Z$^1$ and Z$^2$ directly connected to M represents —COO— or —OCO— and that the other of Z$^1$ and Z$^2$ directly connected to M represents the single bond and, when a plurality of Z$^1$ groups and/or a plurality of Z$^2$ groups are present, they may be identical to or different from one another;

M represents a group selected from Formulae (M-1) to (M-8) below,

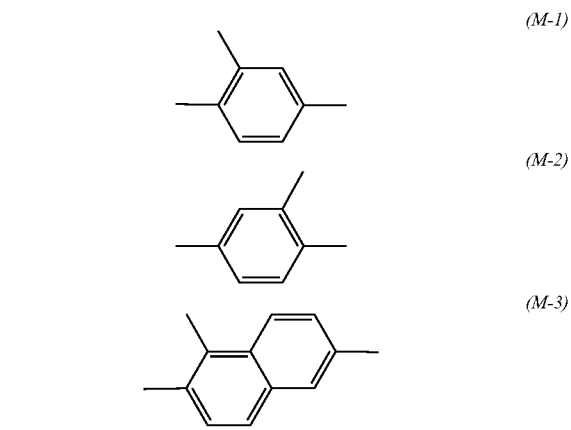

(M-1)
(M-2)
(M-3)

-continued (M-4)
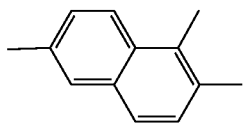

(M-5)
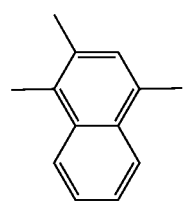

(M-6)
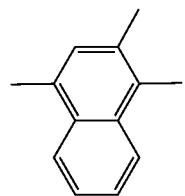

(M-7)
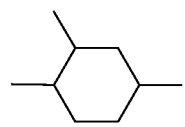

(M-8)
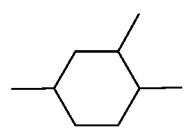

the above groups may be optionally substituted with one or more $L^M$ substituents, $L^M$ represents a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, some hydrogen atoms included in the alkyl group may be replaced with fluorine atoms, and, when a plurality of $L^M$ substituents are present, they may be identical to or different from one another;

$R^1$ represents a hydrogen atom, a fluorine atom, a chlorine atom, a bromine atom, an iodine atom, a pentafluorosulfanyl group, a cyano group, a nitro group, an isocyano group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, some hydrogen atoms included in the alkyl group may be replaced with fluorine atoms;

G represents a group selected from Formula (G-1) below, (G-1)
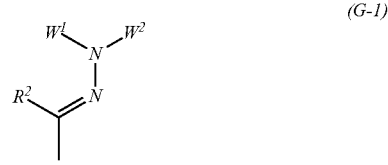

wherein, $R^2$ represents a hydrogen atom or a linear or branched alkyl group having 1 to 20 carbon atoms in which one —$CH_2$—group or two or more —$CH_2$— groups that are not adjacent to one another may be each independently replaced with —O—, —S—, —CO—, —COO—, —OCO—, —CO—S—, —S—CO—, —O—CO—O—, —CO—NH—, or —NH—CO—, and some hydrogen atoms included in the alkyl group may be replaced with fluorine atoms;

$W^1$ represents a group having 2 to 30 carbon atoms, the group including at least one aromatic group, the group may be optionally substituted with one or more $L^W$ substituents, $L^W$ represents a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— group or two or more —$CH_2$— groups that are not adjacent to one another may be each independently replaced with —S—, —CO—, —COO—, —OCO—, —CO—S—, —S—CO—, —O—CO—O—, —CO—NH—, or —NH—CO—, some hydrogen atoms included in the alkyl group may be replaced with fluorine atoms, and, when a plurality of $L^W$ substituents are present, they may be identical to or different from one another;

$W^2$ represents a linear or branched alkyl group having 1 to 20 carbon atoms, the group may be optionally substituted with one or more $L^W$ substituents; and k represents an integer of 0 or 1, m1 and m2 each independently represent an integer of 0 to 4, and m +m2 is an integer of 1 to 5.

14. The polymerizable compound represented by General Formula (I) according to claim 13, selected from the group consisting of the compounds represented by Formulae (I-66), (I-77), (I-81), (I-115), (I-117) and (I-118).

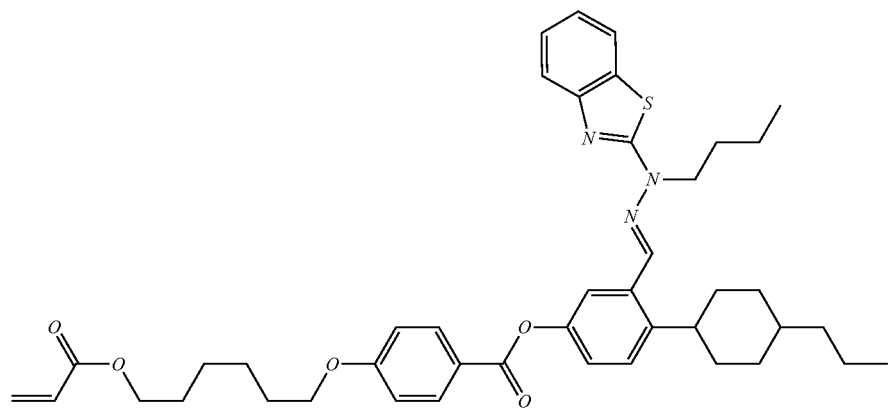
(I-66)
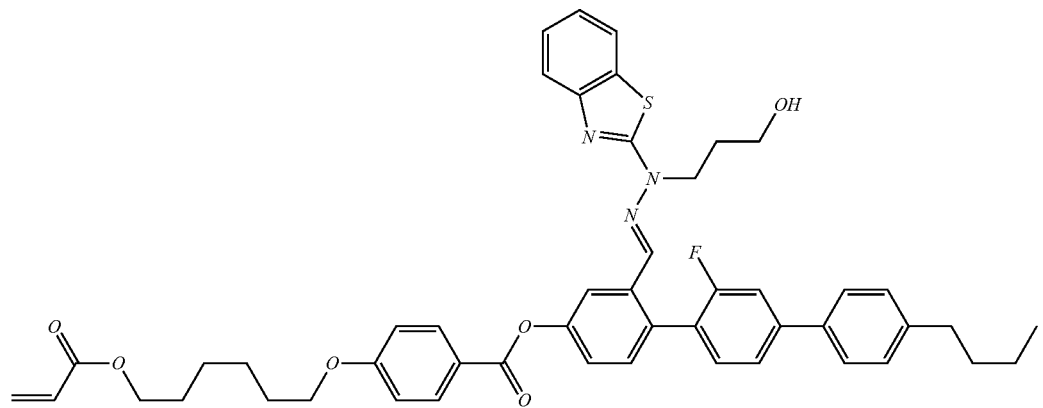
(I-77)
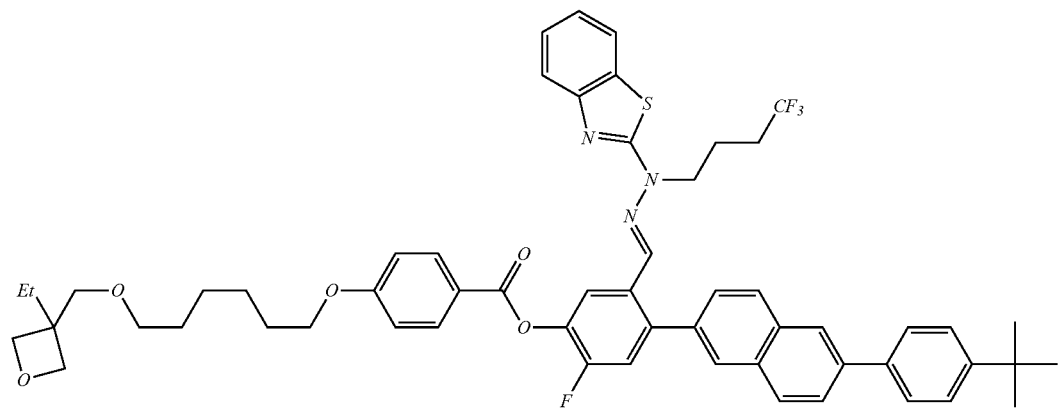
(I-81)

-continued
(I-115)
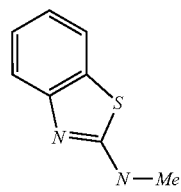
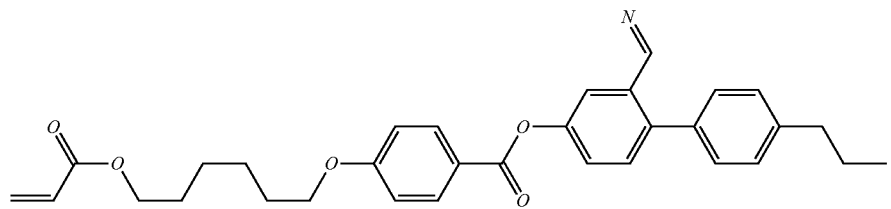
(I-117)
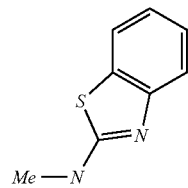
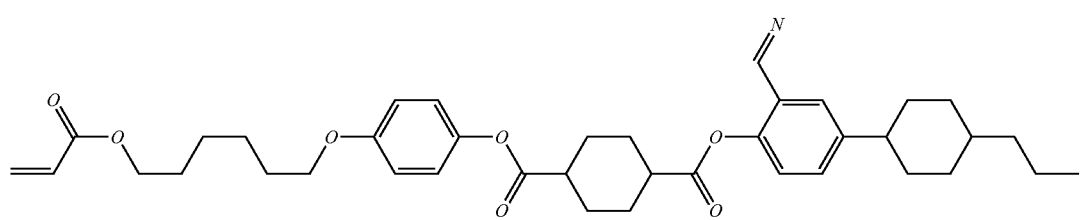
(I-118)
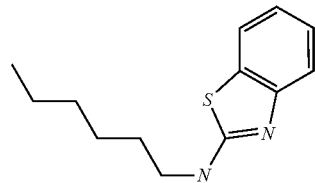
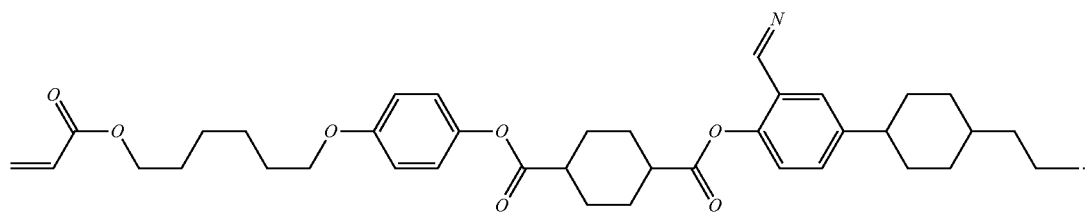

15. The polymerizable compound represented by Formula (I-118):

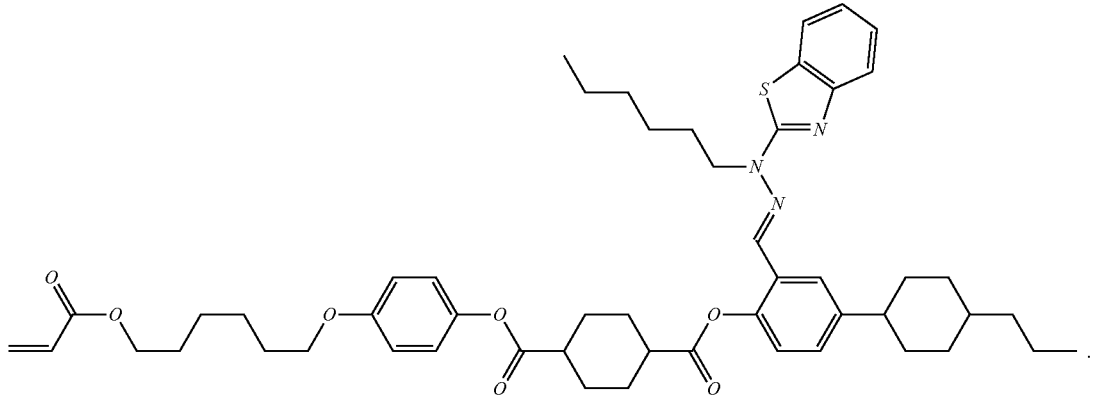

16. The polyymerizable compound represented by General Formula (I) according to claim 1, wherein $R^1$ represents the hydrogen atom, the fluorine atom, the chlorine atom, the bromine atom, the iodine atom, the pentafluorosulfanyl group, the cyano group, the nitro group, the isocyano group, the thioisocyano group, or the linear or branched alkyl group having 1 to 20 carbon atoms.

17. The polymerizable compound represented by General Formula (I) according to claim 13, wherein $R^1$ represents the hydrogen atom, the fluorine atom, the chlorine atom, the bromine atom, the iodine atom, the pentafluorosulfanyl group, the cyano group, the nitro group, the isocyano group, the thioisocyano group, or the linear or branched alkyl group having 1 to 20 carbon atoms.

18. The polymerizable compound represented by General Formula (I) according to claim 1, wherein P represents the polymerizable group selected from the group consisting of groups represented by Formulae (P-1), (P-2), (P-3) and (P-18).

* * * * *